United States Patent [19]
Nakazawa et al.

[11] Patent Number: 5,569,157
[45] Date of Patent: Oct. 29, 1996

[54] ENDOSCOPE

[75] Inventors: Masaaki Nakazawa; Hideo Ito; Koji Nakamoto; Yasuhito Kura; Seiji Kitano; Hisao Yabe; Tatsuya Furukawa, all of Tokyo, Japan

[73] Assignee: Olympus Optical Co., Ltd., Tokyo, Japan

[21] Appl. No.: 237,000

[22] Filed: May 2, 1994

[30] Foreign Application Priority Data

| | | | |
|---|---|---|---|
| May 7, 1993 | [JP] | Japan | 5-106426 |
| May 7, 1993 | [JP] | Japan | 5-106990 |
| May 10, 1993 | [JP] | Japan | 5-108456 |
| May 10, 1993 | [JP] | Japan | 5-108509 |
| May 7, 1993 | [JP] | Japan | 5-130110 |
| May 11, 1993 | [JP] | Japan | 5-109570 |
| Dec. 27, 1993 | [JP] | Japan | 5-333217 |
| Dec. 27, 1993 | [JP] | Japan | 5-333218 |
| Dec. 27, 1993 | [JP] | Japan | 5-333219 |
| Dec. 28, 1993 | [JP] | Japan | 5-353932 |
| Dec. 28, 1993 | [JP] | Japan | 5-354156 |
| Dec. 28, 1993 | [JP] | Japan | 5-354157 |

[51] Int. Cl.$^6$ .................................................... A61B 1/00
[52] U.S. Cl. ........................... 600/107; 600/104; 600/106
[58] Field of Search ................... 128/4, 6, 7; 600/104, 600/106, 107

[56] References Cited

U.S. PATENT DOCUMENTS

| | | | |
|---|---|---|---|
| 3,896,793 | 7/1975 | Mitsui et al. | 128/4 |
| 3,924,608 | 12/1975 | Mitsui | 128/4 |
| 4,190,041 | 5/1983 | Chikama . | |
| 4,407,273 | 10/1983 | Ouchi | 128/6 |
| 4,452,236 | 6/1984 | Utsugi | 128/4 |
| 4,589,403 | 5/1986 | Ouchi et al. . | |
| 4,593,680 | 6/1986 | Kubokawa | 128/4 |
| 4,841,949 | 6/1989 | Shimizu et al. | 128/4 |
| 4,949,706 | 8/1990 | Thon | 128/4 |

FOREIGN PATENT DOCUMENTS

| | | |
|---|---|---|
| 52-67790 | 5/1977 | Japan . |
| 56-8030 | 1/1981 | Japan . |
| 57-75629 | 5/1982 | Japan . |
| 59-15601 | 5/1984 | Japan . |
| 60-220031 | 11/1985 | Japan . |
| 4-314439 | 11/1992 | Japan . |

*Primary Examiner*—Richard J. Apley
*Assistant Examiner*—Beverly M. Flanagan
*Attorney, Agent, or Firm*—Frishauf, Holtz, Goodman, Langer & Chick

[57] ABSTRACT

An endoscope includes an operating portion placed outside a living body, an insertion portion having a proximal end portion coupled to the operating portion, a distal end portion inserted in the living body, and an instrument insertion channel extending through the insertion portion, a raising mechanism having an operation wire and designed to direct the distal end portion of an instrument, caused to extend through the channel, to a predetermined position, and an operation means for operating the operation wire. The endoscope includes a distal end body portion arranged at the distal end portion of the insertion portion and incorporating an observation means for observing the interior of the living body, a support member for forming at least a portion of the outer surface of the distal end portion. The support member is detachable from the distal end body portion. The endoscope further includes a raising base which is supported on the support member such that the angle at which the raising base is arranged can be adjusted. The angle of the raising base is adjusted by the operation wire. The operation wire is detachable from the operation means.

15 Claims, 83 Drawing Sheets

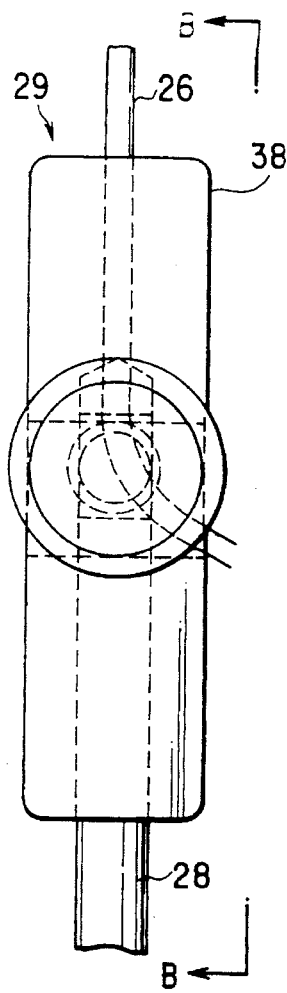 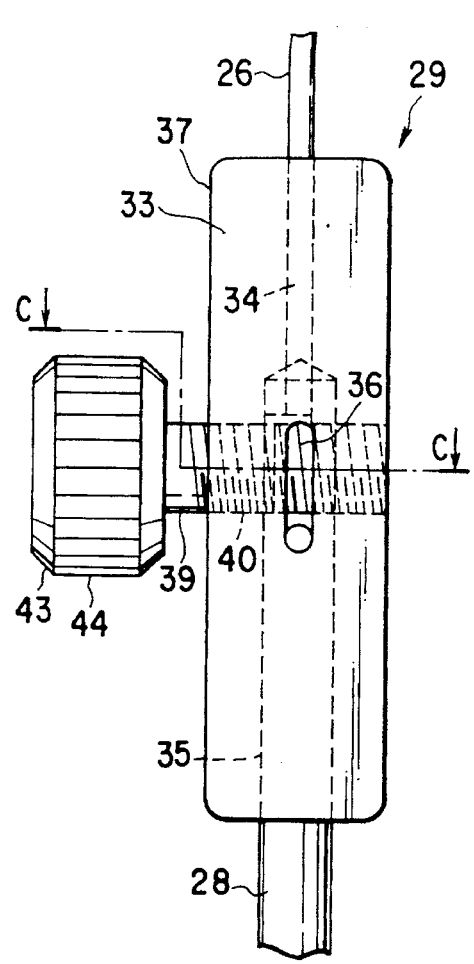 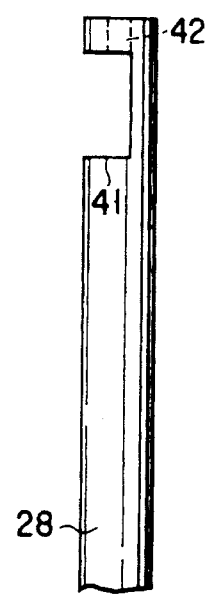
FIG. 2A    FIG. 2B    FIG. 2D
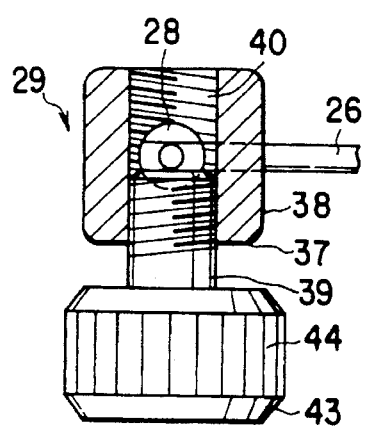 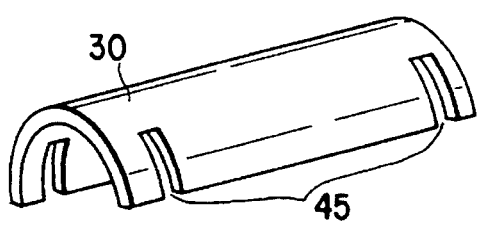
FIG. 2C    FIG. 3

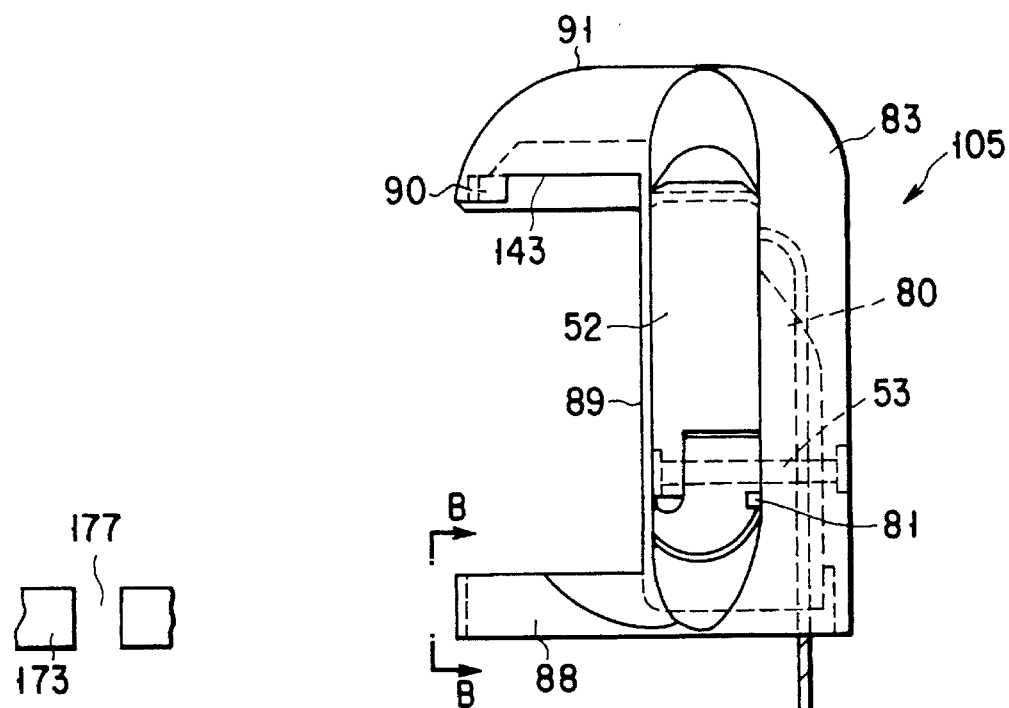
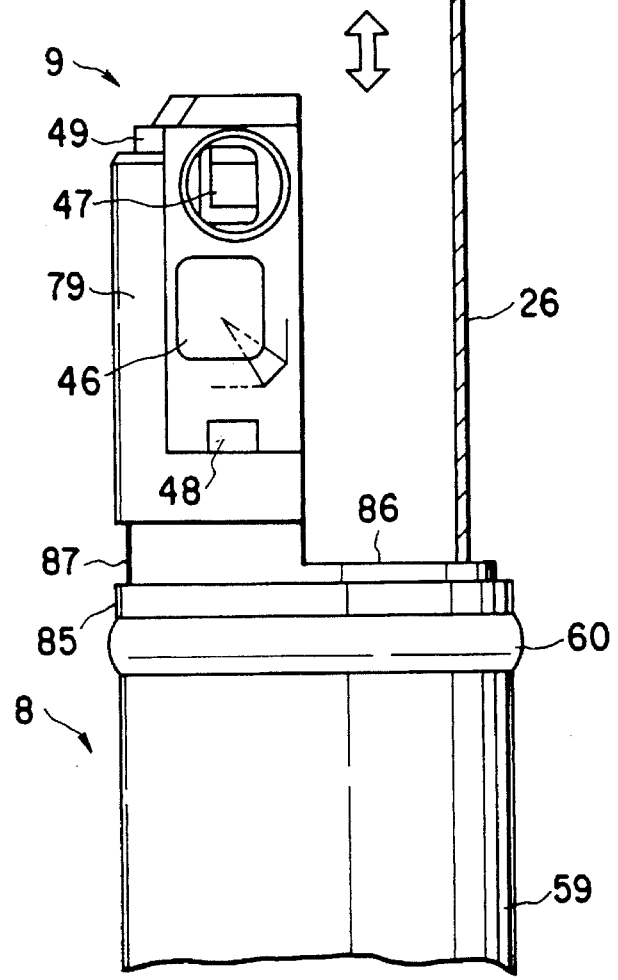
FIG. 4B
FIG. 4A

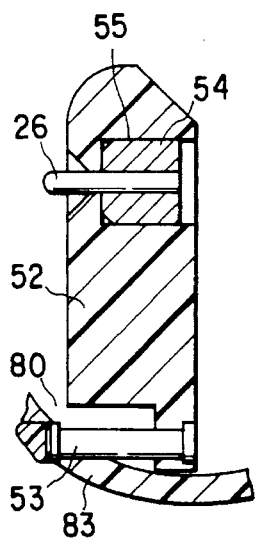
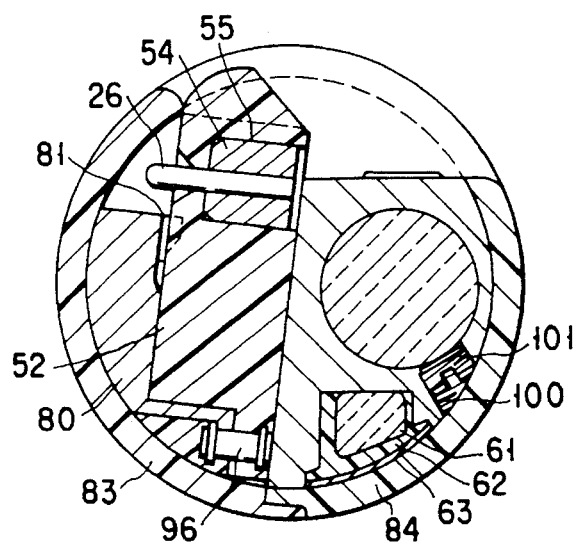
F I G. 10    F I G. 11
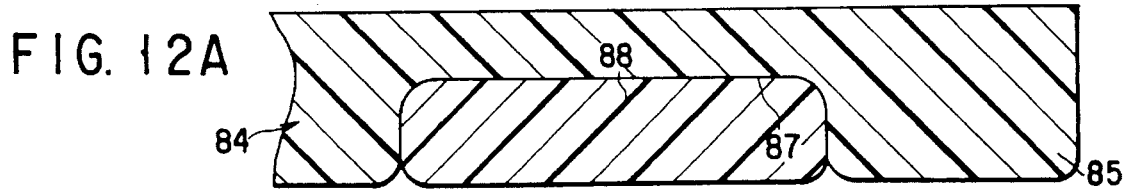
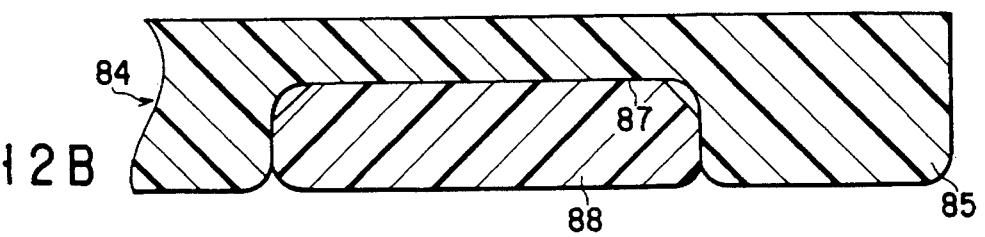
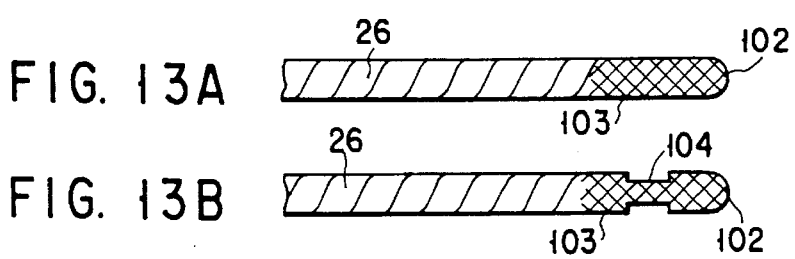
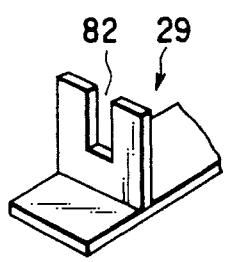
F I G. 13C

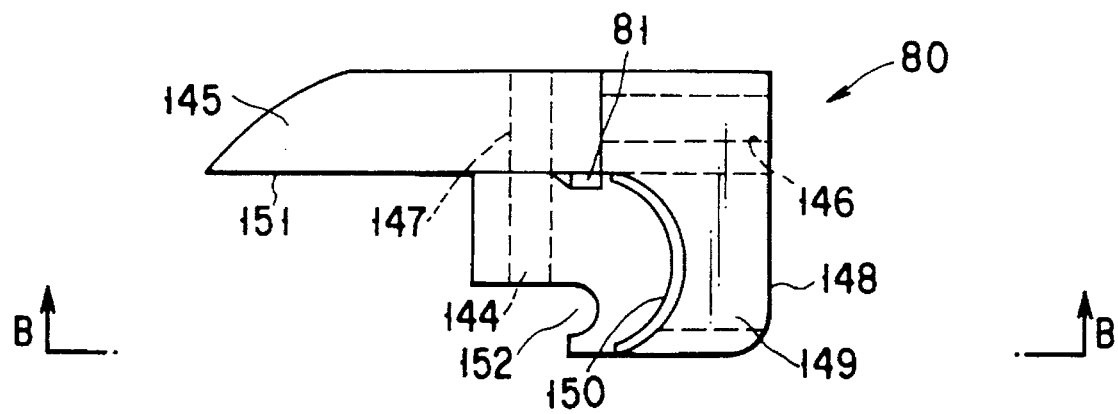
F I G. 26A
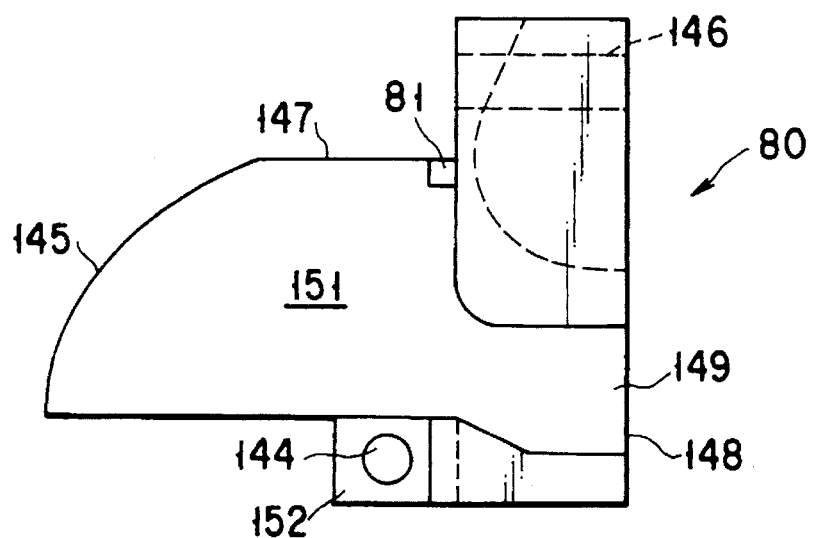
F I G. 26B

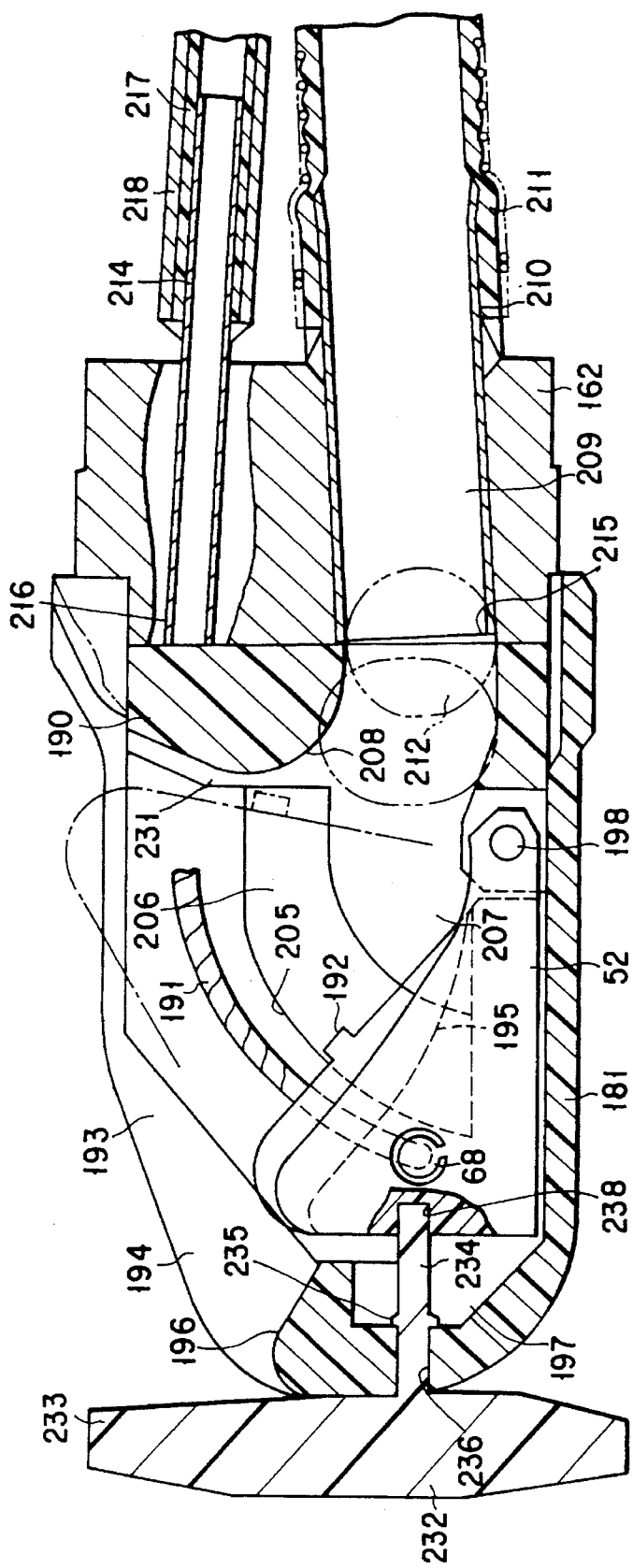
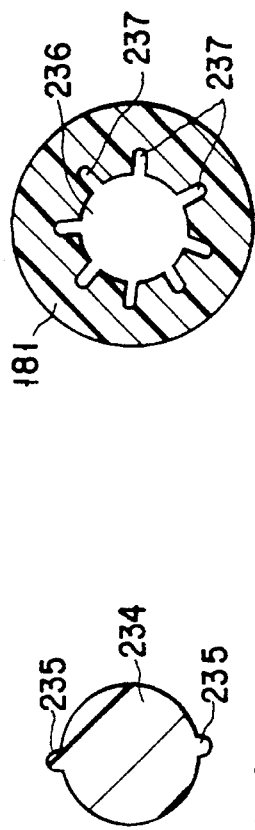
FIG. 32A
FIG. 32C
FIG. 32B

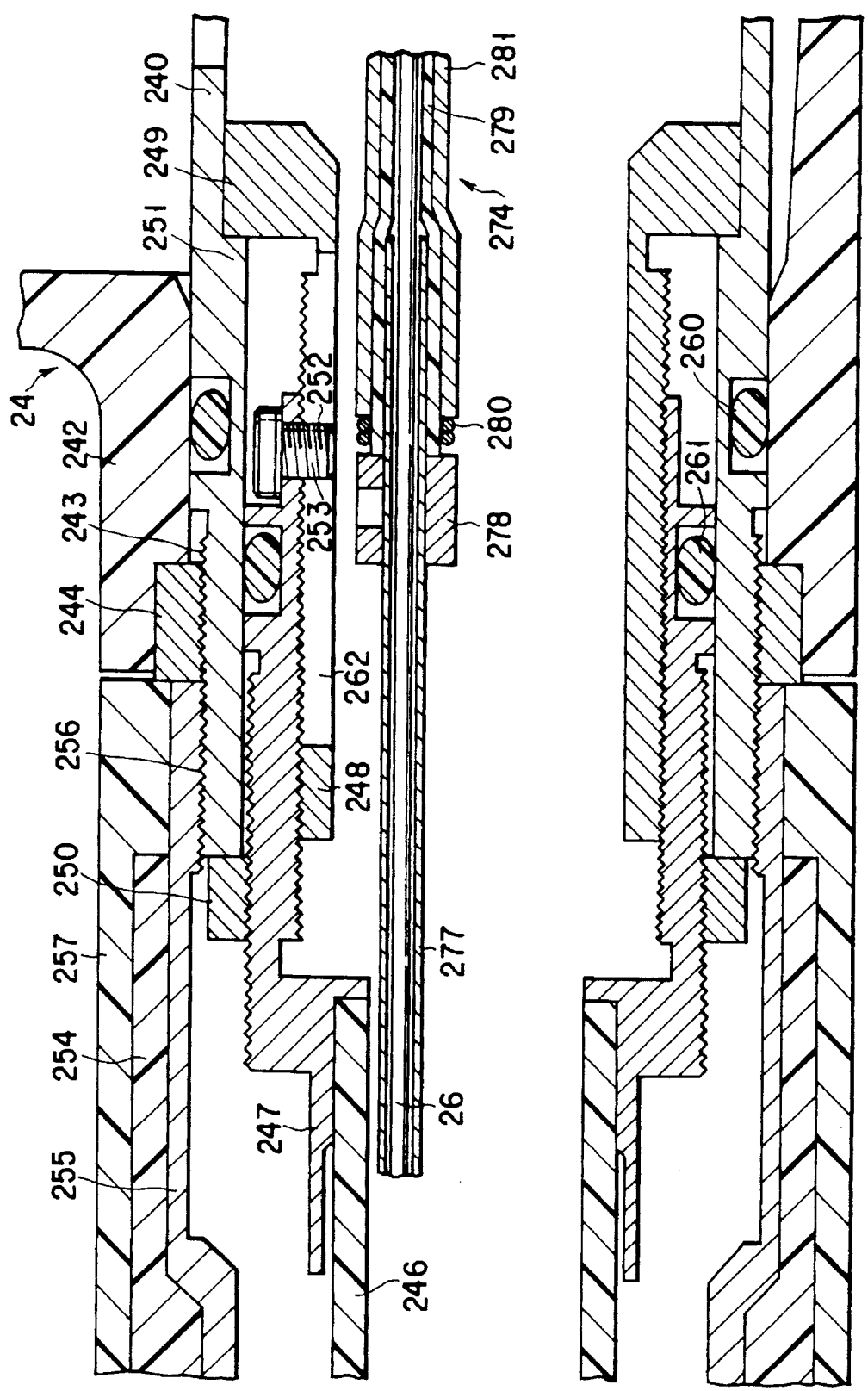
F I G. 35

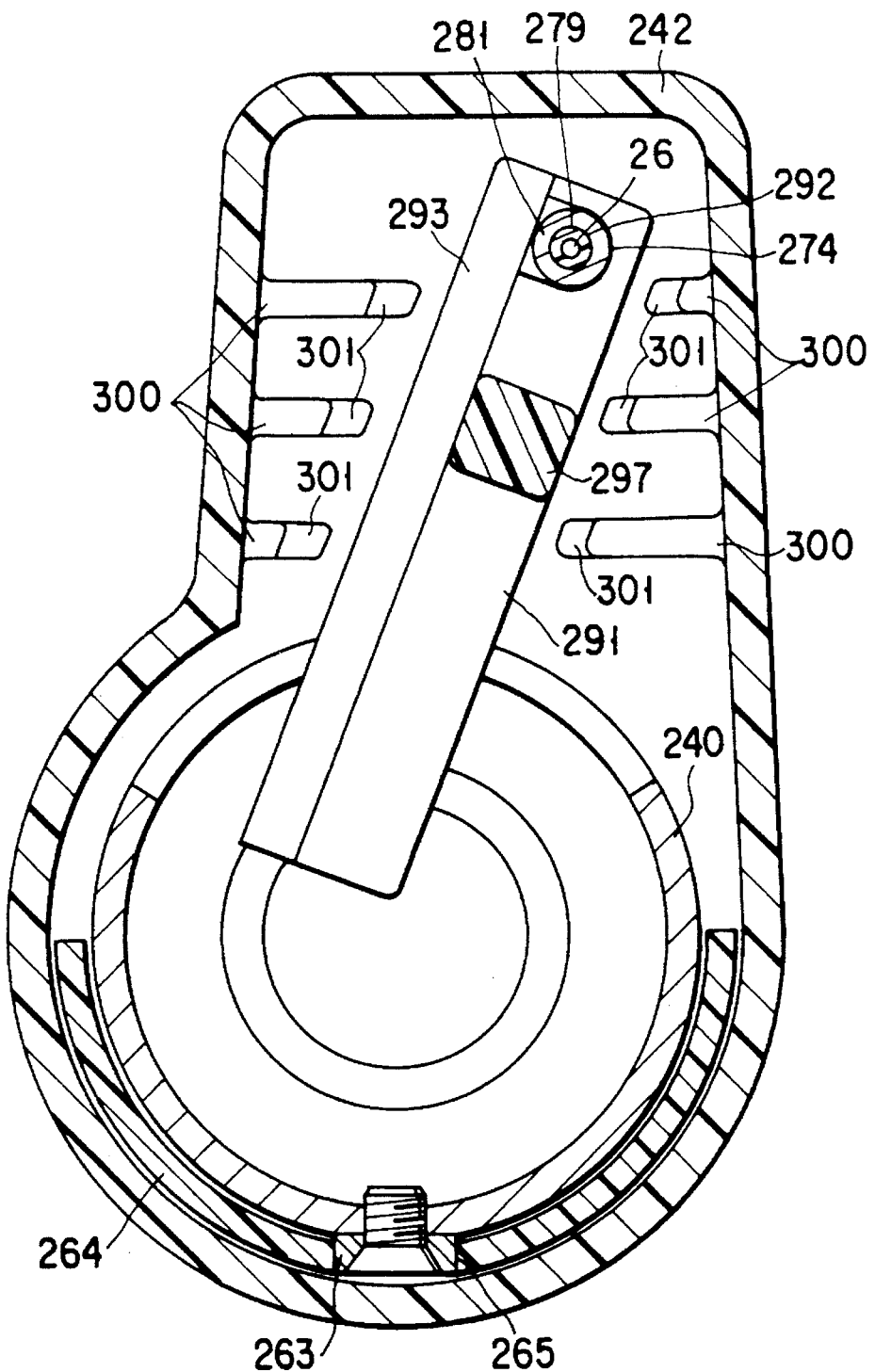
F I G. 37

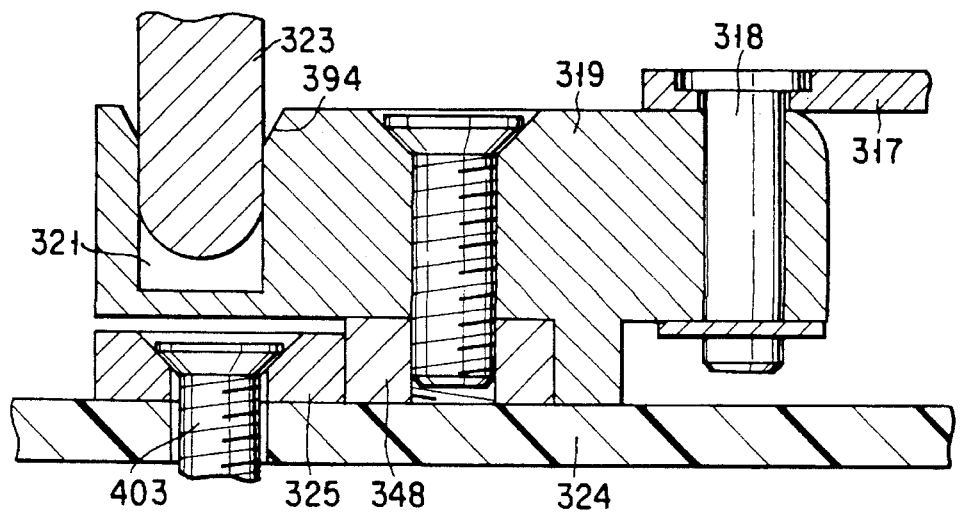
F I G. 40
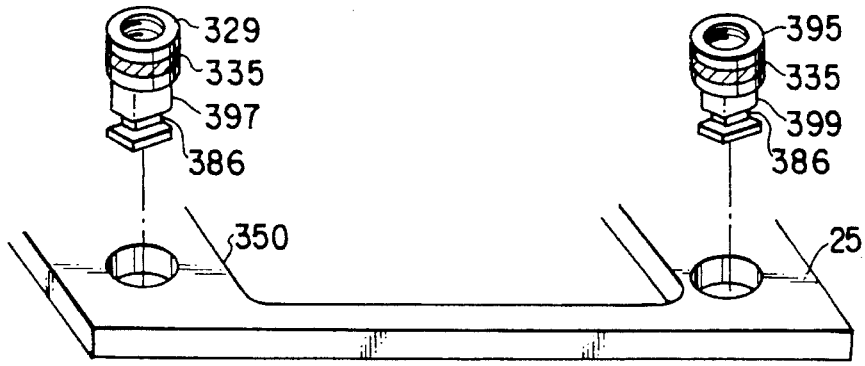
F I G. 42A
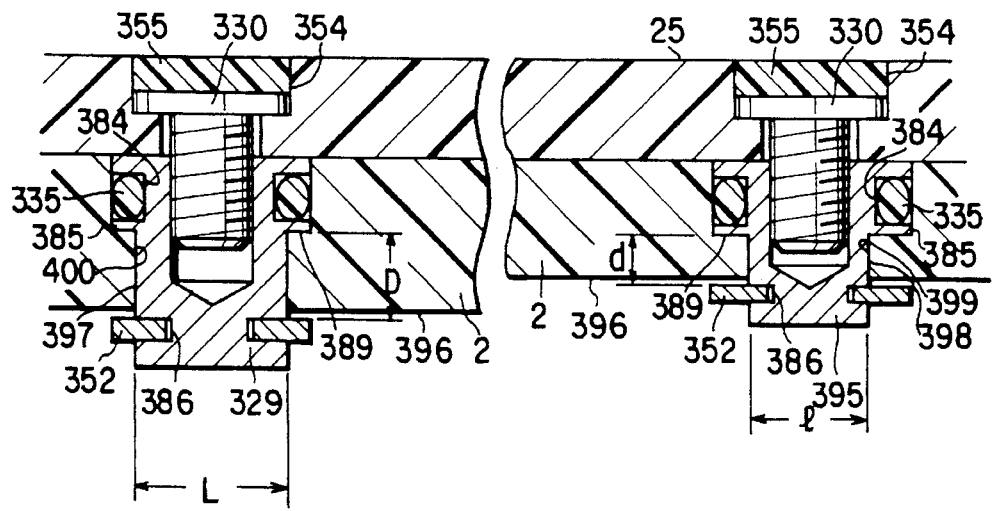
F I G. 42B

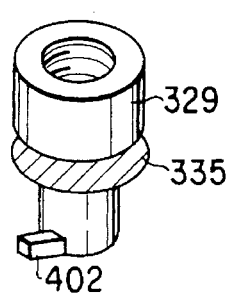 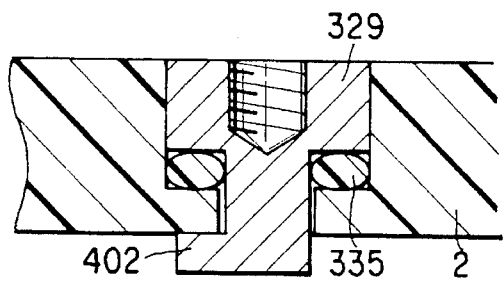
F I G. 43A  F I G. 43B
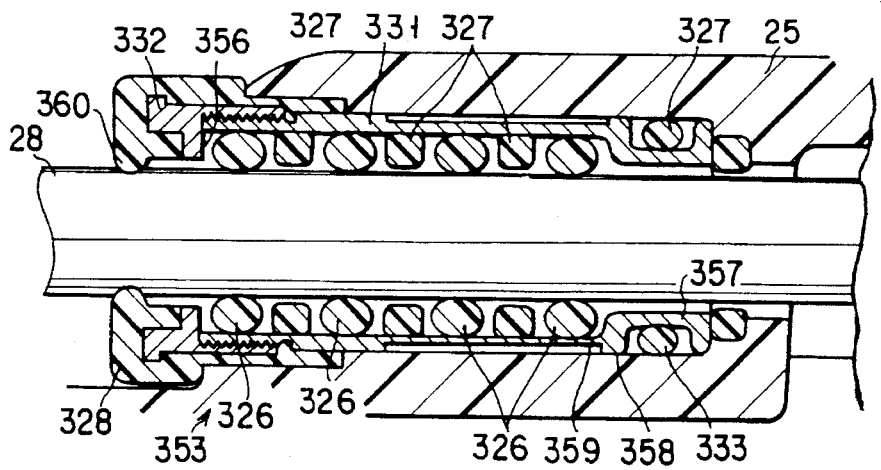
F I G. 44
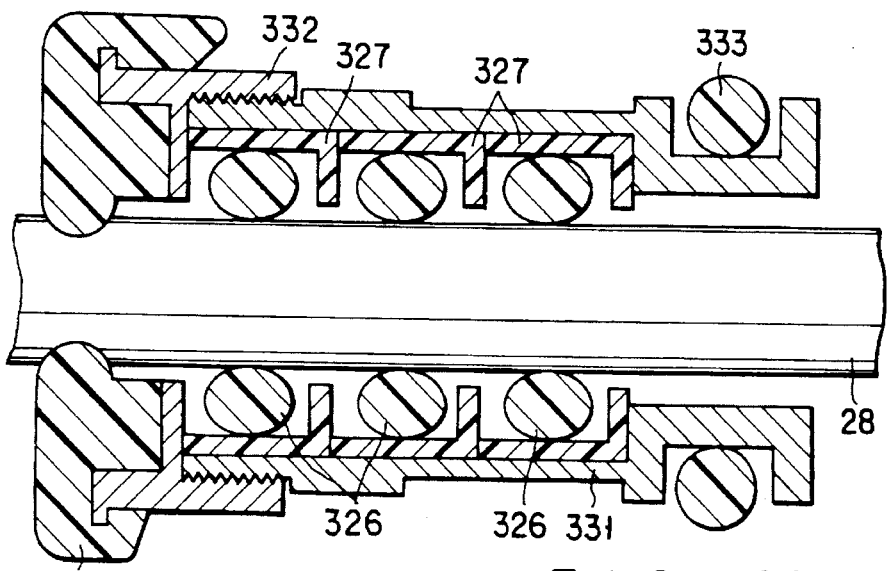
F I G. 45

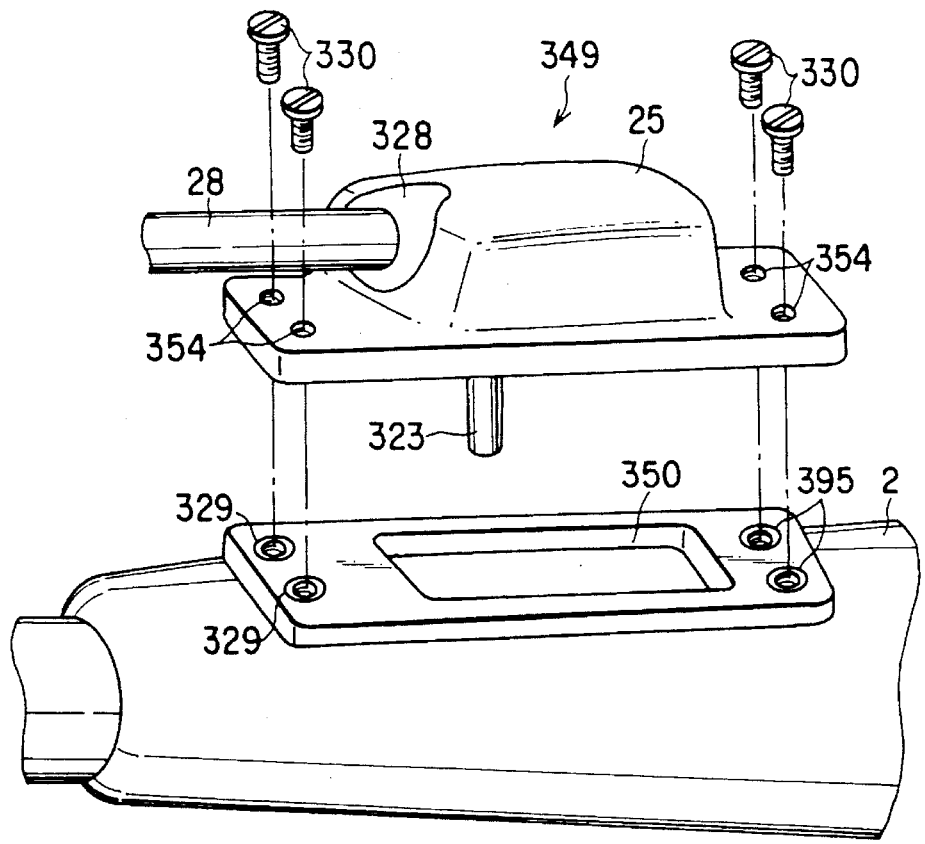
F I G. 64
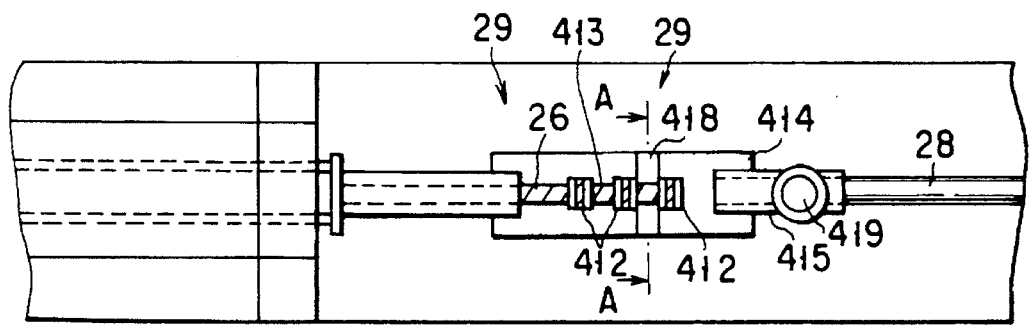
F I G. 65
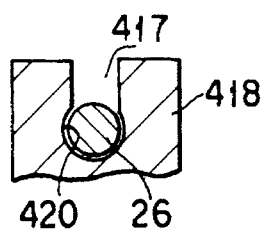
F I G. 66

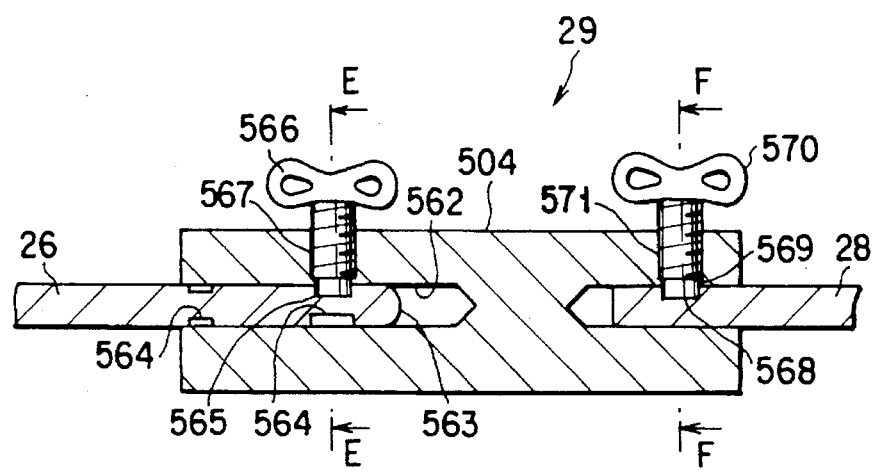
F I G. 73A
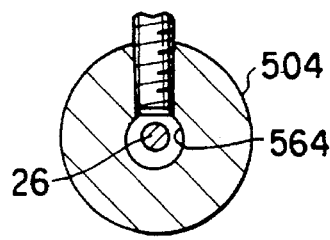
F I G. 73B
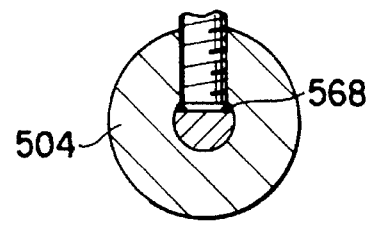
F I G. 73C
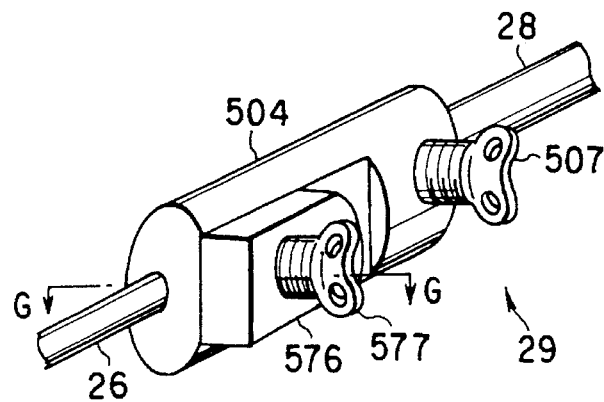
F I G. 74

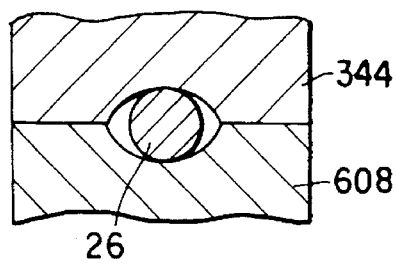
F I G. 87A
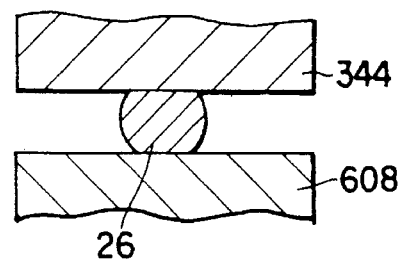
F I G. 87B
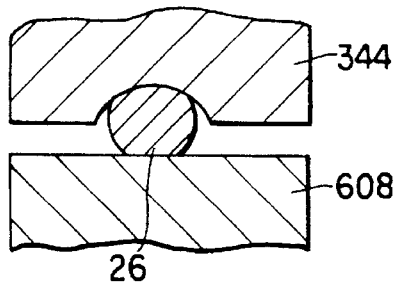
F I G. 87C
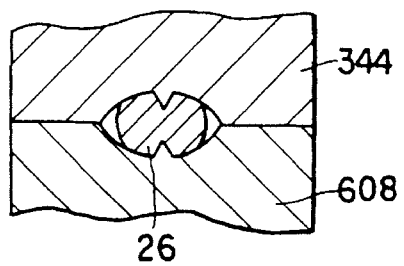
F I G. 87D
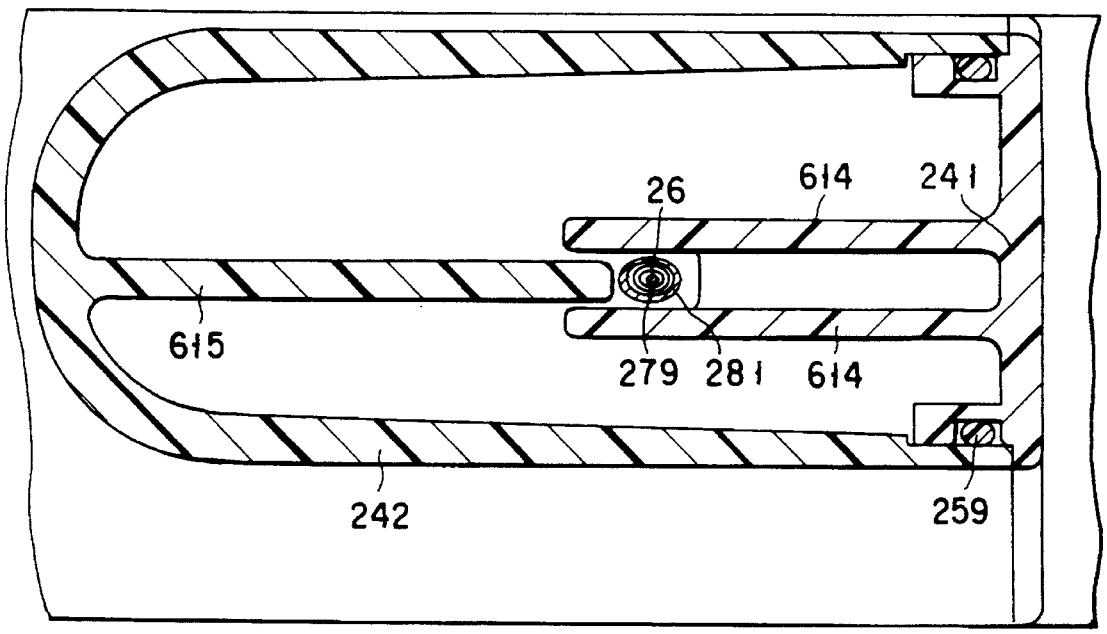
F I G. 89

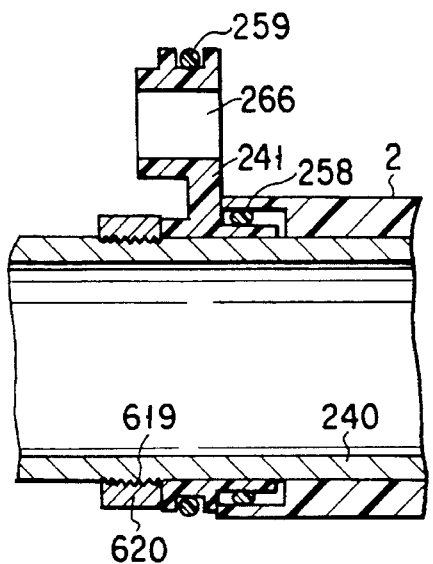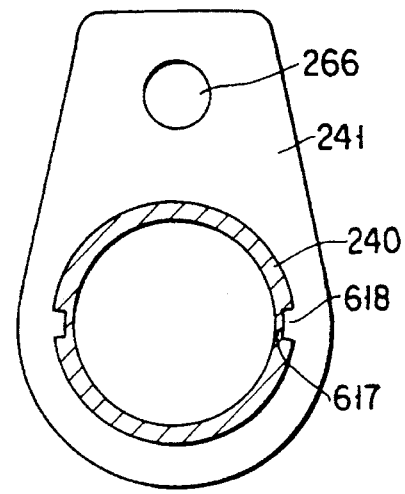
FIG. 91A  FIG. 91B
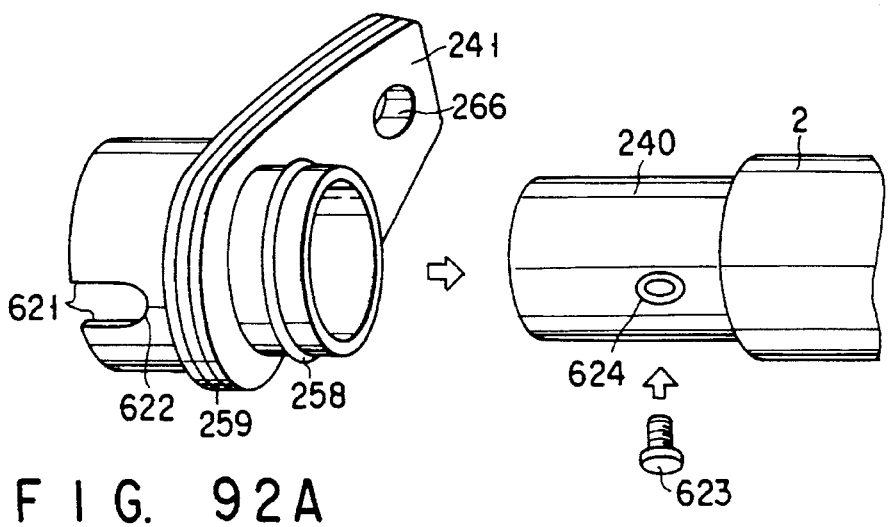
FIG. 92A
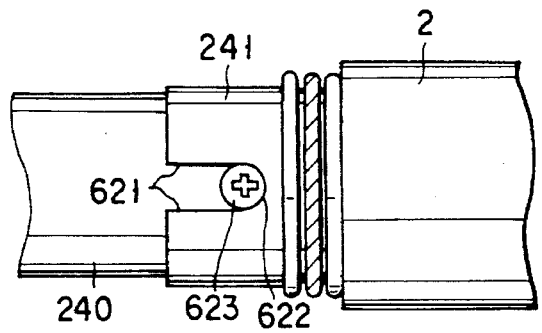
FIG. 92B

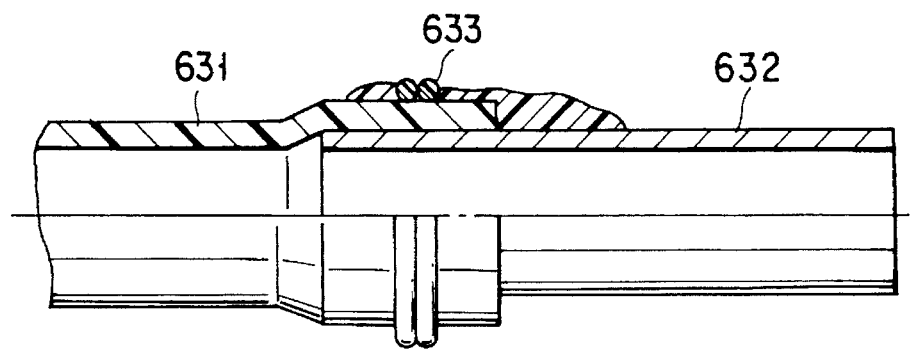
F I G. 95
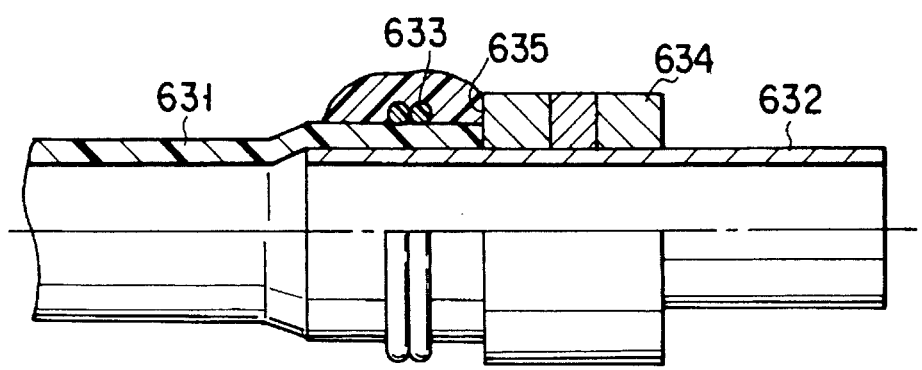
F I G. 96
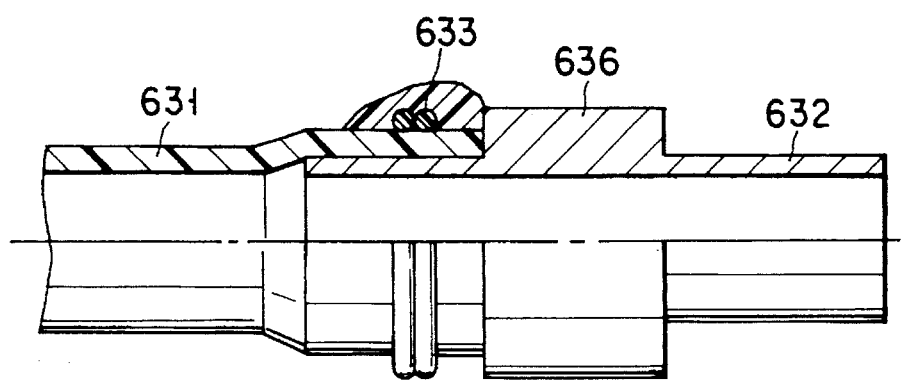
F I G. 97

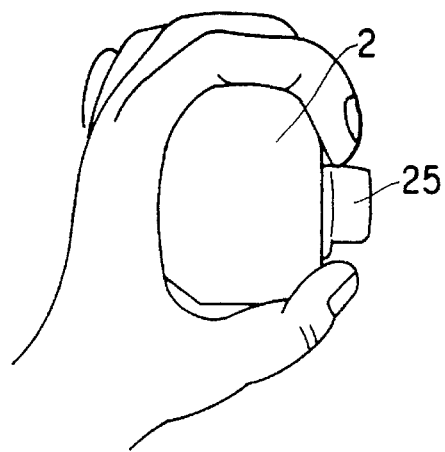
F I G. 101
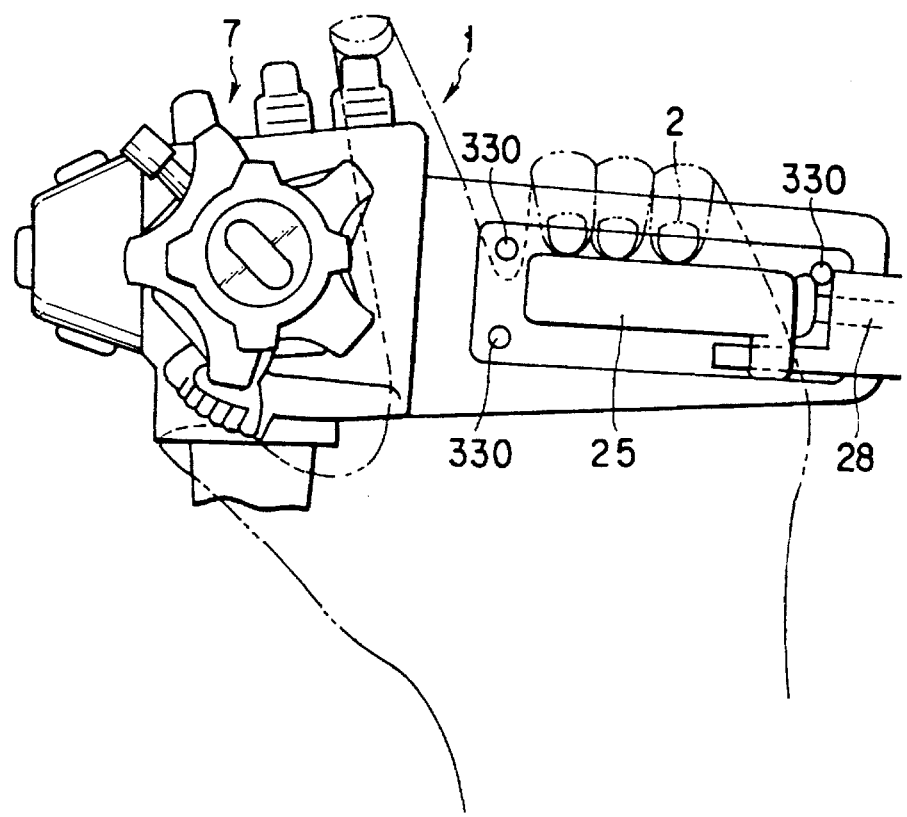
F I G. 102

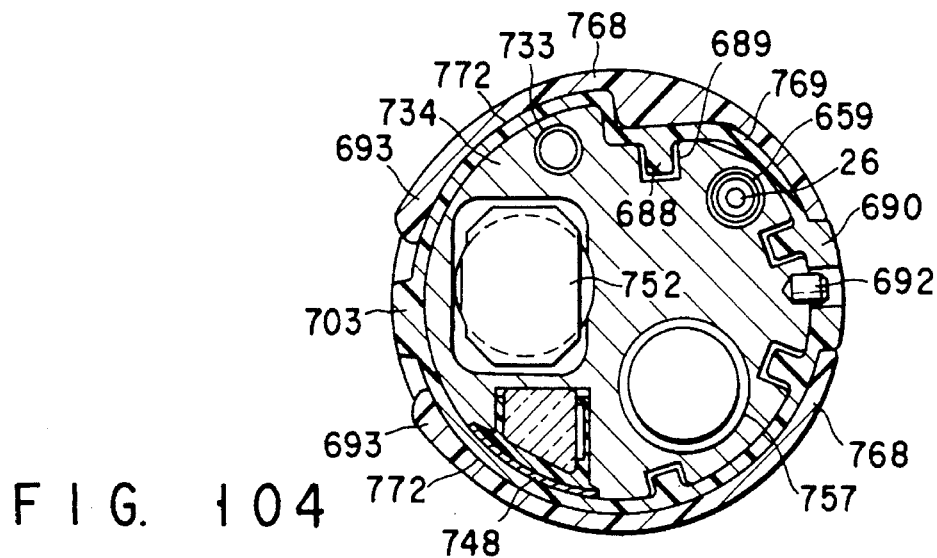
F I G. 104
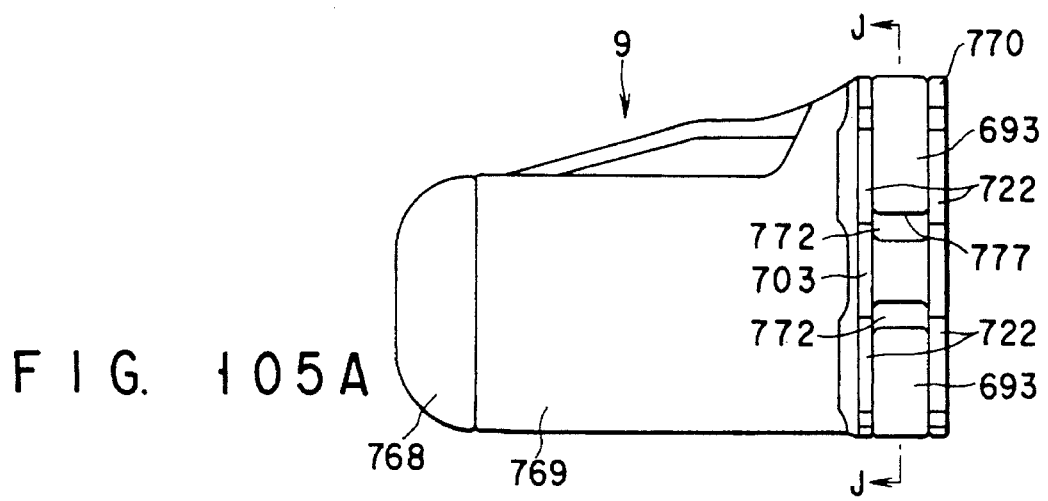
F I G. 105A
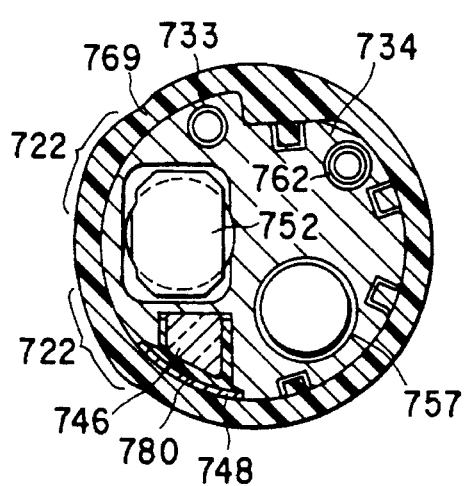
F I G. 105B
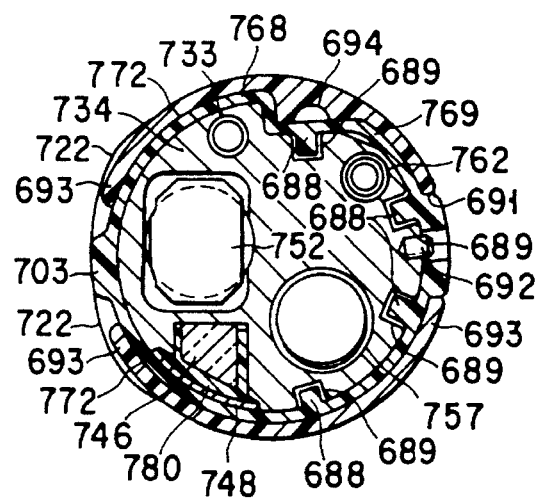
F I G. 105C

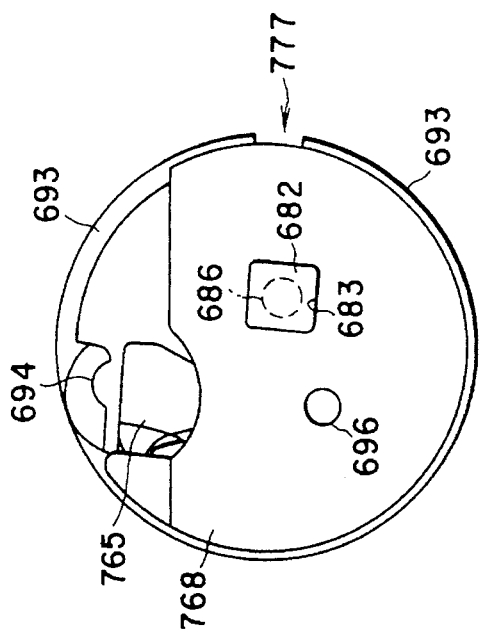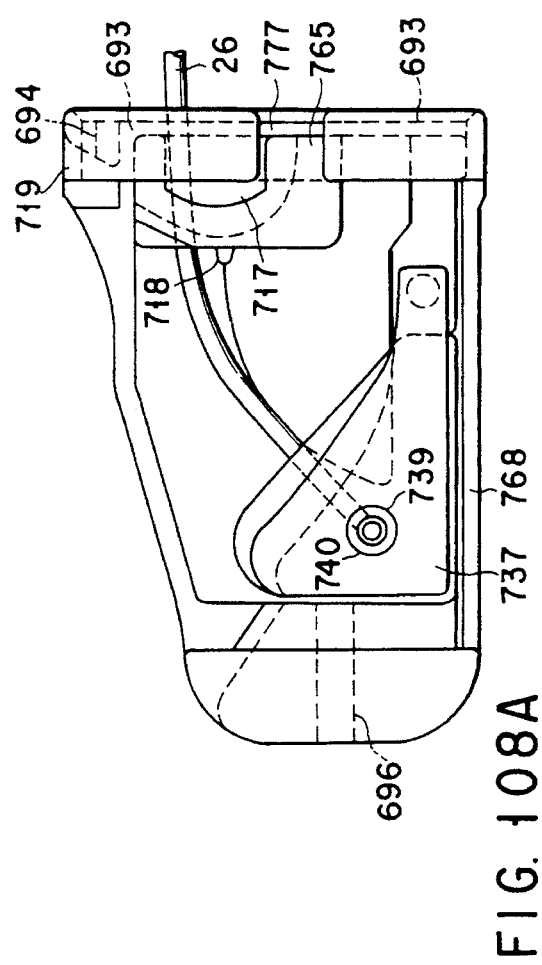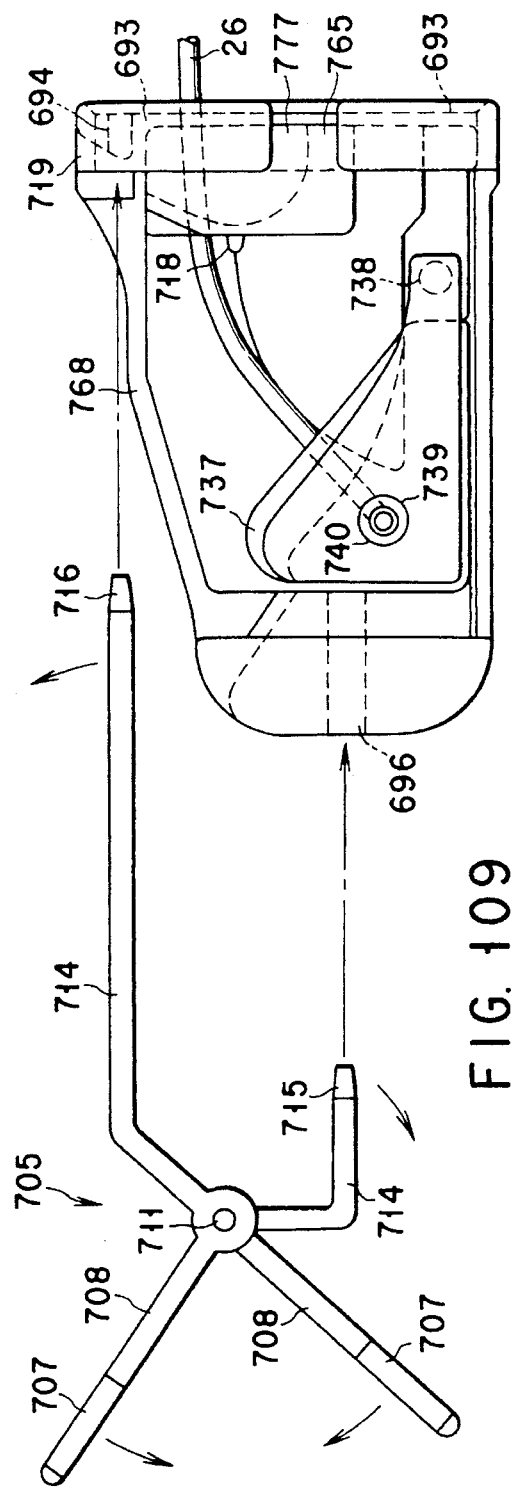

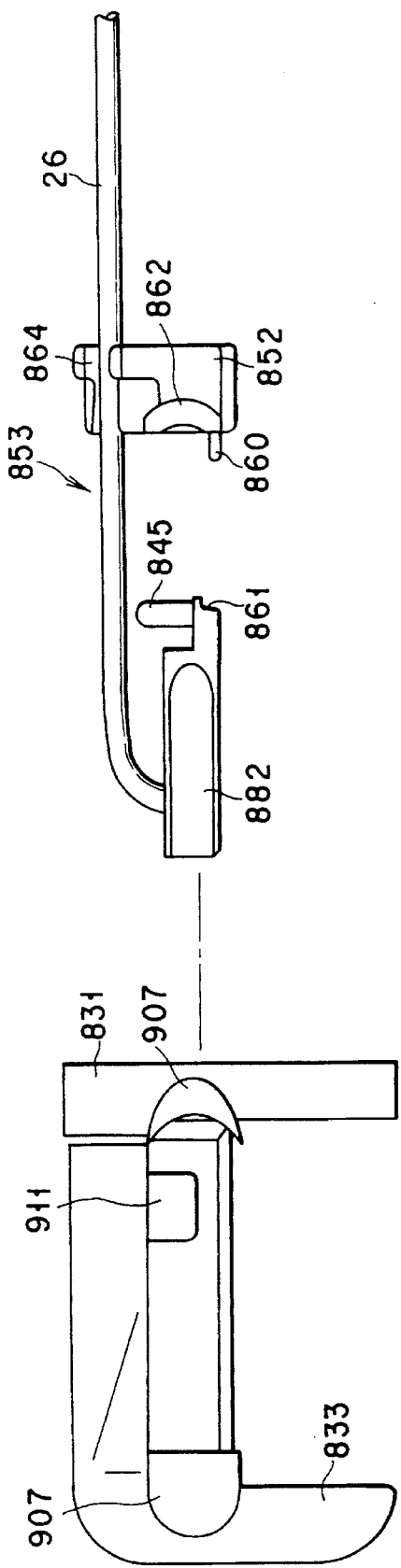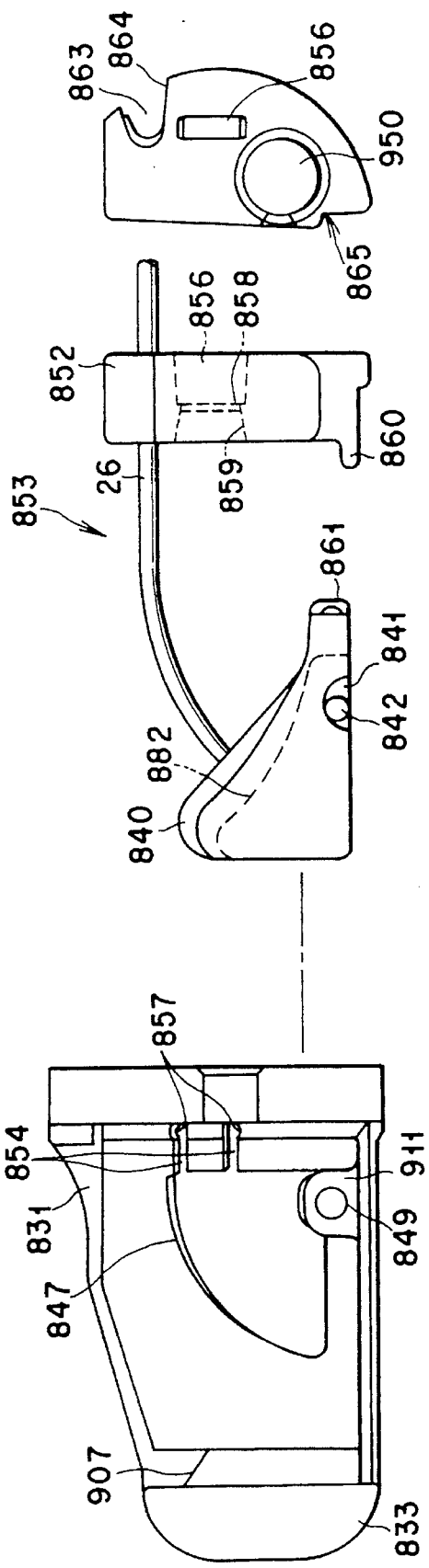
FIG. 117A
FIG. 117B

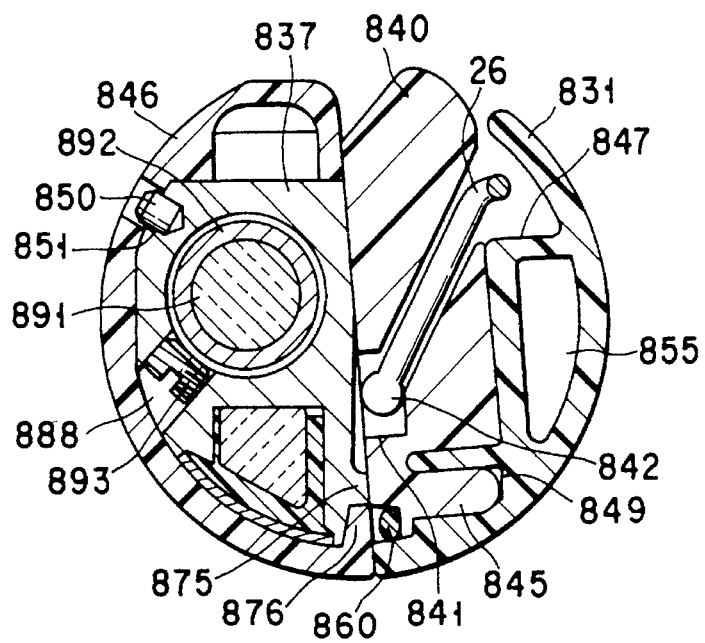
FIG. 118
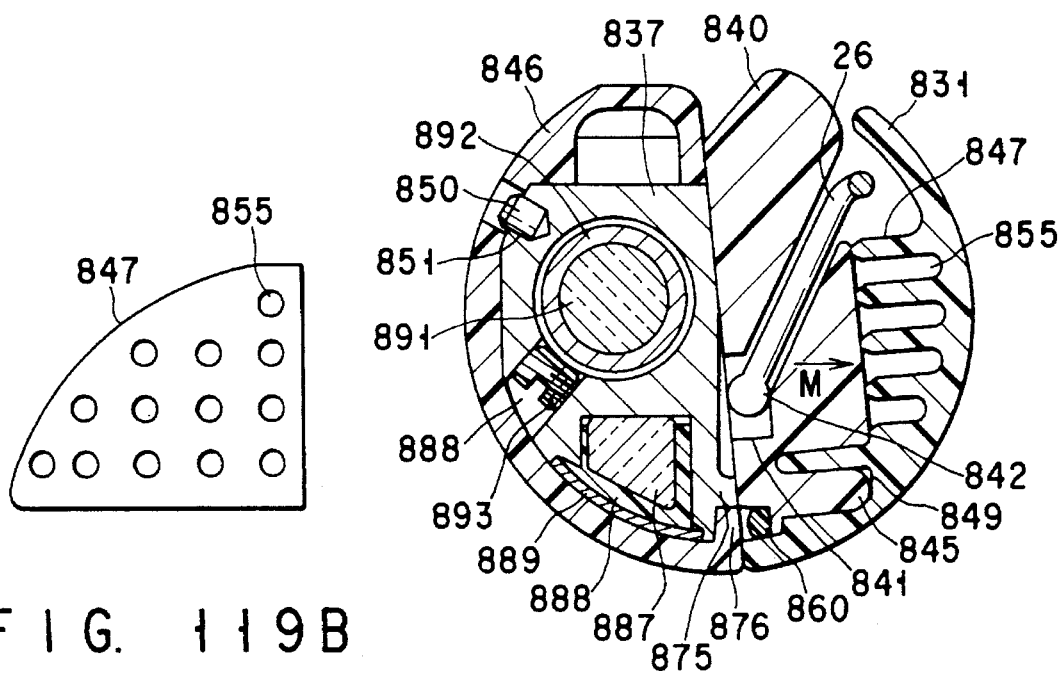
FIG. 119B
FIG. 119A

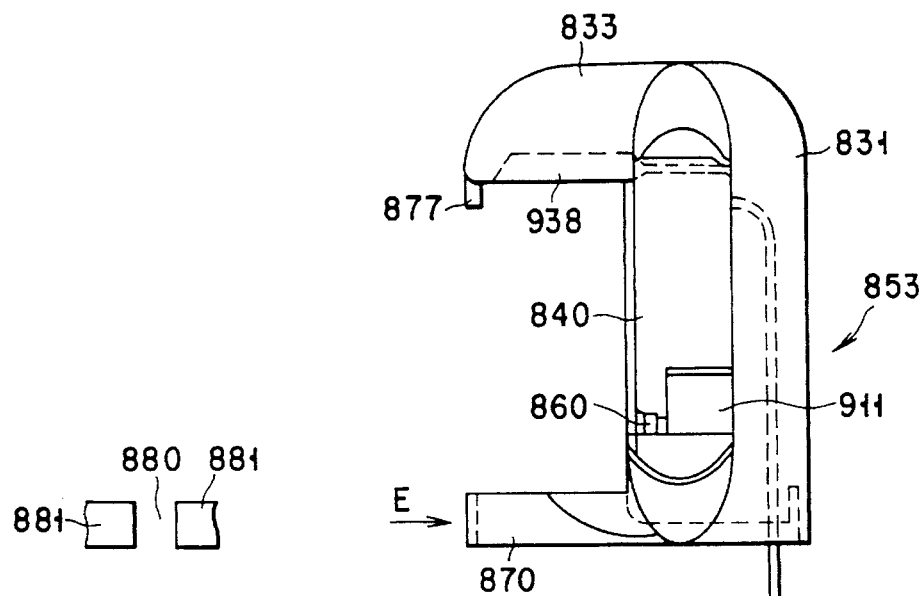
FIG. 122B
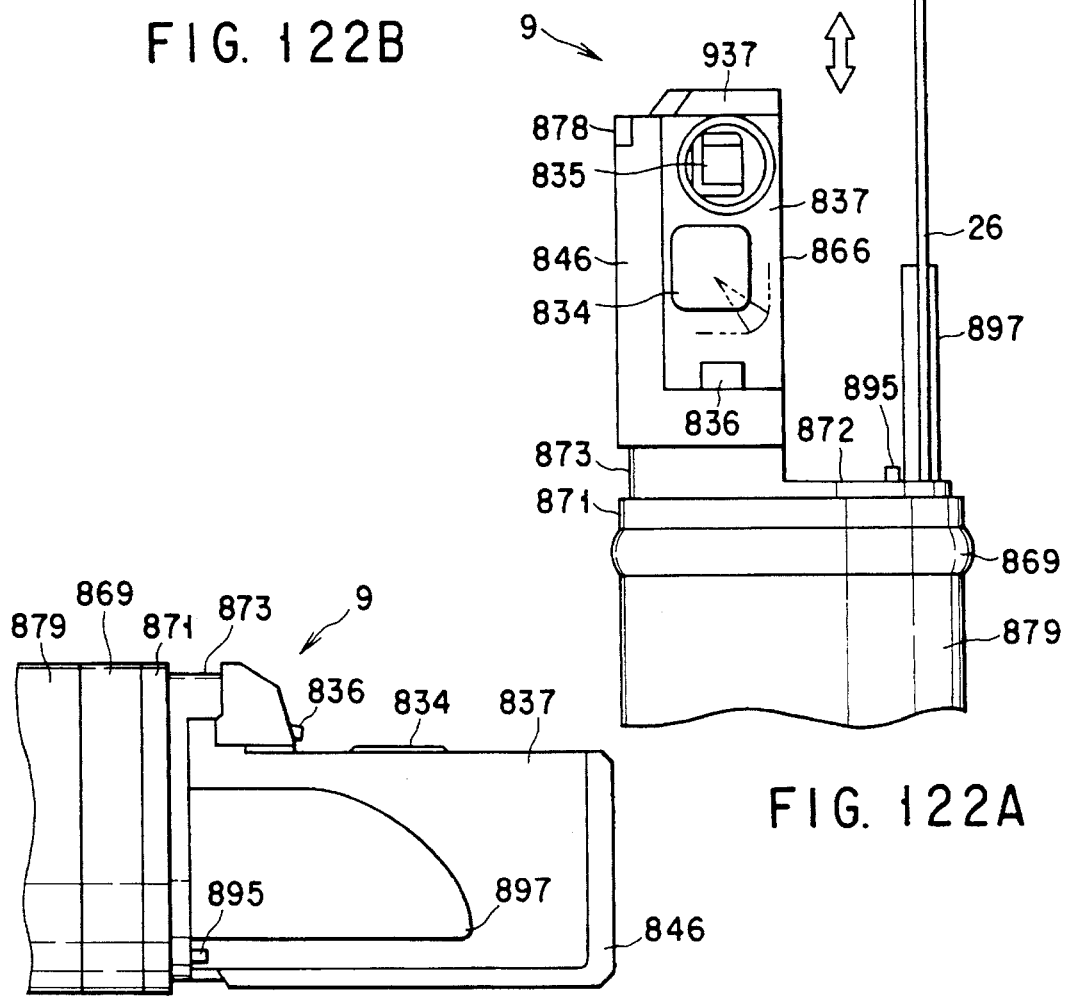
FIG. 122A
FIG. 123

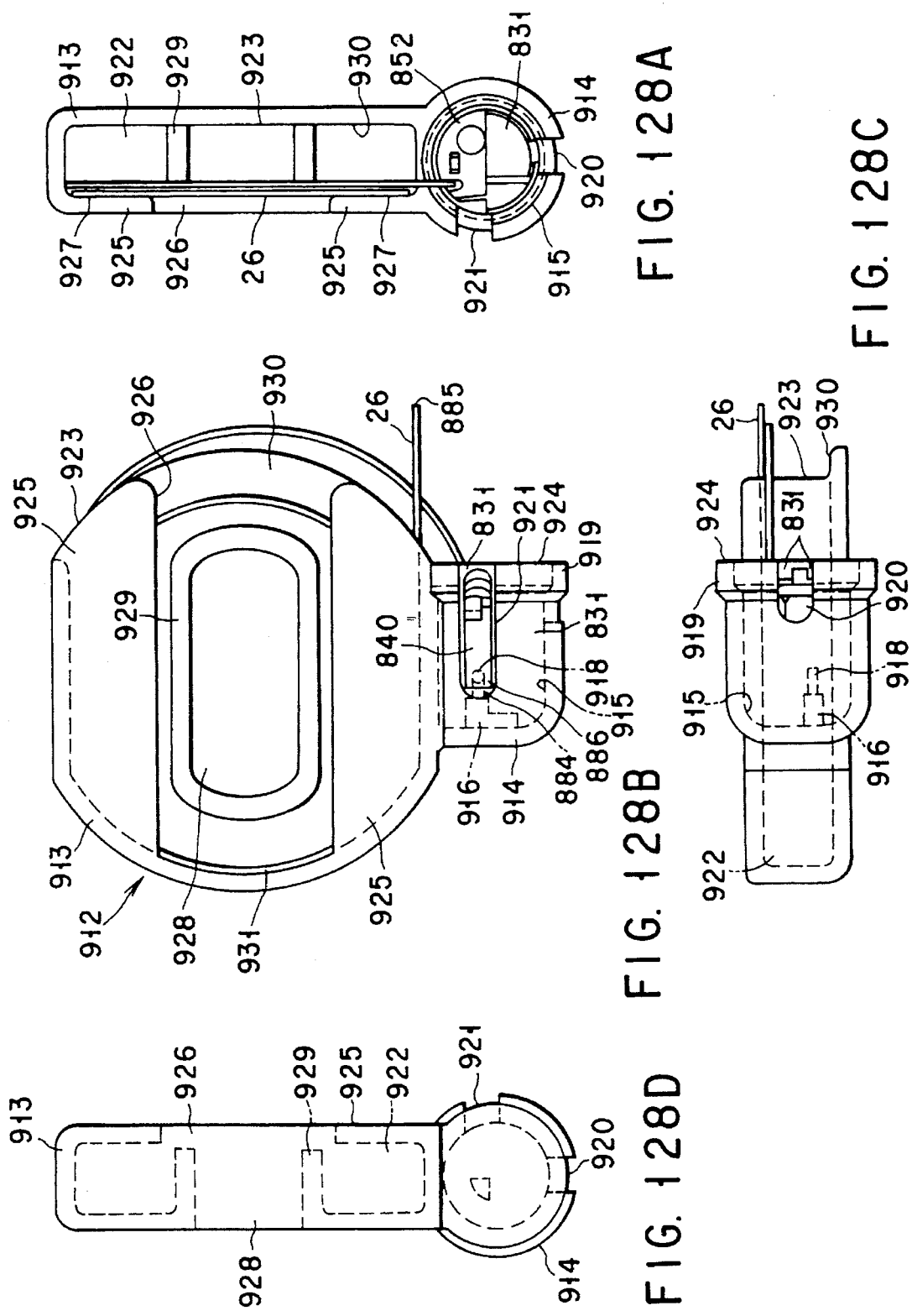

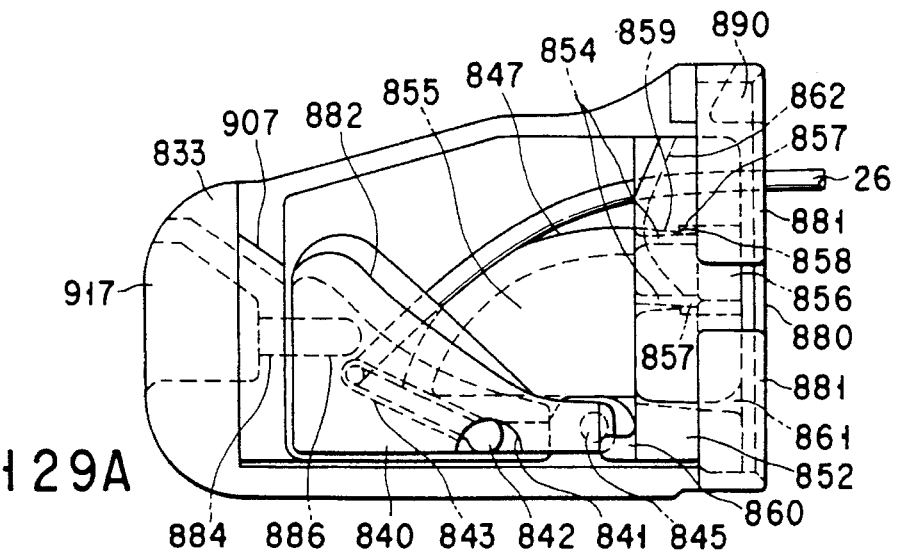
FIG. 129A
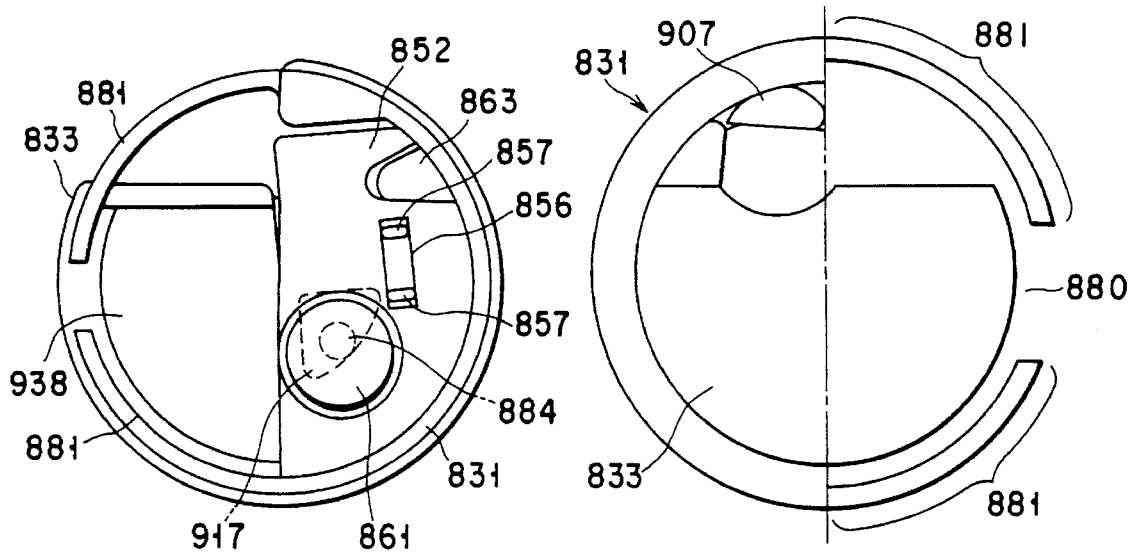
FIG. 129B
FIG. 130B
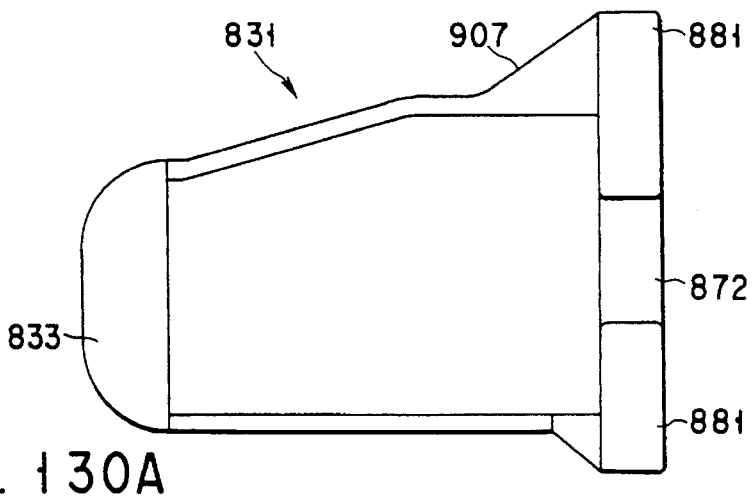
FIG. 130A

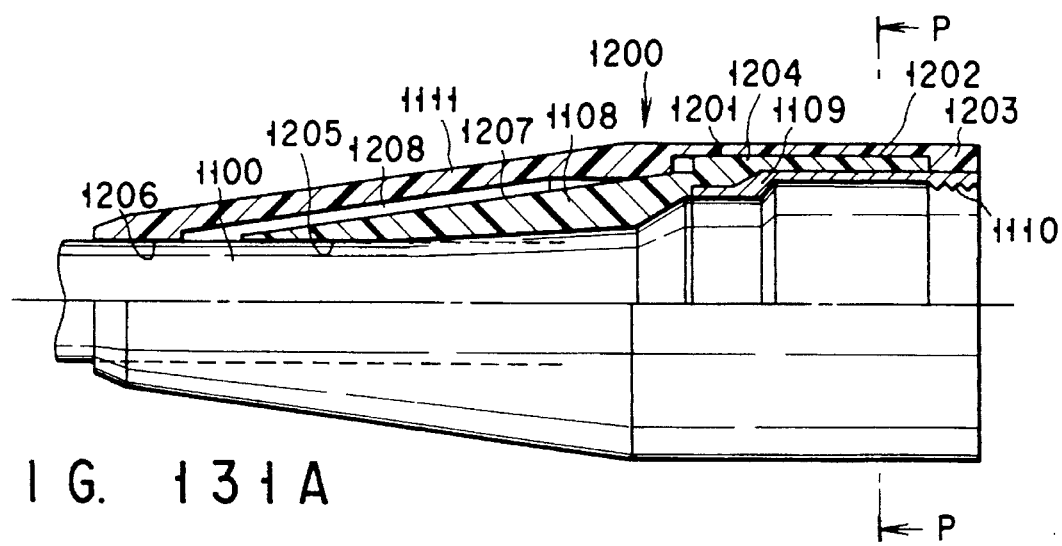
F I G. 131A
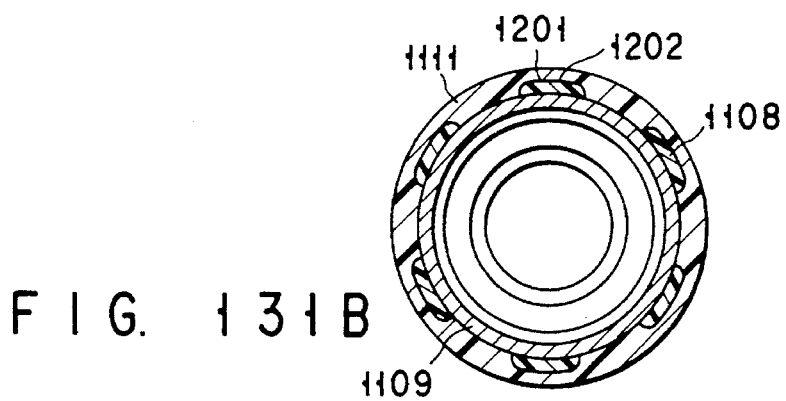
F I G. 131B
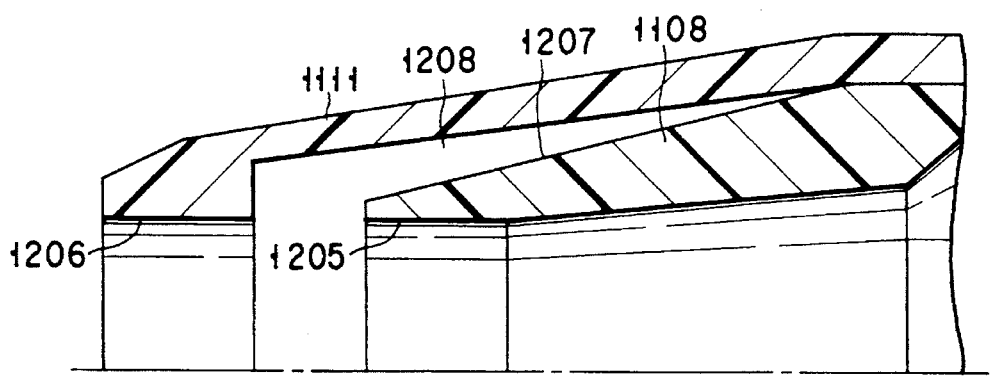
F I G. 132

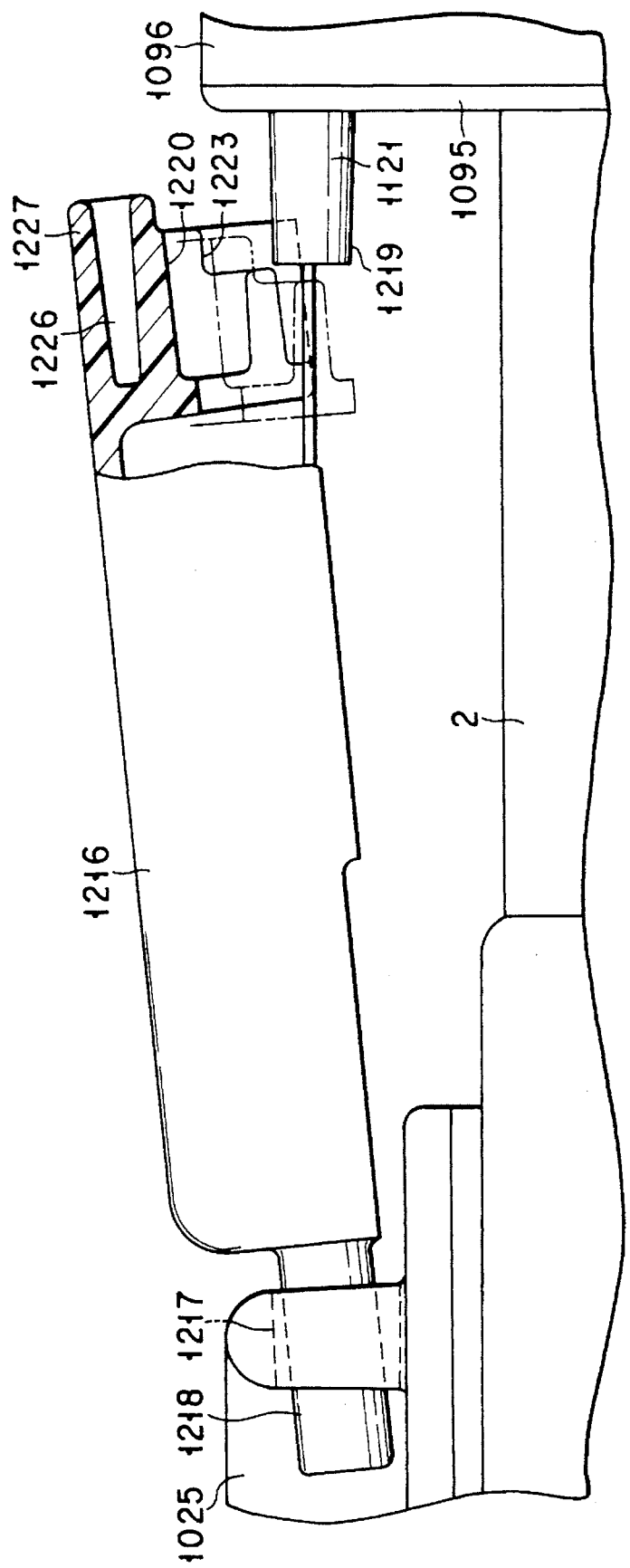
F I G. 136

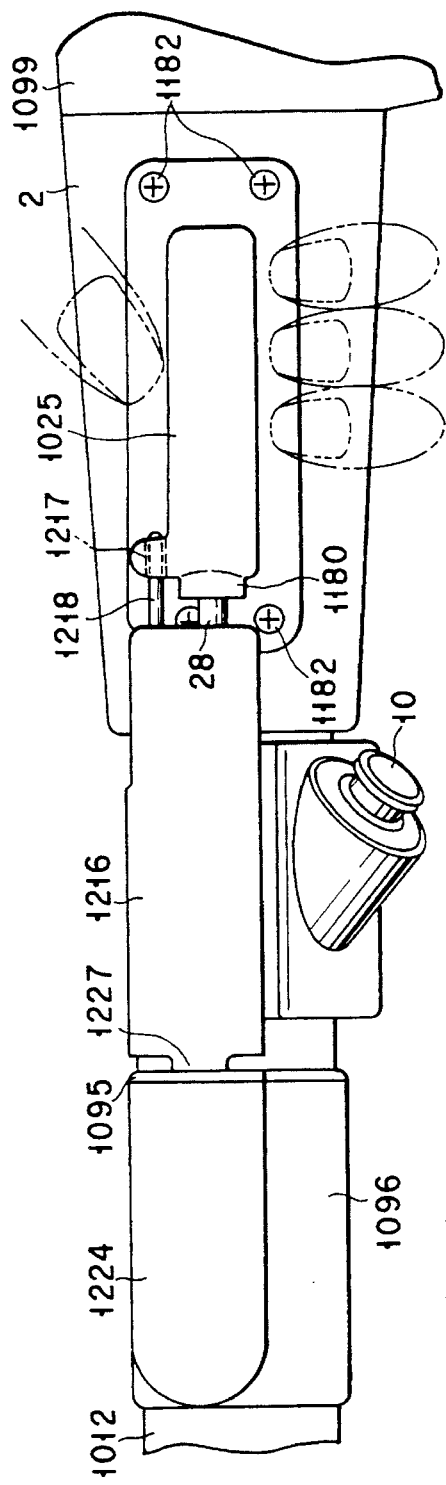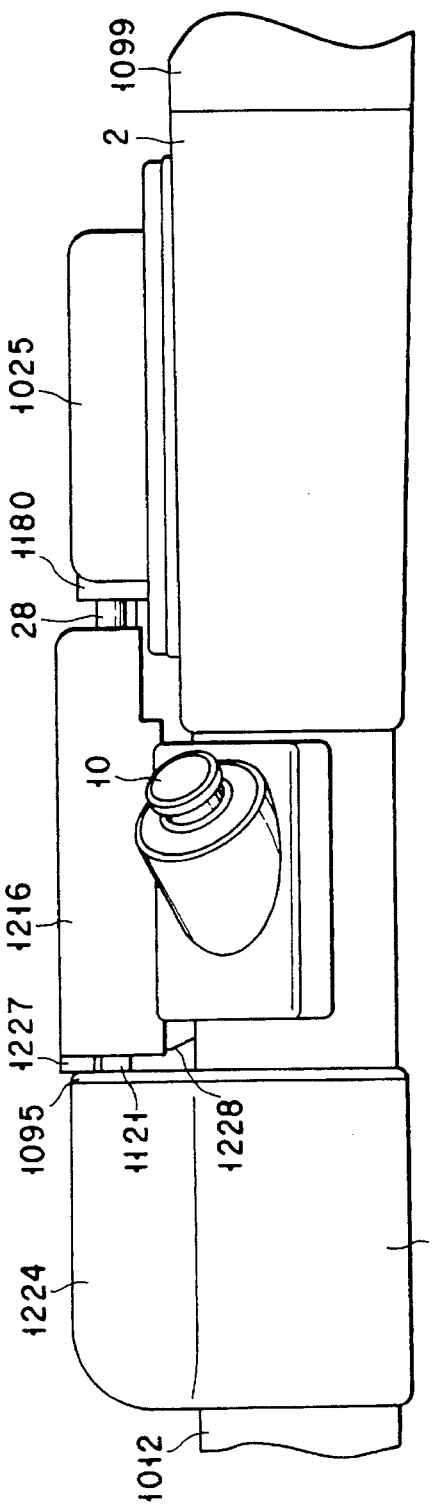
FIG. 137A
FIG. 137B

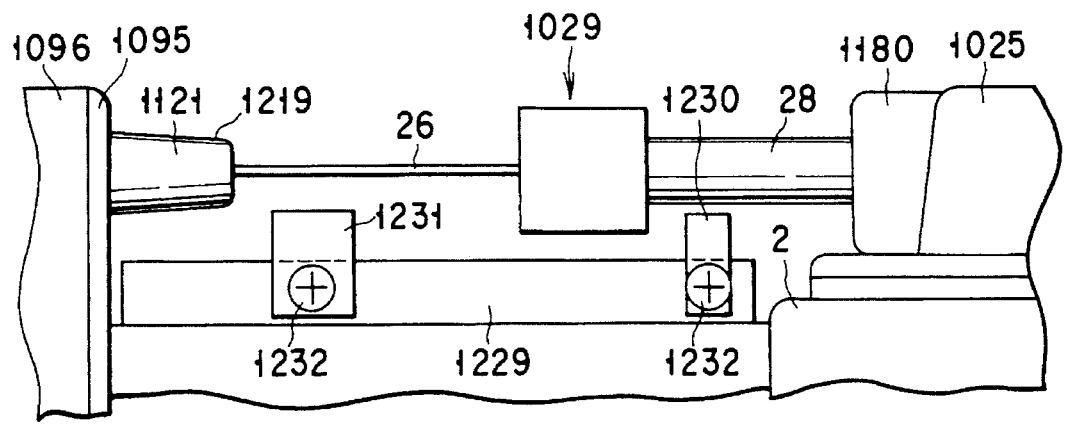
F I G. 144
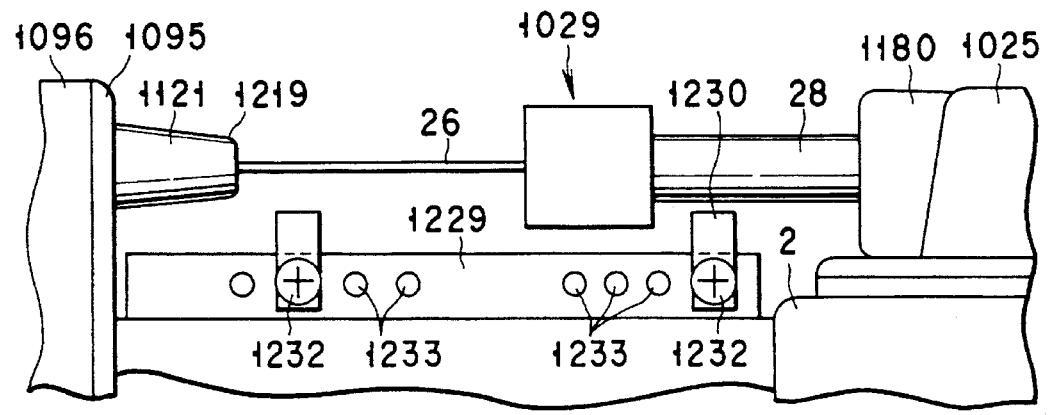
F I G. 145
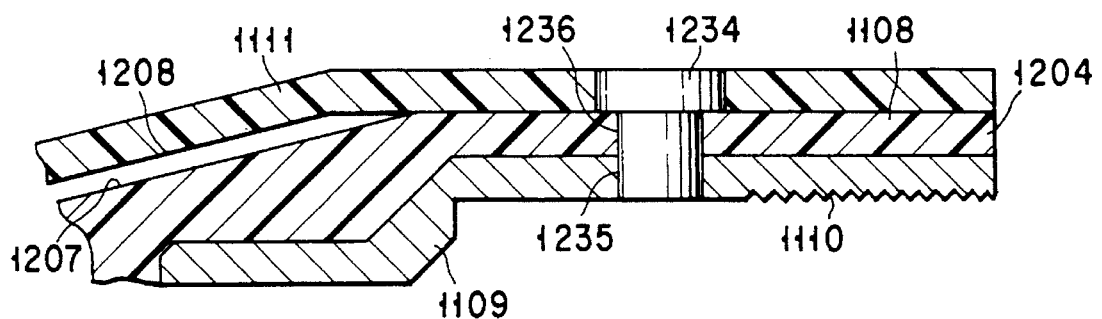
F I G. 146

ENDOSCOPE

BACKGROUND OF THE INVENTION

1. Field of the Invention

The present invention relates an endoscope and, more particularly, to an endoscope having an instrument raising device for adjusting the direction of an instrument such as forceps inserted in a living body cavity by using the endoscope.

2. Description of the Related Art

As is known, a medical endoscope such as a gastroscope or a duodenal scope is used to perform observation, treatment, and the like of a morbid portion upon insertion of the insertion portion of the endoscope into a cavity of a patient. When sampling of tissue for biopsy or medical treatment is to be performed by using forceps while a morbid portion is observed, a forceps raising device is used to direct the forceps toward the morbid portion. The forceps raising device is basically constituted by a forceps raising base rotatably mounted at the distal end portion of the insertion portion, and an operation wire coupled to the forceps raising base. The angle of the forceps raising base is adjusted by reciprocating the operation wire using a manual operating portion. The direction of the forceps is set by this adjustment.

While the endoscope is in use, fluids in a body cavity enter a forceps raising base housing chamber, in which the forceps raising base is housed, and the guide tube of the operation wire. Therefore, the device must be cleaned after it is used. A cumbersome operation is required for the cleaning of the device, especially the guide tube of the operation wire, because the tube is thin, and the operation wire is inserted therein.

In order to solve such a problem, a device having an entrance preventing member (packing) formed at the opening portion of the distal end of a guide tube is disclosed in Jpn. UM Appln. KOKAI Publication Nos. 52-67790 and 52-38986.

Another device is disclosed in Jpn. Pat. Appln. KOKAI Publication No. 56-8030, in which a forceps raising base, an operation wire, and a tubular inner layer member (a guide tube is constituted by a tubular outer layer member (tube member) and the tubular inner layer member (closed coil member)) are designed to be detachable so as to facilitate a cleaning operation.

Still another device is disclosed in Jpn. Pat. Appln. KOKAI Publication Nos. 4-314439 and 57-75629, in which a distal end cover is designed as a detachable member to facilitate the cleaning of a forceps raising base housing chamber.

According to Jpn. UM Appln. KOKAI Publication Nos. 52-67790 and 52-38986, however, entrance of intracavity fluids cannot be prevented completely in practice.

According to Jpn. Pat. Appln. KOKAI Publication No. 56-8030, since the forceps raising base housing chamber serves as a blind alley, a cumbersome operation is required to clean the chamber, and intra-cavity fluids leaking from the closed coil member enter the tubular outer layer member. For this reason, it cannot be said that the cleaning of this device is extremely facilitated as compared with the device disclosed in Jpn. UM Appln. KOKAI Publication Nos. 52-67790 and 52-38986. That is, in the device disclosed in Jpn. Pat. Appln. KOKAI Publication No. 56-8030, since the opening portions of the two ends of the guide tube are narrow, and the inner diameter of the tube is larger than the diameter of each opening portion, a cleaning operation is difficult to perform. In addition, a stopper member must be removed.

A cumbersome operation is also required for the cleaning of the device disclosed in Jpn. Pat. Appln. KOKAI Publication Nos. 4-314439 and 57-75629.

SUMMARY OF THE INVENTION

It is an object of the present invention to provide an endoscope having a forceps raising device, which allows easy cleaning of a forceps raising base housing chamber and the guide tube of an operation wire.

According to the present invention, there is provided an endoscope having an adjustment mechanism, including a forceps raising base rotatably mounted in a distal end portion of an insertion portion, for adjusting an angle of the forceps raising base by reciprocating an operation wire coupled thereto using a manual operating portion, thereby adjusting a direction of forceps inserted from the manual operating portion and transferred out of the distal end portion of the insertion portion, wherein a distal end cover for covering the distal end portion of the insertion portion, the forceps raising base, and the operation wire are detachably mounted.

In the present invention, the distal end cover, the forceps raising base, the operation wire are detachably mounted. When a cleaning operation is to be performed, all these members are detached. Therefore, the guide tube of the operation wire becomes empty, and no dead end space is formed in a chamber to receive the forceps raising base.

Therefore, according to the present invention, since the distal end cover, the forceps raising base, and the operation wire can be removed from the distal end portion of the insertion portion of the endoscope, the inner surface of the guide tube of the operation wire and the forceps raising base housing chamber can be easily cleaned and sterilized. In addition, the time required to dry the members can be shortened. Furthermore, since detachable members such as the operation wire can be easily replaced when they are worn, repairs can be quickly performed at low cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A to 2D show the detailed structure of a connecting unit which can be applied to the endoscope in FIG. 1, in which FIG. 2A is a plan view of the member, FIG. 2B is a side view of the member, FIG. 2C is a sectional view taken along a line C—C in FIG. 2B, and FIG. 2D is a side view of a connecting end portion of a driving shaft;

FIG. 3 is a perspective view of a protective cover for covering the connecting unit;

FIG. 4A is a plan view of the distal end portion of the first embodiment in a disassembled state;

FIG. 4B is a view taken along a line B—B in FIG. 4A;

FIGS. 5A to 5C show the distal end portion of the first embodiment in an assembled state, in which FIG. 5A is a plan view of the portion, FIG. 5B is a sectional view taken along a line B—B in FIG. 5A, and FIG. 5C is a sectional view taken along a line C—C in FIG. 5B;

FIGS. 7A and 7B show a stationary cover, in which FIG. 7A is a view taken from the direction indicated by an arrow E in FIG. 5B, and FIG. 7B is a view taken along a line B—B in FIG. 7A;

FIG. 10 is a view of a raising base along a line H—H in FIG. 6;

FIG. 11 is a sectional view taken along the line H—H of the distal end portion in FIG. 6;

FIG. 12A is an enlarged view of a portion I in FIG. 6;

FIG. 12B is an enlarged view showing a modification of the portion I;

FIGS. 13A and 13B show an end portion, of a forceps raising operation wire, located on the operating portion side;

FIG. 13C is a perspective view of a connecting unit which can be used in combination with the operation wire;

FIGS. 16A and 16B show the arrangement of the distal end portion of an endoscope according to the third embodiment of the present invention, in which FIG. 16B is a view taken along a line B—B in FIG. 15A;

FIGS. 25A and 25B show the arrangement of the distal end portion of an endoscope according to the eleventh embodiment of the present invention, in which FIG. 25B is a view taken along a line 25B—25B in FIG. 25A;

FIGS. 26A and 26B are plan and side views, respectively, of a slope portion body in FIG. 6;

FIGS. 32A to 32C show the distal end portion of an endoscope according to the fourteenth embodiment of the present invention, in which FIG. 32A is a sectional view similar to FIG. 27, FIG. 32B is a sectional view of a regulating pin, and FIG. 32C is a sectional view of a hole in a cover member in which the regulating pin is inserted;

FIG. 35 is a sectional view showing the details of a portion J in FIG. 34;

FIG. 37 is a sectional view taken along a line I—I in FIG. 34;

FIG. 40 is a view for explaining an example of how the stopper plate of the endoscope in FIG. 1 is arranged;

FIGS. 42A and 42B are views for explaining how the first and second screw bearings of the endoscope in FIG. 1 are fixed;

FIGS. 43A and 43B are views for explaining a modification of the method of fixing the first screw bearing;

FIG. 44 is a view showing the details of the driving shaft bearing unit of the endoscope in FIG. 1;

FIG. 45 is a view showing a modification of the driving shaft bearing unit;

FIG. 64 is a perspective view for explaining the main portion of a forceps raising operation wire opening portion according to the ninth embodiment;

FIG. 65 is a plan view showing a connecting portion between the driving shaft and the forceps raising operation wire according to the second embodiment;

FIG. 66 is a sectional view taken along a line A—A in FIG. 65;

FIG. 73A is a sectional view of a connection portion between the driving shaft and the forceps raising operation wire according to the ninth embodiment;

FIG. 73B is a sectional view taken along a line E—E in FIG. 73A;

FIG. 73C is a sectional view taken along a line F—F in FIG. 73A;

FIG. 74 is a perspective view showing a connecting portion between the driving shaft and a forceps raising operation wire according to the tenth embodiment;

FIGS. 87A to 87D are sectional views showing various shapes, respectively, of the wire bearing portion of a forceps raising operation wire and a wire press portion;

FIG. 89 is a sectional view taken along a line P—P in FIG. 88;

FIGS. 90A and 90B show a modification of the connecting portion between the driving shaft and the forceps raising operation wire, in which FIG. 90A is a sectional view of the connecting portion, and FIG. 90B is an enlarged sectional view showing a pressed state of the forceps raising operation wire;

FIGS. 91A and 91B show an example of the fixing structure of a mouthpiece stationary cover;

FIGS. 92A and 92B show another example of the fixing structure of the mouthpiece stationary cover;

FIG. 95 is a sectional view showing a conventional connecting structure of a tube and a pipe;

FIG. 96 is a sectional view showing a modification of the connecting structure of a tube and a pipe, which is used in the present invention;

FIG. 97 is a sectional view showing another modification of the connecting structure of the tube and the pipe, which is used in the present invention;

FIG. 101 is a view showing an operating portion 1 viewed from the axial direction;

FIG. 102 is a side view showing the arrangement of the operating portion 1;

FIGS. 103A and 103B show the schematic arrangement of an endoscope according to another embodiment, in which FIG. 103A is a sectional view taken along the axial direction, and FIG. 103B is a sectional view taken along a line Q—Q in FIG. 103A;

FIG. 104 is a sectional view of an embodiment having a hook engaging portion for a removing jig at the detachable cover of an endoscope distal end portion;

FIGS. 105A to 105D show the arrangement of an endoscope distal end portion upon completion of assembly, in which FIG. 105A is a partially cutaway side view of the portion, FIG. 105B is a view taken from the direction indicated by an arrow J in FIG. 105A, FIG. 105C is a sectional view taken along a line H—H in FIG. 105D, and FIG. 105D is a side view of the opposite side to that shown in FIG. 105A;

FIGS. 106A to 106C show the first embodiment of an endoscope distal end cover, in which FIG. 106A is a side view of a detachable cover, FIG. 106B is a front view taken from the right direction of FIG. 106A, and FIG. 106C is a plan view of a stripping jig;

FIGS. 108A and 108B show another embodiment of the endoscope distal end cover, in which FIG. 108A is a side view of a detachable cover, and FIG. 108B is a view taken from the right direction of FIG. 108A;

FIG. 109 is a side view showing the detachable cover and a stripping jig in the embodiment shown in FIGS. 108A and 108B;

FIG. 112 is a rear view showing still another embodiment of the endoscope distal end cover, and more specifically the relationship between a stationary cover, a detachable cover, and a stripping jig;

FIG. 113 is a view for explaining a packed state of a forceps raising unit in FIG. 107;

FIGS. 114A to 114D are views for explaining another packed state of the forceps raising unit;

FIGS. 115A and 115B are views for explaining still another packed state of the forceps raising unit;

FIGS. 116A and 116B are plan and side views, respectively, showing a cover member according to still another embodiment of the endoscope distal end portion;

FIGS. 117A and 117B are plan and side views, respectively, showing the cover member in FIGS. 116A and 116B and various members fitted to the cover member;

FIG. 118 is a sectional view showing the endoscope distal end portion on which the cover member shown in FIGS. 116A and 116B is mounted;

FIGS. 119A and 119B are sectional views showing a modification of the endoscope distal end portion in FIG. 118;

FIG. 120 is a front view showing a state wherein members such as a raising base are fitted to the cover member;

FIGS. 121A and 121B are side views showing the cover member to explain a method of protecting a wire distal end portion;

FIGS. 122A and 122B are plan views showing a modification of the endoscope distal end portion, in which FIG. 122B shows a portion indicated by an arrow E in FIG. 122A;

FIG. 123 is a side view of a distal end body in FIGS. 122A and 122B;

Figure 34:
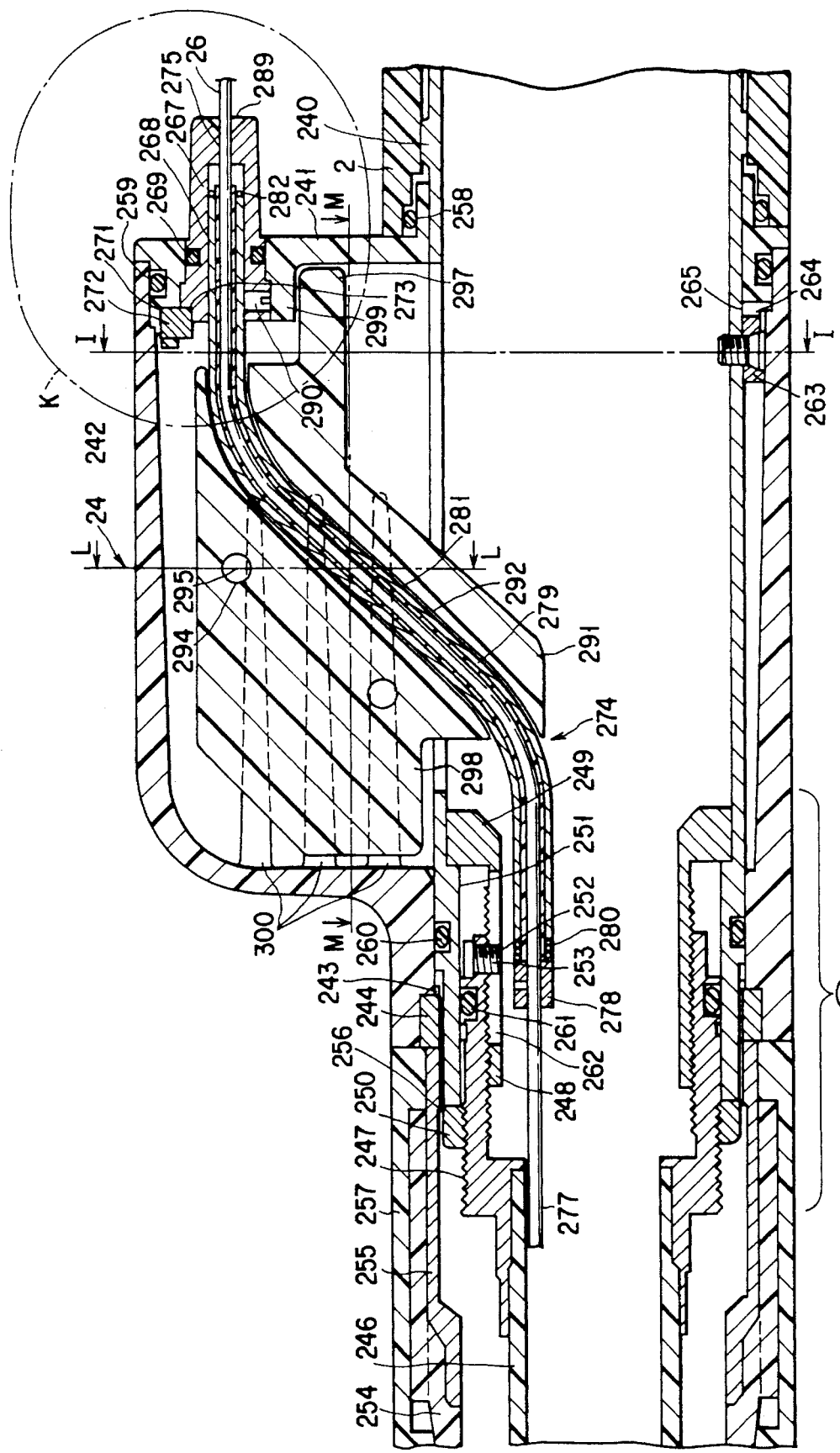
FIG. 34 is a sectional view showing the details of the opening portion of the forceps raising operation wire of the endoscope in FIG. 1.
Figure 124:
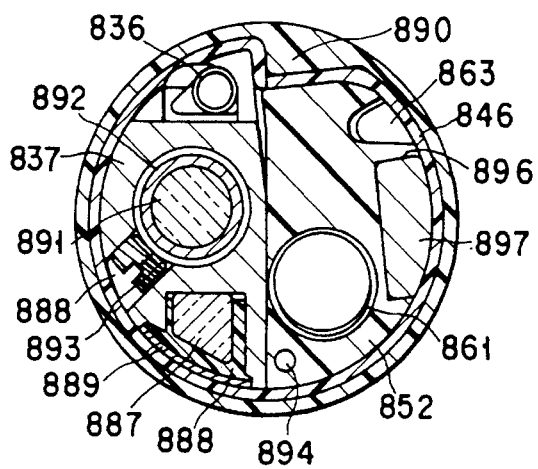
Figure 125:
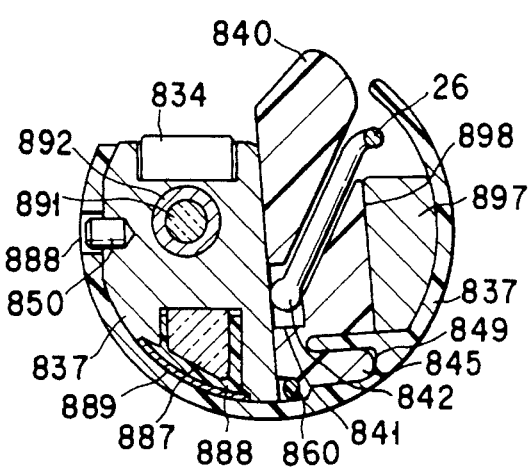
Figure 126:
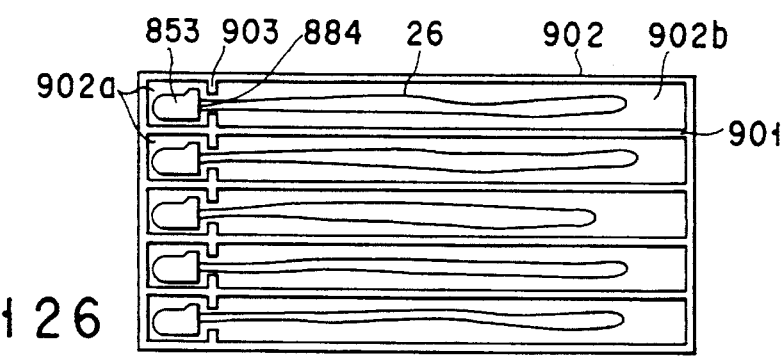
Figure 127:
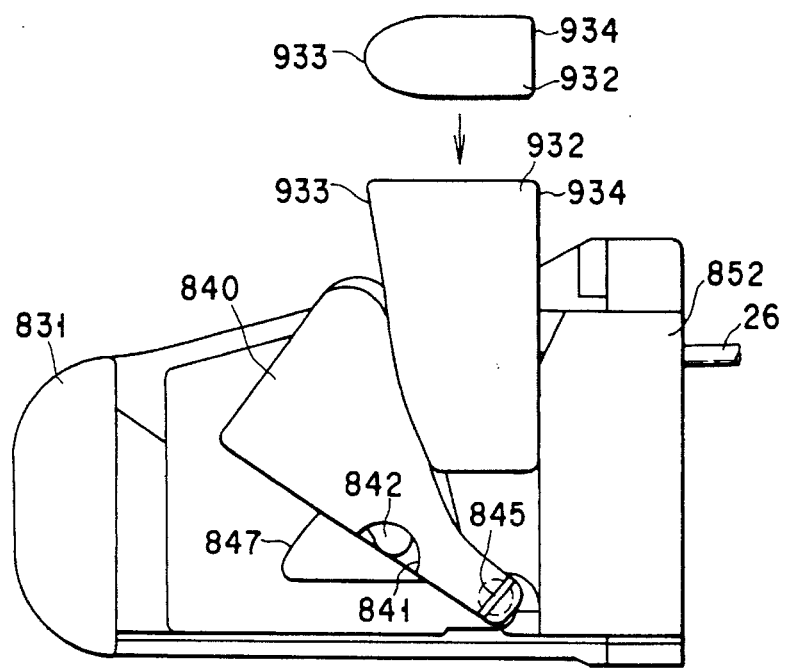
Figure 133A:
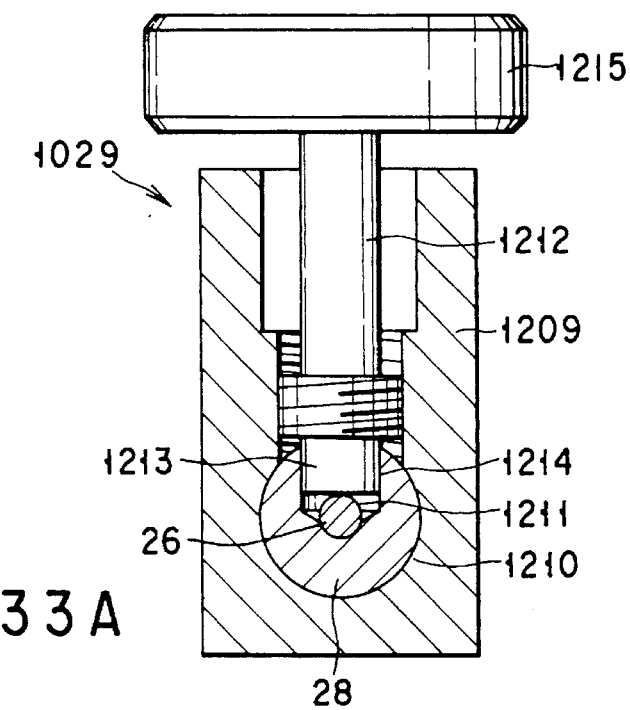
Figure 133B:
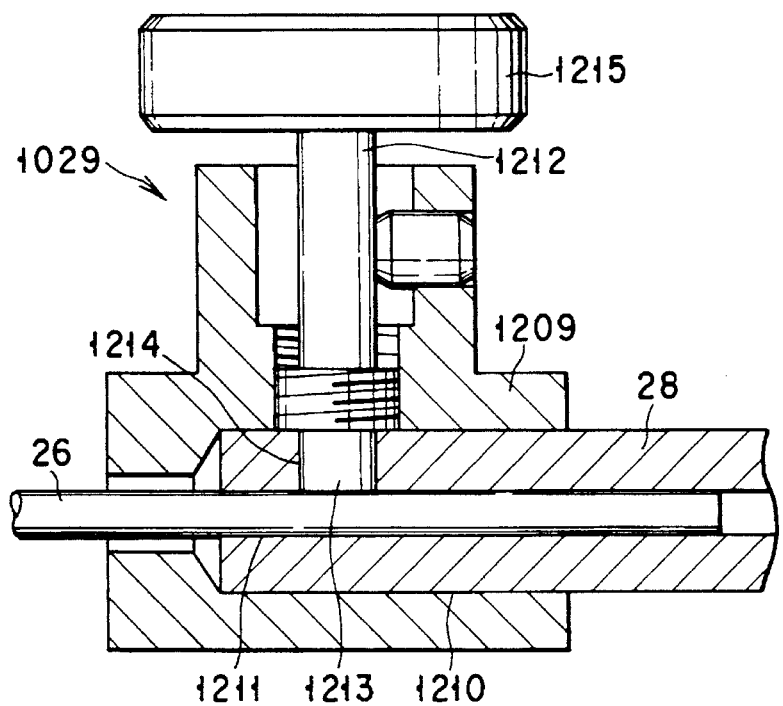
Figure 134:
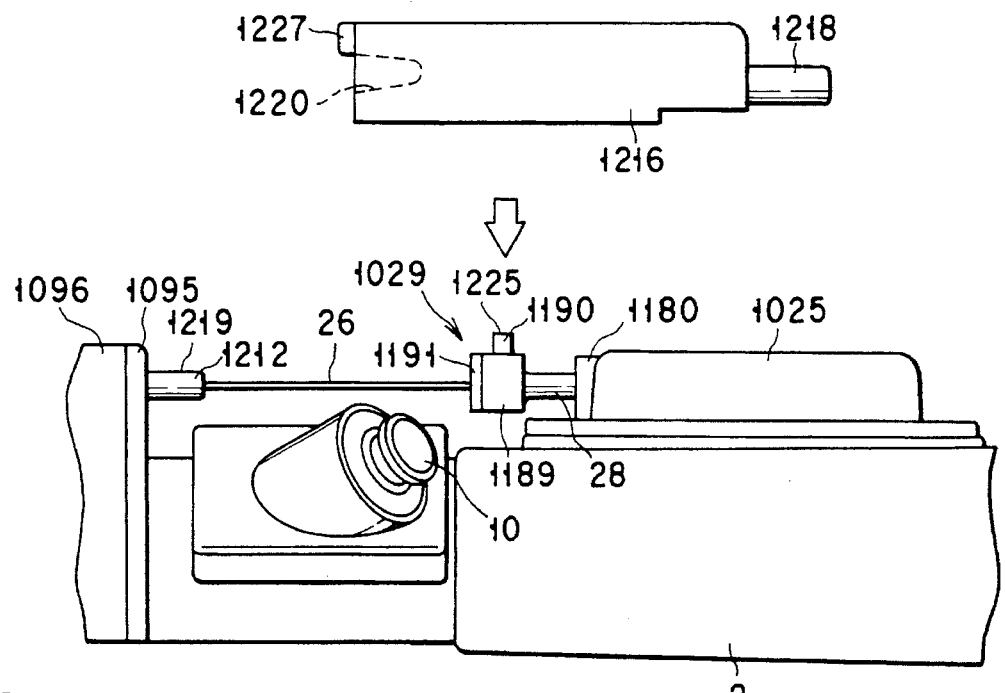
Figure 135A:
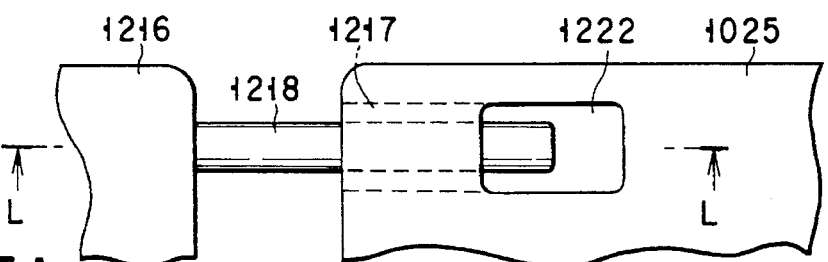
Figure 135B:
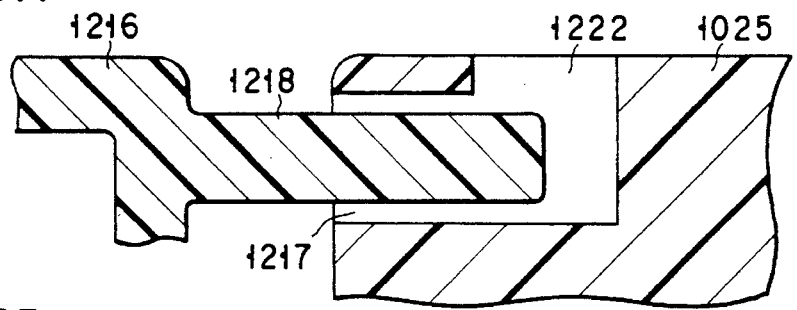
Figure 138:
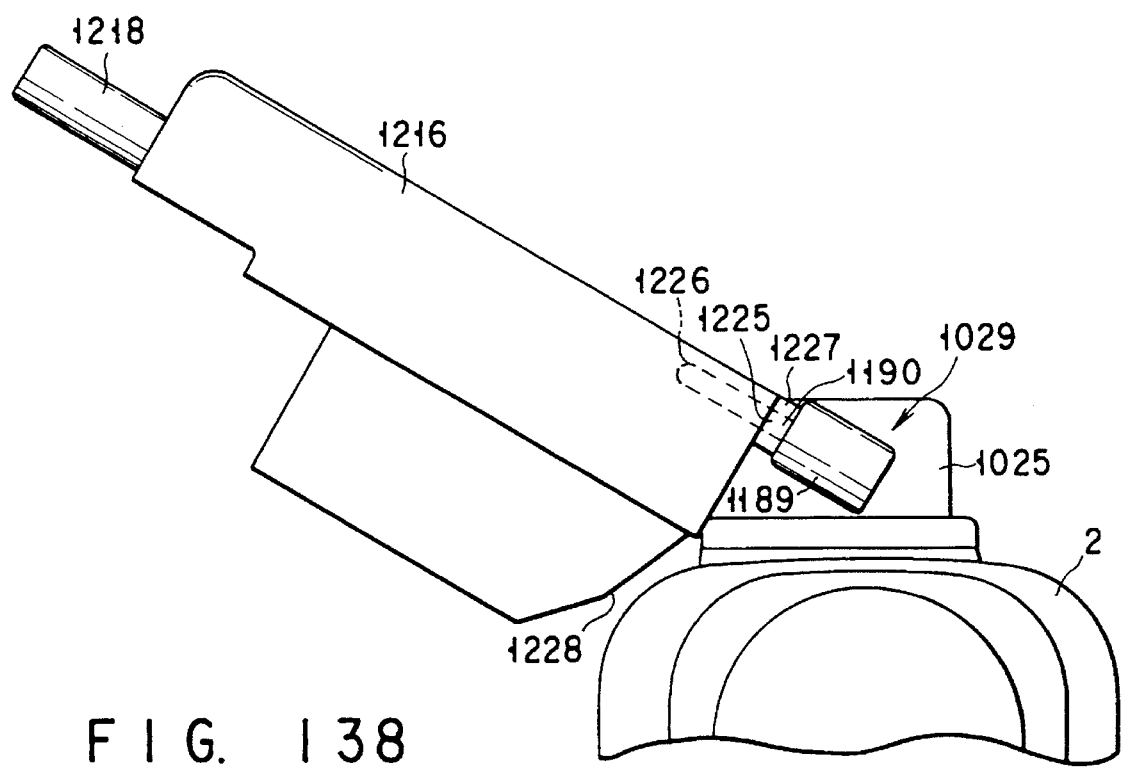
Figure 139:
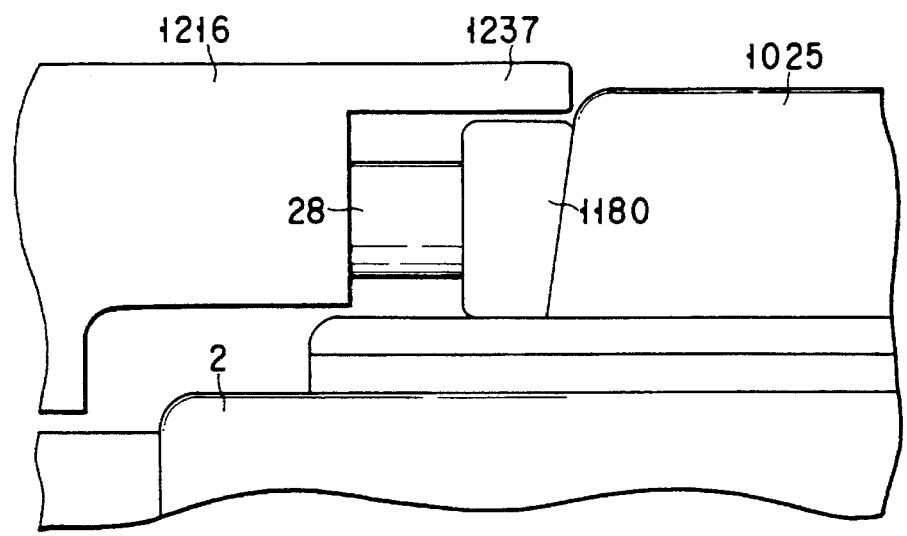
Figure 140A:
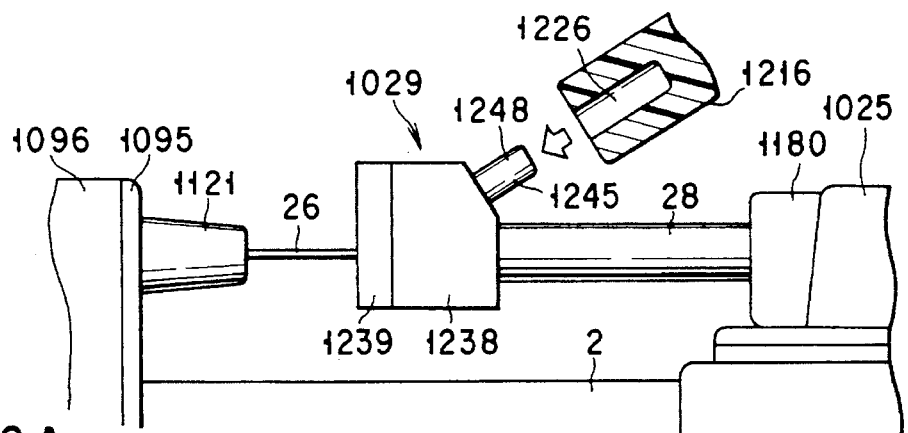
Figure 140B:
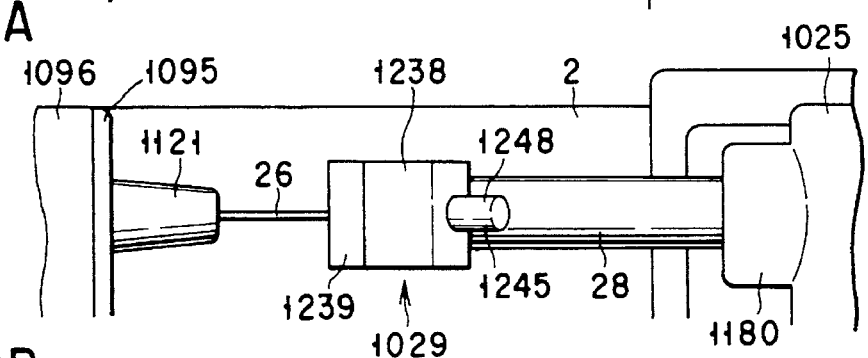
Figure 140C:
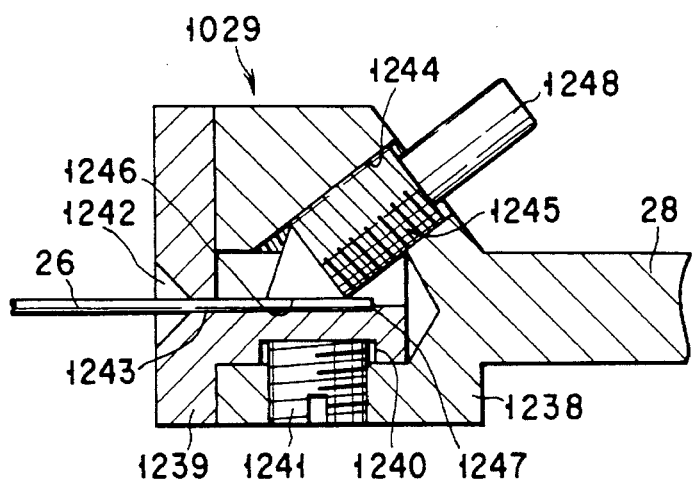
Figure 141:
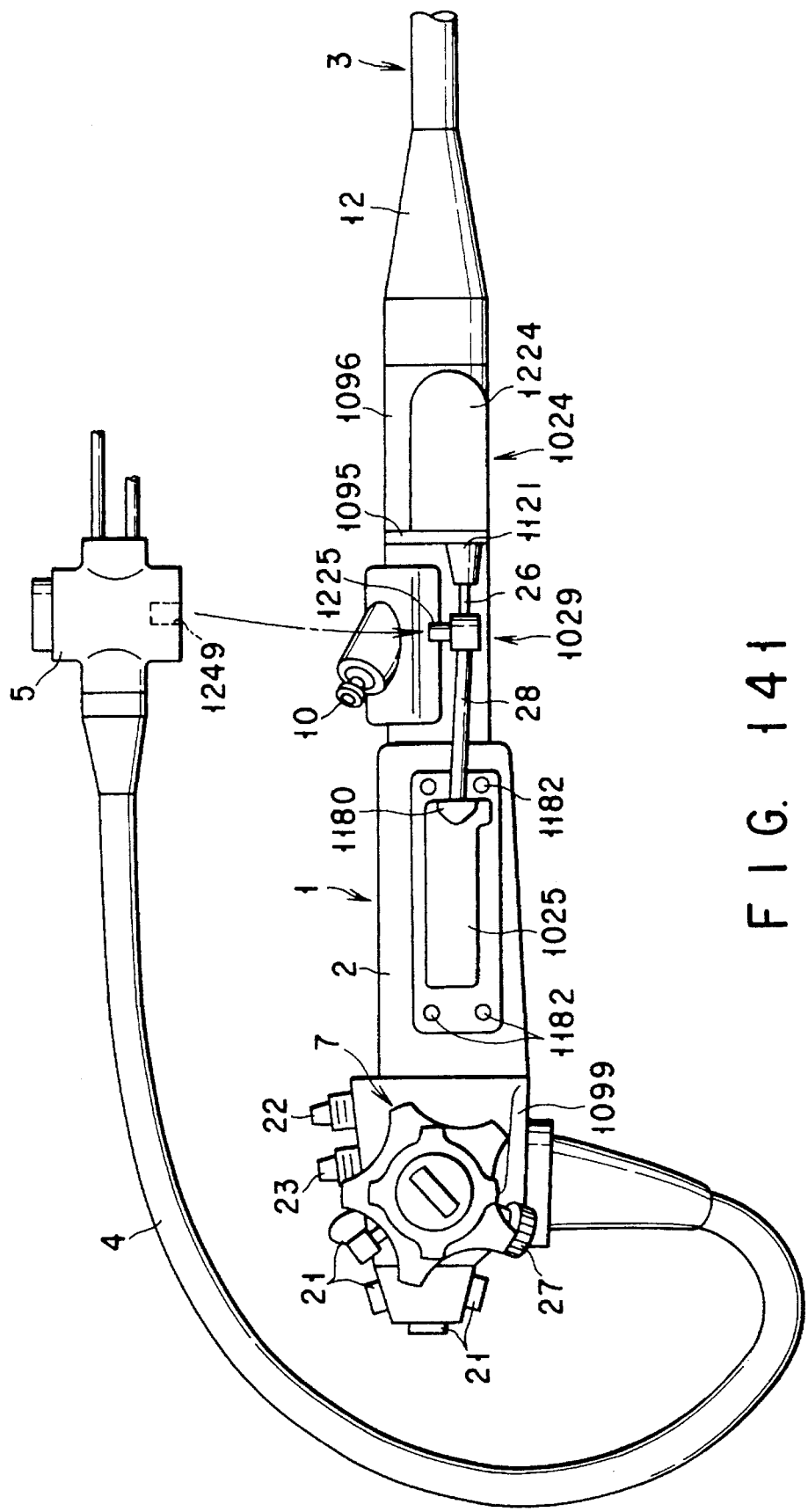
Figure 142:
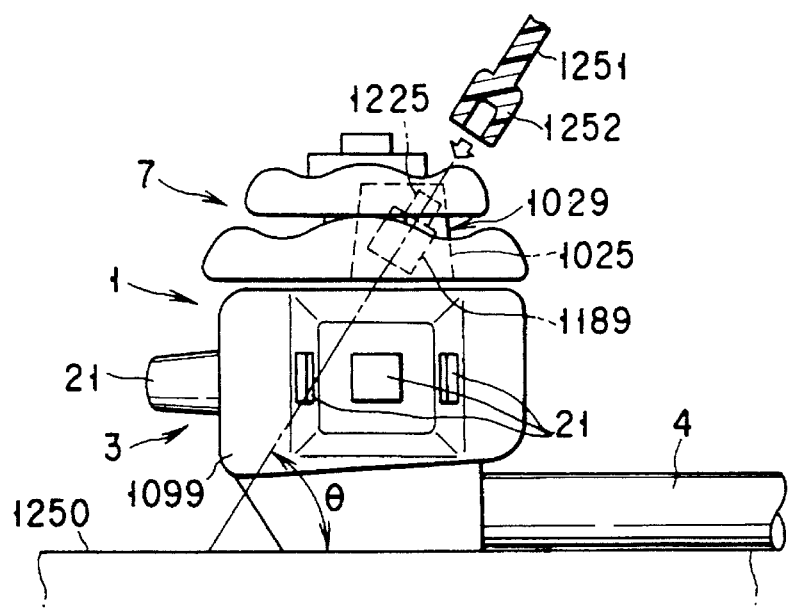
Figure 143:
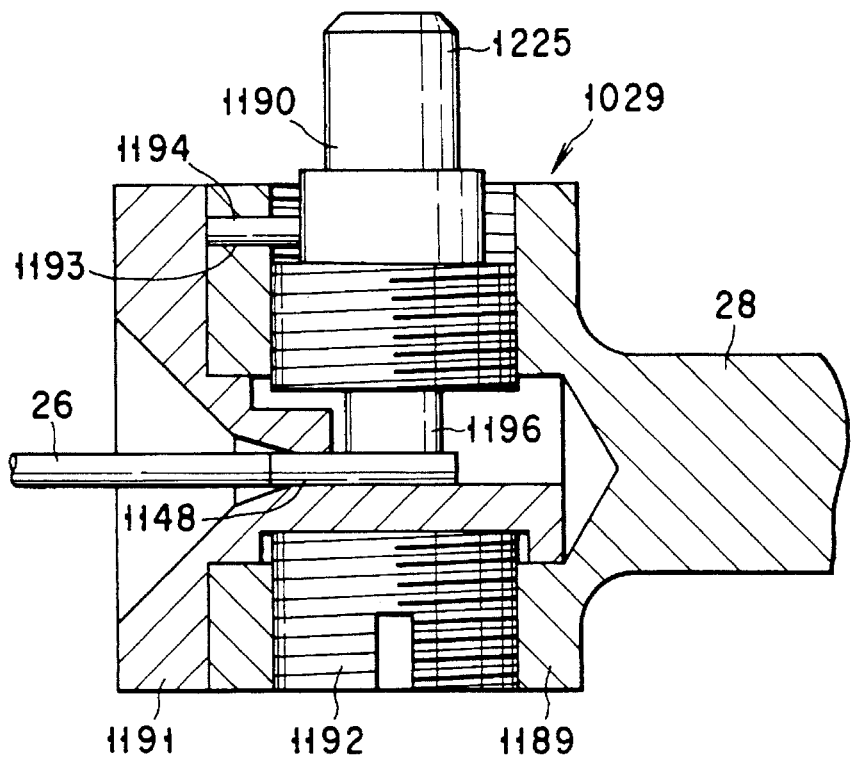
Figure 147:
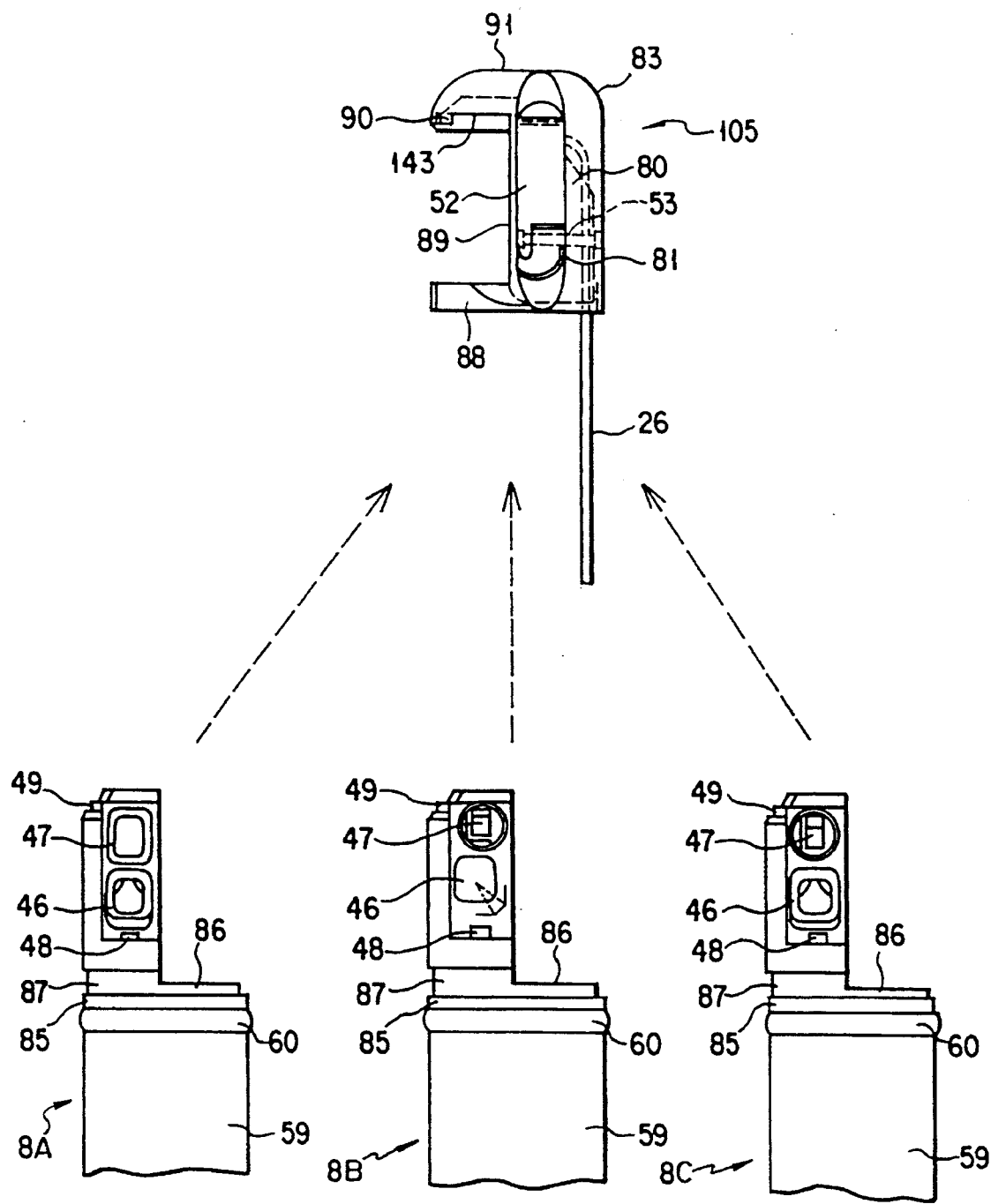

FIG. 124 is a sectional view taken at the position of an insulating member in a state wherein a cover member in FIG. 123 is mounted on a distal end portion body in FIGS. 122A and 122B;

FIG. 125 is a sectional view taken at the position of a raising base in a state wherein the cover member in FIG. 123 is mounted on the distal end portion body in FIGS. 122A and 122B;

FIG. 126 is a schematic view showing a packed state of a forceps raising unit;

FIG. 127 is a view for explaining a method of adjusting the connected state of a wire by using a wire connection inspection member;

FIGS. 128A to 128D are views showing a forceps raising base unit housing member;

FIGS. 129A and 129B are side and sectional views, respectively, showing another embodiment of the cover member;

FIGS. 130A and 130B are side and front views, respectively, showing still another embodiment of the cover member;

FIGS. 131A and 131B show the arrangement of a breakage preventing member and a breakage preventing cover in FIG. 34, in which FIG. 131A is a sectional view taken along the axis direction, and FIG. 131B is a sectional view taken along a line P—P in FIG. 131A;

FIG. 132 is an enlarged sectional view of FIG. 131A;

FIGS. 133A and 133B are sectional and plan views showing a modification of the arrangement of the connecting portion for connecting the driving shaft to the operation wire;

FIG. 134 is a view showing a state wherein the protective cover is removed from the endoscope;

FIGS. 135A and 135B are views showing a modification of the positioning hole formed in the driving shaft opening portion;

FIG. 136 is a partially sectional view showing a state wherein the protective cover is mounted on the endoscope;

FIGS. 137A and 137B are plan views showing the protective cover after it is mounted;

FIG. 138 is a view showing the concept of an embodiment of the endoscope of the present invention in a state wherein a wire press portion body is rotated by the protective cover;

FIG. 139 is a side view showing a modification of the protective cover;

FIGS. 140A to 140C show a modification of the connecting portion, in which FIG. 140A is a side view of the modification, FIG. 140B is a plan view of the modification, and FIG. 140C is a sectional view of the modification;

FIG. 141 is a plan view showing another embodiment of the endoscope;

FIG. 142 is a side view showing still another modification of the connecting portion;

FIG. 143 is a side view showing still another embodiment of the connecting portion;

FIG. 144 is a side view showing a modification of the operating portion;

FIG. 145 is a side view showing another modification of the operating portion;

FIG. 146 is a sectional view showing other modifications of the breakage preventing member and the breakage preventing cover in FIG. 34; and FIG. 147 is a view showing a distal end portion compatible with various types of endoscopes.

DETAILED DESCRIPTION OF THE PREFERRED EMBODIMENTS

A plurality of embodiments of the present invention will be described below with reference to the accompanying drawings.

Figure 1:
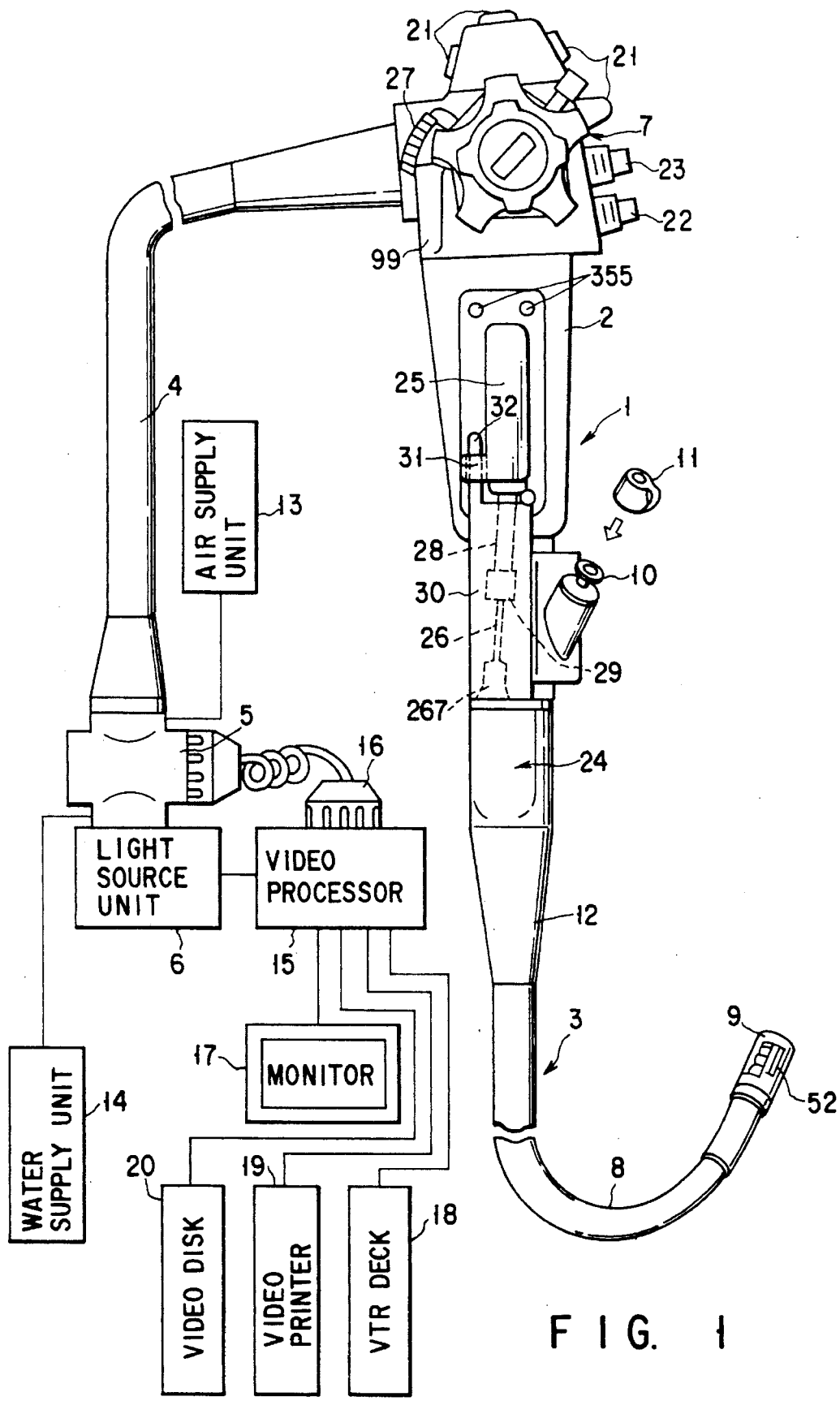
FIG. 1 is a schematic view showing the overall arrangement of an endoscope according to the first embodiment of the present invention.

As shown in FIG. 1, an endoscope has an operating portion 1. The operating portion 1 has a grip portion 2 which is held by an operator with his/her hand. An insertion portion 3 and a universal cord 4 are connected to the operating portion 1. The universal cord 4 has a connector 5 at its end portion. A light source unit 6 for providing illumination light and the like are connected to the connector 5. The insertion portion 3 has a flexible portion 8 which is freely bent when an angle knob 7 mounted on the operating portion 1 is rotated. A distal end portion 9 is mounted on the distal end of the flexible portion 8.

The distal end portion 9 has an opening of a forceps channel extending through the insertion portion 3. The other opening of the forceps channel is formed, as a forceps opening portion 10, in the operating portion 1. A forceps plug 11 is mounted on the forceps opening portion 10 as needed. A breakage preventing member (not shown) for preventing breakage is arranged on the opposite side of the insertion portion 3 to the distal end, and a breakage preventing cover 12 covering the breakage preventing member is mounted on an end portion on the operating portion 1 side.

An air supply unit 13 and a water supply unit 14 are connected to the connector 5. In addition, a video processor 15 for processing a video signal is connected to the connector 5 via a connection adaptor 16. A monitor 17, a VTR deck 18, a video printer 19, a video disk 20, and the like are connected to the video processor 15. For example, the monitor 17 displays an object image by using a processed video signal. The VTR deck 18 records/reproduces a video signal. The video printer 19 prints an object image by using a video signal. The video disk 20 serves as a large-capacity memory device for recording video signals. A switch 21 for operating the video processor 15 is arranged on the operating portion 1. The operating portion 1 also has an air/water supply switching valve 22 for supplying air and water to the distal end portion 9 of the insertion portion 3, and a suction switching valve 23 for a suction operation. A suction operation is performed by a suction pump (not shown) via a suction mouthpiece (not shown) mounted on the connector 5.

The operating portion 1 also has a forceps raising wire opening portion 24 located below the grip portion 2. A forceps raising wire is accessed through the opening portion 24. A driving shaft opening portion 25 for accessing a driving shaft 28 is formed in the grip portion 2. One end of a forceps raising wire 26 as the second transmission means extends from the forceps raising wire opening portion 24, whereas one end of the driving shaft 28 as the first transmission means, which is moved by a forceps raising lever 27 arranged to be coaxial with the angle knob 7, extends from the driving shaft opening portion 25. The driving shaft 28 and the forceps raising wire 26 are detachably coupled to each other via a connecting unit 29. The connecting unit 29 is covered with a detachable protective cover 30 made of an electrically insulating material.

FIGS. 2A to 2D show the details of the connecting unit 29. Holes 34 and 35 are formed in a connecting unit body 33. The forceps raising wire 26 is inserted in the hole 34. The driving shaft is inserted in the hole 35. The depth of the hole 35 is larger than ½ the length of the connecting unit body 33. A through hole 36 communicating with the hole 35 is formed in a central portion side wall 38 of the connecting unit body 33. A set screw 39 is threadably engaged with a threaded portion 40 to be rotatable on an upper surface 37 at a position almost the middle of the through hole 36. A notched portion 41 is formed in an end portion, of the driving shaft 28, located on the connecting unit side, and a hole 42 communicating with the notched portion 41 is formed in the end face of the driving shaft 28. A knurled portion 44 is formed on a head portion 43 of the set screw 39 to allow easy rotation of the set screw 39. Brazing or soldering, for example, is applied to an end face of the forceps raising wire 26 to prevent it from loosening and increasing in diameter. The connecting unit 29 is made from insulating material such as polysulfone or modified PPO and so on.

As shown in FIG. 1, the protective cover 30 made from insulating material, such as plastic, rubber member or other material, is detachably fixed on the operating portion 1 to be located above the connecting unit 29 upon elastic deformation by inserting a positioning projection 32 of the protective cover 30 in a positioning hole 31 formed in the driving shaft opening portion 25. When the protective cover 30 is made of a plastic member, slit portions 45 may be formed as shown in FIG. 3 to facilitate elastic deformation of the protective cover 30. In this case, the protective cover 30 can be fixed with its elasticity instead of engagement between the positioning hole 31 and the positioning projection 32. The length of each slit portion 45 is preferably set to be slightly larger than the distance between the connecting unit 29 and the opening portion on the upper side.

FIGS. 4A to 11 show the details of the distal end portion 9.

As shown in FIGS. 4A and 4B, the distal end portion 9 includes an objective lens 46, an illumination lens 47, and a distal end portion body 49 having a nozzle 48 for spraying air, water, and the like to the objective lens 46 and the illumination lens 47. The distal end portion 9 has a forceps opening portion 51 (see FIG. 6) arranged at a channel 50 (see FIG. 6) communicating with the forceps opening portion 10 of the operating portion 1. A forceps raising base 52 for raising forceps (not shown) extending through the channel 50 is arranged at the distal end of the forceps opening portion 51.

Figure 8:
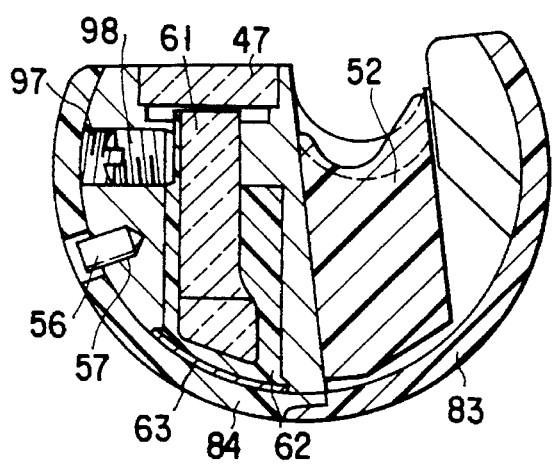
FIG. 8 is a sectional view taken along a line F—F in FIG. 5B.
Figure 9:
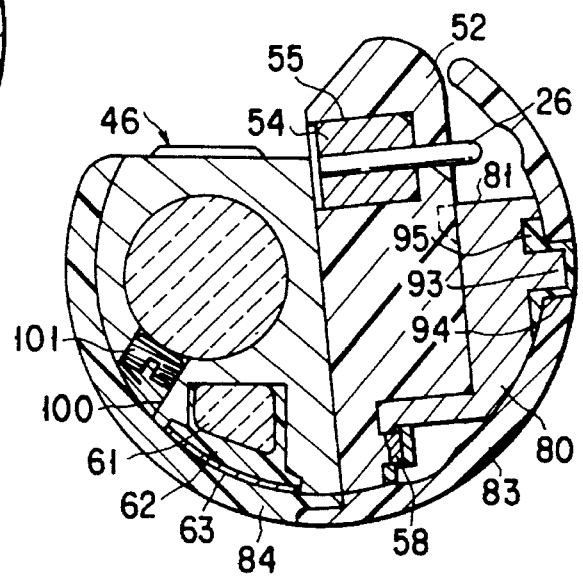
FIG. 9 is a sectional view taken along a line G—G in FIG. 5B.

As shown in FIG. 9, the forceps raising base 52 has a chip housing portion 55. A chip 54 formed on the distal end of the forceps raising wire 26 by swaging is inserted in the chip housing portion 55. The forceps raising base 52 is mounted on a slope portion body 80 via a raising shaft 53 made of a plastic material to be rotatable within a predetermined angle range. The forceps raising base 52 is mounted at an end portion of the forceps raising wire 26. A detachable cover 83 and a stationary cover 84 are arranged on the distal end portion body 49. Each cover is made of an insulating material such as modified PPO. The stationary cover 84 is mounted on the distal end portion body 49 by bonding/fixing a set pin 56, shown in FIG. 8, in a side hole 57 of the distal end portion body 49. The detachable cover 83 is mounted on the distal end portion body 49 to be detachable from the distal end portion 9 together with the forceps raising base 52, the forceps raising wire 26, and the slope portion body 80.

FIGS. 26A and 26B show the details of the slope portion body 80.

The slope portion body 80 has a raising shaft pivotal hole 144 at its bottom portion. The raising shaft 53 extends through the raising shaft pivotal hole 144. The slope portion body 80 has a smooth slope 145 extending, from the left side in FIG. 26B to an upper portion, along the travel path of the forceps raising wire 26. The slope 145 is formed to be continuous with an upper surface 147 extending almost parallel to a raising wire guide hole 146 extending through the upper portion. A stopper projection 81 for defining the range in which the forceps raising base 52 can be raised is formed on a side wall on the forceps raising base 52 side at a position near the upper surface 147.

The slope portion body 80 also has a distal end opening portion surface 148, to which the channel 50 is open, on the left side in FIGS. 26A and 26B to constitute a forceps path portion 149 smoothly extending from the surface 148 to the forceps raising base 52. The upper surface of the forceps path portion 149 constitutes a raising guide portion 150 extending along the bent shape of forceps when the forceps are raised. In this embodiment, the central lines of the raising wire guide hole 146 and the forceps path portion 149 are almost parallel to each other and are almost perpendicular to the raising shaft pivotal hole 144. In addition, a contact surface 151, of the slope 145, which is contact with the forceps raising base 52 is formed to be almost parallel to a side wall of the forceps raising base 52. The slope portion body 80 also has a notched portion 152 at which the bottom portion of the forceps raising base 52 is located.

Figures 5A, 5B, 5C:
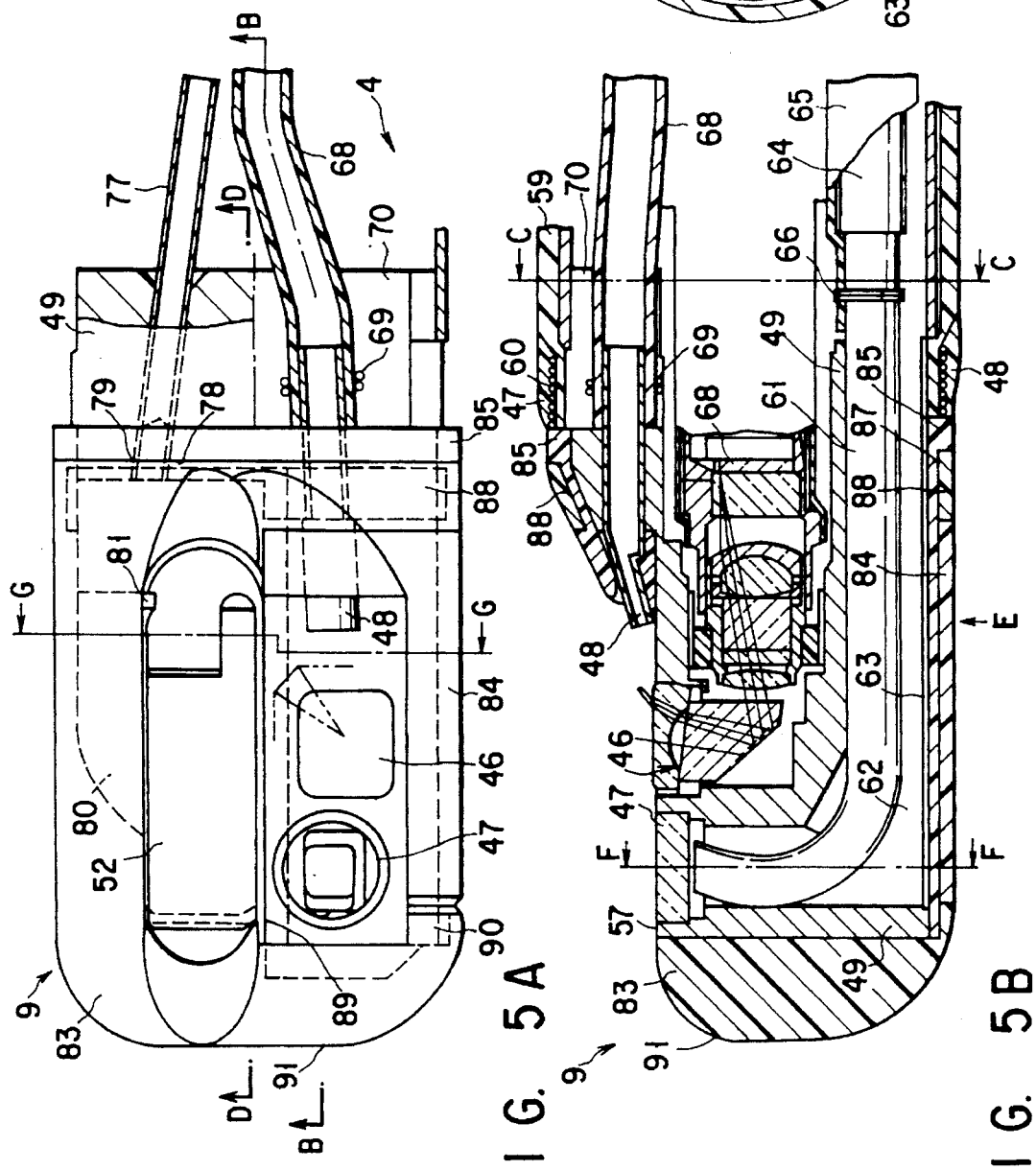

As shown in FIGS. 4A to 11, and especially in FIG. 5B, the portion, of the distal end portion body 49, which has the objective lens 46, the illumination lens 47, and the nozzle 48 is formed such that at least a surface on the forceps raising base 52 side becomes a flat surface. In addition, the opening ends of a channel mouthpiece 72 and a guide tube 77 are formed to have an L shape with respect to a spool bonding portion 60 so that the channel mouthpiece 72 and the guide tube 77 can be arranged within the same plane.

Figure 7A:
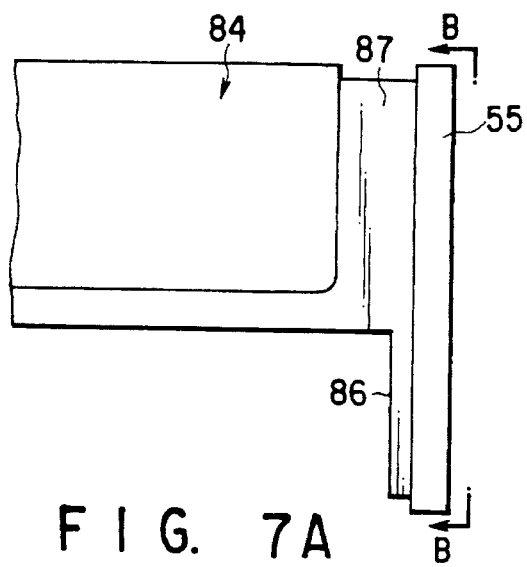
Figure 7B:
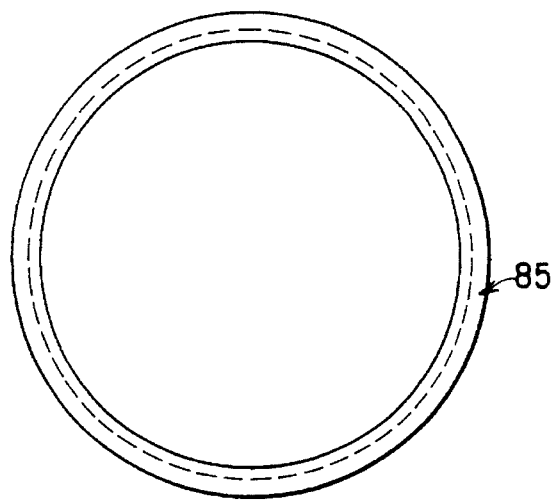

FIG. 7 shows the stationary cover 84 corresponding to this arrangement. The stationary cover 84 is formed into an L shape when viewed from the direction indicated by an arrow E in FIG. 5B. A bottom portion 85 located on the spool bonding portion 60 side is formed into an O-ring shape. A recess groove 87 having a partly notched portion 86 is formed above the bottom portion 85. An upper portion of the stationary cover 84 is formed to cover the distal end portion body 49 except for the objective lens 46, the illumination lens 47, the nozzle 48, and the like. The spool bonding portion 60 serves to fix flexible rubber 59 (FIG. 4A) consisting of an elastic material such as fluororubber and arranged in the flexible portion 8 to be easily bent.

As especially shown in FIGS. 5A, 8, and 9, the detachable cover 83 has a bottom portion 88 with a partly notched portion 92. The bottom portion 88 is formed into a C-shaped ring. The detachable cover 83 is elastically deformed and fitted in the recess groove 87 of the stationary cover 84. In this case, the detachable cover 83 may be made of a plastic member having higher elasticity and better slip properties than the material used for the stationary cover 84 to facilitate a detaching operation. These two covers may be made of the same material having high elasticity. More specifically, polyethylene, polypropylene, and the like have high elasticity, whereas polysulfone, modified PPO, and the like have lower elasticity than that of polyethylene and polypropylene.

The detachable cover 83 has a notched portion 89, which is engaged with the stationary cover 84, above the bottom portion 88. An upper end portion 91 is formed into a smooth R shape.

As shown in FIG. 10, the slope portion body 80, the forceps raising base 52, the detachable cover 83 are formed such that at least the forceps raising base 52 can be rotated within a predetermined angle range with respect to the raising shaft 53. Alternatively, as shown in FIG. 9, the forceps raising base 52 may be integrally formed with a raising pin 58 by using a plastic material or the like, and the raising pin 58 may be inserted in a hole formed in the slope portion body 80 so that the forceps raising base 52 can be rotated with respect to the slope portion body 80. Thereafter, the head of the raising pin 58 may be melted with heat to fix the forceps raising base 52. The slope portion body 80 and the detachable cover 83 are positioned and bonded to each other with a projection 93 formed on a slope portion body 75 and a positioning hole 94 formed in the detachable cover 83. For this reason, an adhesive well portion 95 is formed in the slope portion body 80.

As shown in FIG. 11, the forceps raising base 52 and the slope portion body 80 may be rotatably coupled to each other via a raising shaft 96, and the slope portion body 80 may be bonded to the detachable cover 83, so that the three members are integrated into one unit.

Figure 6:
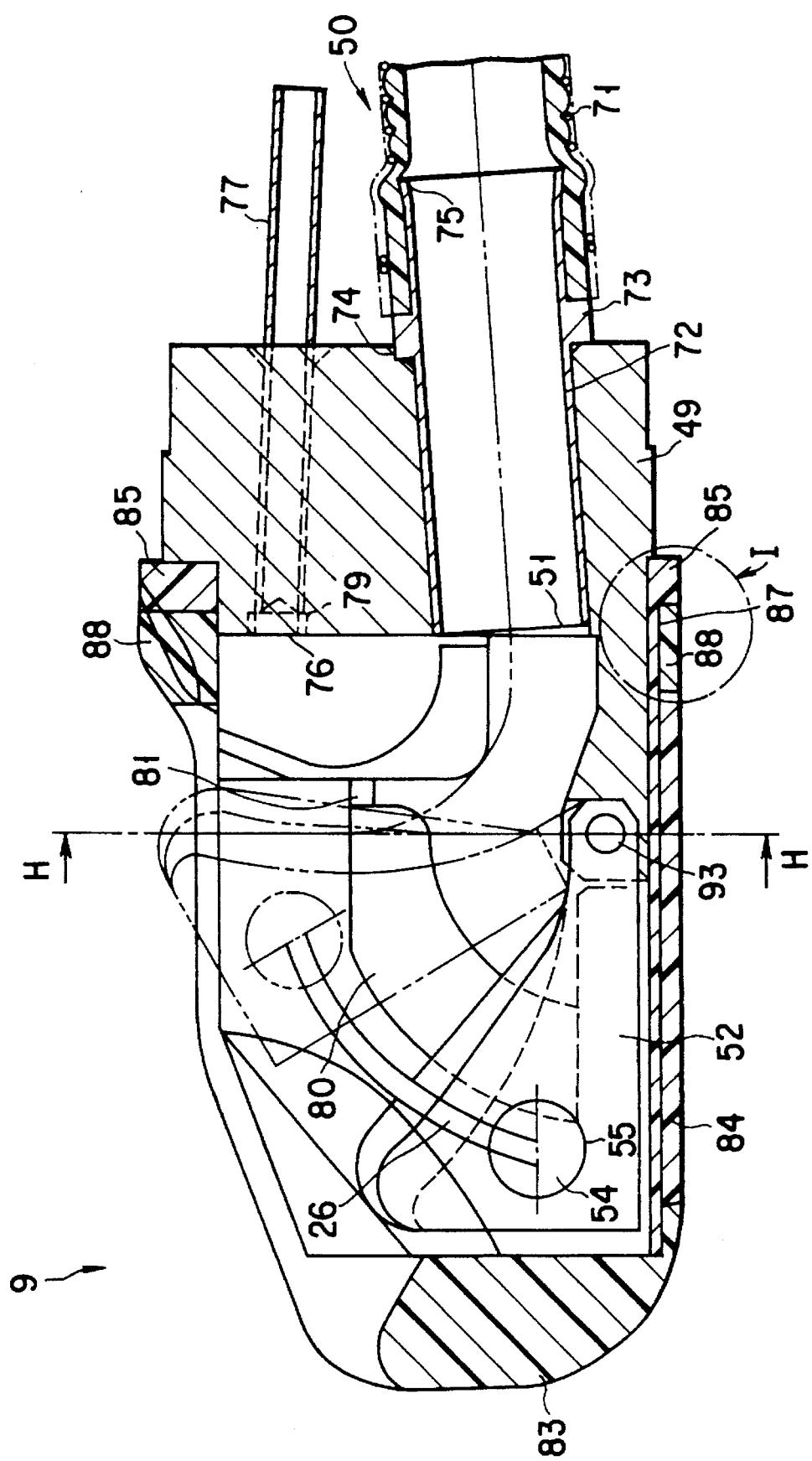
FIG. 6 is a sectional view taken along a line D—D in FIG. 5A.

FIGS. 5A to 5C show the arrangement of the distal end portion upon completion of assembly. FIG. 6 is a sectional view of the distal end portion, taken along a plane passing through the forceps raising base to be perpendicular to the drawing surfaces of FIGS. 4A and 4B and parallel to the axis. A light guide fiber 61 for guiding illumination light from the light source unit 6 is arranged to oppose the illumination lens 47. The light guide fiber 61 is fixed to the distal end portion body 49 by filling a notched portion 62 of the distal end portion body 49 with an adhesive. The notched portion 62 is covered with an adhesive cover 63. A protective tube 64 made of silicone or the like is bonded/fixed throughout the total length of the distal end portion body 49, the flexible portion 8, and the insertion portion 3. In addition, a protective tube 65 made of silicone or the like is fixed on only a portion, of the protective tube 64, which corresponds to the flexible portion 8 by binding the protective tube 65 with a string 66.

As shown in FIG. 8, the light guide fiber 61 is fixed to a side wall threaded portion 97 of the distal end portion body 49 with an HU screw 98. Similarly, a CCD 67 to which a conductive line (not shown) connected to the video processor 15 is connected is arranged to oppose the objective lens 46. As shown in FIG. 9, a lens unit 99 of the objective lens 46 is fixed to a side wall threaded portion 100 of the distal end portion body 49 with an HU screw 101. The distal end of the nozzle 48 is narrowed. The nozzle 48 is bonded/fixed to the distal end portion body 49. An air/water supply tube 68 connected to the cylinder (not shown) of the air/water supply switching valve 22 is fixed to the other end of the nozzle 48 with a string 69. A notched portion 70 is formed in the distal end portion body 49 at the connecting portion of the air/water supply tube 68 so that the air/water supply tube 68 can be bent.

As shown in FIG. 6, at least in the flexible portion 8, the channel 50 has a coil 71 wound thereon and are abutted against a projection 73 formed on the outer surface of a channel mouthpiece 72 made of a tubular member so as to be bonded/fixed thereto. The projection 73 of the channel mouthpiece 72 is abutted against a projection 74 of the distal end portion body 49 to be bonded/fixed to the distal end portion body 49. In addition, an adhesive is smoothly coated on an end portion, of the channel mouthpiece 72, located on the forceps raising base 52 side, i.e., the forceps opening portion 51. The channel mouthpiece 72 has a bell mouth portion, which expands outward, on the other end side. A forceps contact surface 76 of the forceps raising base 52 is formed into a U-shaped groove having a gradual slope. The forceps raising wire 26 is guided by the guide tube 77 disposed in the forceps opening portion 51 to extend to the operating portion 1 and the suction switching valve 23 via the insertion portion 3. The guide tube 77 has a bell mouth portion 78 at an end located on the forceps raising base 52 side and is bonded/fixed in a stepped hole 79 formed in the distal end portion body 49. A slope portion 80 is formed in the distal end portion body 49 along the moving path of the forceps raising wire 26. A stopper projection 81 is formed midway along the slope portion 80 to define the range in which the forceps raising base 52 is raised.

FIGS. 12A and 12B show the details of a portion I in FIG. 6. Each corner of the recess groove 87 of the stationary cover 84 is formed into an R shape to facilitate a cleaning operation, and the bottom portion 88, of the detachable cover 83, which is fitted in the recess groove 87 is chamfered such that at least each corner of the outer surface is formed into an R shape, and each corner of the inner surface is formed into an R or C shape.

FIGS. 13A to 13C show an end portion, of the forceps raising wire 26, located on the operating portion 1 side. A stranded wire is melted by a plasma process or the like to form a spherical portion 102, and an integrated portion 103 is formed by soldering or the like. A stepped portion 104 may also be formed.

Figure 14:
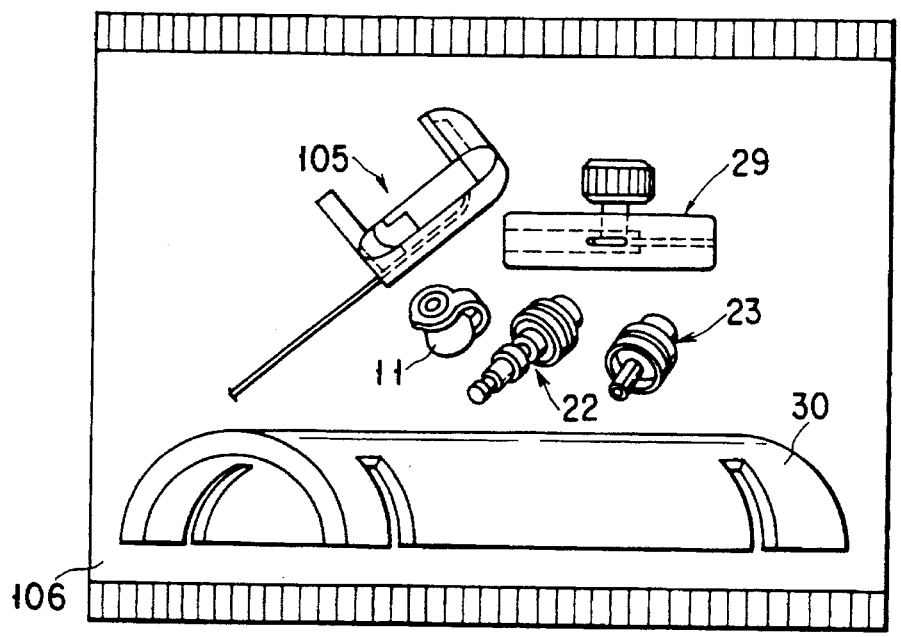
FIG. 14 is a perspective view showing a state wherein a detachable distal end portion, a forceps plug, the connecting unit, a suction piston, air/water supply piston, and a protective cover are incorporated in a sterile pack.

FIG. 14 shows a state wherein a detachable distal end portion 105, the forceps plug 11, the connecting unit 29, the suction switching valve 23, the air/water supply switching valve 22, and the protective cover 30 are arranged in a sterile pack 106. The members in this pack are made of materials which allow autoclaving. In practice, as the sterile pack 106, a sterile pack obtained in the following manner is generally used. The forceps plug 11 and the like are placed on kraft sterile paper, and are heat-sealed with a laminate film.

After one medical treatment, the protective cover 30 shown in FIG. 6 is removed while the forceps raising wire 26 is connected to the electronic endoscope. The forceps raising wire 26 and the driving shaft 28 are removed from the connecting unit body 33 by turning the set screw 39 of the connecting unit 29. In this state, the detachable distal end portion 105 integral with the forceps raising base 52, the detachable cover 83, the forceps raising wire 26, and the slope portion body 80 can be removed from the distal end portion 9 while the notched portion 92 of the bottom portion 88 of the detachable cover 83 which is fitted in the recess groove 87 of the stationary cover 84 fixed to the distal end portion body 49 is elastically deformed.

Subsequently, the sterile pack 106 shown in FIG. 14 is opened, and a new detachable distal end portion 105 and a new connecting unit 29 are removed and mounted in the reverse procedure to that described above. More specifically, the forceps raising wire 26 is first inserted through the opening of the guide tube 77 extending through the distal end portion 9 and the insertion portion 3 and is guided to the outside of the operating portion 1 from an end of the flexible rubber 59 of the suction switching valve 23.

At this time, the bottom portion 88 of the detachable cover 83 is fitted in the recess groove 87 of the stationary cover 84 while the bottom portion 88 is elastically deformed along the outer surface of the stationary cover 84, thus mounting the detachable distal end portion 105 on the distal end portion 9. Thereafter, as shown in FIG. 5, the connecting unit body 33 is inserted in the driving shaft 28 while the forceps raising base 52 is set upside down and the connecting unit 29 is fully pushed toward the switch 21. The forceps raising wire 26 is inserted in the hole 34 of the connecting unit body 33. The forceps raising wire 26 is then guided outside the connecting unit body 33, without slack, via the hole 42 of the driving shaft 28, the side wall 38, and the through hole 36. The set screw 39 is turned to urge the forceps raising wire 26 with the notched portion 41 of the driving shaft 28, thus fixing the forceps raising wire 26. The protective cover 30 is connected to the resultant structure upon elastic deformation.

When the connecting unit 29 shown in FIG. 1 is moved, the movement is transferred to the driving shaft 28, the connecting unit 29, and the forceps raising wire 26 in the order named, thereby raising the forceps raising base 52 of the distal end portion 9.

Members around the forceps raising base 52 can be removed at once together with the detachable distal end portion 105, and the remaining distal end portion body 49 becomes flat. Therefore, the cleaning properties are improved, and the time and labor for a cleaning operation can be reduced. Since the forceps raising wire 26 can be removed, the inside of the guide tube 77 can be easily cleaned. In addition, the forceps raising wire 26 can be easily repaired when it is worn.

The connecting unit 29 can also be sterilized separately. In addition, the operator can easily assemble this portion and can also easily adjust the forceps raising wire 26 when the portion is mounted.

Furthermore, since the connecting unit 29 is located below the grip portion 2, filthy substances such as intracavity fluids do not easily adhere to the hands and face of the operator, allowing a sanitary operation.

Since members detachable with respect to the endoscope are packed in the sterile pack 106 all together, the members are not cleaned between medical treatments. Instead, a new sterile pack 106 is opened to provide clean members, thus saving a cleaning operation.

Moreover, since an end portion of the forceps raising wire 26 is processed into an integral portion, the portion does not loosen. For this reason, the forceps raising wire 26 can be inserted in the guide tube 77 without being stuck therein. In addition, with the connecting unit 29 shown in FIGS. 13A to 13C, since the stepped portion 104 is only required to be hooked on a notched portion 82, the connecting portion can be reduced in size.

The embodiment shown in FIG. 15 will be described next.

In a detachable distal end portion 105, a hook portion 109 is formed on a side surface 108 of a detachable cover 107 on the distal end side of a surface of a forceps raising base 52. A corresponding end portion of a stationary cover 110 is formed into an R-shaped end 111, and a jig hole 112 is formed in the end face of the R-shaped end 111. A hook groove 113 is formed in the end face of a distal end portion body 49 which is perpendicular to the above end face. The stationary cover 10 has an objective lens 46, an illumination lens 47, and an opening window 114 of a nozzle 48. Other arrangements are the same as those in the above embodiment.

Figure 15:
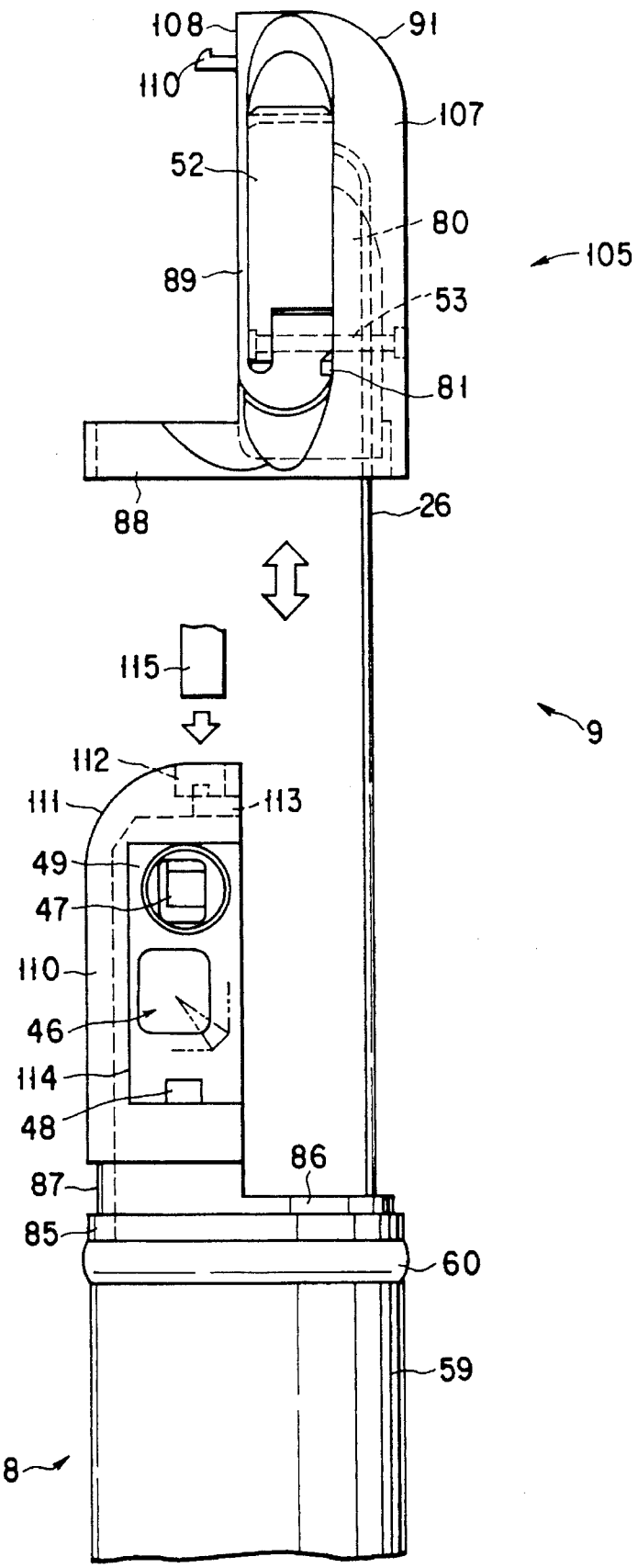
FIG. 15 is a view showing the arrangement of the distal end portion of an endoscope according to the second embodiment of the present invention.

When the detachable distal end portion 105 shown in FIG. 15 is to be removed, a jig 115 is inserted in the jig hole 112, and the hook portion 109 is pushed out of the hook groove 113 to be removed. The detachable distal end portion 105 is mounted in the reverse procedure. That is, the hook portion 109 is inserted in the hook groove 113 upon elastic deformation. Other operations are the same as those in the above embodiment.

In addition to the same effects as those of the above embodiment, in this embodiment, the detachable distal end portion 105 can be more easily removed from a distal end portion 9.

The third embodiment will be described below with reference to FIGS. 16 and 17.

The third embodiment will be described below with reference to FIGS. 16A to 17B.

Figure 16B:
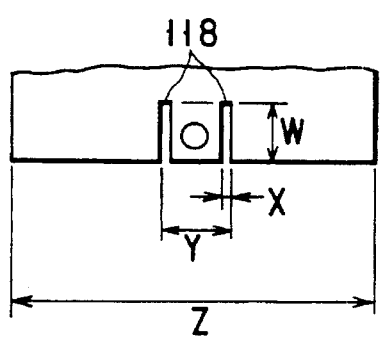
Figure 16A:
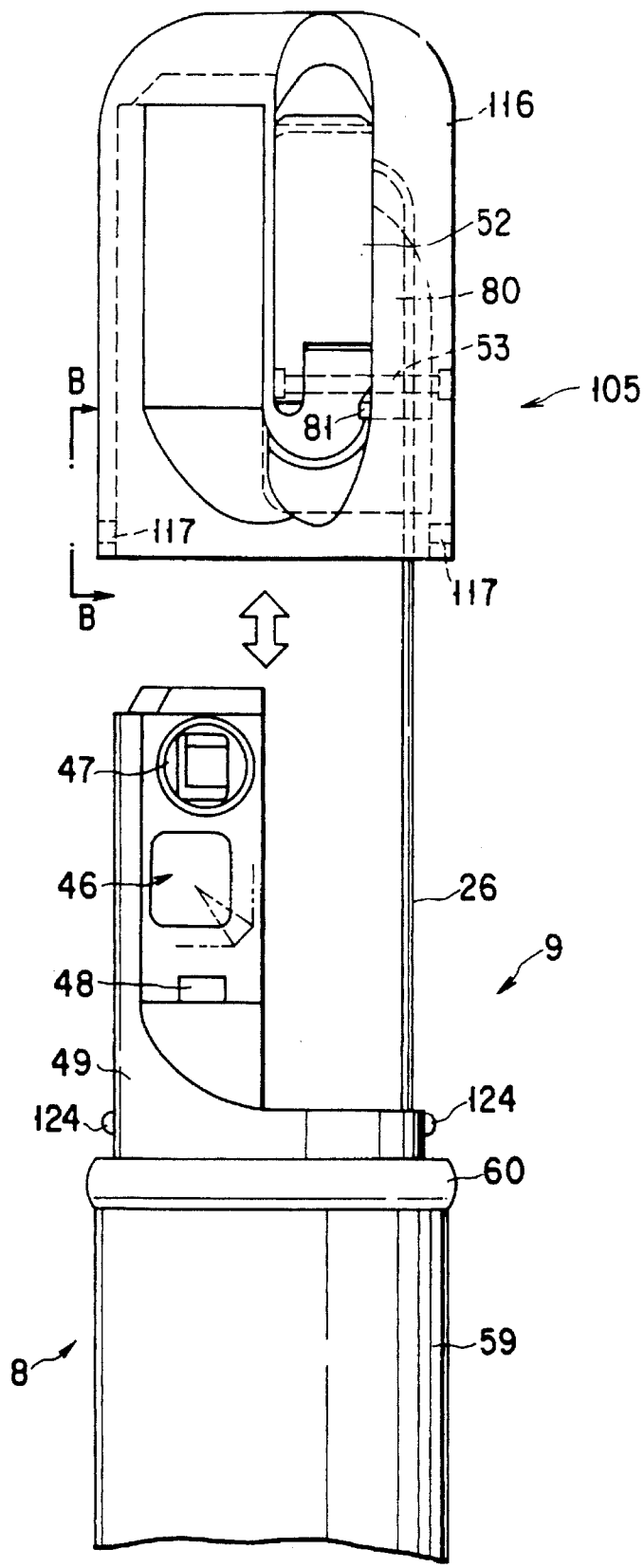

As shown in FIGS. 16A and 16B, in a detachable distal end portion 105, a detachable cover 83 and a stationary cover 84 are constituted by a distal end cover 116 made of an integral elastic plastic member or the like. A forceps raising base 52, a forceps raising wire 26, and a slope portion body are integrally incorporated in the distal end cover 116. The distal end cover 116 is designed to be detachable from a distal end portion body 49 of a distal end portion 9. Click holes 117 and click grooves 118 are formed in the bottom portion of the distal end cover 116 at opposite positions. Projections 124 having a diameter slightly smaller than that of the click holes 117 are formed on an end portion, of the distal end portion body 49, located on a spool bonding portion 60 side at positions corresponding to the click holes 117. In this case, the projections 124 may be formed by forcibly inserting knock pins or the like. Other arrangements are the same as those in the first embodiment.

Figure 17A:
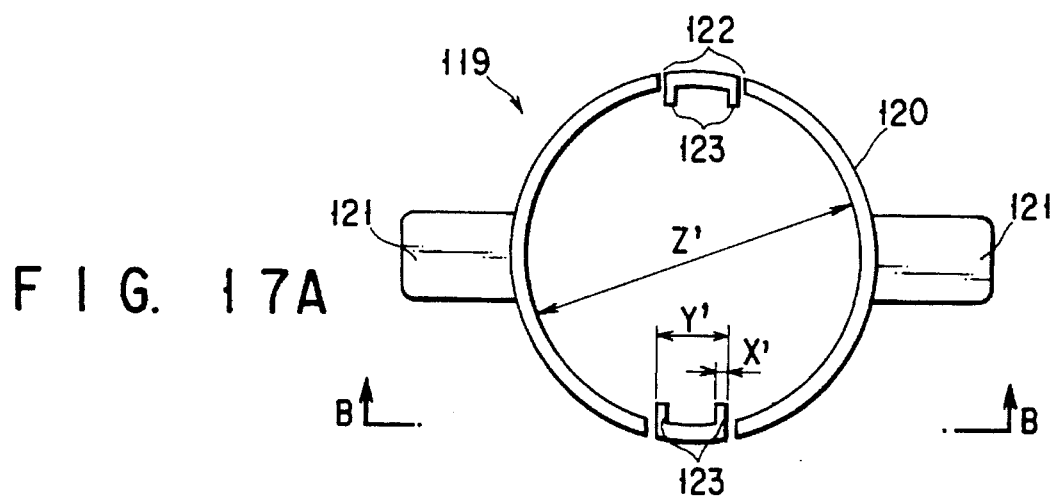
FIGS. 17A and 17B show a detaching jig for the detachable distal end portion in FIG. 16A.
Figure 17B:
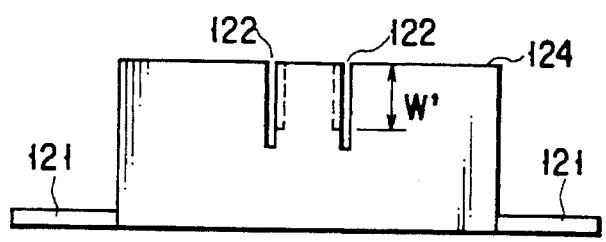

FIGS. 17A and 17B show a detaching jig 119 of the detachable distal end portion 105. The detaching jig 119 is constituted by a ring portion 120 having a diameter Z' slightly larger than an outer diameter Z of the distal end portion. The detaching jig 119 has knob portions 121 at two opposite positions. Two pairs of slit grooves 122 having a pitch Y' slightly smaller than a pitch Y of the click grooves 118 of the distal end cover 116 are respectively formed in the circumferential portion of the ring portion 120 at two opposite positions. Projections 123, each having a width X' slightly smaller than a width X of the click groove 118 and a length W' almost equal to a length W of the click groove 118, extend from the end face of the ring portion 120. In this case, the length of the slit groove 122 is set to be larger than that of the click groove 118.

The detaching jig 119 is inserted in an insertion end 124 and pushed to the end face of a spool bonding portion 245 on the bottom portion of the distal end cover 116. The detaching jig 119 is pulled in a direction opposite to the inserting direction while the projections 123 of the detaching jig 119 are fitted in the click grooves 118 of the distal end cover 116. With this operation, the distal end cover 116 is removed together with the detaching jig 119. After the removal, the R-shaped distal end of the distal end cover 116 is pushed out of the detaching jig 119 to be removed therefrom. Other arrangements are the same as those in the first embodiment.

In this embodiment, the detachable distal end portion 105 can be easily removed from the distal end portion 9 as compared with the first embodiment. Other effects are the same as those of the first embodiment.

The fourth embodiment will be described below with reference to FIG. 18.

This embodiment is basically the same as the third embodiment. Only the difference between the two embodiments will be described below. A partition plate 126 is arranged in a distal end cover 125, and the distal end cover 125, a slope portion body 80, and a forceps raising base 52 are integrally arranged by using a raising shaft 127. The forceps raising base 52 is designed to be rotatable within a predetermined angle range with respect to the raising shaft 127.

The operation of the fourth embodiment is the same as that of the third embodiment.

According to this embodiment, since the raising shaft 127 is supported at two ends, the structure is superior in strength to that in the third embodiment, in which the raising shaft is cantilevered. Other effects are the same as those of the third embodiment.

Figure 19:
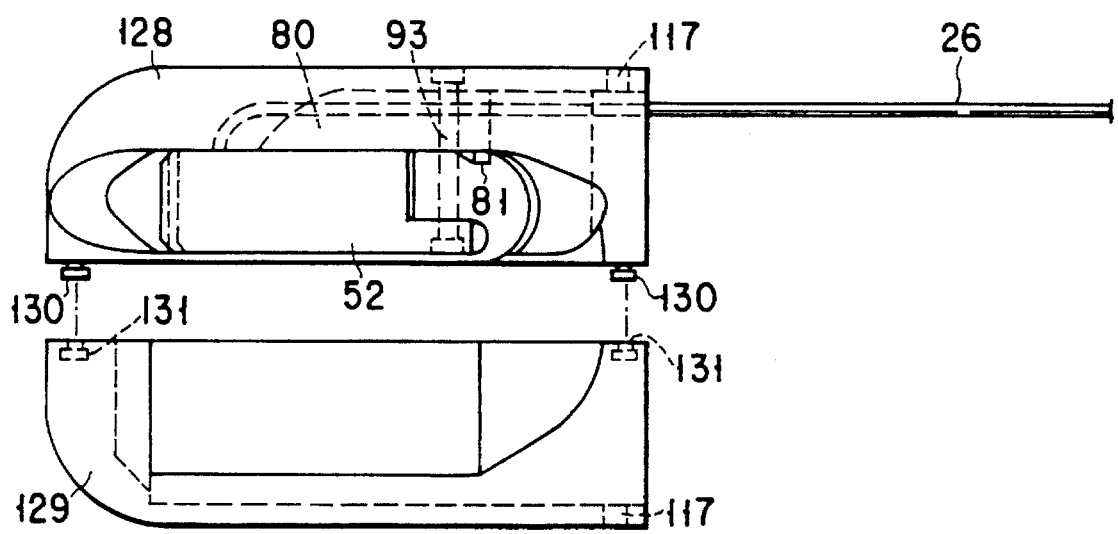
FIG. 19 is a view showing the arrangement of the distal end portion of an endoscope according to the fifth embodiment of the present invention.

The fifth embodiment will be described below with reference to FIG. 19.

This embodiment is similar to the third embodiment. Only the difference between the two embodiments will be described below. In the fifth embodiment, a distal end cover 116 is constituted by two components, i.e., covers 128 and 129. The covers 128 and 129 respectively have a projection 130 and a recess 131 which are engaged with each other.

The covers 128 and 129 can be removed from a distal end portion body 49 without using a jig 119 like the one in the third embodiment. Other arrangements are the same as those in the third embodiment.

Removal of the distal end cover 116 can be easily performed without using a jig. Other effects are the same as those of the first embodiment.

Figure 20:
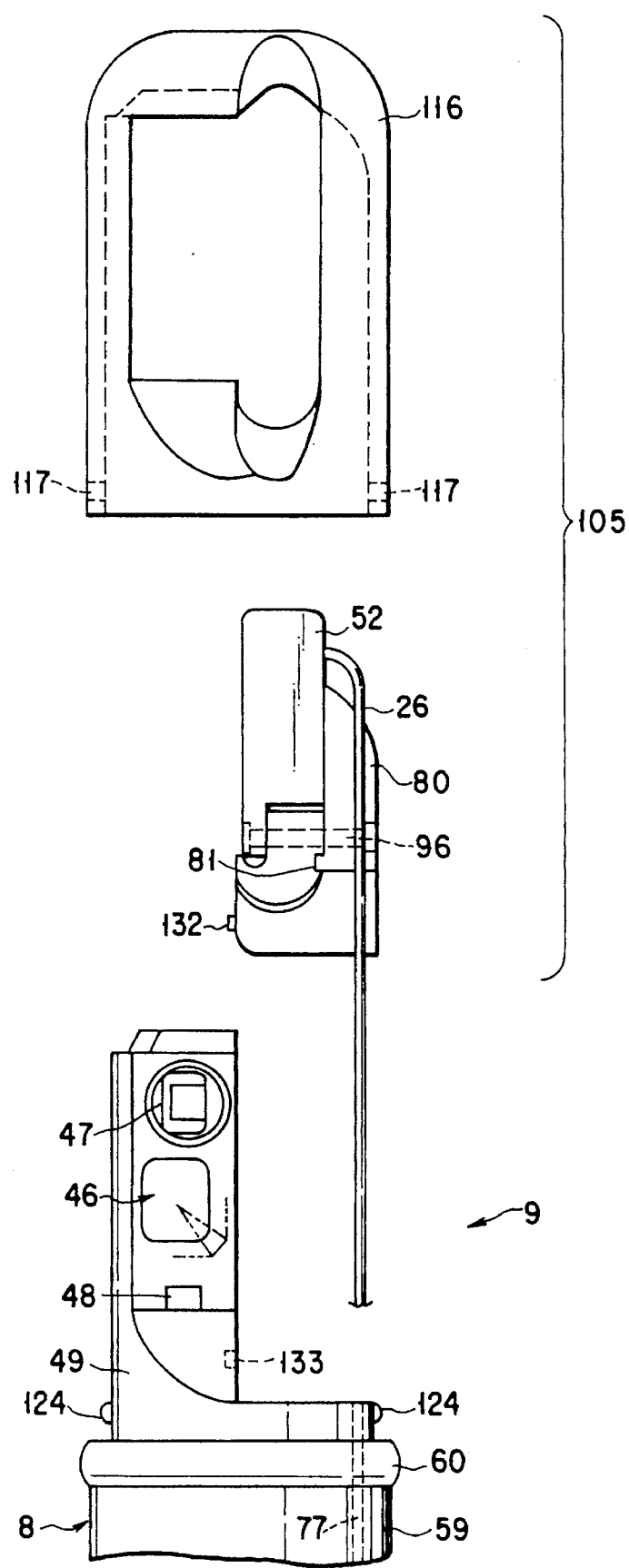
FIG. 20 is a view showing the arrangement of the distal end portion of an endoscope according to the sixth embodiment of the present invention.

The sixth will be described below with reference to FIG. 20.

This embodiment is similar to the third embodiment. Only the difference between the two embodiments will be described below. As shown in FIG. 20, a detachable distal end portion 105 integrally incorporates a forceps raising base 52, a slope portion body 80, and a forceps raising wire 26. The detachable distal end portion 105 is designed to be freely detached from a distal end portion body 49 independently of a distal end cover 116. In this case, the forceps raising base 52 and the slope portion body 80 are coupled to each other via a raising shaft 96 to be rotatable within a predetermined angle range. The slope portion body 80 and the distal end portion body 49 respectively have a projection 132 and a recess 133 which are engaged with each other for positioning. Other arrangements are the same as those in the third embodiment.

The sixth embodiment has the same functions and effects as those of the third embodiment except that the distal end cover 116 can be independently attached/detached.

Figure 21:
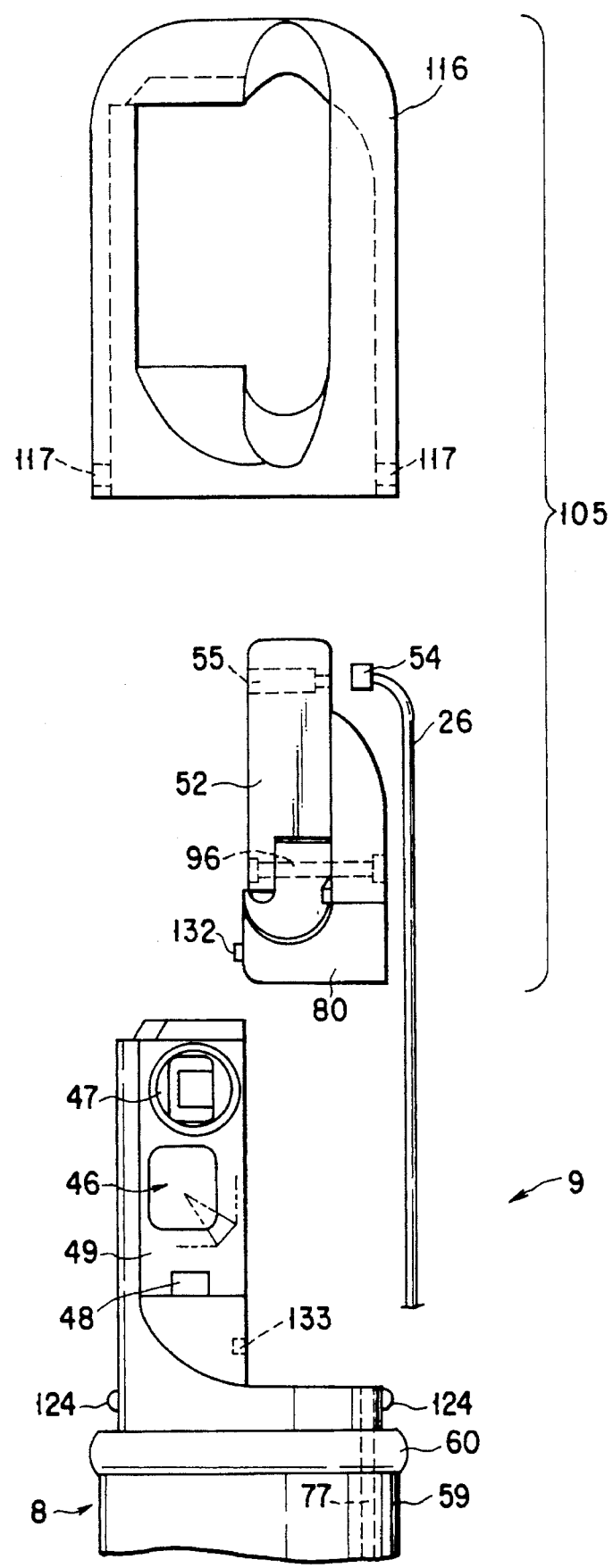
FIG. 21 is a view showing the arrangement of the distal end portion of an endoscope according to the seventh embodiment of the present invention.

The seventh embodiment will be described below with reference FIG. 21.

This embodiment is similar to the sixth embodiment. Only the difference between the two embodiments will be described below. As shown in FIG. 21, a forceps raising wire 26 can be removed from a forceps raising base 52. Other arrangements are the same as those in the sixth embodiment.

Similar to the distal end cover 116 in the sixth embodiment, the forceps raising wire 26 can be independently attached/detached to/from a distal end portion body 49. Other arrangements are the same as those in the third embodiment.

Since the forceps raising wire 26, which wears most, in the third embodiment can be independently attached/detached, only the forceps raising wire 26 can be repaired while other detachable members are kept mounted. Such a repair is economical. Other effects are the same as those of the third embodiment.

Figure 22:
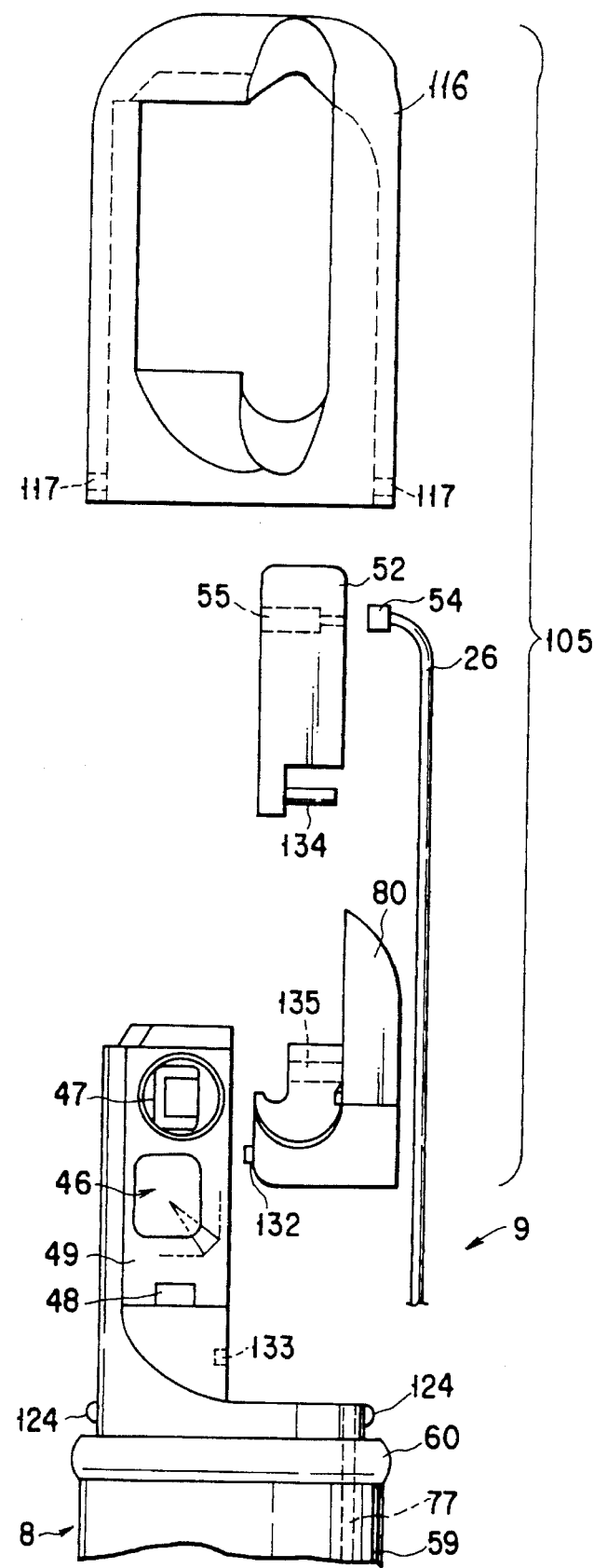
FIG. 22 is a view showing the arrangement of the distal end portion of an endoscope according to the eighth embodiment of the present invention.

The eighth embodiment will be described below with reference to FIG. 22.

This embodiment is similar to the seventh embodiment. Only the difference between the two embodiments will be described below. As shown in FIG. 22, a forceps raising base 52 and a slope portion body 80 are designed to be detachable. In this case, a raising pin projection 134 is formed on the forceps raising base 52, and a corresponding raising pin hole 135 is formed in the slope portion body 80. Other arrangements are the same as those in the seventh embodiment.

The distal end cover 116, the forceps raising wire 26, the forceps raising base 52, and the slope portion body 80 in the third embodiment are all designed to be freely attached/detached to/from a distal end portion body 49 independently. Other operations are the same as those in the third embodiment.

Since all the detachable members are independent of each other, cleaning and repairs can be easily performed. Other effects are the same as those of the third embodiment.

Figure 23:
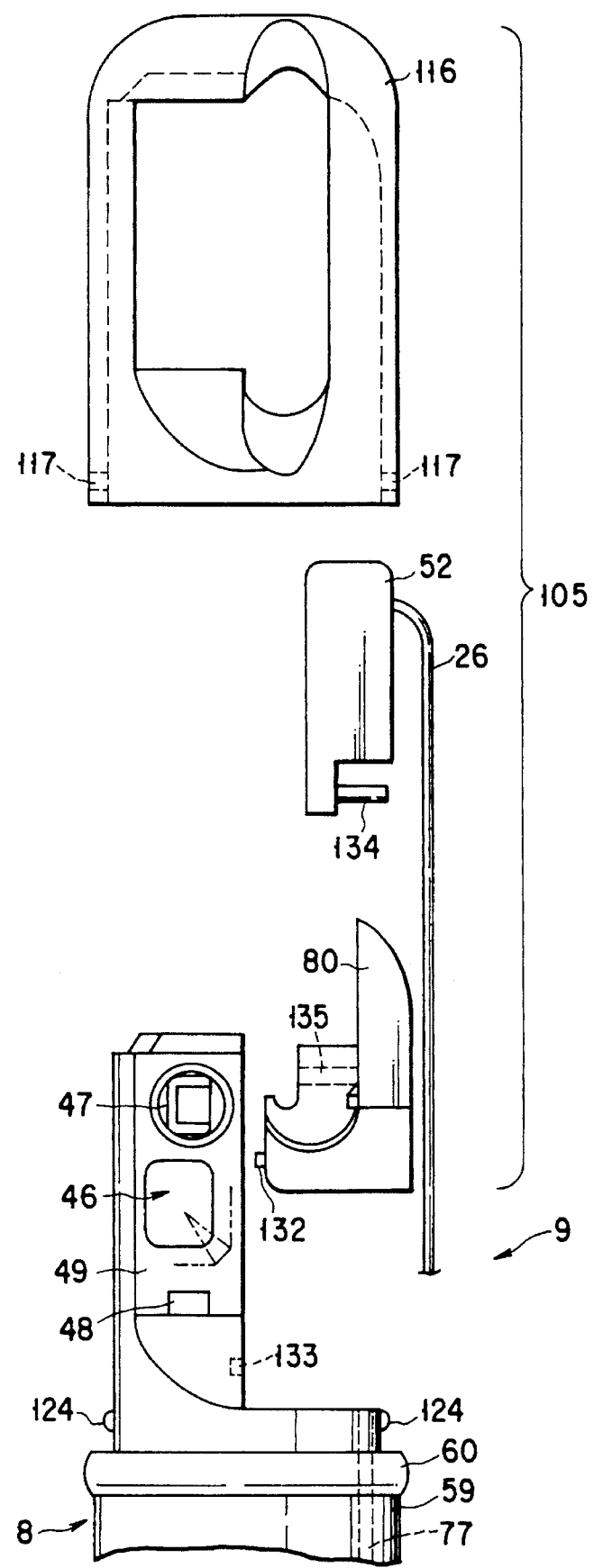
FIG. 23 is a view showing the arrangement of the distal end portion of an endoscope according to the ninth embodiment of the present invention.

The ninth embodiment will be described below with reference to FIG. 23.

In this embodiment, the forceps raising base 52 and the forceps raising wire 26 in the eighth embodiment are designed to be integrally detachable. Other arrangements are the same as those in the eighth embodiment.

The distal end cover 116 and the slope portion body 80 in the third embodiment are designed to be freely attached/detached to/from a distal end portion body 49 independently, whereas the forceps raising wire 26 and the forceps raising base 52 are designed to be freely attached/detached from the distal end portion body 49 integrally. Other operations are the same as those in the third embodiment.

The same effects as those of the third embodiment can be obtained.

Figure 24:
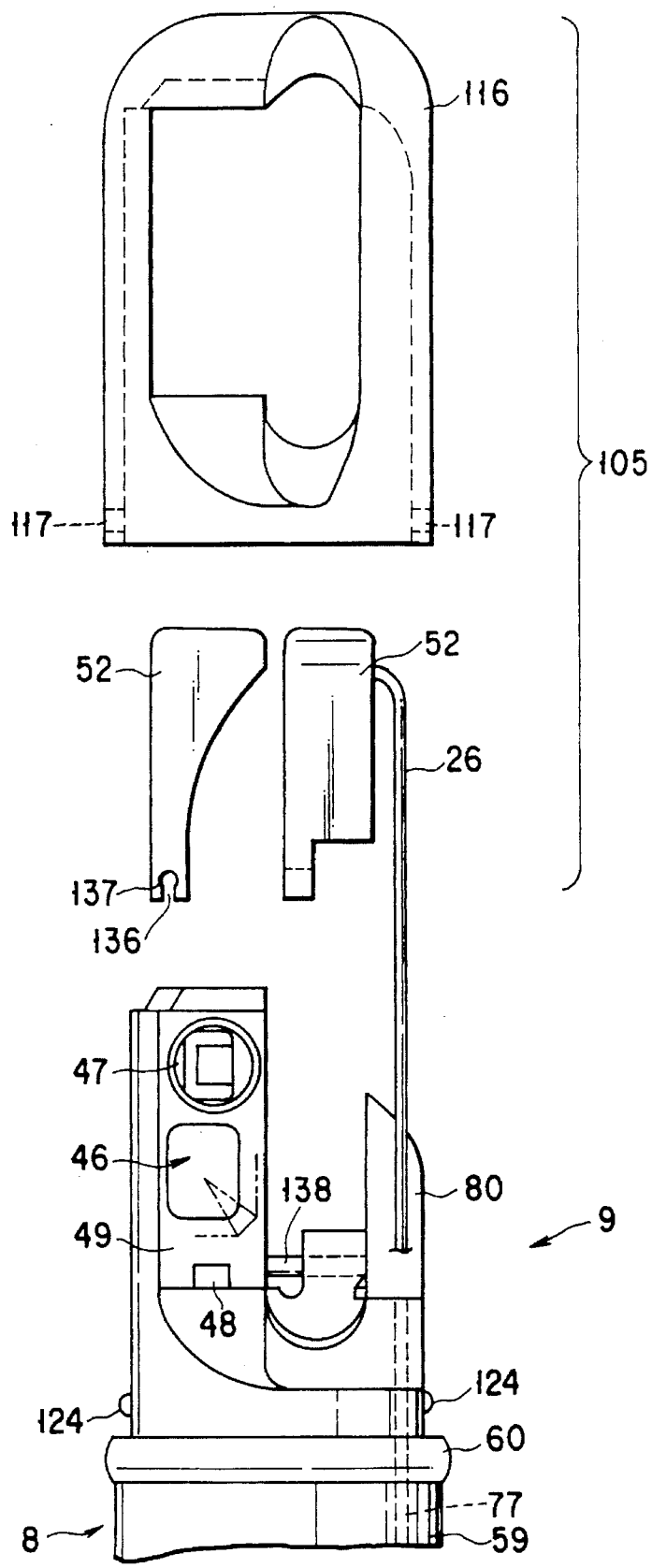
FIG. 24 is a view showing the arrangement of the distal end portion of an endoscope according to the tenth embodiment of the present invention.

The tenth embodiment will be described below with reference to FIG. 24.

A raising pin slit 136, having a width smaller than that of a raising shaft 138, and a raising pin hole 137 are formed in the driving portion of the forceps raising base 52 made of an elastic member such as a plastic member in the ninth embodiment. A slope portion body 80 is integrally formed with a distal end portion body 49, and the raising shaft 138 is arranged therebetween.

The tenth embodiment is the same as the third embodiment except that the slope portion body 80 in the ninth embodiment is not detachable. Note that the forceps raising base 52 can be attached/detached to/from the raising shaft 138 by elastically deforming the raising pin slit 136.

The tenth embodiment has the same effects as those of the third embodiment. In addition, in the tenth embodiment, the forceps raising base 52 can be more easily attached/detached than in the ninth embodiment.

Figures 25A, 25B:
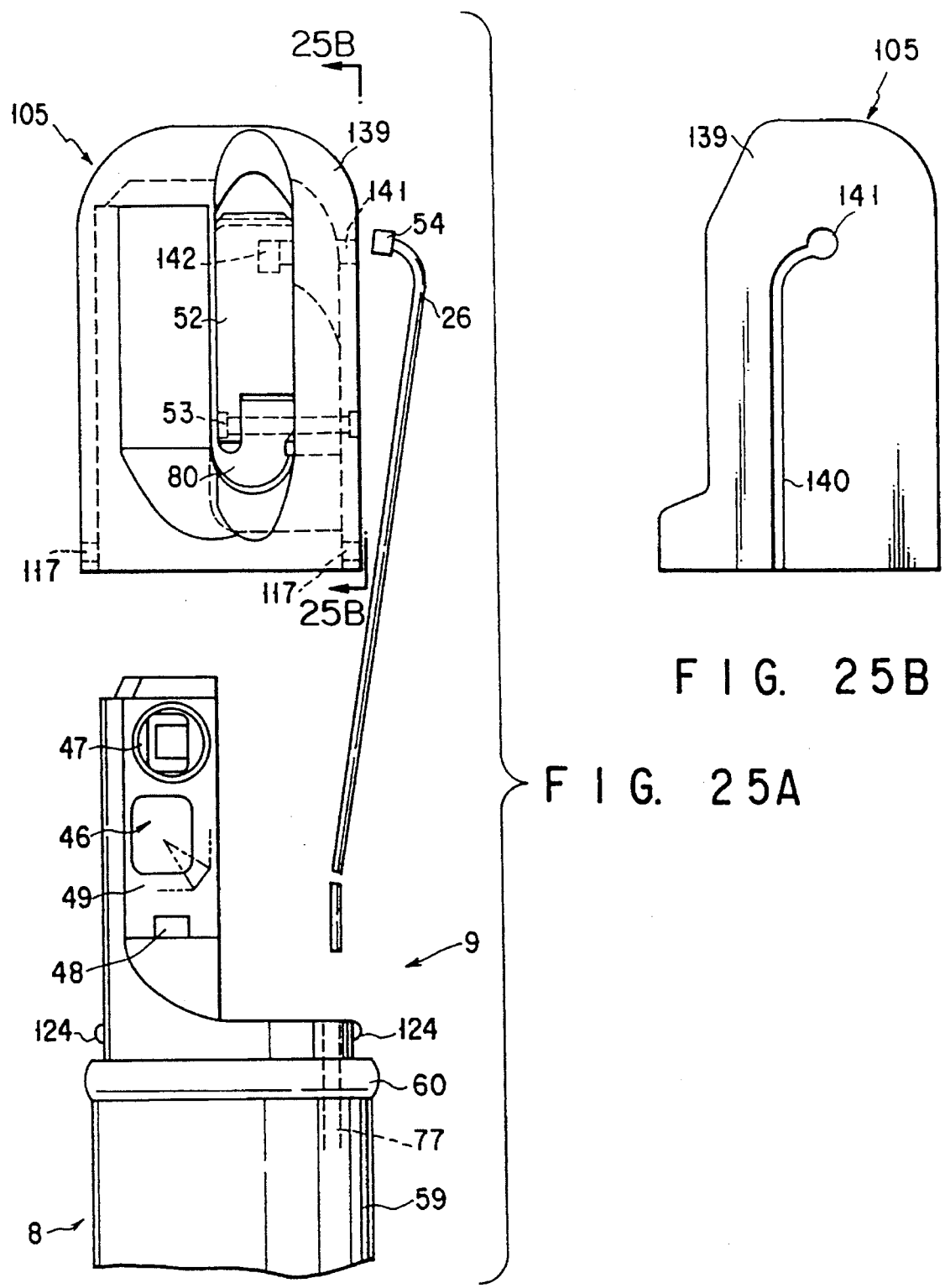

The eleventh embodiment will be described below with reference to FIGS. 25A and 25B.

A forceps raising wire 26 is arranged independently of the detachable distal end portion 105 in the third embodiment. For this reason, a wire groove 140 and a tip hole 141, in which the forceps raising wire 26 can be inserted, are formed in a side wall, of a distal end cover 139, located on the forceps raising base 52 side. In addition, a tip housing portion 142 is formed in a forceps raising base 52.

The forceps raising wire 26 in the third embodiment is designed to be freely attached/detached to/from the distal end portion body 49 independently. Other arrangements are the same as those in the third embodiment.

The eleventh embodiment has the same effects as those of the third embodiment. In addition, since the forceps raising wire 26, which easily wears, is designed to be freely attached/detached independently, the forceps raising wire 26 can be repaired while other detachable members are kept mounted.

Assume that reference symbol A indicates the distal end cover 116; B, the forceps raising base 52; C, the forceps raising wire 26; and D, the slope portion body 80. In addition, assume that two components coupled to each other by "+" are integrated, and constituent elements separated from each other by "," are designed to be attached/detached to/from the distal end portion body independently. In this case, the respective embodiments can be expressed as follows:

First to fifth embodiments: (A, B, C, D)

Sixth embodiment: (A+B, C, D)

Seventh embodiment: (A+C+B, D)

Eighth embodiment: (A+B+C+D)

Ninth embodiment: (A+C, C+D)

Tenth embodiment: (A+B, C)

Eleventh embodiment: (A, B, D+C)

Other combinations, i.e., (A, B+C+D), (A, B, C+D), (A, D+B, C), (A, D+B+C), (A+B+ C), (A, B+C), and (A, B, C) are presented as the twelfth embodiment.

In these cases, only combinations associated with attachment/detachment are different from those described above, but the same functions and operations as those of the third embodiment can be obtained.

Note that the detachable distal end portion 105 can be commonly used for different types of devices (e.g., an electronic scope and a fiber scope), and an abutment portion 143 can be formed as a reference surface.

In this case, the detachable distal end portion 105 need not be provided for each type of device, and hence there is no possibility of erroneous assembly.

It is very useful to make one detachable distal end portion 105 to be common to, i.e., compatible with, two or more types of endoscopes constituted by different components such as optical systems and nozzles, as shown in FIG. 147. For example, as shown in FIG. 147, a scope (endoscope) A, a scope B, and a scope C are endoscopes constituted by different components such as optical systems and nozzles. Assume that the insertion portions of these scopes have substantially the same length and outer diameter, and the channels in the insertion portions have substantially the same diameter. In this case, the same detachable distal end portion 105 can be commonly used for the different types of endoscopes by making recess grooves 87 and distal end bodies 49 of the respective scopes have substantially the same shapes, respectively.

FIGS. 27 to 33 show the thirteenth to fifteenth embodiments of the distal end portion 9.

Figure 27:
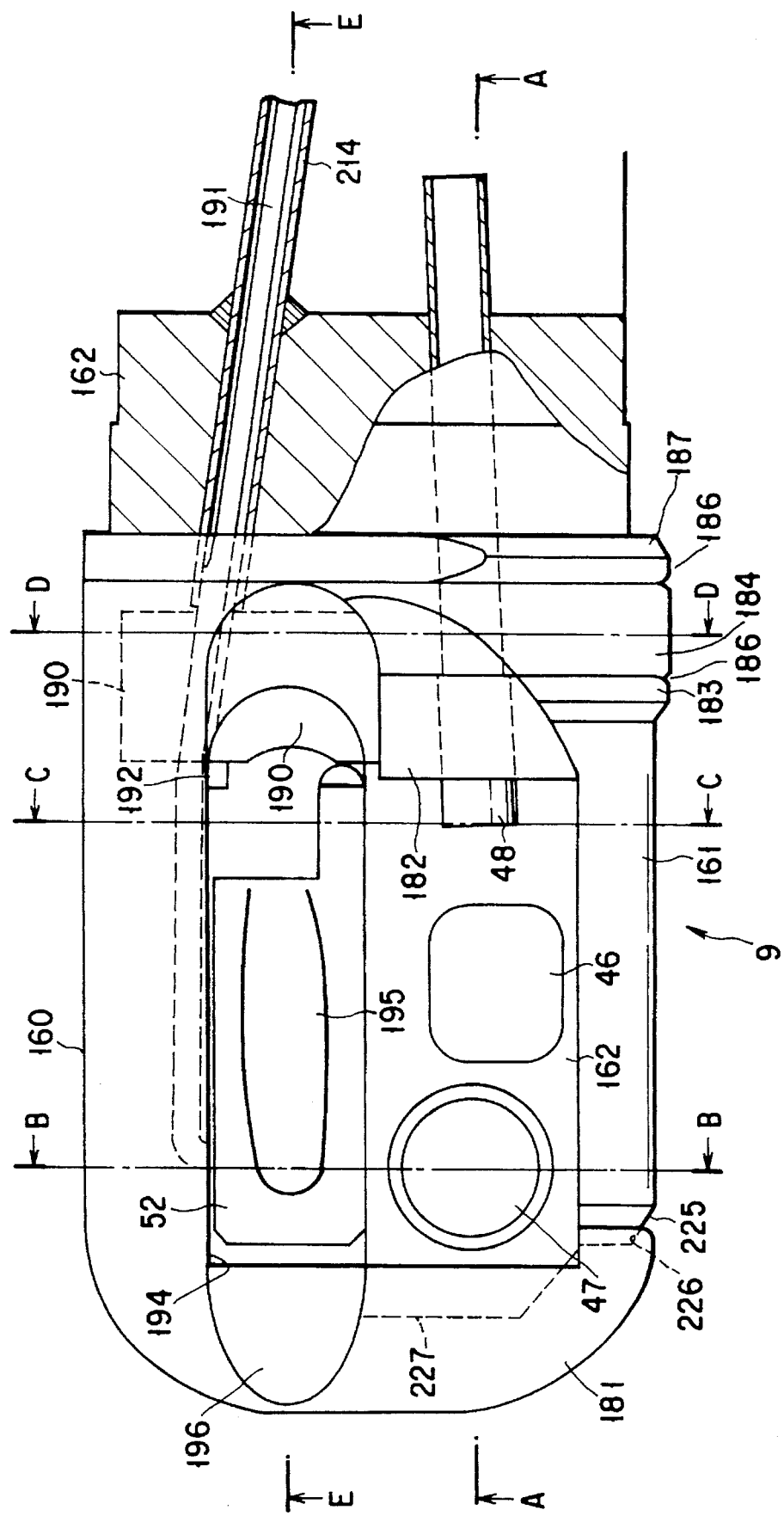
FIG. 27 is a plan view of the distal end portion of an endoscope according to the thirteenth embodiment of the present invention.
Figure 28:
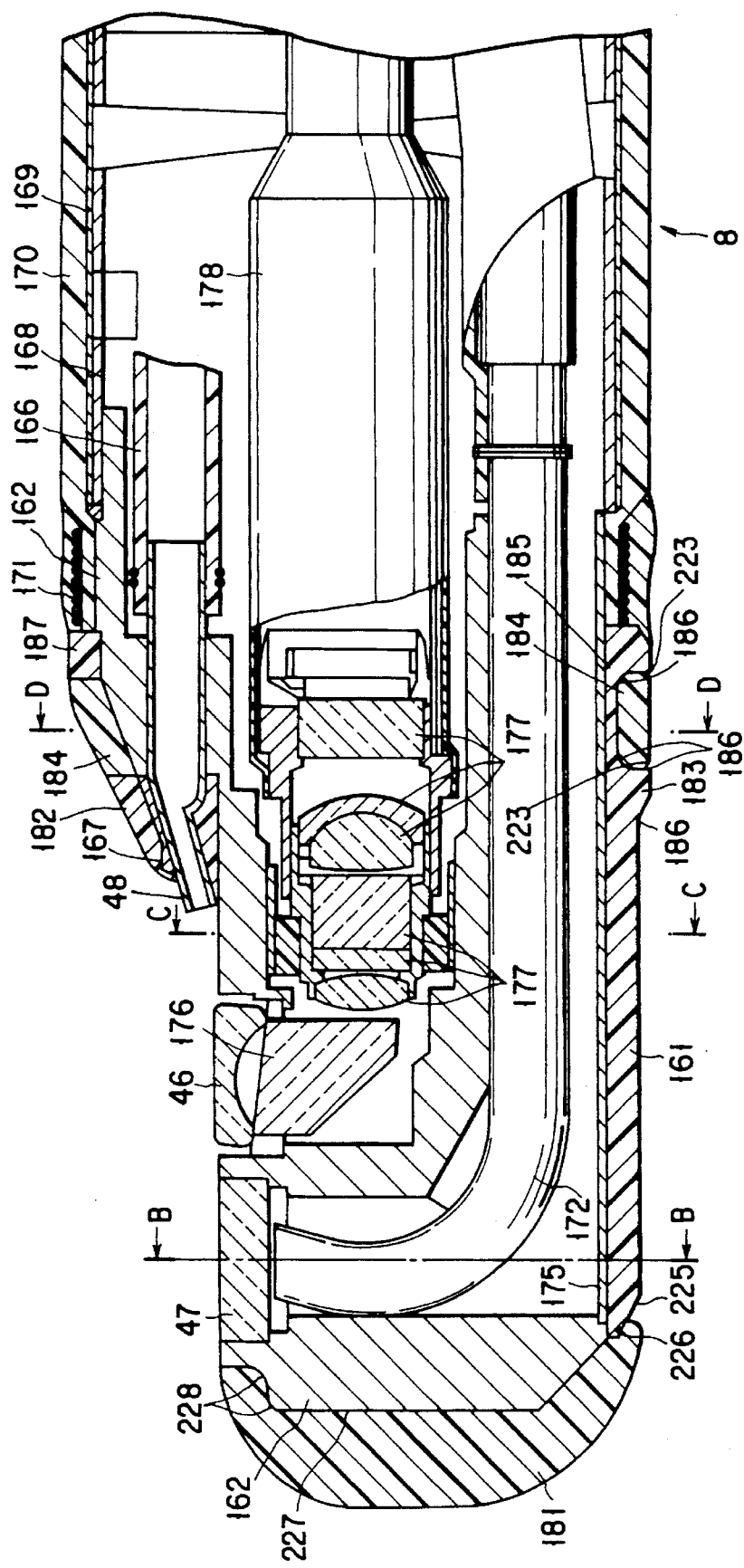
FIG. 28 is a sectional view taken along a line A—A in FIG. 27.
Figure 33:
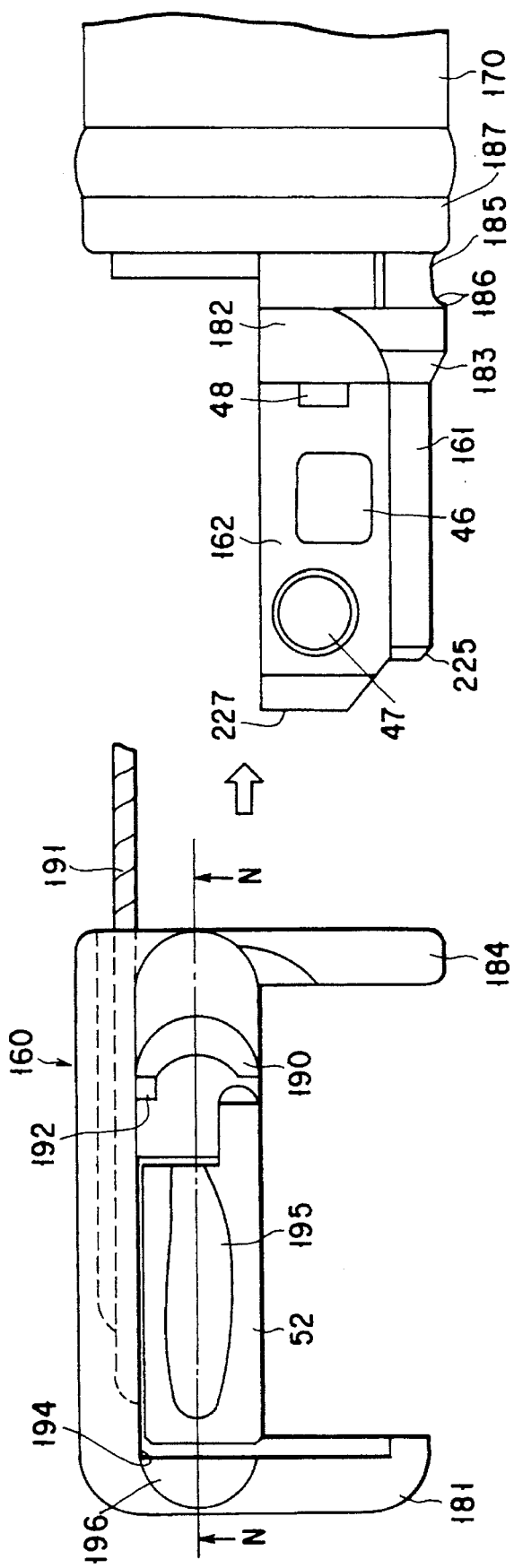
FIG. 33 is a plan view showing the distal end portion of an endoscope according to the fifteenth embodiment of the present invention, with a distal end cover portion being removed from the distal end body.

As shown in FIGS. 27 and 33, the distal end portion 9 is constituted by a distal end portion body 162, integrally formed with an insertion portion 6, and a distal end cover portion 160 detachably mounted on the distal end portion body 162. An illumination lens 47 and an objective lens 46 are arranged on the distal end side of the distal end portion body 162. The distal end of a nozzle 48 is fixed on the proximal end side of the objective lens 46 to oppose the objective lens 46. As shown in FIG. 28, the proximal end of the nozzle 48 is coupled to an air/water supply tube 166, and the proximal end side of the air/water supply tube 166 is connected to an air/water supply switching valve 22 attached to the air/water supply button of an operating portion 3. Water or air can be sprayed from the nozzle 48 by operating the air/water supply button. With this operation, filthy substances on the surface of the objective lens 46 can be removed.

The nozzle 48 is bonded/fixed to the distal end portion body 162, and the gap between the nozzle 48 and a nozzle cover portion 161a of a distal end cover portion 161 (to be described later) of the distal end portion body 162 is filled with an adhesive 167 to be sealed, thus preventing filthy substances from entering the distal end portion 9.

The distal end of a flexible tube portion 168 for controlling a bending operation of a flexible portion 8 is fixed to the proximal end of the distal end portion body 162 with a screw (not shown). The main body of the flexible portion 8 is constituted by the flexible tube portion 168 formed by pivotally connecting a plurality of bending pieces to each other. A net tube 169 and flexible rubber 170 are sequentially fitted on the flexible tube portion 168.

The distal end side of the flexible rubber 170 is fixed with a string 171, and an adhesive is coated on the fixed portion to increase the fixing strength. Note that in this adhesive coating operation, since an annular portion 161b of the distal end cover portion 161 serves as a wall at the distal end side of the bonded portion through the circumference of the distal end cover portion 161, no adhesive leaks out, and the workability is good.

Figure 29:
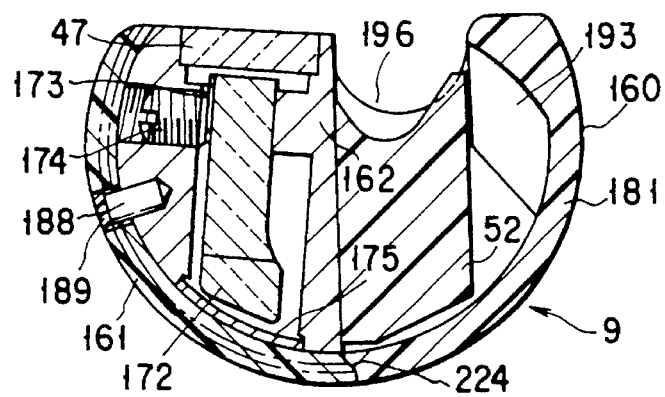
FIG. 29 is a sectional view taken along a line B—B in FIG. 27.

A substantially L-shaped light guide fiber 172 is arranged below the illumination lens 47 disposed in the distal end portion body 162. Since the light guide fiber 172 is simply formed by fixing a plurality of fibers with an adhesive, the distal end portion of the light guide fiber 172 is fixed with a screw 174 via a fixing plate 173 to increase the fixing strength, as shown in FIG. 29. With the presence of the fixing plate 173, the screw 174 is not directly turned into the light guide fiber 172 as glass fibers, and hence damage to the light guide fiber 172 in an assembly operation can be prevented. Note that an arcuated cover member 715 is fixed below the light guide fiber 172 with an adhesive.

Figure 30:
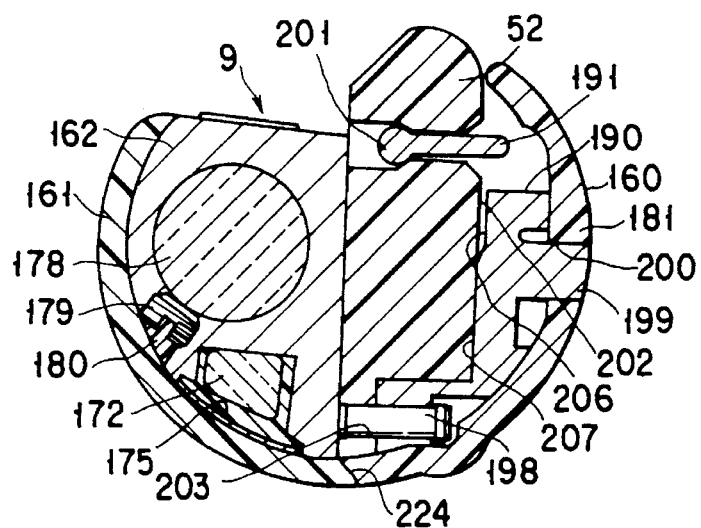
FIG. 30 is a sectional view taken along a line C—C in FIG. 27.

As shown in FIG. 28, in an objective lens system as the other optical system, a tie prism 176 is disposed below the objective lens 46, and an image pickup portion 78 having an objective lens group 177 is disposed along substantially the axis of the insertion portion 6. As shown in FIG. 30, the image pickup portion 178 is fixed with a screw 179. The screw 179 is bonded with an elastic silicone adhesive 180. A recess formed upon fastening of the screw 179 is also filled with the elastic adhesive 180.

As shown in FIG. 29, removal of the distal end cover portion 161 is prevented by a pin 188. The pin 188 is fixed to the distal end portion body 162 with an adhesive. A recess formed between the pin 188 and the distal end cover portion 161 is also filled with an adhesive 189. Note that when the distal end cover portion 161 and the distal end portion body 162 are to be assembled, an adhesive is coated on the inner surface of the distal end cover portion 161 and its outer surface, on which the distal end cover portion 161 is fitted, to prevent entrance of bubbles. In this adhesive coating operation, the adhesive is coated throughout the contact surfaces between the distal end cover portion 161 and the distal end portion body 162 while a leaking adhesive is wiped off, thus bringing the surfaces into tight contact with each other. With this operation, entrance of filthy substances into the distal end portion 9 is prevented.

As shown in FIGS. 29 and 30, the distal end side of the distal end cover portion 161 has a shape obtained by notching a circle by about ¾ the circumference. As shown in FIG. 28, the nozzle cover portion 161a covering the nozzle 48 is formed at the proximal end side of the distal end cover portion 161. In addition, a thick portion 183 is formed on a lower portion of the nozzle cover portion 161a to increase the hooking strength of the distal end cover portion 160, detachably mounted on the distal end portion body 162, with respect to a cover member 181. A thin portion 185, with which a C-shaped deformed portion 184 of the cover member 181 is engaged, is formed on the proximal end side of the thick portion 183.

An R-shaped chamfered portion 186 is formed on the outer surface of the thick portion 183 to prevent damage to a living body. With this R-shaped chamfered portion 186, filthy substances do not easily remain in the corner portions of the outer surface of the thick portion 183, thus improving the cleaning properties of this portion. Similarly, the R-shaped chamfered portion 186 is formed on a stepped portion between the thin portion 185 and the thick portion 183 to improve the cleaning properties of this portion.

In addition, a ring-like annular portion 187 is formed on the proximal end side of the thin portion 185. As described above, since this annular portion 187 serves as a wall when the flexible rubber 170 is fixed with the string 171, and an adhesive is coated on the resultant structure, the adhesive coating operation is facilitated.

The distal end cover portion 160 detachably mounted on the distal end portion body 162 will be described next.

As shown in FIG. 33, the distal end cover portion 160 is formed by disposing a forceps raising base 52 and an insulating block 190 in the cover member 181 as an outer frame. The distal end of an operation wire 191 used to raise the forceps raising base 52 is connected to the forceps raising base 52.

The distal end portion of the cover member 181 has a round shape, as shown in FIGS. 27 and 28, and a cross-section obtained by notching a circle by about ¾ the circumference, as shown in FIG. 29. An inclined flat surface portion 193 (see FIG. 32A) is formed on the distal end side of the cover member 181 to prevent a thin instrument from being caught between the cover member 181 and the forceps raising base 52 when the forceps raising base 52 is raised. An introduction flat surface 194 is formed on the distal end side of the inclined flat surface portion 193 to properly position the instrument in an introduction groove 195 of the forceps raising base 52. In addition, a guide portion 196 is formed to be continuous with the introduction flat surface 194. The guide portion 196 is located below the extended line of the distal end portion of the introduction groove 195 to prevent the instrument from abutting against the guide portion 196 and being caught thereby when the instrument is to be guided out of the distal end portion 9.

Since the cover member 181 is fixed with snap-fit (as will be described later), the member is made of a highly elastic plastic resin such as modified polyphenylene oxide or polyacetal. When the cover member 181 is to be molded by using such a plastic resin, if the cover member 181 is thick, the plastic resin does not properly flow into the mold, resulting in a bad outer appearance. In order to prevent such an inconvenience, a hollow portion 197 is formed on the inner surface of the cover member 181, located below the guide portion 196, to make the thickness of the cover member 181 uniform.

The distal end cover portion 161 is also made of a plastic resin such as polysulfone. Note that the distal end cover portion 161 need not be made of an elastic material because it is fixed. However, the cover member 181 must be made of a material having higher elasticity than that used for the distal end cover portion 161, because the cover member 181 is fixed with snap-fit. The surfaces of the distal end cover portion 161 and the distal end portion body 162 have different colors to allow an operator to recognize, at a glance, that the distal end cover portion 160 is detachable from the distal end portion body 162. With this arrangement, the operator who cleans the endoscope can quickly recognize that the distal end cover portion 160 is detachable, and can clean the endoscope by a cleaning method different from that used for a conventional endoscope. More specifically, the operator can set a good cleaning condition by removing the distal end cover portion 160, which is badly contaminated, from the distal end portion body 162, and can clean the distal end portion body 162 or the distal end cover portion 160 in this state. In this case, if the distal end cover portion 160 is used as a disposable member, a cleaning operation can be simplified and can be performed with high reliability. In order to make the operator recognize that the distal end cover portion 160 is detachable, the luster or touch of the surface of each member may be changed as well as the color of the surface.

As shown in FIG. 30, the forceps raising base 52 is paired with the operation wire 191 connected thereto to constitute a partial assembly, and the insulating block 190 is paired with the forceps raising base 52 to constitute another partial assembly upon fitting/bonding of a shaft 198. The overall assembly constituted by the forceps raising base 52, the operation wire 191, and the insulating block 190 is integrally fixed to the cover member 181 with a boss 199 formed on the insulating block 190. In this case, when the boss 199 is fitted in a hole 200 formed in the cover member 181, the overall assembly constituted by the forceps raising base 52, the operation wire 191, and the insulating block 190 is positioned. When the contact surfaces between the boss 199 and the cover member 181 are bonded to each other, the cover member 181 and the overall assembly are completely fixed. Note that the shaft 198 and the forceps raising base 52 are integrated by bonding their fitting portions 203 to each other. However, the fitting portions of the insulating block 190 and the shaft 198 are not bonded to each other, so that free pivotal movement of the forceps raising base 52 with respect to the insulating block 190 is ensured.

In addition, the shaft 198 and the forceps raising base 52 may be integrally formed, and the head portion of the shaft 198 may be caulked by heat while the shaft 198 is made to extend through the insulating block 190. With this arrangement, the forceps raising base 52 can be freely pivoted about the shaft 198 with respect to the insulating block 190. When caulking is to be performed by heat, the forceps raising base 52 is made of a plastic resin such as polysulfone, modified polyphenylene oxide, or polyacetal. When the shaft 198 and the forceps raising base 52 are to be formed separately, the forceps raising base 52 can be formed by using either the above plastic resin or a metal.

As shown in FIG. 30, the distal end portion of the operation wire 191 connected to the forceps raising base 52 is formed into a fixed portion 201 having a spherical shape and a diameter larger than the wire diameter by a plasma process. The operation wire 191 is bent to be brought into contact with a side surface 202 of the forceps raising base 52.

The insulating block 190 is made of an insulating plastic resin such as polysulfone or modified polyphenylene oxide so as not to be cut by a spark when, for example, the edge of a high-frequency knife blade as a high-frequency instrument is brought into contact with the insulating block 190. The insulating block 190 has an arcuated guide portion 205 (see FIG. 32A) for regulating travel of the operation wire 191 mounted on the forceps raising base 52 to a certain extent. As shown in FIG. 30, a side surface of the guide portion 205 is constituted by a noncontact surface 206 and a guide surface 207. Such an arrangement is employed for the following reason. As the contact area between the forceps raising base 52 and the insulating block 190 increases, the operator feels gritty when the forceps raising base 52 is pivoted. As a result, the operation touch deteriorates. Therefore, the operation touch is improved by minimizing the contact area.

A stopper 192 for regulating the upright position of the forceps raising base 52 extends from the insulating block 190 on the proximal end side of the noncontact surface 206. The stopper 192 extends to such an extent that it stops rotation of the side surface 202 of the forceps raising base 52 halfway. When the stopper 192 is to be formed by forming the insulating block 190 into a projection-like shape, since the insulating block 190 is made of a resin material, the stopper 192 can be formed into any shape within the range in which it can regulate rotation of the forceps raising base 52.

A curved surface 208 is provided for the insulating block 190 at a position closer to the proximal end than the stopper 192. The curved surface 208 serves to define an insertion path together with the forceps raising base 52 when the forceps raising base 52 is raised. A forceps channel 209 is formed on the proximal end side of the curved surface 208. The forceps channel 209 is constituted by a forceps pipe 210 bonded or soldered to the distal end portion body 162. The distal end portion body 162 is smoothly connected to the distal end portion of the forceps pipe 210 without any stepped portion by filling a stepped portion 215 with an adhesive. With this structure, filthy substances do not easily remain in the stepped portion 215. Therefore, filthy substances can be easily removed in a cleaning operation using a brush or fluid, facilitating the cleaning operation.

In addition, a forceps channel tube 211 is connected to the proximal end of the forceps pipe 210.

This forceps channel tube 211 is connected to a suction switching valve 23 (see FIG. 1) of the suction button 21. The forceps channel tube 211 is branched at a forceps opening portion 10 so that an instrument can be inserted/removed in/from the forceps channel 209.

An opening portion 212 of the forceps channel 209, defined by the insulating block 190, gradually changes its shape from a circle to an elliptical shape (indicated by the chain double-dashed lines in FIG. 32A), when viewed from the boundary portion as the stepped portion 215 in the direction of the distal end side. Such a change in cross-section occurs as the curved surface 208 of the insulating block 190 gradually shifts to the distal end side.

Figure 31:
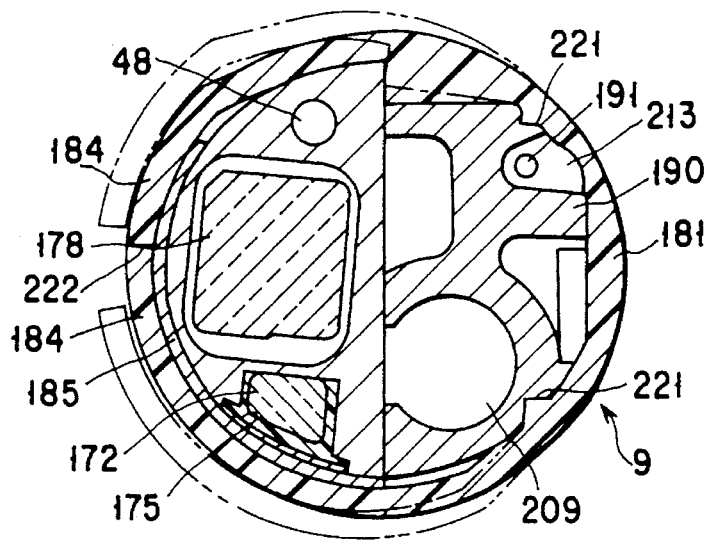
FIG. 31 is a sectional view taken along a line D—D in FIG. 27.

As shown in FIG. 31, the operation wire 191 paired with the forceps raising base 52 extends through a first forceps raising pipe 214 shown in FIG. 32A via a wire path portion 213 of the insulating block 190.

Similar to the forceps pipe 210, the connecting portion between the first forceps raising pipe 214 and the distal end portion body 162 is smoothly connected therebetween without forming any stepped portion by filling a stepped portion 216 with an adhesive. With this structure, since no filth substances easily remain in the stepped portion 216, a cleaning operation is facilitated.

A forceps raising tube 217 made of ethylene tetrafluoride is bonded to the proximal end of the first forceps raising pipe 214, and a rectangular forceps raising coil 218 is fitted on the forceps raising tube 217 to prevent expansion of the forceps raising tube 217. The distal end portion of the forceps raising coil 218 is bonded/fixed to the first forceps raising pipe 214. The proximal end portion of the forceps raising tube 217 is fused, in a thermoforming condition, to the distal end portion of a second forceps raising pipe (not shown). In addition, the proximal end of the forceps raising coil 218 is soldered to the second forceps raising pipe.

As shown in FIGS. 31 and 33, the proximal end portion of the cover member 181 of the distal end cover portion 160 has a C-shaped deformed portion 184. As shown in FIG. 31, the deformed portion 184 defines a boundary together with two projections 221 engaged with the insulating block 190, and a portion 182 (on the opposite side to a notched portion 99) between the two projections 221 is fixed to the insulating block 190 with an adhesive, as described above. The projections 221 serve as adhesive well portions constituting a breakwater for preventing the adhesive from flowing to the deformed portion 184 side.

When the distal end cover portion 160 is mounted on the distal end portion body 162, the C-shaped deformed portion 184 is deformed as indicated by the chain double-dashed lines in FIG. 31 as it crosses over the thick portion 183 of the distal end cover portion 161. Thereafter, the deformed portion 184 is engaged with the thin portion 185 of the distal end cover portion 161.

As shown in FIG. 28, an R-shaped chamfered portion 223 is formed on the outer surface of the C-shaped deformed portion 184 to prevent the corner portions of the outer surface of the deformed portion 184 from damaging a living body. In addition, a notched portion 222 (see FIG. 31) of the deformed portion 184 is located below a plane including an objective lens 46 and an illumination lens 47. With this structure, since the distal end cover is located below the deformed portion 184, the deformed portion 184 can be easily deformed to facilitate a mounting operation of the distal end cover portion 160 with respect to the distal end portion body 162.

As shown in FIGS. 29 and 30, a taper portion 224 is provided at the boundary portion between the cover member 181 and the distal end cover portion 161. The taper portion 224 serves as a guide when the distal end cover portion 160 is engaged with the distal end portion body 162. As is apparent, since the taper portion 224 has an inclined surface, the boundary portion between the cover member 181 and the distal end cover portion 161, which can serve as a path through which a high-frequency current leaks, can be set to be larger than in a case wherein the portion 224 has a vertical surface. As a result, leakage of a high-frequency current through the taper portion 224 can be prevented. Hence, this structure is advantageous in terms of safety.

As shown in FIG. 28, on the distal end side, a taper portion 225 of the distal end cover portion 161 and a taper portion 226 of the cover member 181 are stacked on each other to reduce the gap in the engaging portion between the cover member 181 and the distal end cover portion 161. The fixing strength of the cover member 181 in a direction perpendicular to the drawing surface of FIG. 27 is increased by engaging a projection 227 on the distal end of the distal end portion body 162 with the cover member 181. Furthermore, an R-shaped chamfered portion 228 is formed on a corner portion of the projection 227 to prevent filthy substances from easily remaining in the corner portion, thereby facilitating a cleaning operation.

As shown in FIG. 33, when the distal end cover portion 160 is moved along the direction indicated by the arrows to be mounted on the distal end portion body 162, the state shown in FIG. 27 is obtained. In addition, as shown in FIG. 33, since the surface, of the distal end portion body 162, which corresponds to the forceps raising base 52 is flat, the cleaning properties are very good.

As described above, in the endoscope of this embodiment, since the stopper 192 for regulating a raising operation of the forceps raising base 52 is provided on the insulating block 190 of the detachable distal end cover portion 160, when the distal end cover portion 160 is removed from the distal end portion body 162, the distal end portion body 162 takes a simple shape, thus providing good cleaning properties. In addition, if the detachable distal end cover portion 160 is used as a disposable member, the time and labor for a cleaning operation can be greatly reduced.

If the size of the forceps channel 209 is common to different types of devices, the distal end cover portion 160 as an assembly integrally incorporating the cover member 181, the forceps raising base 52, the insulating block 190, the pin 188, and the operation wire 191 can be commonly used for the different types of devices. Therefore, there is no possibility of erroneous assembly.

Since the surfaces of the detachable distal end cover portion 160 and the distal end portion body 162 integrated with the insertion portion have different colors, an operator who performs a cleaning operation can identify these members at a glance. For this reason, the operator can clean the endoscope by a cleaning method different from that used for a conventional endoscope. More specifically, the operator can set a good cleaning condition by removing the distal end cover portion 160, which is badly contaminated, from the distal end portion body 162, and can clean the distal end portion body 162 or the distal end cover portion 160 in this state. Therefore, a loss of cleaning time caused by a conventional cleaning method can be prevented.

Furthermore, since the stopper 192 is arranged on the detachable distal end cover portion 160 side, the precision of the stopper 192 is determined by only a variation in components in an assembled state. That is, the precision is not influenced by a variation in position of the distal end cover portion 160 relative to the distal end portion body 162 upon a mounting operation. Therefore, the precision can be improved.

FIGS. 32A to 32C show the fourteenth embodiment. In this embodiment, a stopper 192 is arranged on a forceps raising base 52. Since the fourteenth embodiment is basically the same as the thirteenth embodiment, only the difference therebetween will be described below.

As shown in FIG. 32A, the stopper 192 is arranged on the forceps raising base 52. In a raising operation of the forceps raising base 52, the stopper 192 is brought into contact with a flat surface 231 of an insulating block 190 integrally formed with a cover member 181 by bonding so as to regulate the operation of the forceps raising base 52.

when the detachable cover member 181 is mounted on a distal end portion body 162, and the proximal end portion of an operation wire 191 is coupled to a connecting portion 201, if the operation wire 191 is pulled too hard to eliminate a slack, the forceps raising base 52 may be mounted in the distal end portion while the forceps raising base 52 is not fully inverted, as shown in FIG. 32A. Therefore, this embodiment includes a temporary lock member 232 for locking the forceps raising base 52 to a predetermined position.

The temporary lock member 232 has a flange portion 233 having a diameter larger than that of a distal end portion 9. This structure is designed to prevent erroneous use of the endoscope with the temporary lock member 232 being mounted therein. That is, the structure is designed to improve the visual recognizability so as to allow the operator to quickly recognize an abnormality. Therefore, the structure may have a color different from that of the remaining components to be identified.

In addition, a regulating pin 234 for regulating the position of the forceps raising base 52 extends from the temporary lock member 232. A recess 235 is formed midway along the regulating pin 234 at a position above a hole 236 in the cover member 181. Since the temporary lock member 232 is made of a plastic resin, the recess 235 is not formed throughout the circumference of the temporary lock member 232 but is partly formed, as shown in FIG. 32B.

A plurality of notched portions 237 (see FIG. 32C) are formed in the hole 236 of the cover member 181 so that the hole 236 can be easily deformed when the recess 235 of the regulating pin 234 passes therethrough.

In addition, a fitting hole 238 to be fitted on the regulating pin 234 is formed in the forceps raising base 52. When the fitting hole 238 and the regulating pin 234 are fitted together, the forceps raising base 52 is fixed at an inverting position.

Similar to the fifteenth embodiment shown in FIG. 33, the cover member 181 is mounted on the distal end portion body 162 while the temporary lock member 232 is mounted. The operation wire 191 is then connected with the connecting portion 201 while a raising base operating lever 19 is operated to set the forceps raising base 52 in an inverted state. Thereafter, the temporary lock member 232 is pulled out.

As described above, in this embodiment, with the temporary lock member 232, the distal end cover portion 160 can be mounted on the distal end portion body 162 without giving any consideration to the posture of the forceps raising base 52. Therefore, a preparation for the endoscope can be easily performed.

FIG. 33 shows the fifteenth embodiment of the present invention. In this embodiment, a rectangular stopper 192 is formed on a cover member 181. Other arrangements are the same as those in the thirteenth embodiment.

In this arrangement, since the stopper 192 is formed on the cover member 181, the distance from a shaft 198 of a forceps raising base 52 to the stopper 192 increases. Therefore, even if the position of the stopper 192 varies within a part tolerance, since the distance from the stopper 192 to the shaft 198, i.e., the radius of the arc, is large, the forceps raising base 52 is brought into contact with the stopper 192 with a small variation in angle. That is, the lock position precision can be improved.

As described above, according to the thirteenth to fifteenth embodiments of the endoscope distal end portion, since the stopper for regulating a raising operation of the instrument raising base is formed on the detachable distal end cover portion, when the distal end cover portion is removed from the distal end portion of the endoscope, the distal end portion of the endoscope has no complicated three-dimensional shape owing to the stopper. Therefore, a cleaning operation can be performed upon removal of the detachable distal end cover portion. In addition, since the distal end portion of the endoscope has only a small number of recesses/projections, a cleaning operation is facilitated.

FIGS. 34 to 56 show an endoscope according to the sixteenth embodiment of the present invention.

FIGS. 34 to 38 show the details of a guide pipe for guiding a forceps raising wire 26.

As shown in FIG. 34, a frame 240 disposed in an operating portion 1 extends into the forceps raising wire opening portion 24, and a grip portion 2, a mouthpiece fixing cover 241, and a forceps wire opening portion body 242 are clamped and fixed between a stopper ring 244 threadably engaged with a threaded portion 243 and an operating portion body 99, thus constituting an insertion portion 3. In addition, as shown in FIG. 35, an insertion tube 246 is fixed by clamping a projection 251 extending into the frame 240 between a flange portion 249 of a connecting mouthpiece 248 threadably engaged with a proximal end mouthpiece 247 fixed to the operating portion 1 with an adhesive and a fixing ring 250 threadably engaged with the proximal end mouthpiece 247.

Note that the proximal end mouthpiece 247 and the connecting mouthpiece 248 are fixed by fitting a fixing pin 253 in a hole 252 formed in the proximal end mouthpiece 247 and a groove 262 formed in the connecting mouthpiece 248. A breakage preventing member 254 for protecting the insertion tube 246 is fixed by threadably engaging the threaded portion 243 of the frame 240 with a threaded portion 256 formed on the inner surface of a breakage preventing mouthpiece 255 insert-molded in the breakage preventing member 254. A breakage preventing cover 257 is also mounted on the outer surface of the breakage preventing member 254 to ensure watertightness between the breakage preventing member 254 and the insertion tube 246. A portion, of the breakage preventing cover 257, located on the insertion portion 3 side is bonded to the insertion tube 246 to ensure watertightness. An O-ring A 258, a profile packing 259, an O-ring B 260, and an O-ring C 261 are respectively used to ensure watertightness between the grip portion 2 and the mouthpiece fixing cover 241, the forceps wire opening portion body 242 and the frame 240, and the frame 240 and the proximal end mouthpiece 247.

Figure 36:
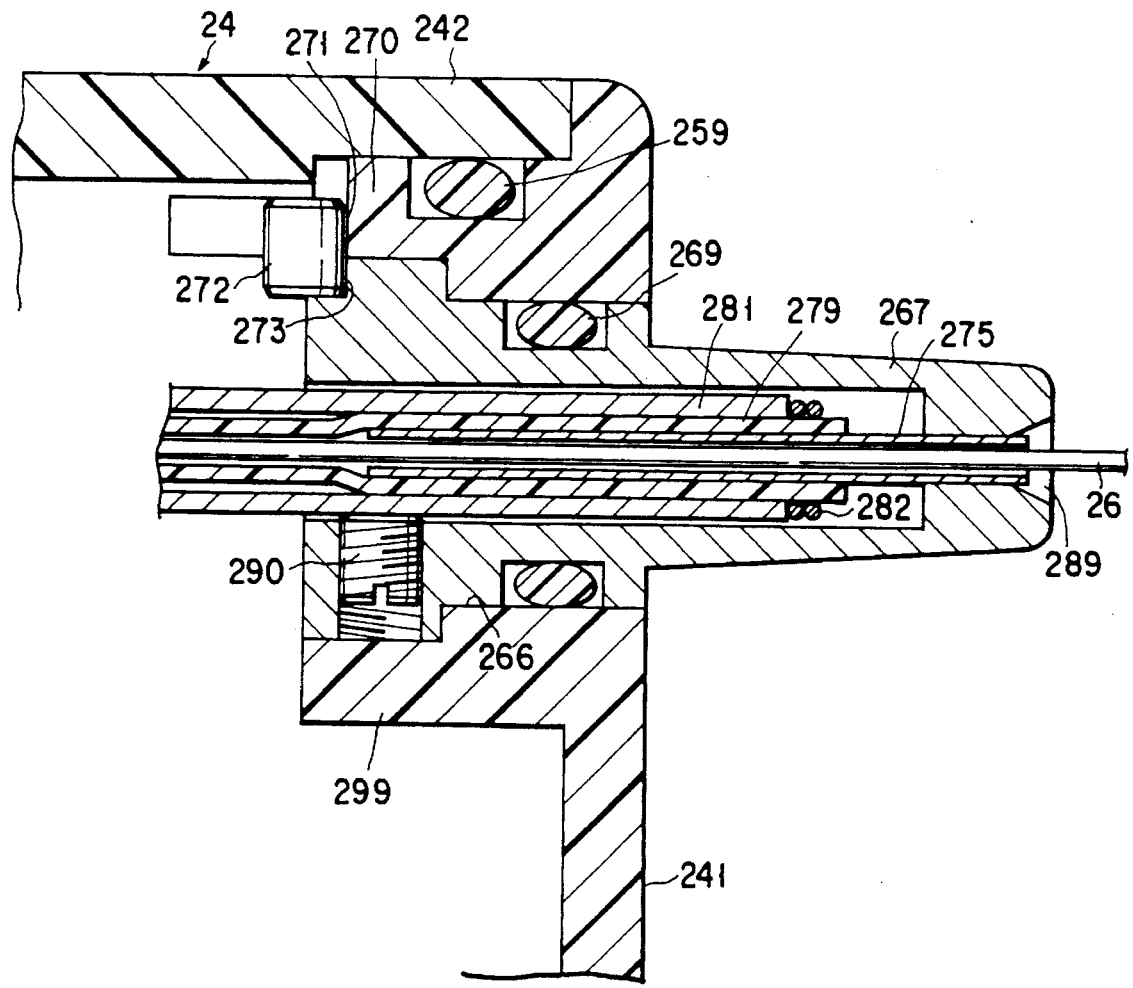
FIG. 36 is a sectional view showing the details of a portion K in FIG. 34.

As shown in FIGS. 34, 36, and 37, the mouthpiece fixing cover 241 is positioned by fitting a groove portion 265, formed by a projection 264 extending from the mouthpiece fixing cover 241, on a fixing member 263 fixed to the frame 240 with a screw. Since the forceps wire opening portion body 242 is fitted in the profile portion of the mouthpiece fixing cover 241 in substantially the same form, the forceps wire opening portion body 242 is also positioned.

As shown in FIGS. 34 and 36, a forceps raising guide tube mouthpiece 267 is seal-fixed to an opening portion 266 of the mouthpiece fixing cover 241 via an O-ring 269 disposed in a recess groove 268 formed in the outer surface of the forceps raising guide tube mouthpiece 267. The forceps raising guide tube mouthpiece 267 is positioned by fitting a pin 272 in a hole 271 of a projection 270 of the mouthpiece fixing cover 241, and in a notched portion 273 of the forceps raising guide tube mouthpiece 267. A proximal end pipe 275 of a forceps raising guide tube 274, in which the forceps raising wire 26 is inserted, is bonded/fixed to the forceps raising guide tube mouthpiece 267, and the other end of the forceps raising guide tube 274 is fastened with a string to a guide tube 77 having a distal end portion 33 mounted with a distal end forceps raising guide tube 276, and is bonded/fixed thereto. The resultant structure is disposed in the insertion portion 3.

Figure 38:
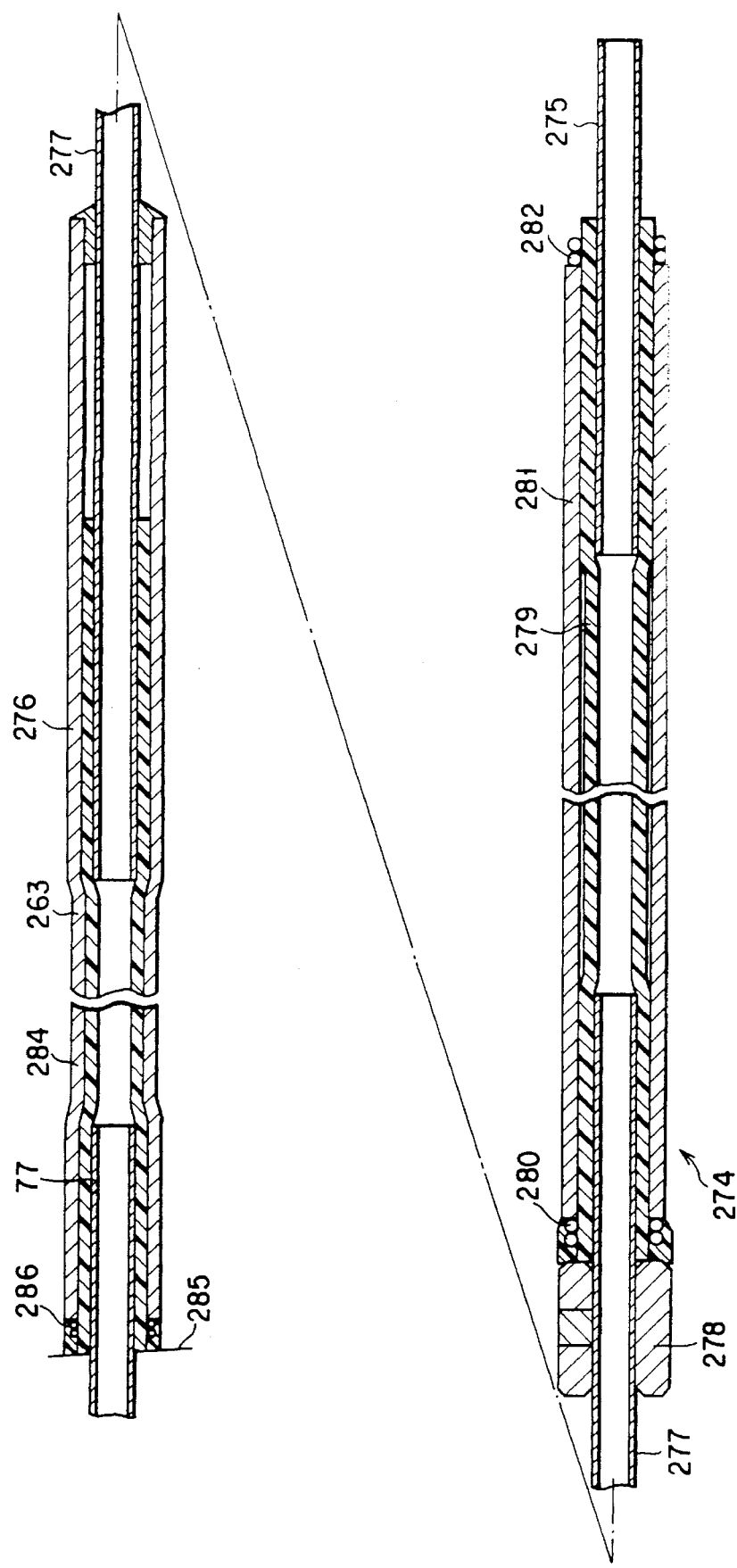
FIG. 38 is a sectional view showing the details of the forceps raising guide tube of the endoscope in FIG. 1.

FIG. 38 shows the arrangement of the forceps raising guide tube 274. In the forceps raising guide tube 274, one end of the distal end forceps raising guide tube 276 connected to a distal end forceps raising guide pipe 277 is fixed to the guide tube 77 connected to a distal end portion body 33 with a tying portion 286 while one end of the distal end forceps raising guide tube 276 is in contact with a distal end portion body end face 285. A distal end coil pipe 284 is fitted on the distal end forceps raising guide tube 276 while the distal end coil pipe 284 is in contact with the tying portion 286. An end, of the distal end coil pipe 284, located on the operating portion 1 side is soldered to the distal end forceps raising guide pipe 277. A tube stop pipe 278 is soldered to the other end of the distal end forceps raising guide pipe 277 while the other end thereof protrudes. A proximal end guide tube 279 for coupling the proximal end pipe 275 to the distal end forceps raising guide pipe 277 is fitted on the protruding end of the distal end forceps raising guide pipe 277 and is abutted against the tube stop pipe 278. A tying portion 280 is further arranged at the tube stop pipe 278, and a proximal end coil pipe 281 as an outer sheath of the proximal end guide tube 279 is abutted against the tying portion 280. The other end of the proximal end coil pipe 281 is fastened with a tying portion 282.

As shown in FIGS. 34 and 37, an end, of the forceps raising guide tube 274, located on the operating portion 1 side is housed in a guide path groove 292 formed in a guide plate 289 and is held by a guide plate cover 293 (see FIG. 37) having a fitting projection 295 corresponding to a fitting hole 294 of the guide plate 289. This end of the forceps raising guide tube 274 is further pressed by a press portion 300 having a rib-like introduction portion 301 arranged in the forceps wire opening portion body 242. A mouthpiece bearing portion 299 formed on the mouthpiece fixing cover 241 presses an upper bearing portion 297 arranged in the guide plate 289. The guide plate 289 and a lower bearing portion 298 of the guide plate cover 293 are disposed on the outer surface of the frame 240.

Figures 39A, 39B:
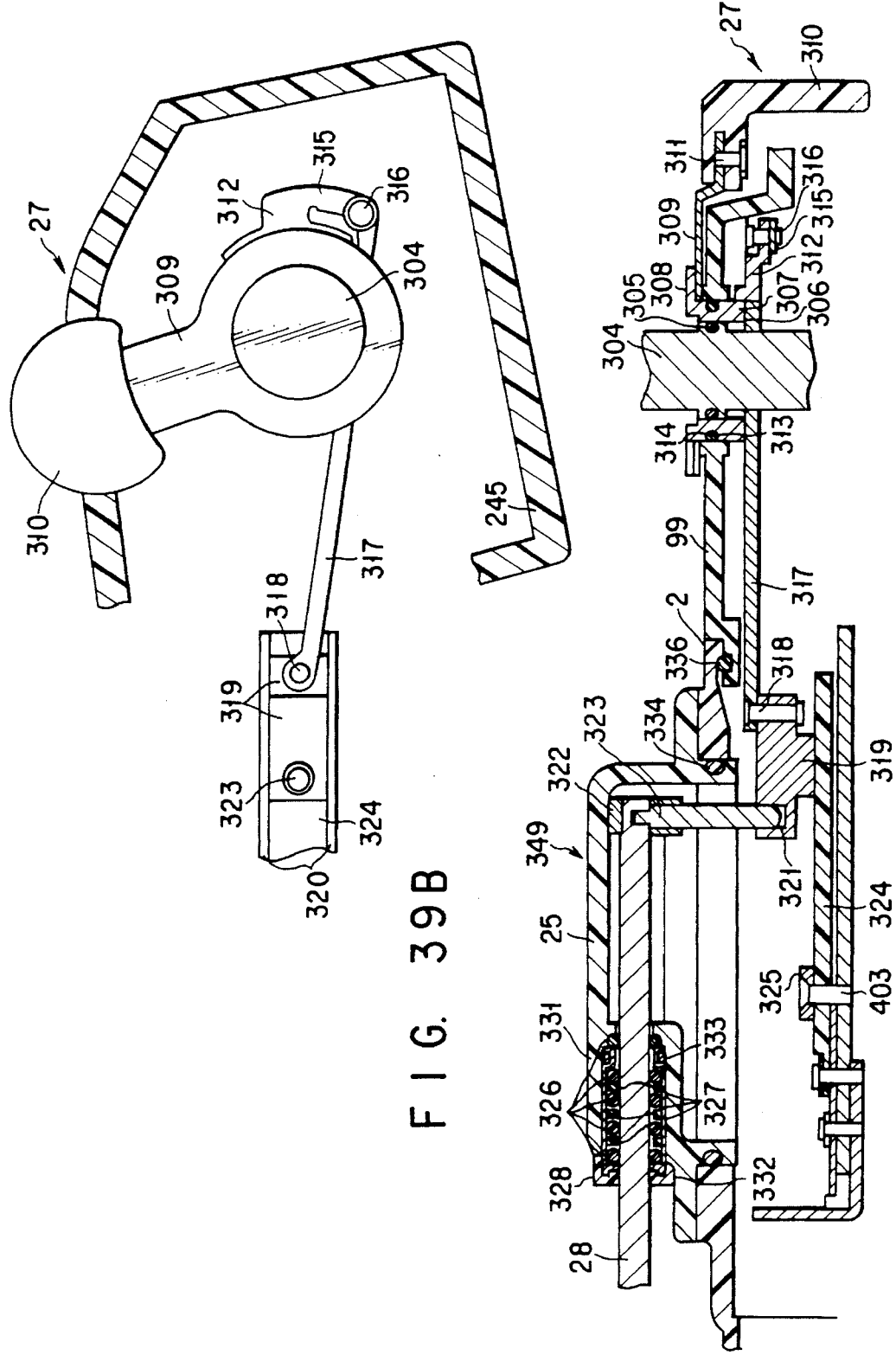
FIGS. 39A and 39B show the details of the opening portion of the driving shaft of the endoscope in FIG. 1.

FIGS. 39A and 39B show the details of portions around the driving shaft opening portion 25 and the forceps raising lever 27 in FIG. 1. FIG. 39A is a longitudinal sectional view. FIG. 39B is a plan view. The forceps raising lever 27 is rotatably mounted on a support shaft 304 common to the angle knob 7 extending into the operating portion 1 via a bearing 307 which is contact with an O-ring 306 arranged in a recess groove 305 of the support shaft 304. The bearing 307 has a press flange 308 at one end, and a threaded portion (not shown) formed in the outer surface of the other end. The press flange 308 serves to press the forceps raising lever 27. The bearing 307 is threadably engaged with a coupling member 309 to be fixed thereto. The forceps raising lever 27 is integrally fixed to the press flange 308 by means of an adhesive or the like. A knob portion 310, on which a finger of the operator is actually placed, is fixed to an arm portion 312 with a screw 311. The bearing 307 has a recess groove 313 formed in its outer surface. An O-ring 314 is fitted in the recess groove 313. The bearing 307 is rotatably mounted on the operating portion body 99 in a watertight state.

One end of the coupling member 309, which is located in the operating portion body 99 and has a hook portion 315, is rotatably connected to a link arm 317 via a pin 316. The other end of the link arm 317 is rotatably mounted on a base seat 319 via a pin 318. A guide wall 320 having a U-shaped cross-section and fixed in the operating portion body 99 is disposed on the two sides of the base seat 319. An engaging hole 321 is formed in a portion, of the base seat 319, located on the insertion portion 3 side. A driving coupling shaft 323 threadably engaged/fixed to a coupling fixing member 322 mounted on a driving shaft 28 is inserted in the engaging hole 321. In this case, a clearance for allowing the driving coupling shaft 323 to move in the axial direction is set between the driving coupling shaft 323 and the engaging hole 321 to prevent the upper surface of the coupling fixing member 322 connected to the driving coupling shaft 323 from interfering with the driving shaft opening portion 25 owing to variations in size and assembly of the respective components. With this structure, since the base seat 319 is reciprocated when the forceps raising lever 27 is rotated, this reciprocal movement is transmitted to a forceps raising base 52 of the distal end portion 9 via the driving coupling shaft 323, the driving shaft 28, and the forceps raising wire 26, thereby raising/inverting the forceps raising base 52.

This reciprocal stroke is determined by a stopper projection 49 formed on the connecting unit body 33 when the forceps raising base 52 is to be raised, and is determined by a stopper plate 325 mounted on a guide plate 324, along which the base seat 319 is reciprocated, when the forceps raising base 52 is to be inverted. In a conventional endoscope, the dimensions of the stopper plate 325 are set independently for each product to conform to differences in stroke between products. In this embodiment, since the above structure conforms to a change in stroke, the dimensions of the stopper plate 325 are set to be common to all products. As shown in FIG. 40, the stopper plate 325 may be arranged such that a stroke adjusting plate 348 is fixed to the base seat 319 with a screw.

Figure 41:
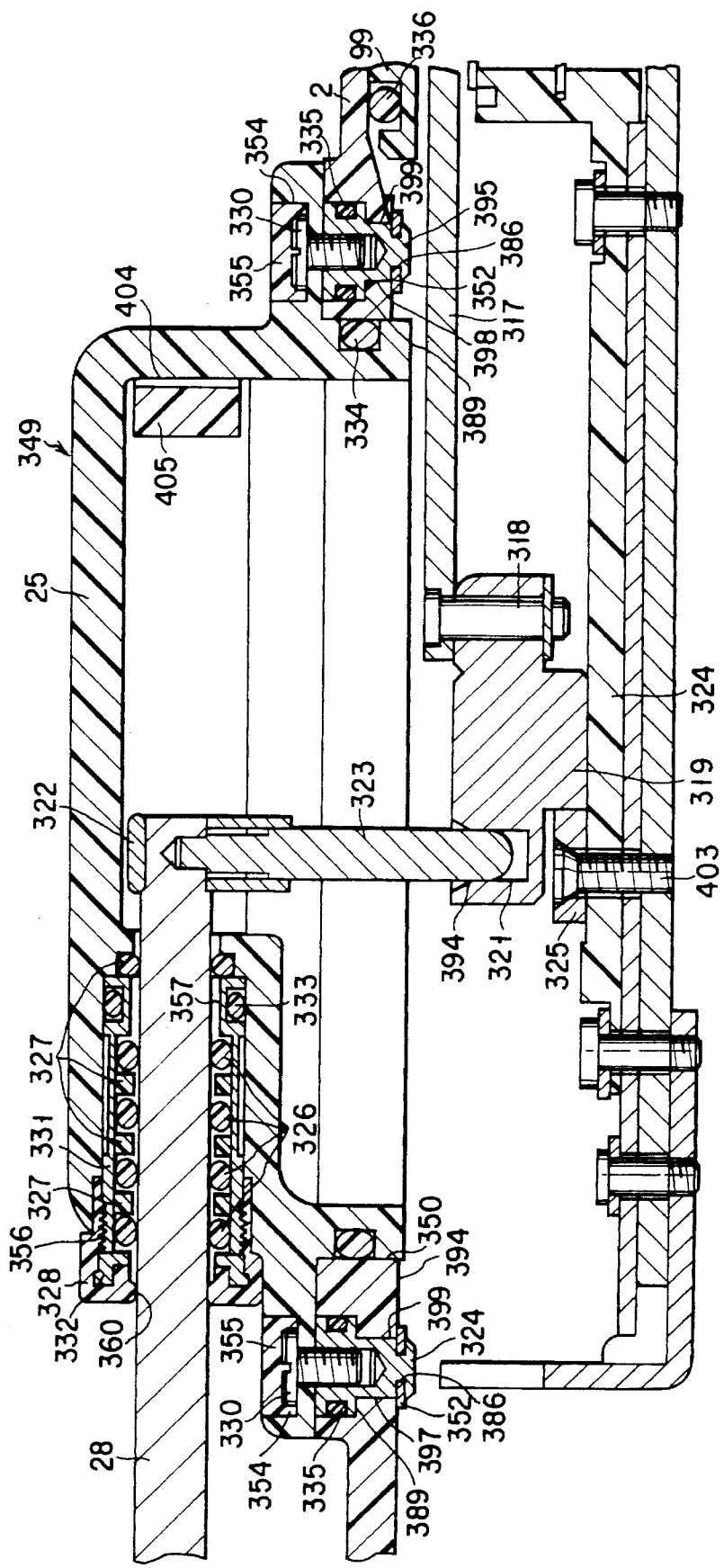
FIG. 41 is an enlarged view of a portion around the opening portion of the driving shaft of the endoscope in FIG. 1.

As shown in FIG. 41, the driving coupling shaft 323 of a driving shaft unit 349 having the driving coupling shaft 323, the driving shaft 28, the driving shaft opening portion 25, and the like is inserted in the engaging hole 321 of the base seat 319 exposed to a opening portion 350 of the grip portion 2. A taper portion 394 is formed in the engaging hole 321 to allow the driving coupling shaft 323 to be easily inserted therein. A profile packing 334 fitted in a recess groove portion 351 of the driving shaft opening portion 25 provides watertightness between the driving shaft unit 349 and the grip portion 2. The driving shaft unit 349 is fixed to the grip portion 2 by threadably engaging screws 330 with first and second screw bearings 329 and 395 fixed to the grip portion 2 with a C-ring 352 so as to sandwich the driving shaft opening portion 25.

Since an upper rapping taper portion 396 is formed in the grip portion 2, the first and second screw bearings 329 and 395 are not identically formed, while an Oring A is commonly used, there is a possibility that the first and second screw bearings 329 and 395 may be erroneously fitted. In order to prevent this erroneous fitting, as shown in FIGS. 42A and 42B, a width L of a rectangular portion A 397 is set to be larger than a width l of a rectangular portion B 398 of the second screw bearing 395 to prevent the first screw bearing 329 from being fitted in a rectangular groove B 399 in which the second screw bearing 395 is fitted. FIG. 42A is a schematic sectional view showing a state before the screw bearings are fitted. FIG. 42B is a sectional view showing a state wherein the screw bearings are fitted. Assume that the second screw bearing 395 is fitted in a rectangular groove A 400 for the first screw bearing 329. In this case, a depth d of the rectangular portion B 398 of the second screw bearing 395 is set to be smaller than a depth D of the rectangular portion A 397 for the first screw bearing 329 so as to prevent the removal preventing C-ring 352 from being fitted. As described above, erroneous fitting of the first and second screw bearings 329 and 395 is prevented by making them have different shapes.

Each fitting hole 354, of the driving shaft opening portion 25, in which the screw 330 is fitted is filled with an insulating filler 355. The four fitting holes 354 formed in the driving shaft opening portion 25 are located on the slidable portion side of the driving shaft 28 to prevent interference with the movement of the driving coupling shaft 323 and make the grip portion 2 compact. Note that an O-ring A 335 and an O-ring B 336 are respectively used to provide watertightness between the first and second screw bearings 329 and 395 and the grip portion 2, and the grip portion 2 and the operating portion body 99. As a simple method of fixing the first screw bearing 329, the following method may be used. As shown in FIGS. 43A and 43B, a removal preventing projection 402 is formed on the bottom portion of the first screw bearing 329. The removal preventing projection 402 is inserted in a fitting hole 385 of the grip portion 2 which has a shape substantially the same as that of the removal preventing projection 402, and is then rotated. With this operation, the grip portion 2 is received by the removal preventing projection 402 against the elastic force of the O-ring A 335 in the direction in which the first screw bearing 329 is removed.

The assembly procedure and arrangement of the driving shaft unit 349 will be described next. The driving shaft unit 349 has a driving shaft bearing unit 353 for holding the driving shaft 28. The assembly procedure and arrangement of the driving shaft bearing unit 353 will be described first. As shown in FIG. 44, O-rings 326 and driving shaft bearings 327 made of a resin so as not to damage the driving shaft 28 are alternately inserted in an O-ring bearing metal member 331. Note that each driving shaft bearing 327 may have an L shape to equalize the gaps between the O-rings 326, as shown in FIG. 45.

Subsequently, as shown in FIG. 44, an insert metal member 332 as an insert component of a seal portion 328 is threadably engaged with the O-ring bearing metal member 331 and bonded/fixed thereto. The insert metal member 332 has an O-ring bearing portion 356 for bearing the O-ring 326 in the sliding direction of the driving shaft 28. Finally, an O-ring 333 is fitted in a recess groove 357 formed on the outer surface of the O-ring bearing metal member 331, thus completing the driving shaft bearing unit 353. The same driving shaft bearing 327 as that used for the driving shaft bearing unit 353 is fitted to a bearing portion 358, and the driving shaft bearing unit 353 having an adhesive filling an adhesive groove 359 formed in the outer surface of the O-ring bearing metal member 331 is inserted in the driving shaft opening portion 25 and bonded/fixed thereto. Even if this adhesive peels off, the watertight state between the driving shaft opening portion 25 and the driving shaft bearing unit 353 is maintained by the 0ring 333. A portion, of the seal portion 328, located on the driving shaft opening portion 25 side is formed into substantially the same shape as the outer surface of the driving shaft opening portion 25 to prevent the insert metal member 332 from being exposed and also prevent a finger of the operator from touching the insert metal member 332.

The driving shaft 28 is inserted in the driving shaft bearing unit 353. Since the inner diameter of the driving shaft bearing 327 is smaller than that of a portion, of the O-ring bearing metal member 331, located on the recess groove 357 side, there is no possibility that the driving shaft 28 is damaged by the O-ring bearing metal member 331. A rubber lining or fluororesin coating may be formed on the driving shaft 28 to prevent damage to the driving shaft 28, insulate it, and protect the O-rings 326. The seal portion 328 is made of a rubber material having a high tear strength because it is exposed on the outer surface. In addition, such a material is used to facilitate supporting of the driving shaft 28. Furthermore, in order to maintain the watertight state between the seal portion 328 and the driving shaft 28, a hemispherical watertight portion 360 is formed on the inner surface of the seal portion 328.

Figure 46:
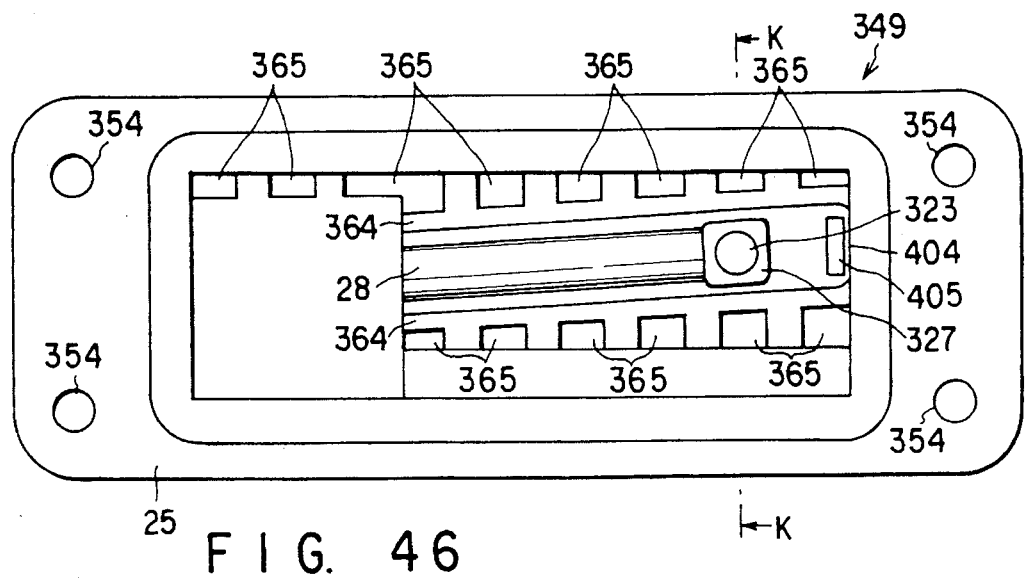
FIG. 46 is a view for explaining the driving shaft bearing unit in FIG. 44.
Figure 47:
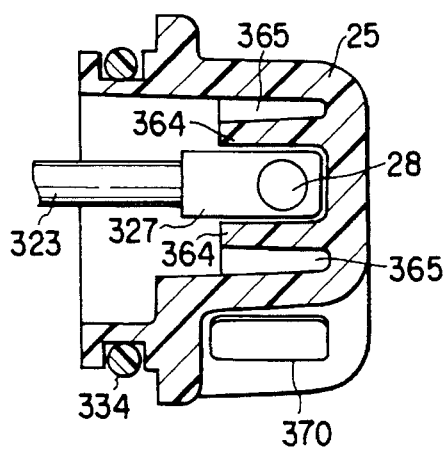
FIG. 47 is a sectional view taken along a line K—K in FIG. 46.

As shown in FIGS. 46 and 47, the coupling fixing member 322 is inserted in the driving shaft 28 while the driving shaft 28 is checked, and the driving coupling shaft 323 is threadably engaged with the coupling fixing member 322, from the lower surface of the driving shaft opening portion 25, and is fixed thereto. The driving shaft 28 and the driving coupling shaft 323 may be fixed to each other by another method shown in FIGS. 48 and 49.

Figure 48:
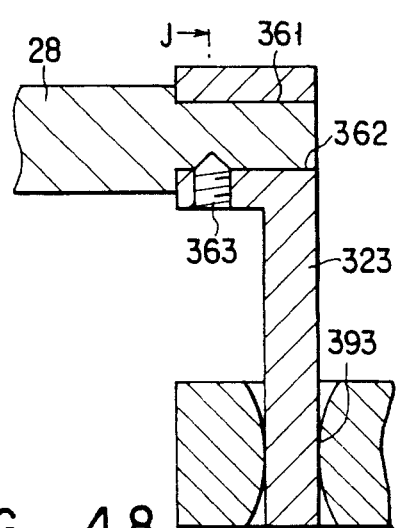
FIG. 48 is a view for explaining the fixing structure of the driving coupling rod of the endoscope in FIG. 1.
Figure 49:
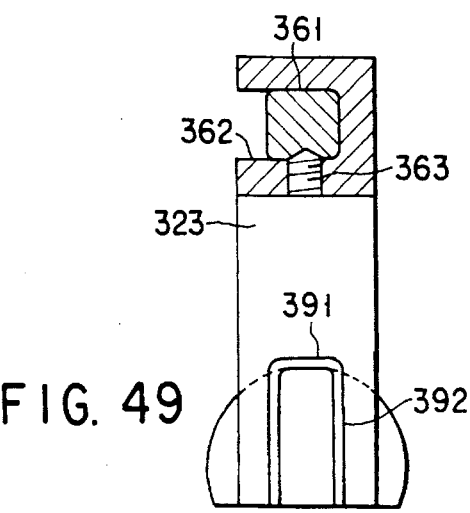
FIG. 49 is a sectional view taken along a line J—J in FIG. 48.
Figure 50:
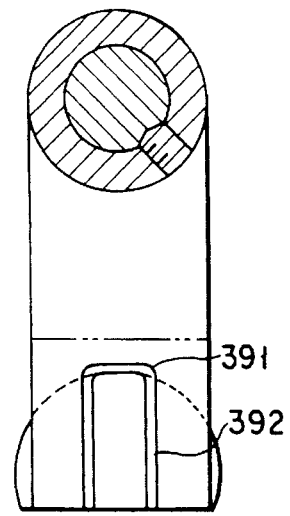
FIG. 50 is a view for explaining a modification of the fixing structure of the driving coupling rod.

FIGS. 48 and 49 will be described. The driving shaft 28 has a rectangular portion 361 for preventing rotation. A fitting groove 362 in which the rectangular portion 361 is fitted is formed in the driving coupling shaft 323. The fitting groove 362 is formed as a groove to have a rectangular shape in consideration of a process. The driving shaft 28 and the driving coupling shaft 323 are fixed to each other by inserting the rectangular portion 361 in the fitting groove 362 and using an NU screw 363. In order to facilitate a screw fastening operation, a screw hole may be formed in an oblique direction instead of a vertical direction as long as it is located on the lower surface side of the driving shaft opening portion 25, as shown in FIG. 50.

As shown in FIG. 49, in order to fix the driving coupling shaft 323 to the base seat 319 further firmly, a recess 391 and a projection 392 are respectively formed in and on the driving coupling shaft 323 and the base seat 319 and are fitted/fixed to each other. In order to diffuse a force acting on the driving coupling shaft 323 in the sliding direction, a fitting groove 393 in which the driving coupling shaft 323 is fitted has a spherical shape to reduce the contact area, as shown in FIG. 48. In addition, as shown in FIG. 47, guide ribs 364 for guiding the driving shaft 28 in the sliding direction extend from the rear surface of the driving shaft opening portion 25, and lattice-like hollow portions 365 are also formed on the rear surface to increase the strength of the driving shaft opening portion 25 or equalize its thickness. Furthermore, the size of a portion, of the coupling fixing member, located in the direction in which it is in contact with the guide ribs 364 is set to be larger than the outer diameter of the driving shaft 28 to prevent the driving shaft 28 from touching the guide ribs 364. In addition, in order to reduce the sliding resistance of the driving shaft 28, clearances are provided between the coupling fixing member 322 and the guide ribs 364.

Figure 51:
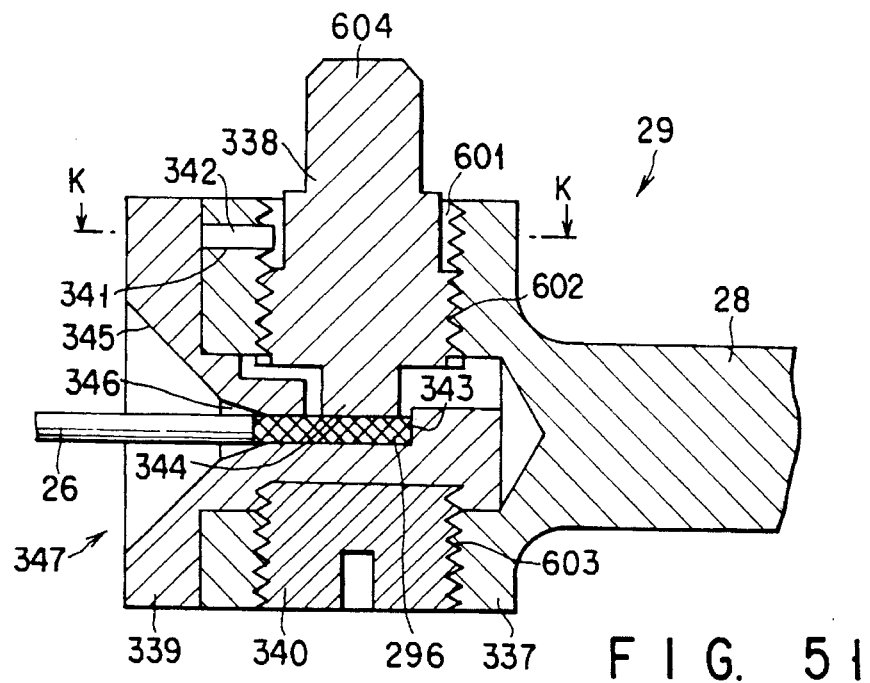
FIG. 51 is a longitudinal sectional view showing a coupled state between the transmission means of the endoscope in FIG. 1 and the second transmission means.
Figure 52:
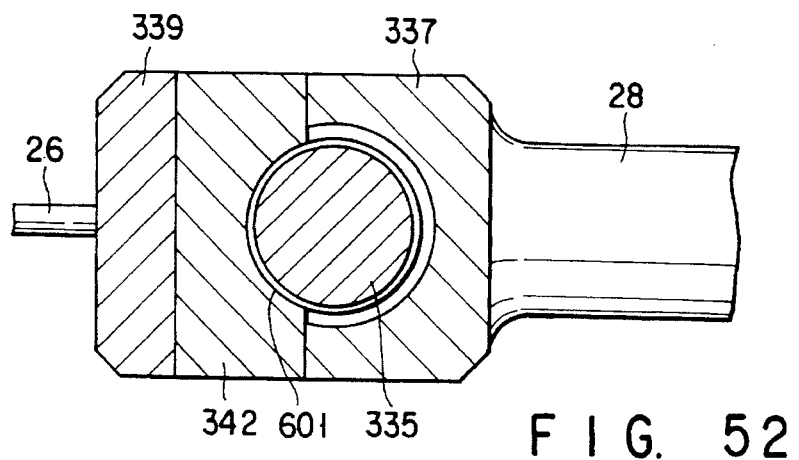
FIG. 52 is a sectional view taken along a line K—K in FIG. 51.

FIGS. 51 and 52 show the structure of the connecting unit 29 arranged on the insertion portion 3 side of the driving shaft 28. FIG. 51 is a longitudinal sectional view of the connecting unit 29. FIG. 52 is a sectional view taken along a line K—K in FIG. 51. A wire press portion body 338 is threadably engaged with a connecting portion body 337 of the driving shaft 28. A wire guide portion 339 for guiding the forceps raising wire 26 is fixed to the connecting portion body 337 with a set screw 340. A removal preventing member 342 for preventing removal of the wire press portion body 338 inserted in a groove 341 formed in the connecting portion body 337 is fixed by the wire guide portion 339 so as not be removed.

Figure 53A:
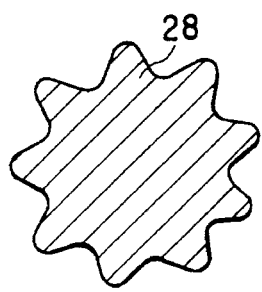
FIGS. 53A to 53C are views for explaining modifications of the cross-sectional shape of the driving shaft.
Figure 53B:
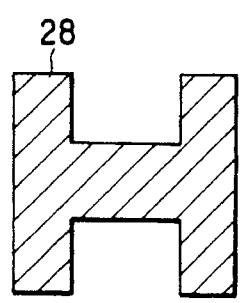
Figure 53C:
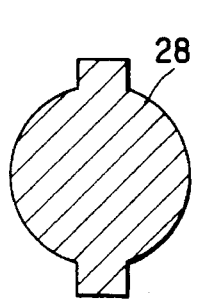

The forceps raising wire 26 is fixed in the following manner. The forceps raising wire 26 is inserted until it is brought into contact with an abutment portion 343 of the wire guide portion 339. The wire press portion body 338 is then rotated to press/deform a wire press portion 344, thus fixing the wire guide portion 339. The driving shaft 28 is exposed to the outside and tends to receive an external force. As a measure to meet such a situation, the cross-sectional shape of the driving shaft 28 may be properly changed, instead of a simple circular shape, to increase the rigidity, as shown in FIGS. 53A to 53C. In addition, the seal portion 328 for watertightly supporting the driving shaft 28 is preferably designed such that the cross-sectional shape of a portion, of the seal portion 328, fitted on the driving shaft 28 is substantially identical to and smaller in size than the driving shaft 28.

Figure 54:
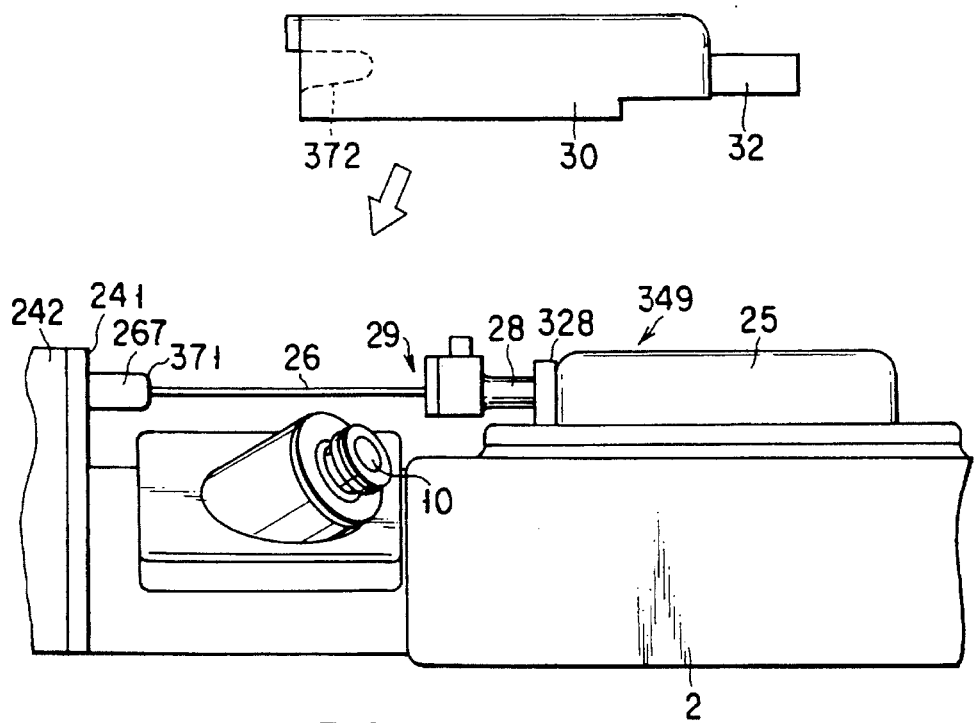
FIG. 54 is a view for explaining a coupling portion between the driving shaft and the forceps raising operation wire in the endoscope in FIG. 1.

As shown in FIG. 54, in order to protect the connecting unit 29, an insulating protective cover 30 is detachably mounted on the operating portion 1. The protective cover 30 is fixed as follows. A positioning projection 32 of the protective cover 30 is inserted in a positioning hole 370 formed in a driving shaft opening portion 25, and the protective cover 30 is forcibly pushed in the operating portion 1. Thereafter, a syringe taper recess 372 of the protective cover 30 is fitted on a syringe taper projection 371 formed on the forceps raising guide tube mouthpiece 267, thus fixing the protective cover 30.

Figure 55:
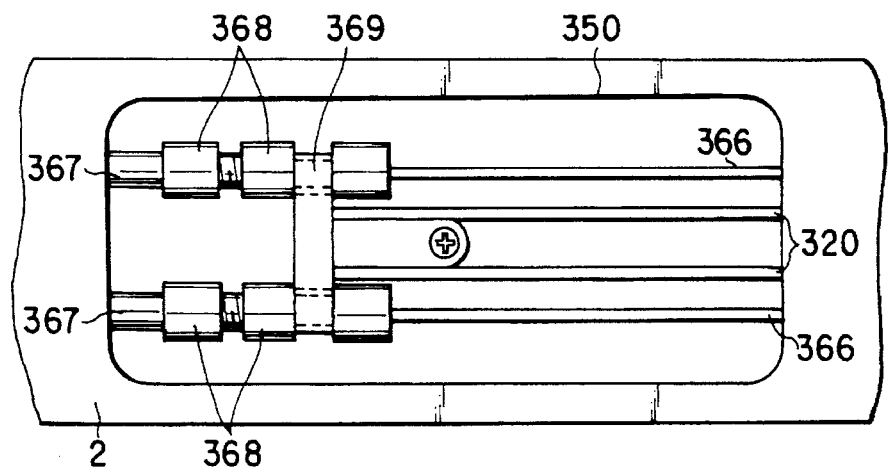
FIG. 55 is a plan view showing the coupling structure of an angle operation wire for operating the flexible portion of the endoscope in FIG. 1.
Figure 56:
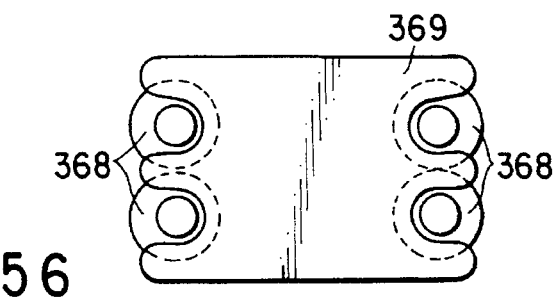
FIG. 56 is a cross-sectional view of the angle operation wire coupling structure in FIG. 55.

As shown in FIGS. 55 and 56, guide tube fixing members 368 are mounted on end portions of wire guide tubes 367 (e.g., coil pipes for guiding angle operation wires 366 for operating a flexible portion 8) on the operating portion 1 side. The fixing positions of the guide tube fixing members 368 with respect to the operating portion 1 are adjusted by an adjustment mechanism which is arranged in an opening portion 350 of the grip portion 2 and designed to adjust the guide tube fixing members 368 by means of threadable engagement.

The functions and effects of the endoscope according to the sixteenth embodiment will be described below with reference to the accompanying drawings.

In the endoscope shown in FIGS. 1 and 34 to 56 as the first embodiment, the distal end portion extends through the insertion portion 3 to be movable along the axis of the insertion portion 3 and is coupled to the forceps raising base 52 as an instrument raising base. In addition, the proximal end portion is coupled to the driving coupling shaft 323 as a conversion means in the grip portion 2 serving as a portion of the operating portion 1 and held by the operator. The transmission means for transmitting the reciprocal movement of this conversion means to the forceps raising base 52 is constituted by the driving shaft 28 as the first transmission means and the forceps raising wire 26 as the second transmission means. The driving shaft 28 has a proximal end portion coupled to the driving coupling shaft 323 in the waterproof structure of the grip portion 2, and a distal end portion extending outside the grip portion 2. The forceps raising wire 26 has a proximal end portion coupled to the distal end portion of the driving shaft 28, and a distal end portion extending through the insertion portion 3 and coupled to the forceps raising base 52.

Materials are selectively used for the first and second transmission means. For example, a shaft member having a high strength, made from precipitation hardened stainless steel, such as SUS 630 etc., is used for the first transmission means, and a flexible wire or the like is used for the second transmission means. In addition, the coupling portion of the second transmission means using a wire which may be disconnected is set outside the grip portion 2. For these reasons, even if the second transmission means must be replaced, the grip portion 2 need not be removed. Therefore, mounting and replacement of the transmission means can be easily performed to ensure excellent assembly operability and maintainability.

The coupling portion between the driving coupling shaft 323 as the distal end portion of the conversion means and the proximal end portion of the driving shaft 28 as the first transmission means is housed in the waterproof structure of the grip portion 2 watertightly held by the seal means properly, and the grip portion 2 does not have a structure in which a metal material is exposed. For this reason, the insulating properties required for the grip portion 2 can be ensured. Furthermore, the conversion means having a complicated structure is housed in the grip portion, and the coupling portion between the driving shaft 28 and the forceps raising wire 26 is covered with the protective cover 30. Even if, therefore, the endoscope is dropped or a similar accidence occurs, no shocks directly act on the conversion means and the coupling portion. Hence, the conversion means and the coupling portions are not easily damaged.

In addition, since the conversion means and the coupling portion between the conversion means and the first transmission means are arranged in the grip portion and covered with the waterproof structure of the grip portion, complicated structure portions are not exposed. Therefore, a cleaning operation or the like is facilitated.

Furthermore, the coupling portion between the distal end of the conversion means and the driving shaft 28 as the first transmission means is formed as a driving shaft unit 349, and the driving shaft unit 349 can be easily attached/detached to/from the grip portion 2. Even if, therefore, a portion of the transmission means is damaged, replacement or the like can be quickly performed.

Figure 57:
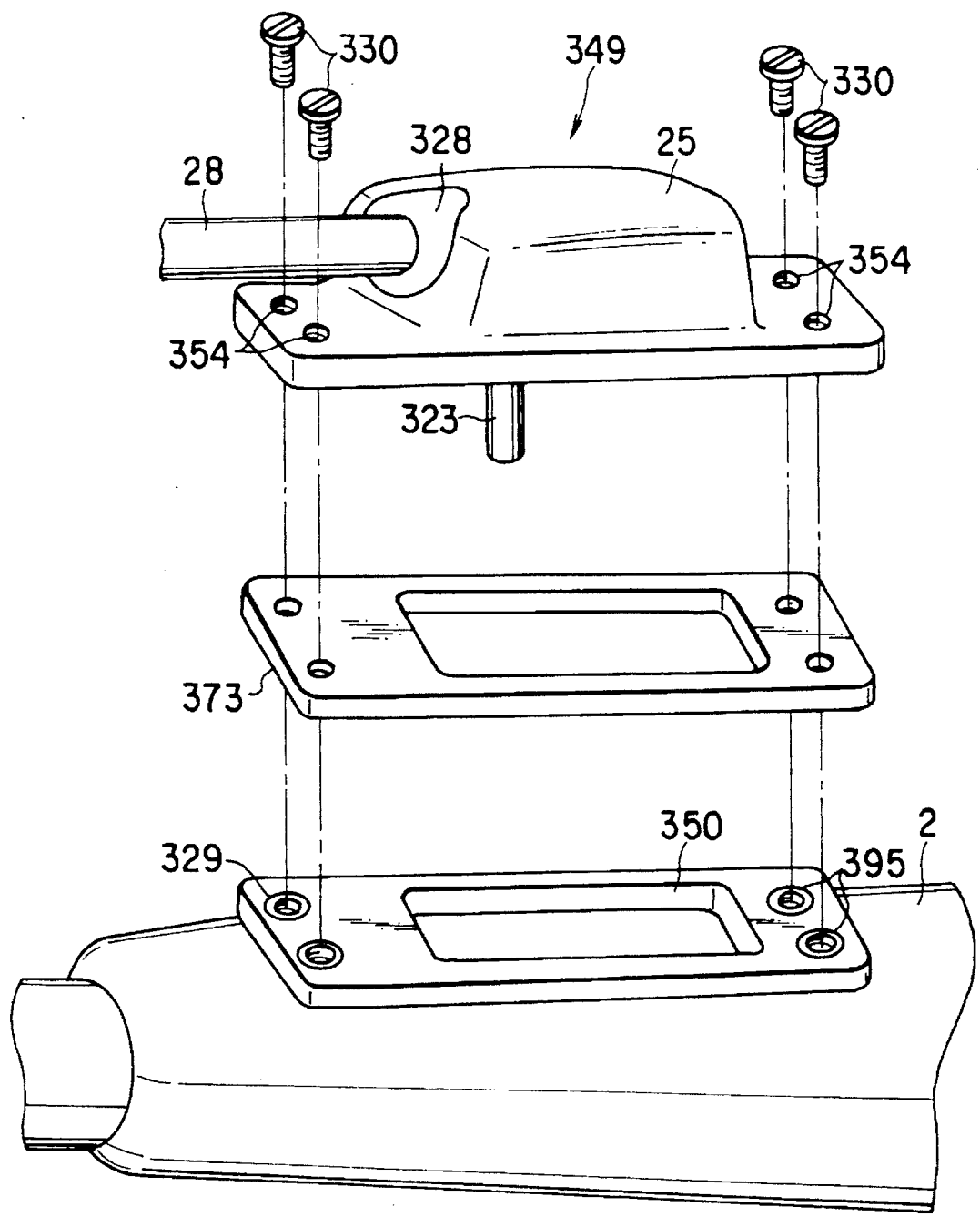
FIG. 57 is a perspective view showing the main portion of a forceps raising operation wire opening portion according to the second embodiment.

FIG. 57 is a schematic perspective view showing the main part of a forceps raising operation wire opening portion of an endoscope according to the seventeenth embodiment of the present invention.

In the seventeenth embodiment, the forceps raising operation wire opening portion of the driving shaft unit 349 in the sixteenth embodiment is improved. More specifically, a rubber packing 373 is used to provide watertightness between a grip portion 2 and a driving shaft unit 349. With this structure, the O-ring A 335 of the connecting unit 29 is omitted.

Other portions are the same as those in the sixteenth embodiment.

The seventeenth embodiment, therefore, has the same effects as those of the sixteenth embodiment. That is, for example, the forceps raising mechanism portions such as the conversion means are protected against shocks, the insulating properties of the grip portion is ensured, and a cleaning operation is facilitated.

The eighteenth embodiment of the present invention will be described below.

FIG. 44 shows the main part of the eighteenth embodiment of the endoscope according to the present invention. In the eighteenth embodiment, a plurality of O-rings 326 and a plurality of driving shaft bearings 327, which are made of a resin and designed to prevent contact between the O-rings 326, are arranged inside an O-ring bearing metal member 331, and an insert metal member 332 inserted in a seal portion 328 made of an elastic member is threadably engaged and fixed. The seal portion 328 has a hemispherical watertight portion 360. The inner diameter of each O-ring 326 is set to be smaller than that of each driving shaft bearing 327, and the inner diameter of each driving shaft bearing 327 is set to be larger than the outer diameter of a driving shaft 28. Other portions are the same as those in the first embodiment.

With this structure, since the driving shaft 28 is supported by a plurality of elastic, watertight members, the driving shaft 28 is not deformed by an external force. In addition, since the driving shaft 28 is not brought into contact with any metal member, the driving shaft 28 is free from damage.

Even if, therefore, the driving shaft 28 is supported by a small number of members, or support members are made of hard materials such as metals, troubles, e.g., operation errors caused when the driving shaft 28 is deformed owing to external shocks and the like and leakage of water caused when the driving shaft 28 is damaged, can be reduced.

The nineteenth embodiment of the present invention will be described below.

Figure 58:
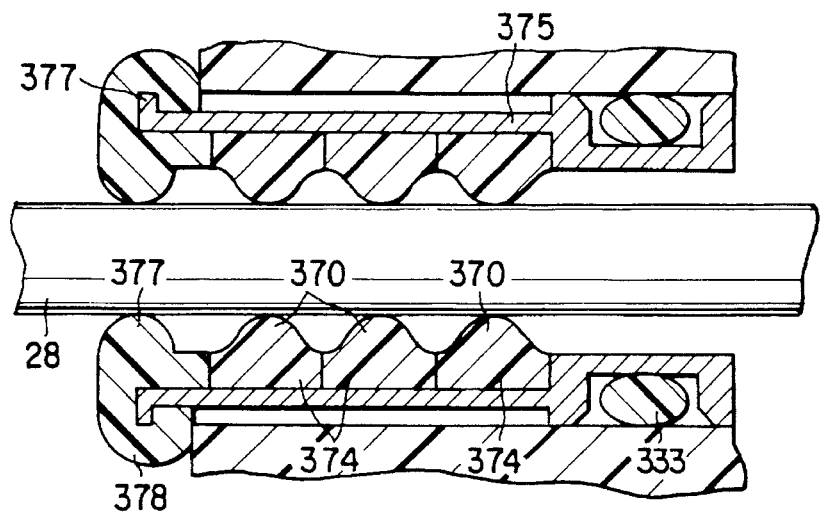
FIG. 58 is a view for explaining the arrangement of the main portion of a forceps raising operation wire opening portion according to the third embodiment.

FIG. 58 shows the main part of the nineteenth embodiment of the endoscope according to the present invention.

In the nineteenth embodiment, a bearing rubber 374 having a plurality of projections 376 is inserted in a rubber bearing metal member 375, and press rubber 378 having a watertight portion 377 is engaged/fixed, as a member for preventing removal of the bearing rubber 374, with/to a flange portion 379 of the rubber bearing metal member 375. Other portions are the same as those in the sixteenth embodiment.

with this arrangement, the same effects as those of the sixteenth embodiment can be obtained.

The twentieth embodiment of the present invention will be described below.

Figure 59:
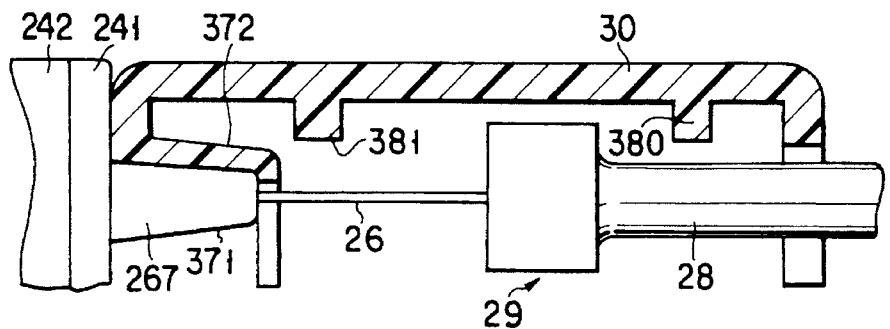
FIG. 59 is a view for explaining the main portion of a forceps raising operation wire opening portion according to the fourth embodiment.

FIG. 59 shows the main part of the twentieth embodiment of the endoscope of the present invention.

In the twentieth embodiment, a raising stopper 380 and an inverting stopper 381 for determining a raising/inverting stroke are disposed on a protective cover 30 detachably mounted on an operating portion 1 and made of a resin which protects the connecting portion of a forceps raising wire 26. Other portions are the same as those of the first embodiment. In a conventional endoscope, stoppers 380, 381 for determining the raising/inverting position of a forceps raising base 52 is disposed in the operating portion 1, so that a user cannot adjust the raising/inverting position as he/she desires. In addition, since different types of products have different raising/inverting strokes, the operating portion 1 incorporating stoppers 380, 381 cannot be made to be common to all products owing to different positions of stoppers 380, 381. With the arrangement of the twentieth embodiment, however, since the raising stopper 380 and the inverting stopper 381 are disposed on the detachable protective cover 30, the operating portion 1 can be made to be common to all products, if protective covers 30 corresponding to the raising/inverting strokes of the respective products are used. If protective covers 30 corresponding to different raising/inverting strokes are prepared for the user, he/she can set a desired raising/inverting position of the forceps raising base 52 by only exchanging protective covers 30.

The twenty-first embodiment of the present invention will be described below.

Figure 60:
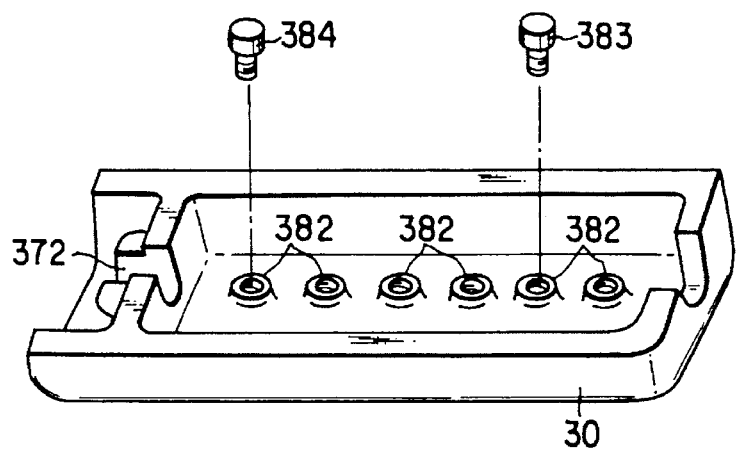
FIG. 60 is a view for explaining the main portion of a forceps raising operation wire opening portion according to the fifth embodiment.

FIG. 60 shows the main part of the twenty-first embodiment of the endoscope according to the present invention.

In the twenty-first embodiment, a plurality of threaded portions 382 are formed on a protective cover 30 so that a raising stopper pin 383 and an inverting stopper pin 384 can be threadably engaged/fixed with/to required portions. Other arrangements are the same as those in the first embodiment.

According to this structure, in addition to the effects of the sixteenth embodiment, an operating portion can be made to be common to all products and a user can set a raising/inverting stroke with the single protective cover 30.

The twenty-second embodiment of the present invention will be described below.

Figure 61:
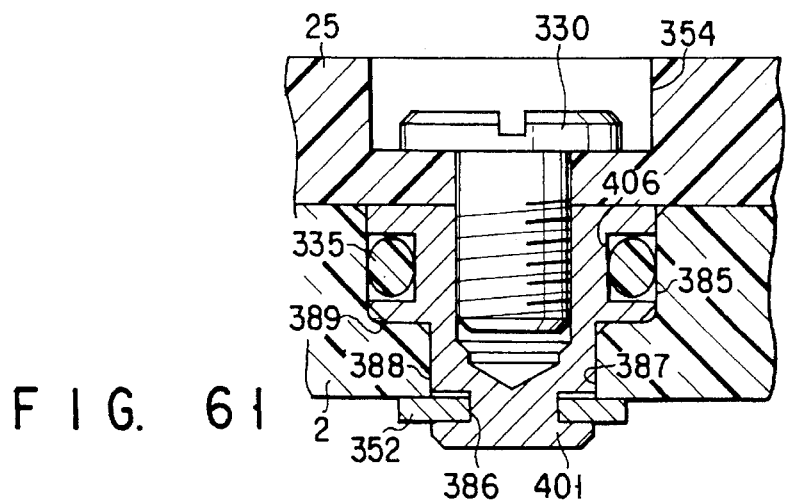
FIG. 61 is a view for explaining the main portion 10 of a forceps raising operation wire opening portion according to the sixth embodiment.

FIG. 61 shows the main part of the twenty-second embodiment of the endoscope according to the present invention.

The twenty-second embodiment will be described with reference to a case wherein a grip portion 2 and a driving shaft opening portion 25 are fixed to each other. An O-ring A 335 is inserted in a recess groove 406 formed in the outer surface of a screw bearing 401 made of a metal and having a screw hole. In this state, the O-ring A 335 is inserted in a fitting hole 385 of the grip portion 2 until it is brought into contact with an abutment portion 389 of the grip portion 2. A C-ring 352 is then inserted in a C-ring groove 386 formed in the screw bearing 401. With this operation, removal of the screw bearing 401 is prevented. In addition, the grip portion 2 has a rectangular hole 387. Since a rectangular portion 388 having substantially the same shape as that of the rectangular hole 387 of the screw bearing 401 is fitted in the rectangular hole 387, the screw bearing 401 is not rotated when a screw 330 is threadably engaged with the screw hole. Watertightness between the grip portion 2 and the screw bearing 401 is maintained by the O-ring A 335. When the screws 330 is inserted in a fitting hole 354 of the driving shaft opening portion 25 and is threadably engaged with the screw bearing 401, the driving shaft opening portion 25 is fixed to the grip portion 2.

In a conventional endoscope, a resin casing is directly fixed with a screw. If, however, the resin casing is fixed with the screw, since a ridge portion of the resin casing is low in strength, the fixing strength is low. In addition, if the screw is repeatedly fastened/loosened, the ridge portion is abraded and cannot be used.

With the structure in the twenty-second embodiment, however, even if a casing is fixed with a screw, the screw can be repeatedly fastened/loosened, and high fixing strength can be achieved. In addition, watertightness can be maintained as high as in a conventional endoscope.

The twenty-third embodiment of the present invention will be described below.

Figures 62A, 62B:
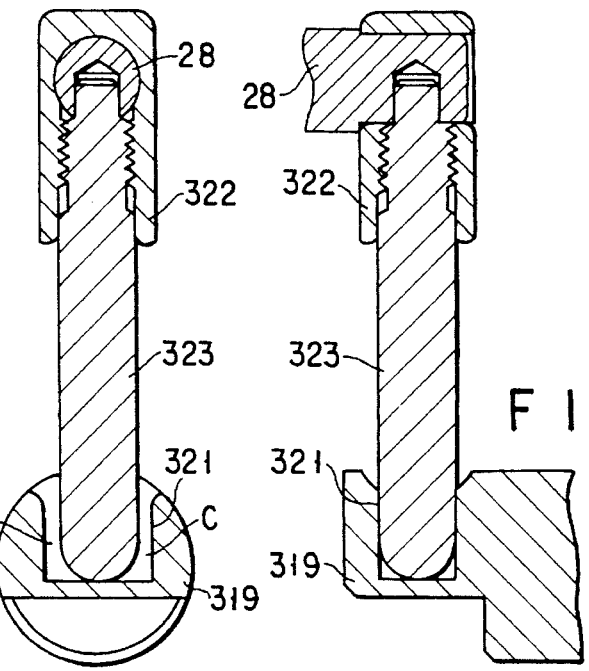
FIGS. 62A and 62B are views for explaining the main portion of a forceps raising operation wire opening portion according to the seventh embodiment.

FIGS. 62A and 62B show the main part of the twenty-third embodiment of the endoscope according to the present invention. FIG. 62A is a sectional front view. FIG. 62B is a sectional side view.

In the twenty-third embodiment, a clearance C is formed in an engaging hole 321 of a base seat 319 engaged with a driving coupling shaft 323 in a direction perpendicular to the sliding direction of a driving shaft 28.

Assume that the driving coupling shaft 323 is fixed in the engaging hole 321 of the base seat 319 with only threadable engagement. In this case, if an overload acts on the driving coupling shaft 323 upon sliding movement of the driving shaft 28 or the like, a failure may occurs in a sliding operation of the driving coupling shaft 323 due to bending thereof because of a lack of an escape. With the arrangement of this embodiment, however, since the clearance is ensured between the driving coupling shaft 323 and the engaging hole 321 of the base seat 319, even if an overload acts on the driving coupling shaft 323, the driving coupling shaft 323 can escape within the clearance, and a failure in a sliding operation of the driving coupling shaft 323 due to bending thereof can be prevented.

The twenty-fourth embodiment of the present invention will be described below.

Figure 63:
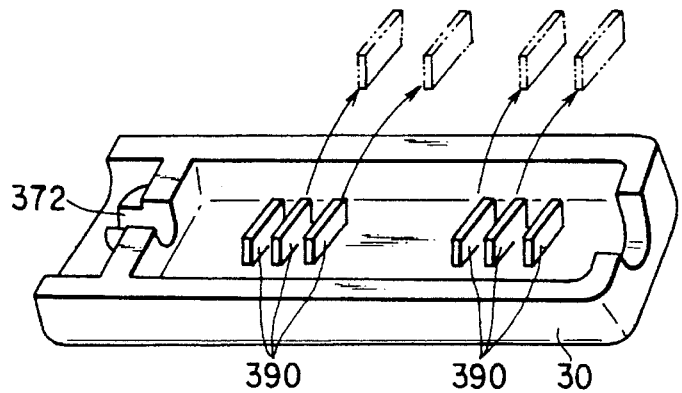
FIG. 63 is a perspective view for explaining the main portion of a forceps raising operation wire opening portion according to the eighth embodiment.

FIG. 63 shows the main part of the twenty-fourth embodiment of the endoscope according to the present invention.

In the twenty-fourth embodiment, a plurality of stopper projections 390 are formed on a protective cover 30. With this structure, stopper projections 390 on the protective cover 30 can be removed, except for those corresponding to a desired inverting/raising position, by, for example, breaking them. Therefore, the manufacturer need not form molds for the respective protective covers 30 having different inverting/raising strokes, even though each protective cover 30 is manufactured by injection molding. That is, a great reduction in process cost can be realized.

The twenty-fifth embodiment of the present invention will be described below.

FIG. 64 shows the main part of the twenty-fifth embodiment of the endoscope according to the present invention.

The twenty-fifth embodiment is characterized in that a portion for sealing the first transmission means, of the first transmission means and a seal means, is formed as a unit.

Of the first transmission means, a portion extending from the seal means is exposed to the outside. For this reason, this portion tends to be damaged and deformed by an external force while the first transmission means is used or cleaned. In addition, the seal portion is not a fixed portion but is a slidable portion, and hence greatly wears. For this reason, it is difficult to maintain a watertight function. Furthermore, it is cumbersome for an operator to mount small parts constituting the seal portion when an endoscope is assembled.

In this embodiment, the portion for sealing the first transmission means, of the first transmission means and the seal means, is formed as a unit. In replacement of the unit, therefore, the watertightness of the seal portion as the unit can be examined. In addition, in assembly of an endoscope, the operator need not mount small parts separately, but can mount them as a unit which is easy to handle, thus facilitating an assembly operation. After the unit is mounted, this seal portion may be watertightly connected to the remaining seal portion. Since the remaining seal portion is a fixed portion, assembly of this portion may be performed while the watertightness is maintained, thus facilitating the assembly operation. Furthermore, when a portion extending from the seal means is damaged or deformed, or a sliding seal portion loses the watertight function, the unit may be replaced with a new one, thus realizing good repair properties.

As shown in FIGS. 41 and 46, a regulation means for regulating the moving range of the first transmission means in the axial direction may be arranged in the opening portion of a portion of the seal means which seals the first transmission means or at the portion for sealing the first transmission means. With this arrangement, the moving range can be easily regulated while the portion for sealing the first transmission means is removed from the seal means.

According to the endoscopes of the sixteenth to twenty-fifth embodiments, materials are selectively used for the first and second transmission means. For example, a shaft member having a high strength is used for the first transmission means, and a flexible wire or the like is used for the second transmission means. In addition, the coupling portion of the second transmission means using a wire which may be disconnected is set outside the grip portion 2. For these reasons, even if the second transmission means must be replaced, the grip portion 2 need not be removed. Therefore, mounting and replacement of the transmission means can be easily performed to ensure excellent assembly operability and maintainability.

The conversion means and the coupling portion between the conversion means and the first transmission means are housed in the grip portion 2, and the grip portion 2 does not have a structure in which a metal material is exposed. For this reason, the insulating properties required for the grip portion 2 can be ensured. Furthermore, the conversion means having a complicated structure is housed in the grip portion 2. Even if, therefore, the endoscope is dropped or a similar accidence occurs, no shocks directly act on the conversion means and the coupling portion. Hence, the conversion means is not easily damaged.

In addition, since the conversion means and the coupling portion between the conversion means and the first transmission means are arranged in the grip portion 2 and watertightly held by the seal means in the grip portion, complicated structure portions are not exposed. Therefore, a cleaning operation or the like is facilitated, and high operability is ensured.

FIGS. 65 and 66 show the twenty-sixth embodiment of the present invention.

In the endoscope of this embodiment, a driving shaft 28 is moved in the axial direction via a wire reciprocating mechanism (not shown) in an operating portion 1 by operating a forceps raising lever 27 (see FIG. 1) disposed in the operating portion 1. The driving shaft 28 and a forceps raising wire 26 are coupled to each other via a connecting unit 29 to be described below. The wire reciprocating mechanism preferably includes a rack/pinion mechanism. In this case, the pinion is coupled to the forceps raising lever 27, and the rack is coupled to the driving shaft 28.

A plurality of stopper ring members 412 are soldered to the outer surface of the proximal end portion of the forceps raising wire 26 via a gap 413. A notched portion is formed in the distal end of the driving shaft 28.

The connecting unit 29 serves to connect the forceps raising wire 26 to the driving shaft 28. A connecting unit body 414 of the connecting unit 29 has a first pipe 415 for receiving the driving shaft 28 and a second pipe 416 for receiving the forceps raising wire 26. A stopper plate 418 (see FIG. 6) having a stopper groove 417 having a width smaller than the outer diameter of the forceps raising wire 26 is disposed between the first pipe 415 and the second pipe 416. The pipes 415 and 416 and the stopper plate 418 are made of an insulating elastic material, e.g., polysulfone.

A set screw 420 is rotatably turned into the first pipe 415. The inner diameter of the second pipe 416 is larger than the outer diameter of the stopper ring members 412.

In the above arrangement, the driving shaft 28 is inserted first in the first pipe 415 while the forceps raising wire 26 is inserted in the second pipe 416, and the set screw 420 is fixed in a notched portion 527 of the driving shaft 28. The forceps raising wire 26 is then fitted in a wire fitting hole 419 of the stopper plate 418 while an instrument raising base 9 is completely inverted. In this case, the forceps raising wire 26 is guided by the stopper groove 417 and fitted in the wire fitting hole 419 while the stopper plate 418 is elastically deformed. In this state, removal of the forceps raising wire 26 in the axial direction is prevented by the stopper ring members 412 located on two sides of the stopper plate 418, and removal of the forceps raising wire 26 in the vertical direction is prevented by the stopper groove 417 having a width smaller than the diameter of the wire fitting hole 419.

In this arrangement, the length of the forceps raising wire 26 can be adjusted by changing the positions of the stopper plate 418 and the gap 413.

As described above, in this embodiment, the reciprocal movement of the driving shaft 28 is transmitted to the instrument raising base 9 in a distal end portion 5 without being attenuated by a slack of the forceps raising wire 26. In addition, when the forceps raising wire 26 is mounted, its adjustment can be easily performed by using the stopper ring members 412.

Figure 67A:
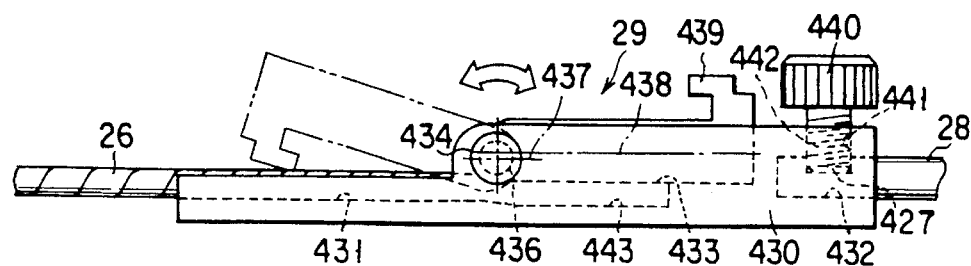
FIGS. 67A ad 67B are side and plan views, respectively, showing a connecting portion between the driving shaft and the forceps raising operation wire according to the third embodiment.
Figure 67B:
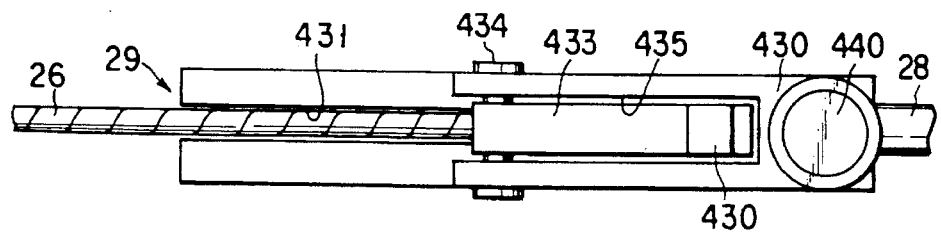

FIGS. 67A and 67B show the twenty-seventh embodiment of the present invention. A connecting unit 29 of the endoscope of this embodiment has the following arrangement.

As shown in FIGS. 67A and 67B, a guide groove 431 for receiving a forceps raising wire 26 is formed in one end of a connecting unit body 430, and a guide hole 432 for receiving a driving shaft 28 is formed in the other end of the connecting unit body 430. The connecting unit body 430 has a housing groove 435 for housing a stopper lever 433. A lever pin 434 for rotatably coupling the stopper lever 433 thereto is mounted near the middle of the connecting unit body 430.

A hook portion 439 on which a finger of an operator is hooked is formed on an end portion of the stopper lever 433. A central line 437 (indicated by a chain line in FIG. 67A) of a hole 436 in which the lever pin 434 is inserted is located below a central line 438 (indicated by a chain line in FIG. 67A) of the stopper lever 433. A communicating hole 441 is formed in the connecting unit body 430 to communicate with the guide hole 432 and extend through the connecting unit body 430 in a direction perpendicular to the guide hole 432. A threaded portion 442 is formed on the inner surface of the communicating hole 441, and a set screw 440 is threadably engaged with the threaded portion 442.

The guide groove 431 communicates with a housing groove 435 while it extends under the housing groove 435, and forms a guide groove 443, which is deeper than the housing groove 435, at a portion where the guide groove 431 communicates with the housing groove 435.

In the above arrangement, first of all, the driving shaft 28 is inserted in the guide hole 432 of the connecting unit body 430 and is fixed by turning the set screw 440 into the notched portion 527 of the driving shaft 28. The forceps raising wire 26 is then inserted in the guide grooves 431 and 443, and the stopper lever 433 is moved to the position indicated by the dotted line in FIG. 72A to fix the forceps raising wire 26.

Figures 68A, 68B:
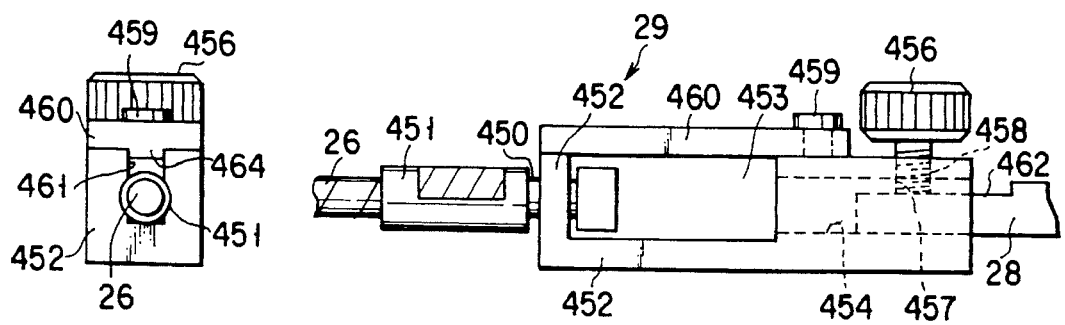
FIGS. 68A to 68C are front, side, and plan views, respectively, showing a connecting portion between the driving shaft and the forceps raising operation wire according to the fourth embodiment.
Figure 68C:
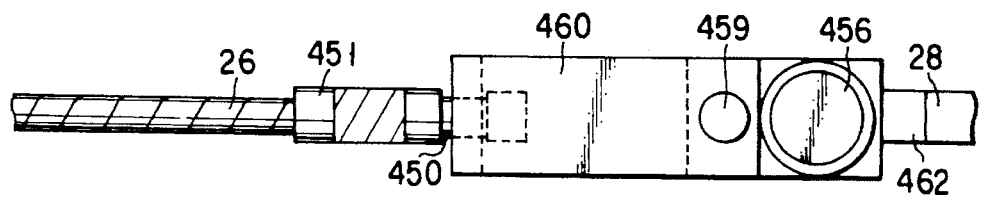

FIGS. 68A to 68C show the twenty-eighth embodiment of the present invention. A connecting unit 29 of the endoscope of this embodiment has the following arrangement.

A wire mouthpiece 451 having a stepped portion 450 is soldered to the proximal end portion of a forceps raising wire 26. A connecting unit body 452 has a notched portion 453 and a through hole 454 open to the notched portion 453. The connecting unit body 452 also has a communicating hole 457 communicating with the through hole 454 and extending through the connecting unit body 452 in a direction perpendicular to the through hole 454. A threaded portion 458 is formed on the inner surface of the communicating hole 457, and a set screw 456 is threadably engaged with the threaded portion 458.

A stopper cover 460 is pivotally mounted on the upper surface of the connecting unit body 452, with which the set screw 456 is threadably engaged, via a support pin 459. A projection 464 is formed on an end portion, of the stopper cover 460, located on the opposite side to the support pin 459. A hook groove 461 having a width larger than the outer diameter of the stepped portion 450 is formed in a distal end portion of the connecting unit body 452. In addition, a notched portion having a horizontal portion 462 is formed in a distal end portion of a driving shaft 28.

In the above arrangement, the stepped portion 450 of the wire mouthpiece 451, disposed on the proximal end portion of the forceps raising wire 26, is fitted in the hook groove 461, and the resultant structure is covered with the stopper cover 460 while the depths at which the forceps raising wire 26 and the driving shaft 28 are inserted are adjusted. With this operation, the forceps raising wire 26 is fixed. Thereafter, the driving shaft 28 is inserted in the through hole 454 and is fixed by pressing the set screw 456 against a notched portion 463 of the driving shaft 28.

As described above, in comparison with the twenty-sixth embodiment, in this embodiment, removal of the forceps raising wire 26 from the connecting unit body 452 can be prevented, and the length of the forceps raising wire 26 can be adjusted on the driving shaft 28 side, thus allowing easy connection and realizing excellent cleaning properties.

Figure 69A:
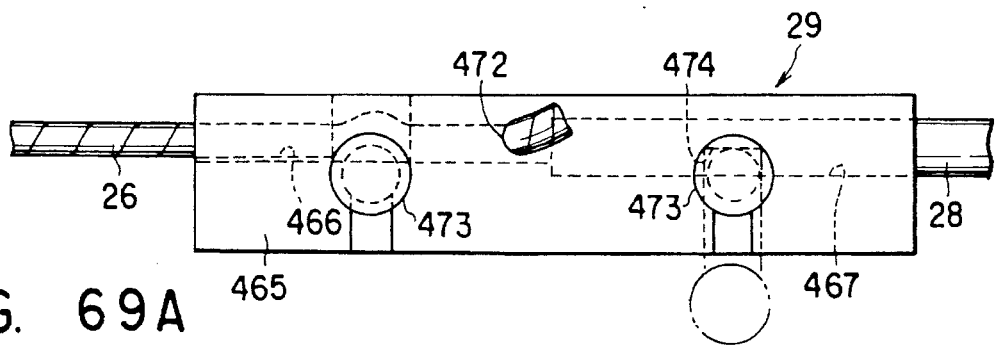
FIGS. 69A and 69B are side and plan views, respectively, showing a connecting portion between the driving shaft and the forceps raising operation wire according to the fifth embodiment.
Figure 69B:
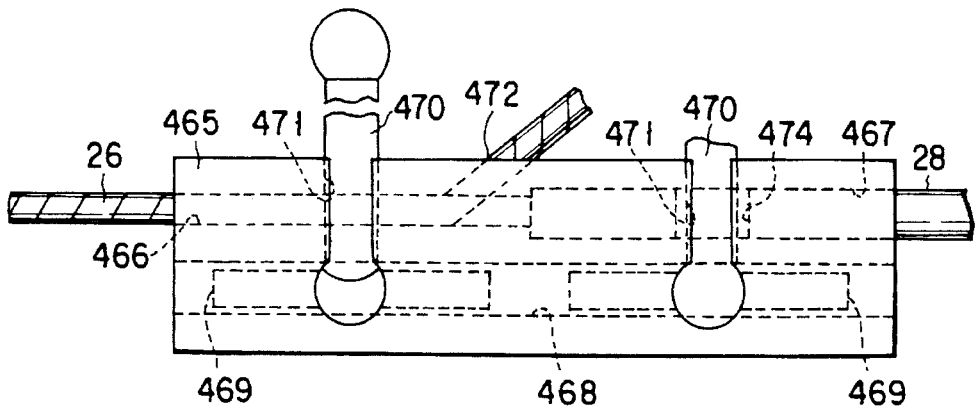

FIGS. 69A and 69B show the twenty-ninth embodiment of the present invention. The connecting portion of the endoscope of this embodiment has the following arrangement.

A connecting unit 29 of the embodiment is constituted by a connecting unit body 465 made of an elastic member such as a plastic member. A first hole 466 for receiving a forceps raising wire 26 is formed in one end of the connecting unit body 465, and a second hole 467 for receiving a driving shaft 28 is formed in the other end of the connecting unit body 465. The first and second holes 466 and 467 are coaxially formed.

A through hole 468 is formed in the connecting unit body 465 in a direction parallel to the holes 466 and 467. Two removal preventing pins 469 and two press levers 470 are inserted/fixed in the through hole 468. A hook groove 471 having a width smaller than the diameter of each press lever 470 is formed in the upper surface of the connecting unit body 465. A hole 472 and a housing hole 473 are formed in a side wall of the connecting unit body. The forceps raising wire 26 is inserted in the hole 472. The two press levers 470 are housed in the housing hole 473. In addition, a hole 474 is formed below the two press levers 470 of the forceps raising wire 26.

In the above arrangement, first of all, the press lever 470 located on the driving shaft 28 side is laid, while the driving shaft 28 is inserted in the second hole 467, and the press lever 470 is fixed in the notched portion 527 of the driving shaft 28 to fix the driving shaft 28.

The forceps raising wire 26 is then inserted in the first hole 466, and the proximal end portion of the forceps raising wire 26 is introduced via the hole 472. The press lever 470 located on the forceps raising wire 26 side is laid, while the instrument raising base 9 is an inverted state, thus fixing the forceps raising wire 26 with the press lever 470 being pressed against the forceps raising wire 26. Note that the two press levers 470 respectively used to fix the driving shaft 28 and the forceps raising wire 26 are fitted in the hook groove 471 while the hook groove 471 of the connecting unit body 465 is elastically expanded.

Figure 70A:
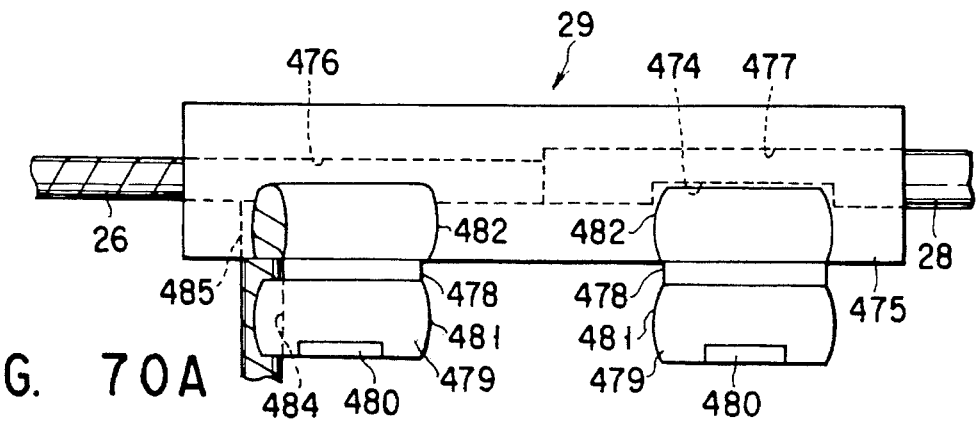
FIGS. 70A and 70B are side and plan views, respectively, showing a connecting portion between the driving shaft and the forceps raising operation wire according to the sixth embodiment.
Figure 70B:
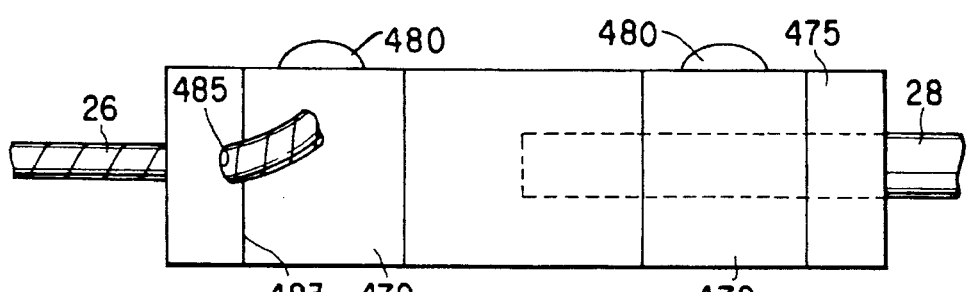

FIGS. 70A and 70B show the thirtieth embodiment of the present invention. A connecting unit 29 of this embodiment is constituted by a connecting unit body 475 made of an elastic member such as a plastic member. A first hole 476 for receiving a forceps raising wire 26 is formed in one end of the connecting unit body 475. A second hole 477 for receiving a driving shaft 28 is formed in the other end of the connecting unit body 475. The first and second holes 476 and 477 are coaxially formed.

The connecting unit body 475 has two hinge portions 478. The hinge portions 478 respectively have press covers 479. These press covers 479 respectively have collars 480. Each press cover 479 has a barrel-like cross-section, and each fitting portion 482, in which the press cover 479 is housed in a fitted state, also has a barrel-like shape. Notched portions 484 and 485, through which the forceps raising wire 26 extends, are formed in a boundary portion 483 between the press cover 479, located on the forceps raising wire 26 side, and the fitting portion 482 fitted on the press cover 479.

In the above arrangement, the driving shaft 28 is inserted in the hole 477 of the connecting unit body 475, and the notched portion 527 of the driving shaft 28 is aligned with the fitting portion 482. In this state, the press cover 479 located on the driving shaft 28 side is elastically deformed and fitted in the fitting portion 482, thus fixing the driving shaft 28. The forceps raising wire 26 is inserted in the hole 476 of the connecting unit body 475 and is caused to extend out of the connecting unit body 475 via the notched portions 484 and 485. The press cover 479 located on the forceps raising wire 26 side is elastically deformed and fitted in the fitting portion 482, thus fixing the forceps raising wire 26.

In this embodiment, since the connecting unit 29 has a simple structure, an inexpensive endoscope can be realized, and the endoscope can be easily assembled. In addition, excellent cleaning properties can be obtained.

Figure 71A:
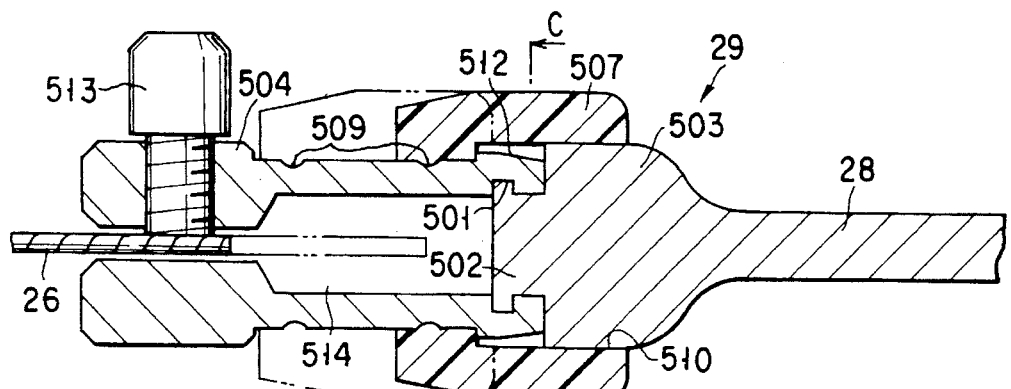
FIGS. 71A and 71B are side and plan views, respectively, showing a connecting portion between the driving shaft and the forceps raising operation wire according to the seventh embodiment.
Figure 71B:
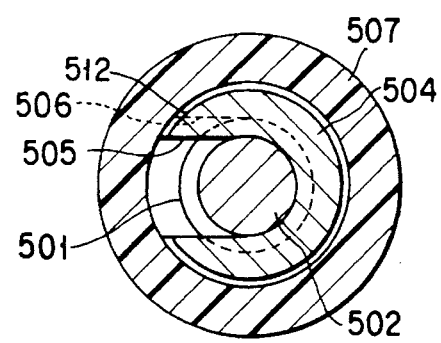

FIGS. 71A and 71B show the thirty-first embodiment of the present invention. A connecting unit 29 of this embodiment has the following arrangement.

As shown in FIG. 71A, a flange portion 501 is disposed on the distal end side of a driving shaft 28. A small-diameter portion 502 is formed at the proximal end of the flange portion 501, and a large-diameter portion 503 is formed at the proximal end of the small-diameter portion 502. A connecting member 504 is detachably mounted on the distal end portion of the driving shaft 28.

As shown in FIG. 71B, horseshoe-shaped notched portions 505 and 506 are formed in the proximal end portion of a connecting member 504 fitted between the small-diameter portion 502 of the driving shaft 28 and the flange portion 501. With this structure, attachment/detachment of the connecting member 504 can be performed from a side of a raising operation rod 487. In addition, a cap 507 for holding such connection between the driving shaft 28 and the connecting member 504 is disposed around the connecting portion between the driving shaft 28 and the connecting member 504. The cap 507 is made of a plastic material having high elasticity, e.g., polyacetal, polyethylene, or polypropylene. A projection 508 is formed on the inner surface of the cap 507. When this projection 508 is engaged with a recess portion 509 formed in the outer surface of the connecting member 504, the cap 507 is positioned, and a sense of clicking can be obtained.

The driving shaft 28 is engaged with the connecting member 504 while the cap 507 is moved to the position indicated by the chain double-dashed line in FIG. 71A. Thereafter, the cap 507 is moved to the position indicated by the solid line in FIG. 71A. With this operation, the large-diameter portion 503 of the driving shaft 28 is engaged with an engaging portion 510 formed in the inner surface of the cap 507, thereby fixing the driving shaft 28.

As described above, since the cap 507 is made of a plastic resin, the cap 507 is pushed by using its wide range of elasticity to be fitted on the connecting member 504. As a result, the cap 507 is set in the state shown in FIG. 71A. In this case, a taper surface 512 is formed on the outer surface of the proximal end portion of the connecting member 504 to improve the assembly properties. This taper surface 512 allows the cap 507 to easily expand when it is forcibly fitted on the connecting member 504.

A set screw 513 is turned into the distal end portion of the connecting member 504 to fix the forceps raising wire 26 at an arbitrary position. The chain double-dashed line in FIG. 71A indicates that the forceps raising wire 26 can be adjusted even if an insertion portion 6 varies in length. For this purpose, a space portion 514 is formed.

Figure 72C:
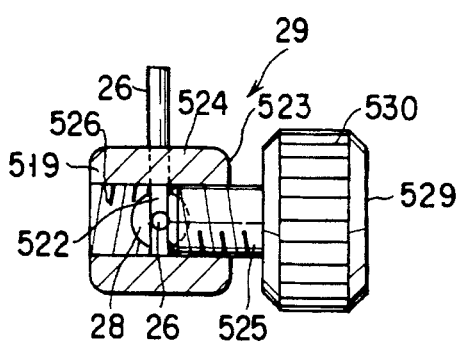
FIGS. 72A to 72C are front, side, and plan views, respectively, showing a connecting portion between the driving shaft and the forceps raising operation wire according to the eight embodiment.
Figure 72A:
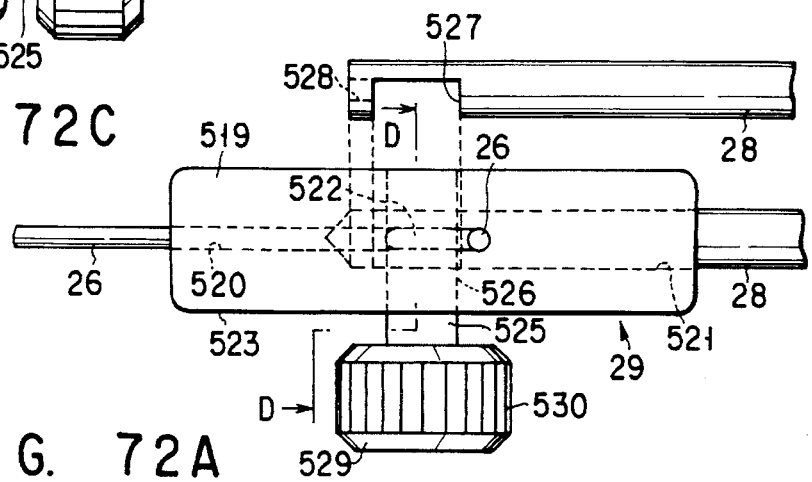
Figure 72B:
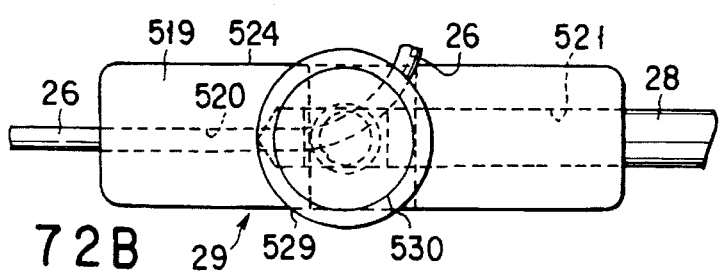

FIGS. 72A to 72C show the thirty-second embodiment of the present invention. A connecting unit 29 of this embodiment has the following arrangement.

A connecting unit body 519 has a first hole 520, through which a forceps raising wire 26 extends, and a second hole 521, through which a driving shaft 28 extends. The second hole 521 extends to a position exceeding a central portion of the connecting unit body 519, and a through groove 522 communicating with the second hole 521 is formed in a side wall 524 of the central portion of the connecting unit body 519.

A set screw 525 is rotatably and threadably engaged with an upper surface 523 of the connecting unit body 519, at which a substantially central portion of the through groove 522 is located, in the vertical direction via a threaded portion 526. Note that a notched portion 527 is formed in the distal end portion of the driving shaft 28, and a third hole 528 communicating with the notched portion 527 is formed in the distal end face of the driving shaft 28. In addition, a knurled portion 530 is formed on a head portion 529 of the set screw 525 to facilitate rotation of the set screw 525.

An end face of the forceps raising wire 26 is soldered so as not to be loosened and increase in diameter. The connecting unit 29 is made of an insulating plastic member such as polysulfone or modified PPO to allow autoclaving.

The driving shaft 28 is inserted in the second hole 521 of the connecting unit body 519, and the forceps raising wire 26 is inserted in the first hole 520 of the connecting unit body 519. The forceps raising wire 26 is introduced into the notched portion 527 via the third hole 528 of the driving shaft 28. In this state, the forceps raising wire 26 is pulled out of the through groove 522 of the side wall 524 of the connecting unit body 519 without any slack. The forceps raising wire 26 is then pressed/fixed between the end face of the notched portion 527 of the driving shaft 28 and the set screw 525 by pivoting the set screw 525.

FIGS. 73A to 73C show the thirty-third embodiment of the present invention. A connecting unit 29 of this embodiment has the following arrangement.

In the embodiment, a hole 562 is formed in a connecting member 504, and a forceps raising wire 26 is inserted in the hole 562. The proximal end portion of the forceps raising wire 26 is formed into a spherical end portion 563, and annular grooves 564 are formed in the distal end portion of the spherical end portion 563. A screw member 566 having a distal end portion 565 having substantially the same size as the width of each annular groove 564 is detachably and threadably engaged with a threaded portion 567 of the connecting member 504.

A plurality of annular grooves 564 are formed in the axial direction so that the coupling position of the forceps raising wire 26 can be adjusted. In addition, an end portion of the forceps raising wire 26 is hardened by soldering.

On the wire reciprocating unit 14 side, a slit 568 is formed in the distal end portion of a driving shaft 28, and a screw member 570 having a distal end portion 569 having substantially the same width as that of the slit 568 is detachably and threadably engaged with a threaded portion 571.

In the above arrangement, a connecting portion 201 can be completely disassembled to allow sterilization at a high water vapor pressure, e.g., autoclaving, thereby facilitating a cleaning operation.

Figure 75A:
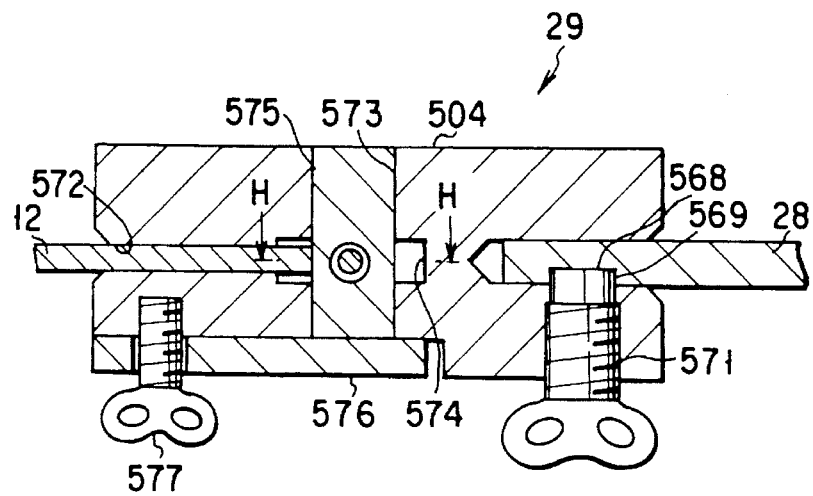
FIG. 75A is a sectional view taken along a line G—G in FIG. 74.
Figure 75B:
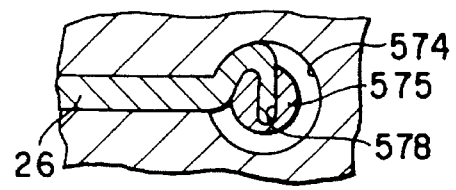
FIG. 75B is a sectional view taken along a line H—H in FIG. 75A.
Figure 75C:
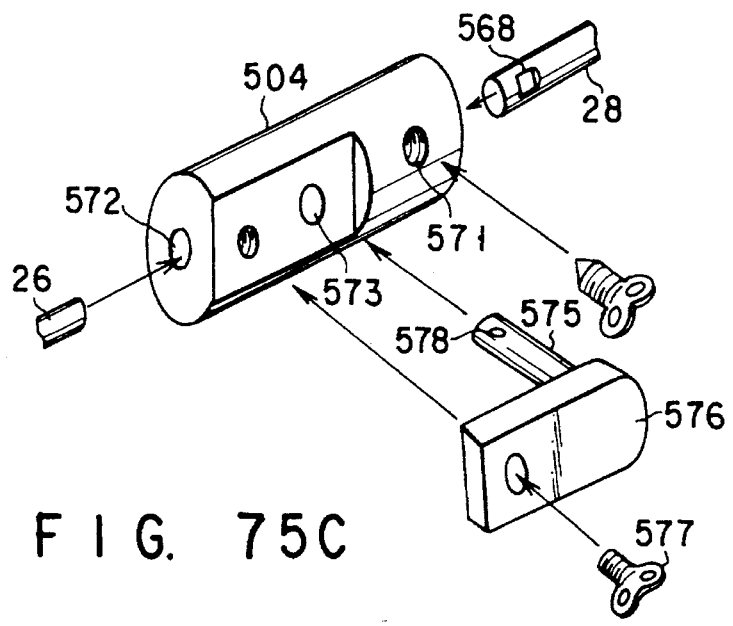
FIG. 75C is a perspective view showing the connection portion in FIG. 74 in a disassembled state.

FIGS. 74 to 75C show the thirty-fourth embodiment of the present invention. A connecting unit 29 of this embodiment has the following arrangement.

A hole 572 through which a forceps raising wire 26 extends is formed in the distal end portion of a connecting member 504. A first communicating hole 573 is formed in the connecting member 504 to cross the hole 573 at a right angle, and a second communicating hole 574, which is coaxial with the first communicating hole 573, is formed at a portion where the first communicating hole 573 crosses the hole 572. A fixing member 576 having a shaft portion 575 which has a circular cross-section and is almost fitted in the first communicating hole 573 is mounted on the connecting member 504 to be pivotal about the shaft portion 575. A through hole 578 shown in FIG. 75B is formed in the shaft portion 575 at a position where the through hole 578 coincides with the axis of the hole 572 when the fixing member 576 is fixed to the connecting member 504 with a screw member 577.

The forceps raising wire 26 is inserted in the hole 572 while the fixing member 576 is rotated through 90° from the position in FIG. 74 to cause the through hole 578 of the shaft portion 575 to communicate with the hole 572. Thereafter, the fixing member 576 is rotated through 90° to set the state shown in FIG. 75B. At this time, the forceps raising wire 26 is clamped and fixed between the second communicating hole 574 and the shaft portion 575.

In the above arrangement, as shown in FIG. 75C, since the connecting portion between the forceps raising wire 26 and a driving shaft 28 can be disassembled to the part level, autoclaving of the parts in the disassembled state can be performed at once. Therefore, the time required for a cleaning/sterilizing operation can be shortened, and the labor can be reduced.

As described above, according to the endoscopes of the twenty-sixth to thirty-fourth embodiments, the position in the axial direction where the forceps raising wire is connected to the operating mechanism can be adjusted by the adjusting means arranged in the connecting portion between the forceps raising wire and the operating mechanism. For this reason, the forceps raising base can be properly raised or inverted by correcting variations in length of the forceps raising wire and the endoscope in an assembly operation. That is, the instrument raising base can be properly raised and inverted with any combination of a forceps raising wire and an operating mechanism.

Since the forceps raising wire and the operating mechanism are detachably connected to each other, the user can repair/replace the forceps raising wire by himself/herself.

Figure 76:
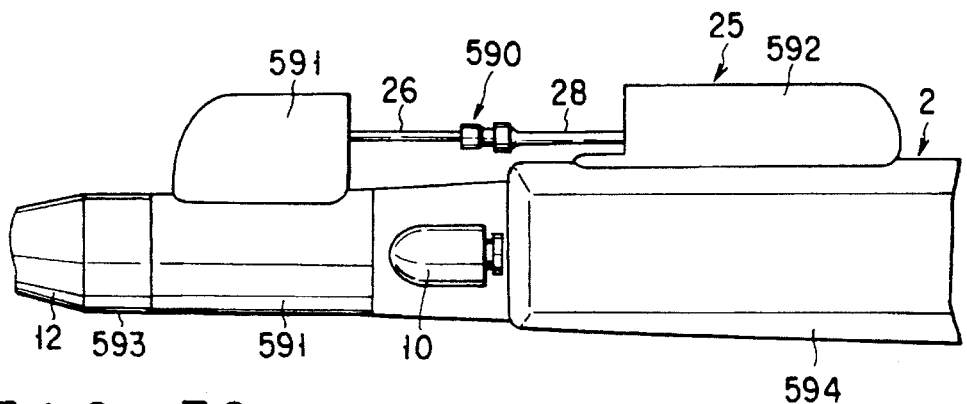
FIG. 76 is a side view showing an operation wire outlet portion.

FIG. 76 shows the thirty-fourth embodiment of the present invention.

In the endoscope of this embodiment, the proximal end portion of a forceps raising wire 26 is detachably connected to a driving shaft 28 at a position near a forceps opening portion 10 while the connecting portion is located outside an endoscope 1. The connecting portion between the forceps raising wire 26 and the driving shaft 28 is denoted by reference numeral 590.

As shown in FIG. 76, a stationary cover 591 and an assembly consisting of a breakage preventing cover 12 and a cover 593, which are disposed on the distal end portion side of the stationary cover 591 and coupled to each other by a fixing member (not shown), are fixed to the distal end portion of a grip 594 constituting a grip portion 2. A cover member 592 is mounted on a driving shaft opening portion 25 formed in the grip 594 and having a substantially rectangular shape.

The stationary cover 591 is sealed with respect to the grip 594. For example, the grip 594 may have an internal structure like the one in the sixteenth embodiment described with reference to FIGS. 34 to 37. In addition, the driving shaft opening portion 25 and the cover member 592 may have structures like those described with reference to FIGS. 57 to 64.

The forceps raising wire 26 and the driving shaft 28 are caused to extend from the stationary cover 591 and the cover member 592 while they are sealed with respect to the stationary cover 591 and the cover member 592. In addition, looseness of the forceps raising wire 26 and the driving shaft 28 with respect to the stationary cover 591 and the cover member 592 is prevented.

In the endoscope of this embodiment, the connecting portion 590 between the forceps raising wire 26 and the driving shaft 28 is located at a forceps opening portion 5 located near an end portion, of an operating portion 3, located on the insertion portion side. With this arrangement, filthy substances jetting out from a body cavity via an operation wire outlet portion 200 can scarcely reach the operator.

Figure 77:
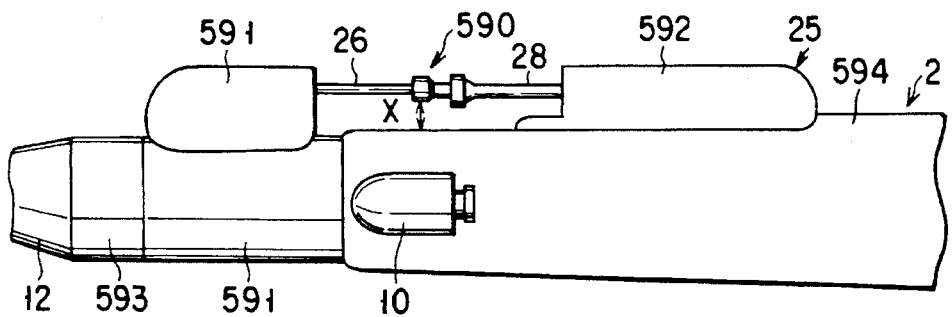
FIG. 77 is a side view showing a modification of the operation wire outlet portion.

FIG. 77 shows the thirty-fifth embodiment of the present invention. In this embodiment, the positions of a forceps raising wire 26, a driving shaft 29, and a connecting portion 590 are different from those of the corresponding components in the first embodiment. In this arrangement, a grip 594 extends to a forceps opening portion 5, and the connecting portion 590 is disposed near the distal end portion of the grip 594. In addition, a surface, of the grip 594, which corresponds to the connecting portion 590 is formed into a flat surface within the range in which the connecting portion 590 is moved upon reciprocating operations of the operation wire 26 and the driving shaft 29. Note that other arrangements are the same as those in the thirty-fourth embodiment.

with this arrangement, the same functions and effects of the above embodiment can be obtained. In addition, since the surface, of the grip 594, which corresponds to the connecting portion 590 is formed into the flat surface within the moving range of the connecting portion 590, even if a size X in FIG. 77 is decreased, the connecting portion 590 does not interfere with the surface of the grip 594. That is, since no portion extends from the grip 594 toward the connecting portion 590, and a predetermined gap is formed between the connecting portion 590 and the surface of the grip 594, reciprocating operations of the operation wire 26 and the driving shaft 29 can be smoothly performed. Note that the size X may be set to be 0 when the connecting portion 590 is to be reciprocated while it is in contact with the surface of the grip 594 serving as a guide.

Figure 78:
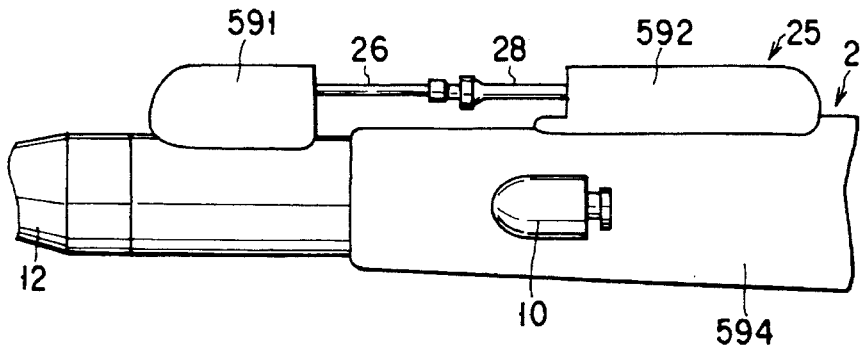
FIG. 78 is a side view showing another modification of the operation wire outlet portion.

FIG. 78 shows the thirty-sixth embodiment. In this embodiment, a connecting portion 590 between an operation wire 26 and a driving shaft 28 is disposed near a breakage preventing member 12. That is, the connecting portion 590 is located closer to the insertion portion side than a forceps opening portion 5.

with this arrangement, the same functions and effects as those of the thirty-fourth embodiment can be obtained. In addition, since the connecting portion 590 is located near the breakage preventing member 12, a wire outlet portion 200 open to the outside is located farther from the operator, the operator is seldom contaminated by filthy substances from a body cavity. In this arrangement, since a projection 246 of the breakage preventing member 12 is pressed against the distal end face of a second stationary cover 591 to eliminate the gap between the breakage preventing member 12 and the second stationary cover 591, no filthy substances enter between the breakage preventing member 12 and the second stationary cover 591. This ensures a sanitary condition.

In the endoscopes of the thirty-fourth to thirty-sixth embodiments, since the connecting portion between the operation wire and the wire driving means is disposed near an end portion, of the operating portion, located near the insertion portion, filthy substances jetting out from a body cavity via the connecting portion between the operation wire and the wire driving means cannot reach the operator.

In addition, the operation wire and the wire driving means are detachably connected to each other, and the forceps raising wire can be detached from the endoscope. Hence, excellent cleaning properties can be obtained.

Figure 79:
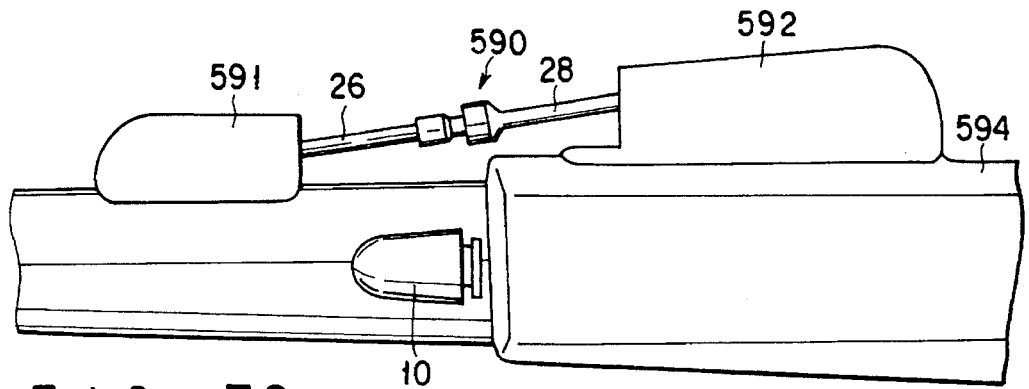
FIG. 79 is a side view showing still another modification of the operation wire outlet portion.

FIG. 79 shows the thirty-seventh embodiment of the present invention. This embodiment is different from the thirty-fourth embodiment in the direction in which a driving shaft 28 is reciprocated. A forceps raising wire 26 is guided in an inclined state, as shown in FIG. 79. Other arrangements are the same as those in the thirty-fourth embodiment.

The driving shaft 28 is moved by operating a forceps raising lever 27 (FIG. 1). The stroke of the driving shaft 28 is increased by an amount corresponding to the inclination shown in FIG. 79. Letting l1 be the stroke length along the axis of a grip 594, and l2 be the stroke length along the axis of the driving shaft 28, $l2=l1/\cos\theta$. Since $0 \leq \cos\theta \leq 1$, $l1/\cos\theta \geq 1$. That is, the length l2 is larger than the length l1, and the stroke increases. Therefore, a large rod displacement amount can be obtained with a small stroke.

According to the endoscope of this embodiment, excellent cleaning properties and operability can be obtained. That is, since a displacement amount transmitted from the raising driving unit to the driving shaft can be reliably transmitted to the raising base in the distal end portion, good response characteristics and operability can be obtained. Furthermore, since the path from the transmission rod to the operation wire is made to be substantially straight, no buckling of the operation wire occurs to improve the durability. Moreover, since the operation wire and the transmission rod are designed to be detachable, good cleaning properties can be obtained.

The thirty-eighth embodiment of the present invention will be described next with reference to FIGS. 34 to 38 and 80 to 84C. An assembly procedure and an arrangement which are designed to suppress variations in the total length of a forceps raising guide tube 274 will be described with reference to FIG. 38. A repetitive description with respect to the sixteenth embodiment described with reference to FIGS. 34 to 56 will be avoided.

A tube stop pipe 278 having a desired size is soldered to a forceps raising guide pipe 277 from the operating portion 1 side. A variation in size in this fitting operation is set to be about ±0.5 mm. An adhesive is sufficiently coated on the outer surface of the forceps raising guide pipe 277, and a proximal end guide tube 279 whose dimensional tolerance of the total length is ±0.5 mm is fitted on the adhesive-coated portion of the forceps raising guide pipe 277. The outer surface of the proximal end guide tube 279 is then tied with strings at three positions to sufficiently spread the adhesive throughout the circumference. After the adhesive is dried, the strings are cut except for the string at a tying portion 280 on the tube stop pipe 278 side.

An adhesive is sufficiently coated on the outer surface of a proximal end pipe 275 whose total length is longer than a length after a fitting operation by 20 mm. The proximal end pipe 275 is then inserted in the proximal end guide tube 279. The outer surface of the proximal end guide tube 279 is then tied with strings at three positions to sufficiently spread the adhesive throughout the circumference. In this case, a mark is formed on the proximal end pipe 275 at a position corresponding to a dimensional tolerance of ±0.5 mm to clarify the length of a portion to be inserted. The proximal end pipe 275 is inserted in the proximal end guide tube 279 to the position of this mark. After the adhesive is dried, all the strings at the three positions are cut.

When the adhesive on the proximal end guide tube 279, the forceps raising guide pipe 277, and the proximal end pipe 275 is dried, a proximal end coil pipe 281 whose dimensional tolerance of a total length is about ±1 mm is inserted in the proximal end guide tube 279 having the adhesive coated on its portion located on the tube stop pipe 278 side until the proximal end coil pipe 281 is brought into contact with the tying portion 280. As is apparent, the total length of the proximal end coil pipe 281 is set to be smaller than that of the proximal end guide tube 279. An end portion, of the proximal end coil pipe 281, located on the operating portion 1 side is bonded to the proximal end guide tube 279 in the following manner. The proximal end coil pipe 281 with the proximal end guide tube 279 being fitted thereon is looped. The proximal end coil pipe 281 in a looped state becomes shorter, relative to the proximal end guide tube 279, than the proximal end coil pipe 281 in a straight state. As a result, some portion of the proximal end guide tube 279 is exposed. An adhesive is coated on this portion. When the looped state is restored to the straight state, the adhesive is spread over the end portion, of the proximal end coil pipe 281, located on the operating portion 1 side, thus completing the bonding operation. A tying portion 282 is formed at the end face, of the proximal end coil pipe 281, located on the operating portion 1 side to position the proximal end coil pipe 281 with respect to the proximal end guide tube 279. In addition, an adhesive is sufficiently coated between the tube stop pipe 278 and the proximal end coil pipe 281 to firmly fix the proximal end coil pipe 281 to the proximal end guide tube 279.

A distal end guide tube 283 whose total length is larger than a length after a fitting operation by about 20 mm is inserted in a portion, of the forceps raising guide pipe 277, located on the distal end portion 9 side by a length within a range of about ±2 mm with respect to a desired length, and the distal end guide tube 283 is thermally welded to the forceps raising guide pipe 277. The distal end guide tube 283 is cut from the end, of the proximal end guide tube 279, located on the operating portion 1 side with a width tolerance of about ±1 mm with respect to a desired width. In addition, the proximal end pipe 275 is cut from the end, of the distal end guide tube 283, located on the distal end portion 9 side with a width tolerance of about ±0.5 mm with respect to a desired width. By assembling the forceps raising wire guide tube 274 in accordance with the above assembly procedure, the variation in total length can be minimized.

The forceps raising wire guide tube 274 is connected to a guide tube 77 (FIG. 5A) mounted in a distal end portion body 33 in the following manner. After the distal end coil pipe 284 is inserted in the distal end guide tube 283, the distal end guide tube 283 is inserted in the guide tube 77, which has an adhesive sufficiently coated on its entire outer surface, until the distal end guide tube 283 is brought into contact with a distal end body end face 285. The outer surface of the distal end guide tube 283 is tied with strings at three positions to sufficiently spread the adhesive. After the adhesive is dried, the strings are cut except for the string at a tying portion (not shown) on the distal end portion 9 side. Subsequently, an adhesive is coated on the entire outer surface of the tying portion, of the distal end guide tube 283, located on the operating portion 1 side, and a distal end coil pipe 284 is fitted on the distal end guide tube 283 until the distal end coil pipe 284 is brought into contact with the tying portion. In addition, an adhesive is sufficiently coated between the distal end body end face 285 and the distal end coil pipe 284 to firmly fix the distal end coil pipe 284 to the distal end guide tube 283. Furthermore, on the operating portion 1 side of the distal end coil pipe 284, a solder is applied between the distal end coil pipe 284 and the forceps raising guide pipe 277.

The forceps raising wire guide tube 274 is connected to a forceps raising guide tube mouthpiece 121 in the following manner. An adhesive is sufficiently coated on the entire outer surface of the proximal end pipe 275. As shown in FIG. 34, the proximal end pipe 275 is then inserted in the forceps raising guide tube mouthpiece 121 to a position separated from an opening portion 289 by about 0.5 mm judged by the eye. An adhesive is coated between a taper portion 639 and the proximal end pipe 275, and the forceps raising wire guide tube 274 is fixed with an HU screw 290. The adhesive is then dried. With the above operation, the forceps raising wire guide tube 274 can be fitted to the guide tube 77 and the forceps raising guide tube mouthpiece 121 while the variation in dimension in the fitting operation is minimized.

Figure 80:
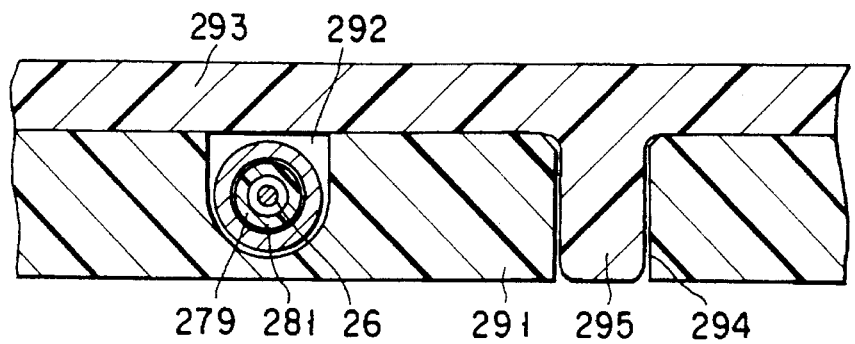
FIG. 80 is a sectional view taken along a line L—L in FIG. 34.
Figure 81:
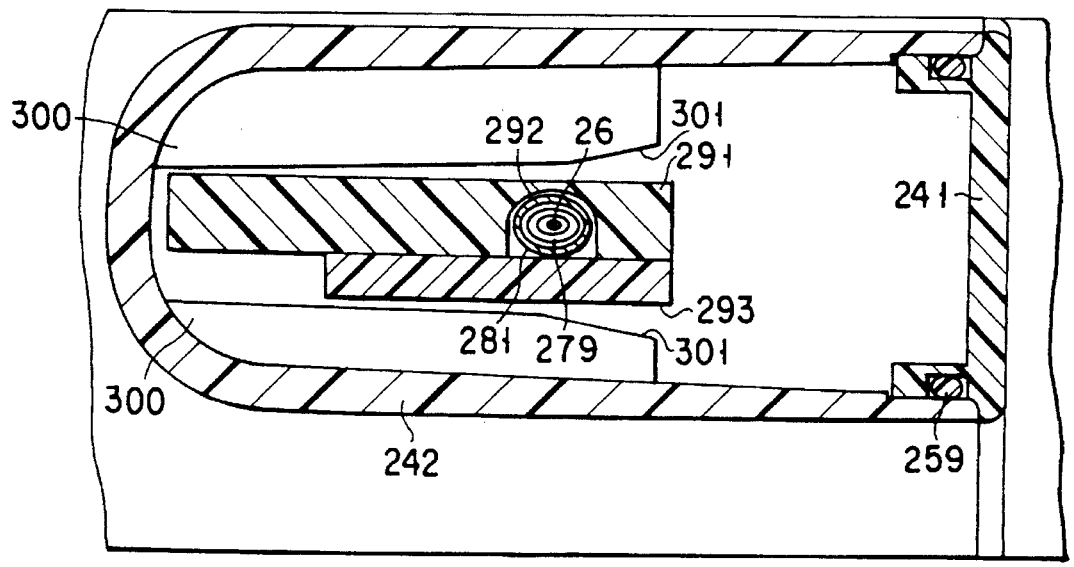
FIG. 81 is a sectional view taken along a line M—M in FIG. 34.
Figure 82:
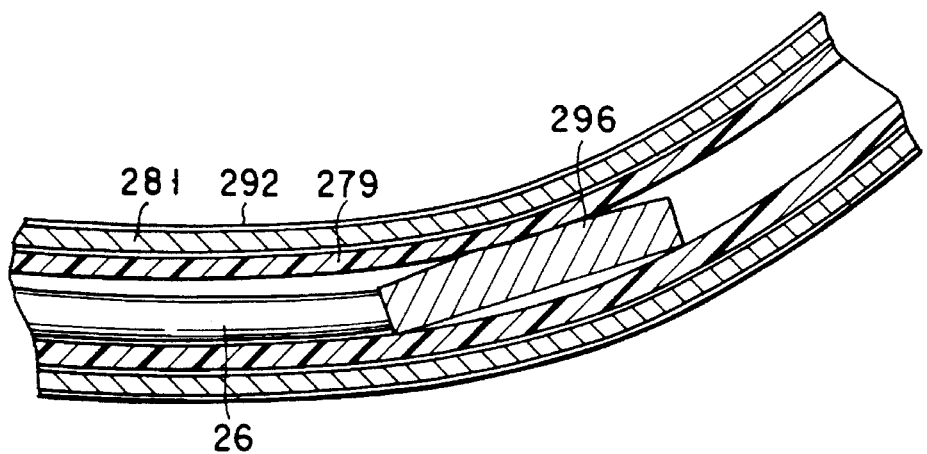
FIG. 82 is an enlarged sectional view showing a state wherein a forceps raising operation wire extends through a forceps raising operation wire guide tube.

The forceps raising wire guide tube 274 is constituted by a flexible member and extends outside a grip portion 2. As shown in FIGS. 34 and 37, a guide plate 291 is disposed in a forceps wire opening portion body 242 to guide the path through which the forceps raising wire guide tube 274 is displaced. A guide path groove 292 is formed in the guide plate 291. The forceps raising wire guide tube 274 is fitted in the guide path groove 292, and a guide plate cover 293 (FIG. 37) is mounted on the guide path groove 292 to prevent the forceps raising wire guide tube 274 from coming out of the guide path groove 292. The guide plate 291 and the guide plate cover 293 are positioned by a fitting hole 294 formed in the guide plate 291 and a fitting projection 295 formed on the guide plate cover 293 (FIG. 80). The guiding radius of the guide path groove 292 formed in the guide plate 291 is set such that the length and outer diameter of a hard portion 296 (FIG. 82) formed on the distal end of a forceps raising wire 26 are set with respect to the inner diameter of the proximal end guide tube 279 to allow the hard portion 296 to extend therethrough.

A method of mounting the guide plate 291 and the guide plate cover 293 will be described below. After the forceps raising guide tube mouthpiece 121 mounted on the forceps raising wire guide tube 274 is fixed to a mouthpiece fixing cover 241, the forceps raising wire guide tube 274 is fitted in the guide path groove 292 of the guide plate 291. In this case, upper and lower bearing portions 297 and 298 of the guide plate 291 are respectively positioned in a direction perpendicular to the plane of FIG. 34 by a mouthpiece bearing portion 299 of the mouthpiece fixing cover 241 and the outer surface of a frame 240. The fitting projection 295 of the guide plate cover 293 is fitted in the fitting hole 294 of the positioned guide plate 291 to clamp the forceps raising wire guide tube 274 between the guide plate 291 and the guide plate cover 293. In this state, the forceps wire opening portion body 242 is mounted on the mouthpiece fixing cover 241 from the insertion portion 3 side. The forceps wire opening portion body 242 has press portions 300 for clamping the guide plate 291 and the guide plate cover 293 to position them in a direction perpendicular to the drawing surface of FIG. 34. In addition, introducing portions 301 (FIGS. 37 and 81) are formed on the press portions 300 on the operating portion 1 side to facilitate introduction of the guide plate 291 and the guide plate cover 293.

Figure 83:
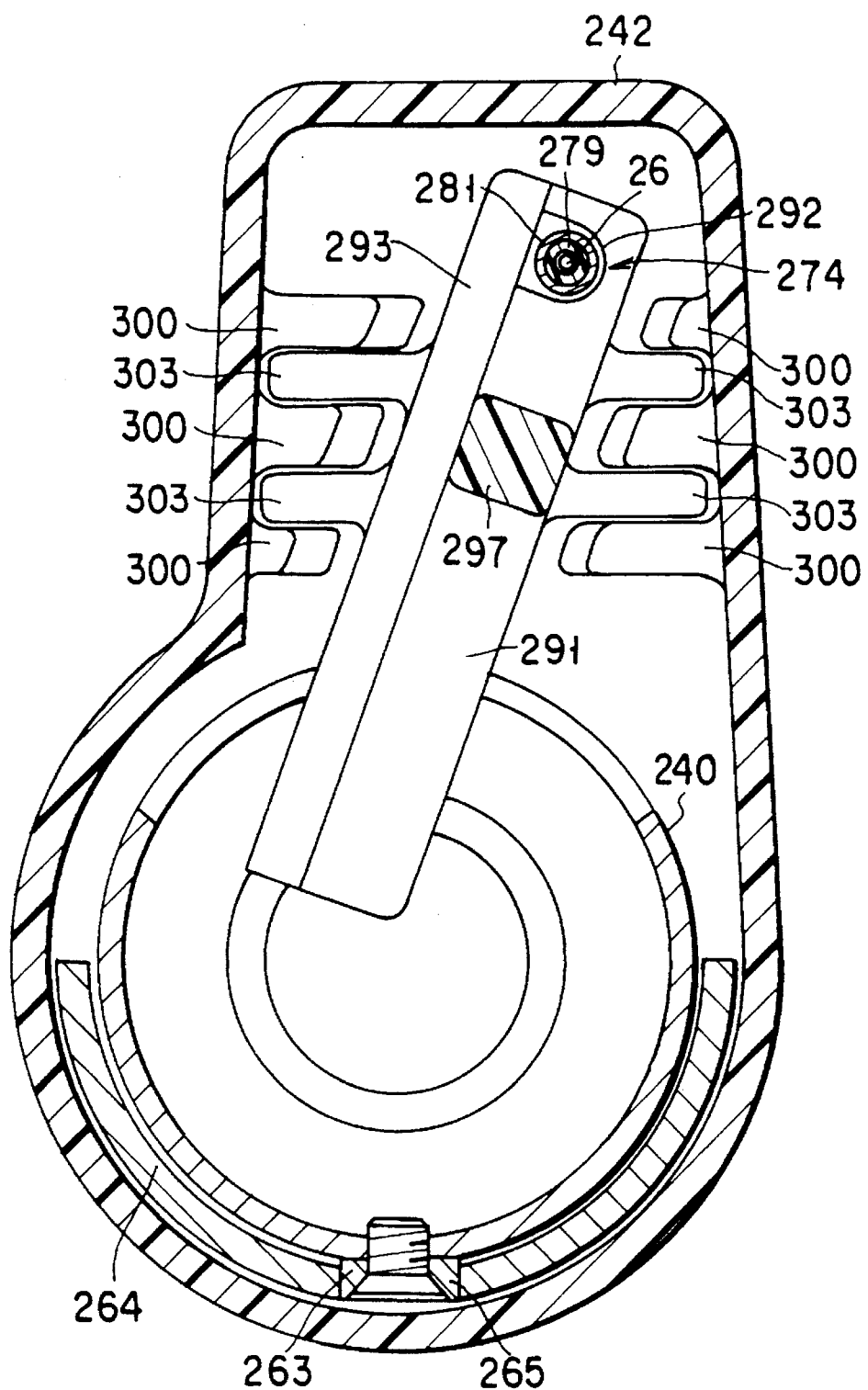
FIG. 83 is a sectional view taken along a line I—I in FIG. 34, in which the lock projection of a guide plate is added.
Figure 84A:
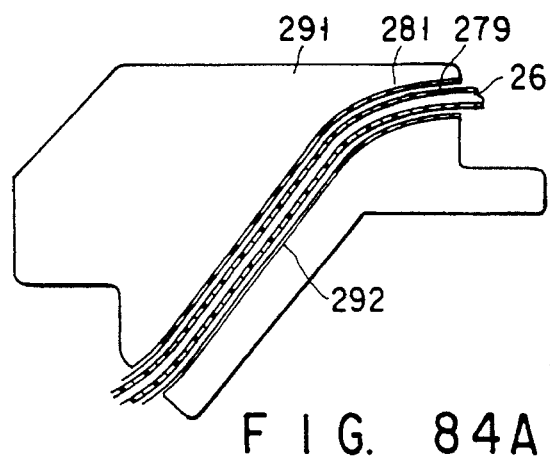
FIGS. 84A to 84C show modifications of the guide plate and a guide plate cover.
Figure 84B:
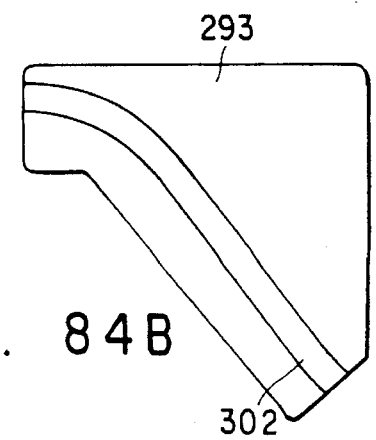
Figure 84C:
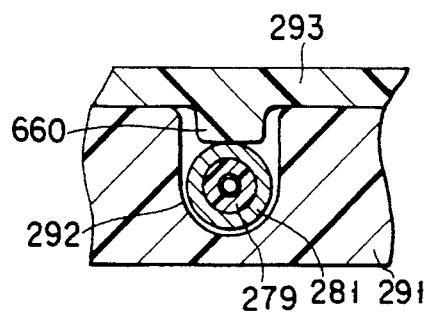

Note that the end portion, of the guide path groove 292 of the guide plate 291, located on the insertion portion 3 side extends to a limit at which interference of the components incorporated in the insertion portion 3 can be avoided and a bent state of the forceps raising wire guide tube 274 can be protected. A groove opening portion 302, of the guide path groove 292 of the guide plate 291, located on the insertion portion 3 side is positioned to conform to all endoscopes having forceps raising mechanisms and also correspond to one of the endoscopes having the forceps raising mechanisms which has the insertion portion 3 with the minimum inner diameter so as to minimize meandering of the forceps raising wire guide tube 274 in the insertion portion 3. In addition, the shapes of the groove opening portion 302 of the guide plate 291 and the press portions 300 of the forceps wire opening portion body 242 are determined (FIG. 37) such that the groove opening portion 302 is located at substantially the same position as that of the guide tube 77 (FIG. 5A) for guiding the forceps raising wire 26 in the distal end portion 9. Positioning means for the guide plate 291 and the guide plate cover 293 may be positioned as follows. As shown in FIG. 83, lock projections 303 are respectively formed on the guide plate 291 and the guide plate cover 293, and positioning is performed by fitting the lock projections 303 in the press portions 300 of the forceps wire opening portion body 242. In addition, as shown in FIG. 18, the guide plate 291 and the guide plate cover 293 may be positioned by forming a guide path projection 620 having substantially the same shape as that of the guide path groove 292 of the guide plate 291 on the guide plate cover 293, instead of using the fitting hole 294 and the fitting projection 295.

As described above, in the endoscope in which the position of the flexible forceps raising wire guide tube 274 having the forceps raising wire 26 inserted therein on the operating portion 1 side is displaced with respect to the position of the forceps raising wire guide tube 274 on the insertion portion 3 side, since a guide means is arranged in the displacing portion, and the forceps raising wire guide tube 274 is flexible, good assembly operability can be obtained. In addition, since the guide plate 291 has a means for guiding the displacement path, no special means needs to be arranged in the forceps raising wire guide tube 274 itself. Therefore, the same insertion portion outer diameter as that in a conventional endoscope can be maintained. In addition, in a cleaning operation, the forceps raising wire 26 is removed, and a syringe containing a detergent solution is mounted on a syringe taper projection 267 (FIG. 36) of the forceps raising guide tube mouthpiece 121, thus cleaning the forceps raising wire guide tube 274. With this operation, cleaning can be easily and simply performed. Note that a syringe taper recess may be used instead of the syringe taper projection 267.

The arrangement of a connecting portion 29 disposed on the insertion portion 3 side of a driving shaft 28 will be described next with reference to FIGS. 51, 52, and 85.

A wire press portion body 338 is threadably engaged with a connecting portion body 337 of the driving shaft 28, and a wire guide portion 339 for guiding the forceps raising wire 26 is fixed to the connecting portion body 337 with a set screw 340. A removal preventing member 342 for preventing removal of the wire press portion body 338 inserted in a groove 341 formed in the connecting portion body 337 is fixed by the wire guide portion 339 so as not to be removed.

The forceps raising wire 26 is fixed as follows. The forceps raising wire 26 is inserted in the wire guide portion 339 until it is brought into contact with an abutment portion 343 of the wire guide portion 339. The wire press portion body 338 is then rotated to cause a wire press portion 344 to press/deform the forceps raising wire 26, thereby fixing the forceps raising wire 26. In this case, in FIG. 51, a detachable distal end portion 93 (FIG. 4A) is mounted on the distal end portion 9 while a forceps raising lever 27 is rotated in the direction of inversion until a base seat 31 is brought into contact with a stopper plate 325. Thereafter, a jig for inverting a forceps raising base 36 is mounted on the distal end portion 9. With this operation, as described above, since a variation in the total length of a forceps raising wire guide tube 274 is minimized, if a variation in the total length of the forceps raising wire 26 is minimized, the forceps raising wire 26 is naturally brought into contact with the abutment portion 343 of the wire guide portion 339. In an inverted state, since the connecting portion 29 and the forceps raising guide tube mouthpiece 121 are located closest to each other, a space corresponding to about two fingers of an operator is formed between the connecting portion 29 and the forceps raising guide tube mouthpiece 121 in this state to allow easy insertion of the forceps raising wire 26.

The wire guide portion 339 has a first wire guide portion 345 and a second wire guide portion 346. A first guide opening portion 347 of the first wire guide portion 345 is made to be large to allow an operator to easily insert the forceps raising wire 26 in the wire guide portion 339. A second guide opening portion 600 of the second wire guide portion 346 is made to be small and the angle of its taper portion is made to be acute to prevent the forceps raising wire 26 from being abruptly bent. The removal preventing member 342 is clamped between a removal preventing engaging portion 601 of the wire press portion body 338 and the wire guide portion 339 to regulate the movement of the removal preventing member 342. In addition, since the removal preventing engaging portion 601 is always engaged with the removal preventing member 342, the movement of the removal preventing member 342 is regulated in a direction perpendicular to the clamping direction.

In order to facilitate the process of forming the connecting portion body 337, a threaded portion 602 for the wire press portion body 338 and a threaded portion 603 for the set screw 340 are formed coaxially, i.e., processed at once. The forceps raising wire 26 has a hard portion 296 as a portion to be pressed/deformed. The relationship between the outer diameter of the wire press portion 344 of the wire press portion body 338 and the total length of the hard portion 296 of the forceps raising wire 26 is expressed by (outer diameter of wire press portion 344)<(total length of hard portion 296). In order to reduce the size of the connecting portion 29, no rotation means (e.g., knurled portion) is formed on the wire press portion body 338, but a rotation engaging projection 604 is formed, in which a rotation means is engaged to be rotated.

Figure 85:
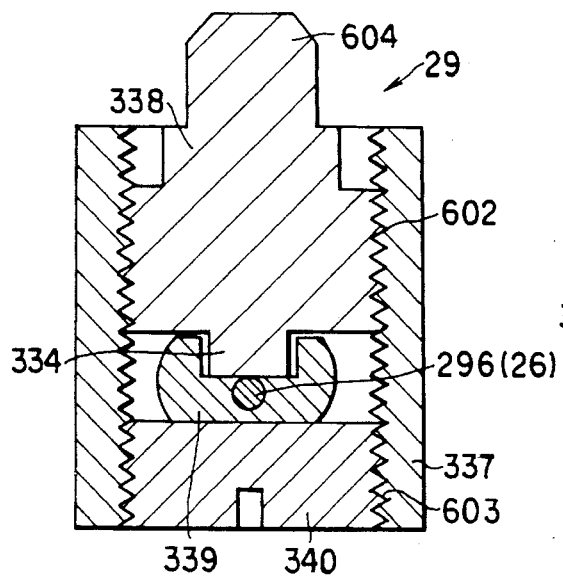
FIG. 85 is a sectional view showing a modification of the connecting portion between the driving shaft and the forceps raising operation wire.
Figure 86:
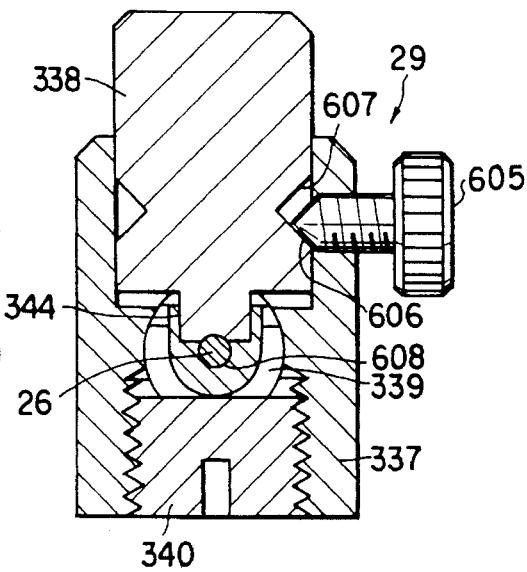
FIG. 86 is a sectional view showing still another modification of the connecting portion.

FIG. 86 is a sectional view showing a modification of the arrangement of the connecting portion 29 in FIGS. 51, 52, and 85. A taper portion 606 of a rotating screw 605 is brought into contact with a taper portion 607 of a wire press portion body 338. With this structure, the wire press portion body 338 is vertically moved by reciprocating the rotating screw 605. A wire bearing portion 608 and a wire press portion 344, which are used for a forceps raising wire 26, may have the shapes shown in FIGS. 87A to 87D. Each of these shapes is designed to fix the forceps raising wire 26 by making it have a circular profile cross-section.

A connecting portion 29 has an insulating protective cover 609 detachably mounted on an operating portion 1 (FIG. 1). The protective cover 609 serves to protect the connecting portion 29. The protective cover 609 is fixed as follows. A positioning projection 611 of the protective cover 609 is inserted in a positioning hole 610 formed in a driving shaft opening portion 25, and the protective cover 609 is pushed into the driving shaft opening portion 25 toward the operating portion 1 side. A syringe taper recess 613 of the protective cover 609 is then fitted on a syringe taper projection 612 formed on a forceps raising guide tube mouthpiece 121 shown in FIG. 51, thus fixing the protective cover 609.

Figure 88:
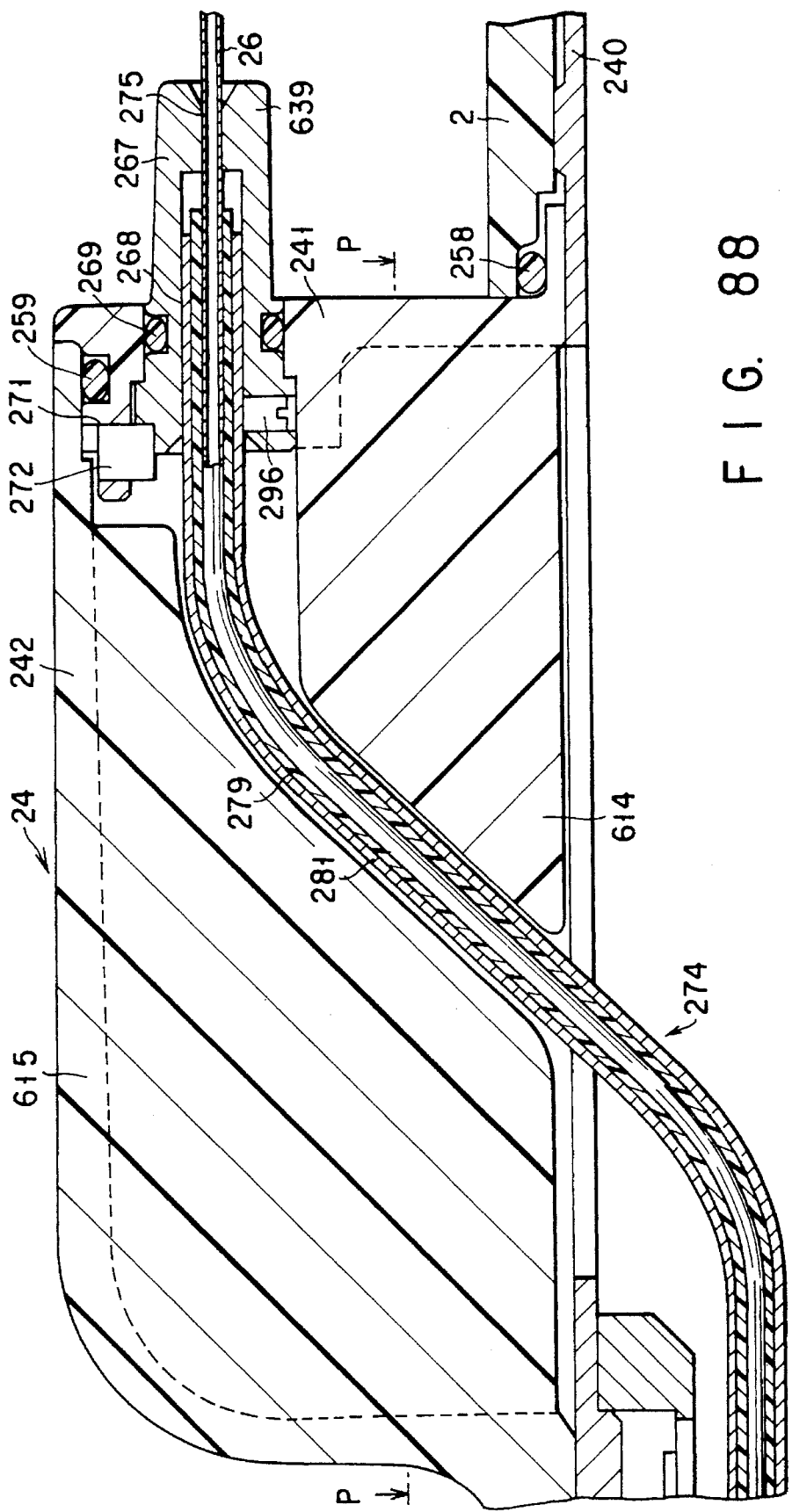
FIG. 88 is a sectional view showing the details of a modification of the forceps raising operation wire opening portion.

FIGS. 88 and 89 show the thirty-ninth embodiment of the present invention. FIG. 88 is a sectional view showing the details of a forceps raising wire opening portion 24. FIG. 89 is a sectional view taken in the direction indicated by the arrow along a line P—P in FIG. 88.

In this embodiment, as a means for displacing a forceps raising wire guide tube 274, the casing of the forceps raising wire opening portion 24 itself is used. The mouthpiece fixing cover 241 has guide projections 614 constituting a displacement path of the forceps raising wire guide tube 274. After a forceps raising guide tube mouthpiece 121 is fixed to the mouthpiece fixing cover 241, the forceps raising wire guide tube 274 is caused to extend between the two guide projections 614. In this state, a forceps wire opening portion body 242 is fitted in the mouthpiece fixing cover 241. With this operation, since the forceps raising wire guide tube 274 is pressed by a press projection 615 formed on the forceps wire opening portion body 242, the forceps raising wire guide tube 274 is fixed to a desired position.

Figure 90A:
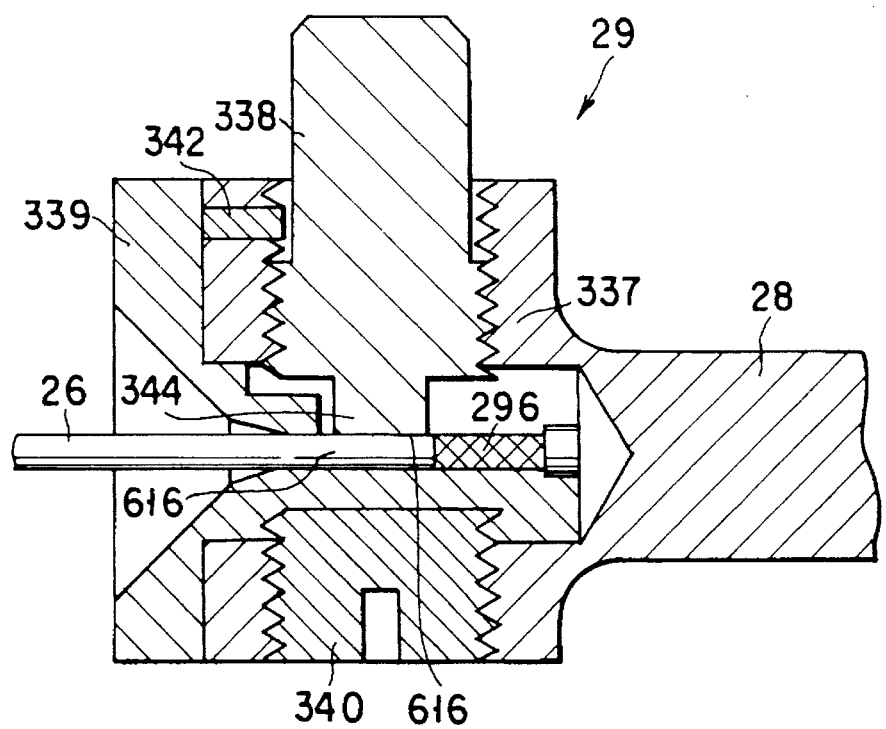
Figure 90B:
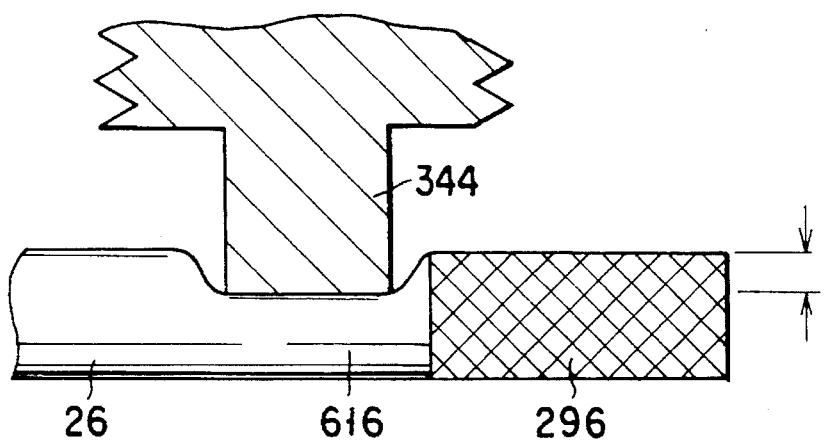

FIGS. 90A and 90B show a modification of the arrangement of the connecting portion 29 in the thirty-eighth embodiment.

FIG. 90A is a sectional view of a connecting portion 29. FIG. 90B is an enlarged sectional view showing a forceps raising wire 26 in a pressed state. In the thirty-eighth embodiment, the forceps raising wire 26 is fixed by pressing the wire portion 344 against the hard portion 296 of the forceps raising wire 26 to deform the hard portion 296 (see FIG. 51). If the hard portion 296 is too hard, the hard portion 296 may not be sufficiently deformed upon pressing by the wire press portion 344, and sufficient tensile resistance may not be obtained.

As shown in FIG. 90A, therefore, instead of the hard portion 296, a hard portion 616 is formed as a portion for pressing the forceps raising wire 26, and a hard portion 296 is formed on the opposite side to the side where a tension is applied. With this arrangement, when the forceps raising wire 26 is pressed by the wire press portion 344, the hard portion 616 is considerably deformed to form a stepped portion as a hook portion between the hard portion 616 and the hard portion 296. As a result, the forceps raising wire 26 is not easily removed and hence can be firmly fixed.

FIGS. 91A to 92B show other examples of the fixing structure of the mouthpiece fixing cover 241 in FIG. 34.

In the example shown in FIGS. 91A and 91B, rotation preventing projections 618 of a mouthpiece fixing cover 241 are fitted in rotation preventing recesses 617 formed in a frame 240, thus preventing rotation of the mouthpiece fixing cover 241. In addition, the mouthpiece fixing cover 241 is clamped/fixed between a grip portion 2 and a stopper ring 620 threadably engaged with a threaded portion 619 formed on the frame 240, thus preventing removal of the mouthpiece fixing cover 241. According to this structure, however, since a rotation preventing operation and a removal preventing operation must be independently performed, an assembly operation is complicated.

In the example shown in FIGS. 92A and 92B, therefore, a rotation preventing portion 621 and a removal preventing portion 622 are provided for a mouthpiece fixing cover 241. After the mouthpiece fixing cover 241 is fitted in a frame 240, a set screw 623 is threadably engaged with a screw hole 624 formed in the frame 240. In this case, the set screw 623 is in contact with both the rotation preventing portion 621 and the removal preventing portion 622 of the mouthpiece fixing cover 241. That is, rotation and removal of the mouthpiece fixing cover 241 can be prevented by fitting only one component, i.e., performing only one operation, thereby eliminating the difficulty in the assembly operation. Note that this example can be applied to not only fixing of the mouthpiece fixing cover 241 but also all casings requiring prevention of rotation and removal.

Figure 93:
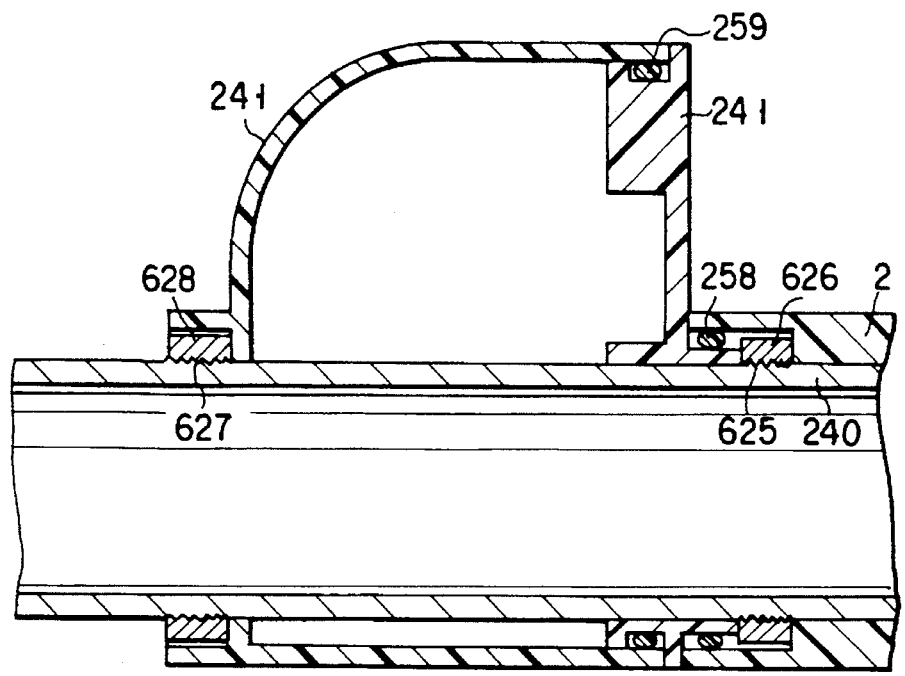
FIG. 93 is a sectional view showing an example of the fixing structure of a grip portion, the mouthpiece stationary cover, and a forceps raising operation wire opening portion body.
Figure 94:
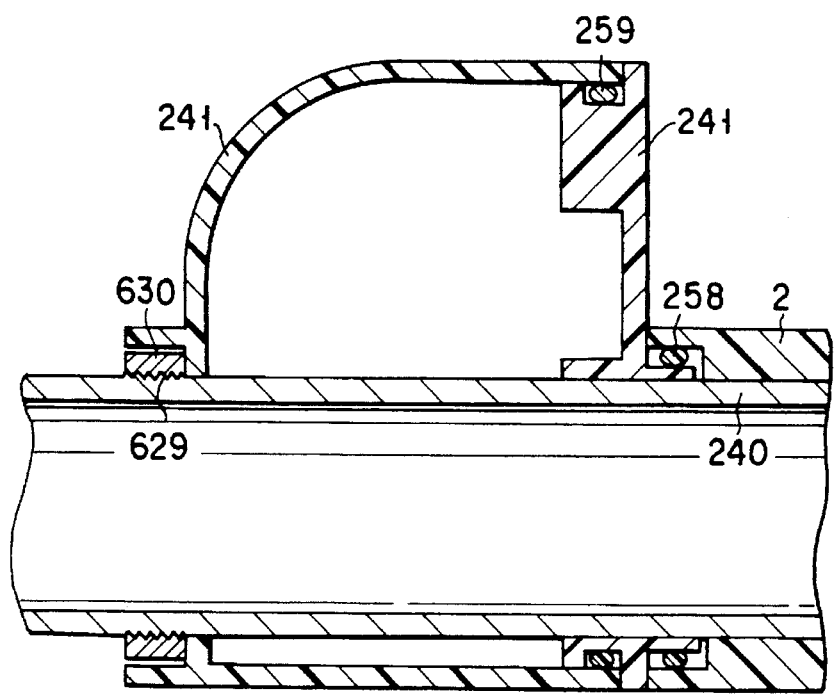
FIG. 94 is a sectional view showing another example of the fixing structure of the grip portion, the mouthpiece stationary cover, and the forceps raising operation wire opening portion body.

FIG. 93 is a sectional view showing an example of the fixing structure of a grip portion 2, a mouthpiece fixing cover 241, and a forceps wire opening portion body 242. FIG. 94 is a sectional view showing another case of the fixing structure.

In the case shown in FIG. 93, the grip portion 2 is clamped/fixed between an operating portion body 99 (FIG. 1) and a first threaded portion 625 formed on a frame 240. The mouthpiece fixing cover 241 and the forceps wire opening portion body 242 are clamped/fixed between the grip portion 2 and a second stopper ring 628 threadably engaged with a second threaded portion 627 formed on the frame 240.

If, however, this structure is employed, two fixing members are required to fix three casings. For this reason, a complicated operation is required, and the number of components increases, resulting in an increase in cost.

In the example shown in FIG. 94, a grip portion 2, a mouthpiece fixing cover 241, and a forceps wire opening portion body 242 are clamped/fixed between an operating portion body 99 and a stopper ring 630 threadably engaged with a threaded portion 629 formed on a frame 240. That is, a plurality of casings such as the grip portion 2, the mouthpiece fixing cover 241, and the forceps wire opening portion body 242 can be fixed with one fixing member, thereby eliminating the difficulty in the fixing operation. In addition, since only one fixing member is required, the number of components can be reduced.

A modification of the connecting structure of the tube 631 and the pipe 632 which has been described with reference to FIG. 38 will be described with reference to FIGS. 95 to 97.

FIG. 95 shows a conventional structure for connecting a tube 631 and a pipe 632. In this structure, after an adhesive is coated on the entire outer surface of the pipe 632, and the tube 631 is fitted thereon, the tube 631 is tied and fixed with a string. A reinforcing adhesive is coated on a tying portion 633 to prevent the string from being loosened. In this method, however, since positioning of the tube 631 is performed by an operator upon judgement by the eye, a variation in the length of the overlapping portion between an end of the pipe 632 and an end of the tube 631 is large. In addition, since the reinforcing adhesive leaks out of the tying portion 633, a satisfactory bonding operation is not performed.

As shown in FIG. 96, therefore, a tube stopping tube 634 is soldered to a pipe 632 at a desired position, and an adhesive is coated on the entire outer surface of the pipe 632. Thereafter, a tube 631 is fitted on the pipe 632 until it is brought into contact with the tube stopping tube 634, and is tied/fixed with a string. A reinforcing adhesive is coated on the tying portion 633 to prevent the string from being loosened. With this tube connecting operation, the operator who connects the tube can connect the tube 631 with an accurate length of the overlapping portion between an end portion of the pipe 632 and an end portion of the tube 631 by only bringing the tube 631 into contact with the tube stopping tube 634. Therefore, the variation in the length of the overlapping portion is small. In addition, an adhesive receiving portion 635 for preventing leakage of an adhesive is formed by a stepped portion between the tube stopping tube 634 and the tube 631. Therefore, leakage of the adhesive can be prevented.

FIG. 97 shows another modification of the connection structure of the tube and the pipe. A tube stopping portion 636 is formed on a pipe 632, and a tube 631 is fitted on the pipe 632 until the tube 631 is brought into contact with the tube stopping portion 636. Thereafter, the tube 631 is connected to the pipe 632. With this structure, the same effects as those of the structure shown in FIG. 96 can be obtained. In addition, since the tube stopping portion 636 is formed on the pipe 632 by a mechanical process, a variation in the position of the tube stopping portion 636 is small. Hence, a variation in the length of the overlapping portion between an end portion of the pipe 632 and an end portion of the tube 631 can be suppressed to a small value.

Figure 98:
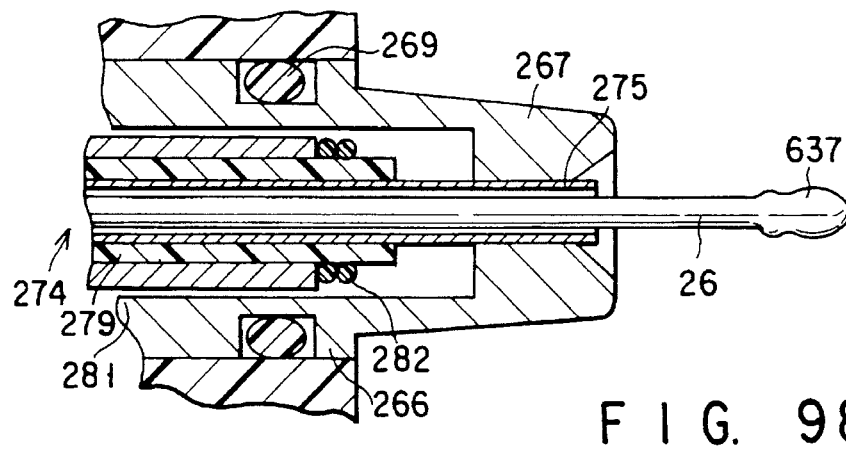
FIG. 98 is a sectional view showing a modification of the forceps raising operation wire guide tube.

FIG. 98 is a sectional view showing a modification of the structure of the forceps raising wire guide tube 274. In an endoscope in which a forceps raising base 36 to which a forceps raising wire 26 is connected is detachably mounted in a distal end portion 9 and is fixed to the end, of the forceps raising wire 26, located on the operating portion 1 side upon deformation by pressing, if the forceps raising wire 26 is removed from the distal end portion 9 of the endoscope while the forceps raising wire 26 is pressed/deformed, the inner surface of a forceps raising wire guide tube 274 may be damaged by the deformed portion.

In order to prevent this, the inner diameter of a proximal end pipe 275, through which a pressed/deformed portion 637 of the forceps raising wire 26 passes first, is set to be slightly larger than the outer diameter of the forceps raising wire 26 and allow the forceps raising wire 26 to pass through the forceps raising wire guide tube 274 without damaging the inner surface of the forceps raising wire guide tube 274.

Assume that the pressed/deformed portion 637 of the forceps raising wire 26 passes through the proximal end pipe 275. In this case, if the maximum diameter of the pressed/deformed portion 637 is larger than the inner diameter of the proximal end pipe 275, the outer diameter of the pressed/deformed portion 637 is made to be smaller than the inner diameter of the proximal end pipe 275. Therefore, the pressed/deformed portion 637 does not damage the inner surface of the forceps raising wire guide tube 274.

Figure 99:
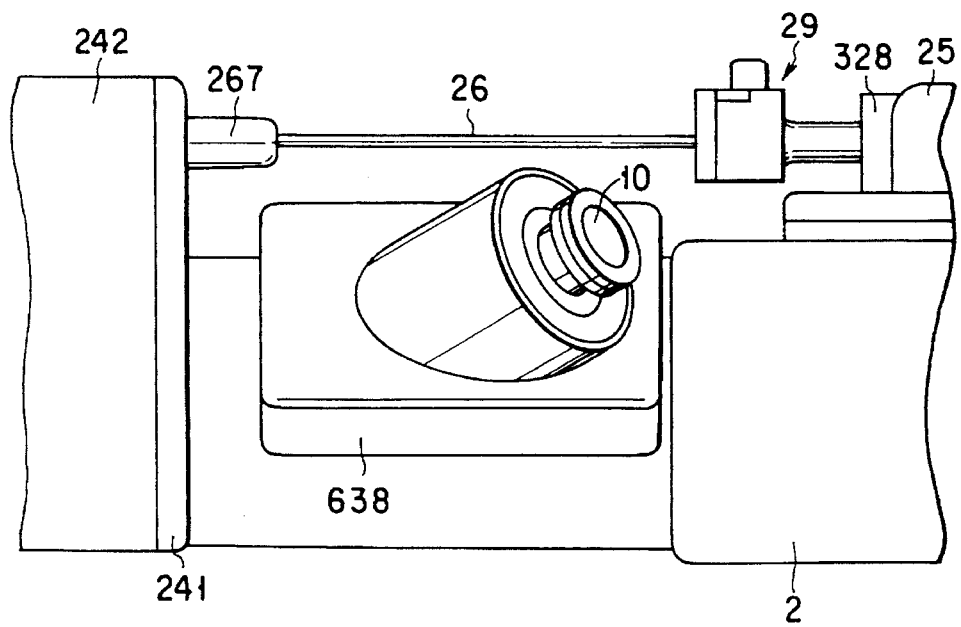
FIG. 99 is a view showing a forceps raising operation wire opening portion body and its modification.
Figure 100:
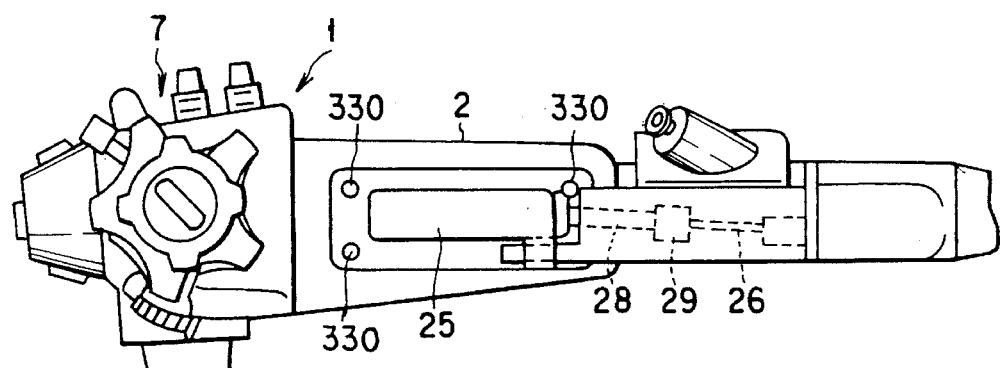
FIG. 100 is a view showing a portion of FIG. 1.

FIG. 99 shows a modification of the arrangement of the forceps wire opening portion body 242 and the forceps opening portion body 638. FIG. 100 shows the main part of the endoscope shown in FIG. 1. As shown in FIG. 100, in an endoscope having a connecting portion 29 of a forceps raising wire 26 outside an operating portion 1, a forceps wire opening portion body 242, which is a portion through which a forceps raising wire guide tube 274 extends outside, and a forceps opening portion body 638 considerably protrudes from the operating portion 1. If, therefore, these two components are formed on the same circumference, the operating portion 1 considerably increases in size. Such an increase in size cannot be allowed in terms of operability and outer appearance. Under the circumstances, only a means for forming both the connecting portion 29 of the forceps raising wire 26 and the forceps opening portion body 638 on the outer surface of the endoscope is to form the forceps wire opening portion body 242 and the forceps opening portion body 638 in a line. If the forceps wire opening portion body 242 is formed on the operating portion 1 side, the forceps opening portion body 638 is located apart from the operating portion 1, resulting in a deterioration in operability associated with insertion of an instrument. In addition, since the stroke of the connecting portion 29 is added to the lengths of the forceps wire opening portion body 242 and the forceps opening portion body 638, the total length of the operating portion 1 increases.

As shown in FIG. 99, therefore, the forceps opening portion body 638 is arranged between the operating portion 1 and the stroke of the connecting portion 29, and the forceps wire opening portion body 242 is arranged on the insertion portion 3 side of the forceps opening portion body 638. With this position of the forceps opening portion body 638, the operability associated with insertion of an instrument can be maintained at the same level as in an endoscope incorporating a forceps raising mechanism, and the total length of the operating portion 1 can be reduced to the minimum.

FIGS. 101 and 102 show the arrangement of the operating portion 1. FIG. 101 is a view taken in the axial direction. FIG. 102 is a side view. In an endoscope having a connecting portion 29 of a forceps raising wire 26 outside the operating portion 1, a driving shaft 28 is disposed on an angle knob 7 side. A driving shaft opening portion 25 mounted on a grip portion 2 with a screw 330 has the minimum width, length, and height, except for a portion otherwise required in consideration of a function. Since a forceps raising mechanism protruding to the outside is arranged on the angle knob 7 side, the operating portion 1 can be held without any interference from the mechanism. Since the dimensions of the driving shaft opening portion 25 are minimized, an operation can be performed without any interference, thus preventing a deterioration in operability. In addition, a portion, of the driving shaft opening portion 25, located on the upper side on the drawing surface of FIG. 102 may be made to be substantially parallel to the grip portion 2 to allow the operator to easily hold his/her finger on the driving shaft opening portion 25.

Figure 103A:
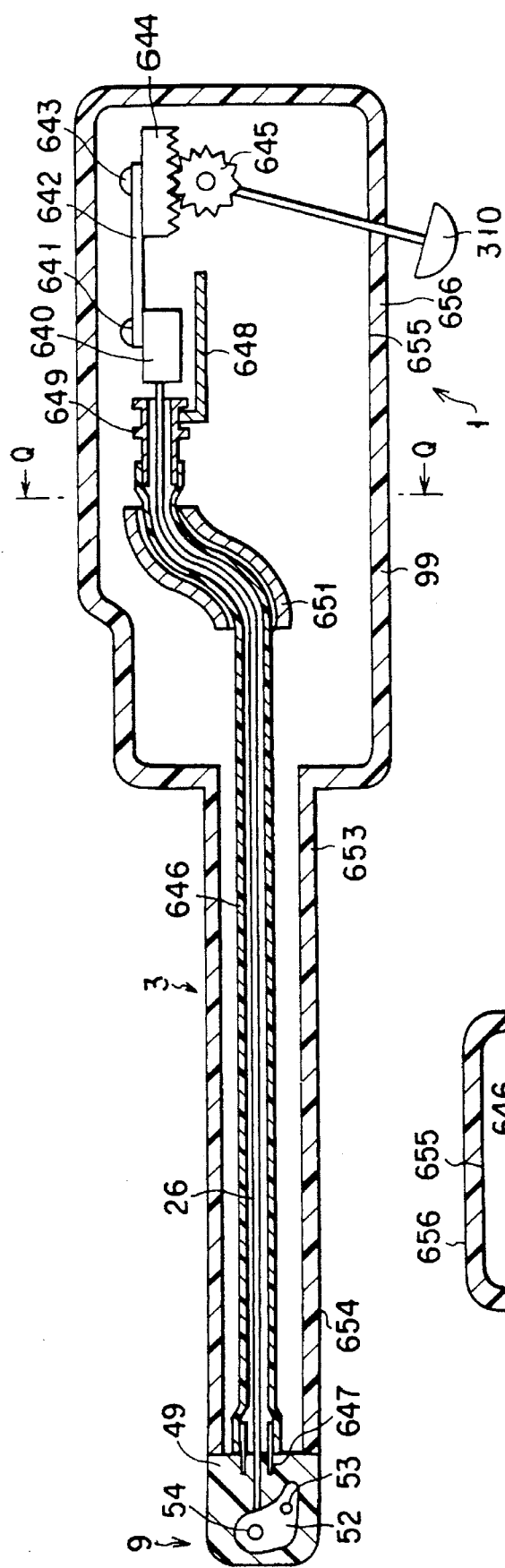
Figure 103B:
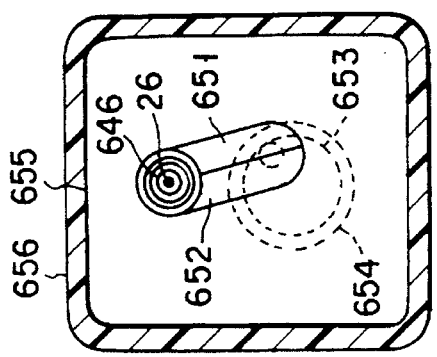

FIGS. 103A and 103B show the fortieth embodiment of the present invention. FIG. 103A is a sectional view taken in the axial direction. FIG. 103B is a sectional view taken in the direction indicated by the arrows along a line Q—Q in FIG. 103A. In the above embodiment, the position of the flexible forceps raising wire guide tube 274, in which the forceps raising wire 26 is inserted, on the operating portion 1 side is displaced with respect to its position on the insertion portion 3 side so as to cause the forceps raising wire guide tube 274 to extend outside the operating portion 1. In this embodiment, the position of a forceps raising wire guide tube 274 on the operating portion 1 side is displaced, within a operating portion 1, with respect to its position on the insertion portion 3.

A forceps raising base 36 is mounted on a distal end portion body 33, and the forceps raising wire 26 is mounted on the forceps raising base 36 via a tip 38. When the forceps raising wire 26 is reciprocated by rotating a knob portion 310, the forceps raising base 36 is pivoted about a raising shaft 39 to be raised/inverted. The forceps raising wire 26 is pressed/fixed against/to a connecting portion 640 arranged in an operating portion body 99 of the operating portion 1, and the connecting portion 640 is connected to a rack portion 644 via a link arm 642. With this structure, when a pinion portion 645 engaged with the rack portion 644 is rotated by using the knob portion 310, the forceps raising wire 26 is reciprocated. In addition, a forceps wire guide tube 246 for guiding the forceps raising wire 26 is arranged in the insertion portion 3 in such a manner that an end portion located on the distal end portion 9 side is connected to a distal end mouthpiece 247 mounted on the distal end portion body 33, and an end portion located on the operating portion 1 side is connected to a distal end mouthpiece 249 mounted on a fixing member 248 in the operating portion body 99. Since a driving rod 250 is made to have a long arm to reduce the required raising force, the distal end mouthpiece 249 is located at an upper position on the drawing surface of FIG. 40 and is displaced from the position of the distal end mouthpiece 247. For this reason, a guide A 651 and a guide B 652 are arranged on this displaced portion to guide the displacement. The guide A 651 and the guide B 652 are fixed with an adhesive.

As is apparent from the above description, according to the thirty-eighth to fortieth embodiments, the position of the forceps raising wire guide tube, in which the forceps raising wire is inserted, on the operating portion side is displaced with respect to the position of the forceps raising wire guide tube on the insertion portion side, and the guide means for almost fixing the displaced portion of the forceps raising wire guide tube are arranged. With this structure, since the forceps raising wire guide tube is flexible, good assembly operability can be ensured. In addition, since only the guide means is required to be formed at the displaced portion of the forceps raising wire guide tube, no special treatment is required for the forceps raising wire guide tube itself. Therefore, the outer diameter of the insertion portion can be maintained at the same diameter as that of a conventional endoscope. In addition, a satisfactory cleaning operation can be performed by only removing the forceps raising base and the forceps raising wire. That is, a cleaning operation is facilitated.

FIG. 104 shows the structure of the distal end portion of an endoscope in which each lock piece 693 of a detachable cover 768 can be fitted in a corresponding recess groove 772, formed in the bottom portion of a stationary cover 769, upon elastic deformation. The detachable cover 768 can be easily removed by breaking only the lock piece 693.

Referring to FIG. 104, reference numeral 659 denotes a mouthpiece pipe through which a forceps raising wire 26 extends; 734, a distal end portion body; 752, a CCD connected to a conductive line (not shown) extending to a video processor 15 (FIG. 1); and 757, the mouthpiece of a channel through which an instrument extends.

This endoscope distal end portion has the following advantages over a conventional distal end portion.

Unlike a conventional method of manually removing a distal end cover, the hands of the operator of this endoscope are not contaminated, and are free from damage in breaking the distal end cover.

In the removing method of the embodiment, no large force is required, and there is no possibility that the parts in the distal end portion are damaged, unlike the conventional method of breaking a distal end cover by clamping it with a pair of pliers.

In addition, since no screw is used to fix the distal end cover, there is no possibility that small screws are lost or loosened in a living body.

According to the endoscope distal end portion shown in FIG. 104, however, if the end portion of the lock piece 693 is made to protrude from the outer diameter of the distal end portion to allow easy breakage of the lock piece 693, a body wall may be damaged by the end portion of the lock piece 693 when the endoscope is inserted in a living body.

FIGS. 105A to 115B show the forty-first embodiment of the present invention, which has an endoscope distal end cover which can solve this problem and allows a detachable cover to be easily and reliably attached/detached to/from the endoscope distal end portion.

Figure 105D:
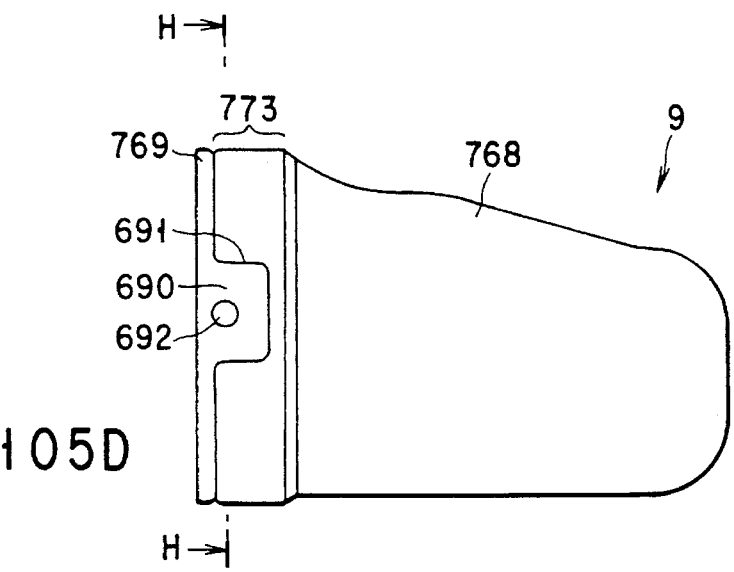

FIGS. 105A to 105D show the arrangement of a distal end portion 9 in an assembled state. FIG. 105A is a partially cutaway side view of the distal end portion 9. FIG. 105B is a view taken from the direction indicated by an arrow J in FIG. 105A. FIG. 105C is a sectional view taken from the direction indicated by the arrows along a line H—H in FIG. 105D. FIG. 105D is a side view of the opposite side of the distal end portion 9 to that shown in FIG. 105A.

A plurality of ribs 688 radially extend from a bottom portion 770 of a stationary cover 769. In addition, recess groove portions 689 are formed in a distal end portion body 734 to be fitted on the ribs 688, thereby regulating the rotational movement of the distal end portion body 734 and the stationary cover 769. A projection 690 (FIG. 105D) having a diameter substantially equal to or smaller than the outer diameter of the stationary cover 769 radially protrudes from the bottom portion 770 of the stationary cover 769. The projection 690 is fitted in a fitting groove portion 691 formed in a bottom portion 773 of a detachable cover 768 and serves to regulate the rotational movement of the stationary cover 769 and the detachable cover 768 together with a rectangular projection 682 formed on the distal end portion of the stationary cover 769 and an engaging hole 683 (FIG. 106B) formed in the detachable cover 768. With this structure, removal of the detachable cover 768 in an examination using the endoscope can be prevented. Note that a pin 686 fitted in the distal end portion body 734 is disposed in the projection 682.

The fitting groove portion 691 of the detachable cover 768 is formed in a rigid portion on the opposite side to a notched portion 777 (FIG. 105A). A reinforcing pin 692, which is inserted in the distal end portion body 734, is inserted in the projection 690 of the stationary cover 769. An engaging piece 693 (C-shaped piece) of the detachable cover 768 is elastically deformed and fitted in a recess groove 772 formed in the bottom portion 770 of the stationary cover 769. A partial large-diameter portion 722 is formed around the recess groove 772 of the stationary cover 769 along the end portion of the lock piece 693. The outer diameter of the large-diameter portion 722 is larger than the diameter of the lock piece 693 in a state wherein the lock piece 693 is kept engaged with the recess groove 772. For this reason, there is no possibility that the membrane of a body cavity is caught by the lock piece 693 during an examination using the endoscope.

Reference numeral 746 denotes a light guide fiber bundle for guiding illumination light from a light source unit (FIG. 1). The light guide fiber bundle 746 is fixed to the distal end portion body 734 with an adhesive filling a notched portion of the distal end portion body 734. This notched portion is covered with an adhesive cover 748. Reference numeral 762 denotes a guide tube which is formed in the distal end portion body 734 and through which a forceps raising wire 26 is caused to extend.

Figure 106A:
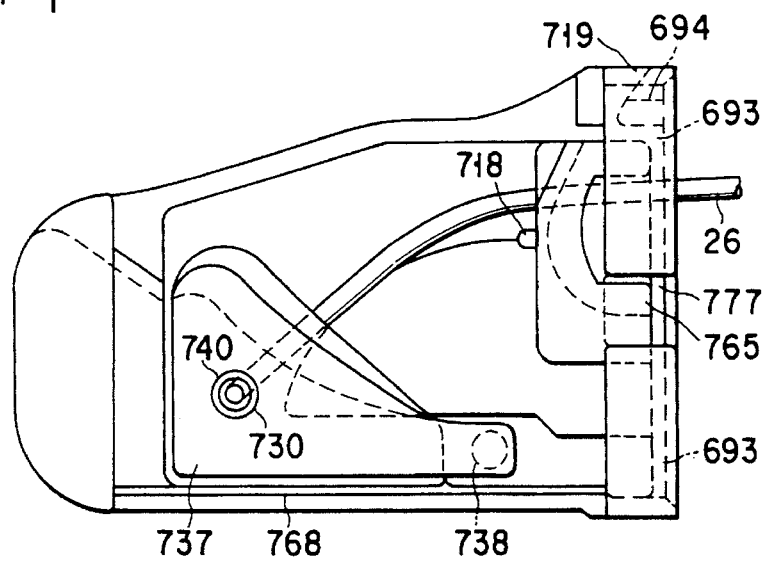
Figure 106B:
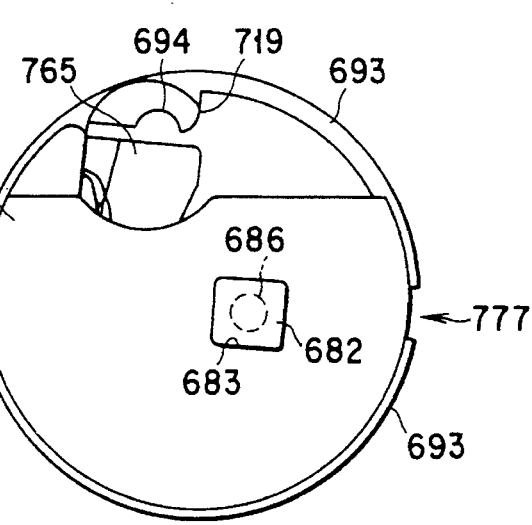
Figure 106C:
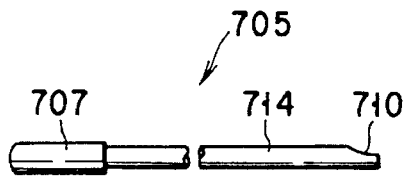
Figure 107:
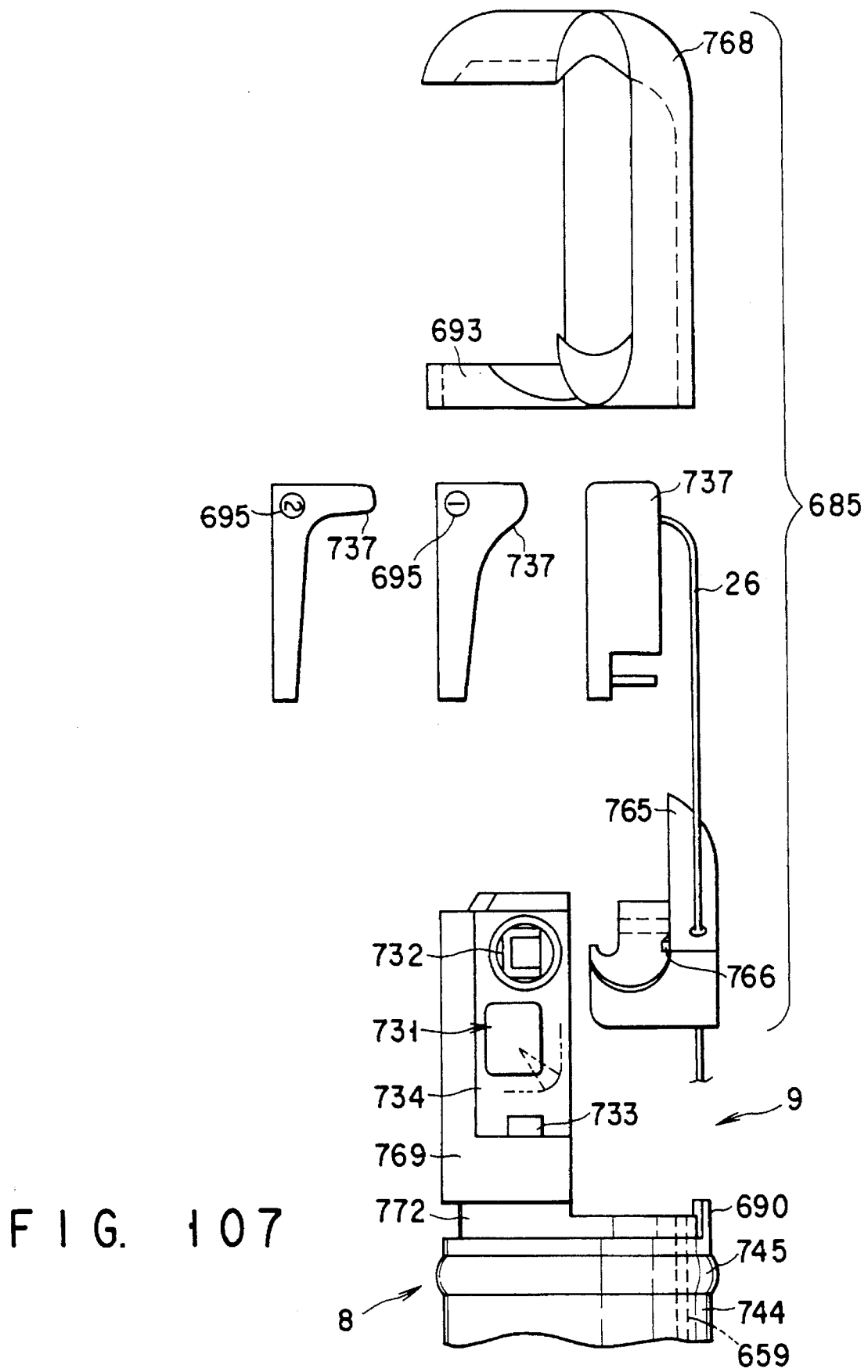
FIG. 107 is an exploded view of the detachable cover and a stationary cover at the distal end portion.

The forty-second embodiment of the present invention will be described next with reference to FIGS. 106A to 107. FIG. 106A is a side view of a detachable cover 768. FIG. 106B is a front view taken from the right direction of the right side of FIG. 106A. FIG. 106C is a plan view of a stripping jig 705. FIG. 107 is an exploded view of the detachable cover 768 and a stationary cover 769 in a distal end portion 9.

As shown in FIG. 107, a forceps base raising unit 685 is designed to be disassembled into the detachable cover 768, a forceps raising base 737, a forceps raising wire 26, and a slope portion body 765. The forceps raising base 737 is replaced with one of other types of forceps raising bases 737 in accordance with the size of an instrument to be caused to extend therethrough and a desired raising angle. An identification mark such as the one denoted by reference numeral 695 is attached to each forceps raising base 737 to discriminate it from the remaining types of forceps raising bases 737. Alternatively, the types of bases may by discriminated by color. Reference numeral 732 denotes an illumination lens; 731, an objective lens; and 733, a nozzle. A stopper projection 766 with which the forceps raising base 737 can be brought into contact is formed on the slope portion body 765. A tying bonding portion 745 serves to fix flexible rubber 744 consisting of an elastic material such as fluororubber, which is provided for a flexible portion 8 (FIG. 1) to allow the flexible portion 8 to be easily bent.

Note that the detachable cover 768 may be made of a plastic member having higher elasticity and better sliding properties than those of the material for the stationary cover 769 to make the detachable cover 768 more detachable. Alternatively, the detachable cover 768 may be made of the same material having high elasticity as that for the stationary cover 769. More specifically, polyethylene, polyacetar, polypropylene, and the like are materials having high elasticity, whereas polysulfone, modified PPO, and the like are materials having lower elasticity than that of polyethylene, polyacetar, polypropylene and the like. The detachable cover 768 has a hook portion 175. The upper end portion of the detachable cover 768 is formed into a smooth R-shaped portion.

The detachable cover 768 is removed by breaking the lock piece 693 and hence is used as a disposable member for each medical treatment. However, the slope portion body 765, the forceps raising base 737, and the forceps raising wire 26 are cleaned and sterilized to be reused. The above disposable member is a resin molded member, and the members to be reused are made of a metal or ceramic material. The forceps raising base 737 is located closer to the circumference of the detachable cover 768 than its center. The length of the forceps raising wire 26 is larger than the distance from the distal end of the distal end portion 9 to the proximal end of the insertion portion 3.

As shown in FIGS. 106A to 106C, an engaging hole (hook portion) 694 in which the stripping jig 705 is inserted is formed on the proximal end side of the lock piece 693. The clamping margin of the lock piece 693 of the detachable cover 768 increases toward the notched portion 777.

When the detachable cover 768 in the state shown in FIG. 107 is to be mounted on the distal end portion 9, the projection 682 on the distal end of the stationary cover 769 is engaged with the engaging hole 683 of the detachable cover 768 before the lock piece 693 is fitted in the recess groove 772 of the stationary cover 769.

The stripping jig 705 shown in FIG. 106C is constituted by a handle portion 707 and a support portion 714. A hook portion 710 is formed at the distal end of the support portion 714. The hook portion 710 is inserted in the engaging hole 694 formed on the proximal end side of the lock piece 693 of the detachable cover 768 to break the lock piece 693 so as to remove the lock piece 693 from the recess groove 772 formed in the bottom portion 770 of the stationary cover 769. With this operation, the detachable cover 768 can be easily removed from the distal end portion body 734, and the distal end portion 9 can be easily cleaned.

FIGS. 108A to 109 show the forty-third embodiment of the present invention.

FIG. 108A is a side view of a detachable cover 768. FIG. 108B is a front view taken from the right direction of FIG. 108A. FIG. 109 is a side view showing the detachable cover 768 and a stripping jig 705.

In this embodiment, as shown in FIGS. 108A and 108B, a first engaging hole (hook portion) 694 is formed on the proximal side of a lock piece 693 of the detachable cover 768, and a second engaging hole (hook portion) 696 for the stripping jig 705 is formed in the distal end portion of the detachable cover 768. The two engaging holes 694 and 696 are arranged on a substantially straight line to be substantially symmetrical.

As shown in FIG. 109, the stripping jig 705 in this embodiment comprises two jig members 708 respectively constituted by handle portions 707, substantially straight support portions 714, and hook portions 715 and 716. The two jig members 708 are connected to each other via a support shaft 711. The hook portion 715 of the stripping jig 705 is engaged with the second engaging hole 696, and the hook portion 716 is engaged with the first engaging hole 694. The handles 707 are then gripped. With this operation, the hook portion 716 is raised with the hook portion 716 serving as a fulcrum, thus breaking the lock piece 693. The lock piece 693 is then removed from a recess groove 772 formed in a bottom portion 770 of a stationary cover 769. With this operation, the detachable cover 768 can be easily removed from a distal end portion body 734.

Figure 110:
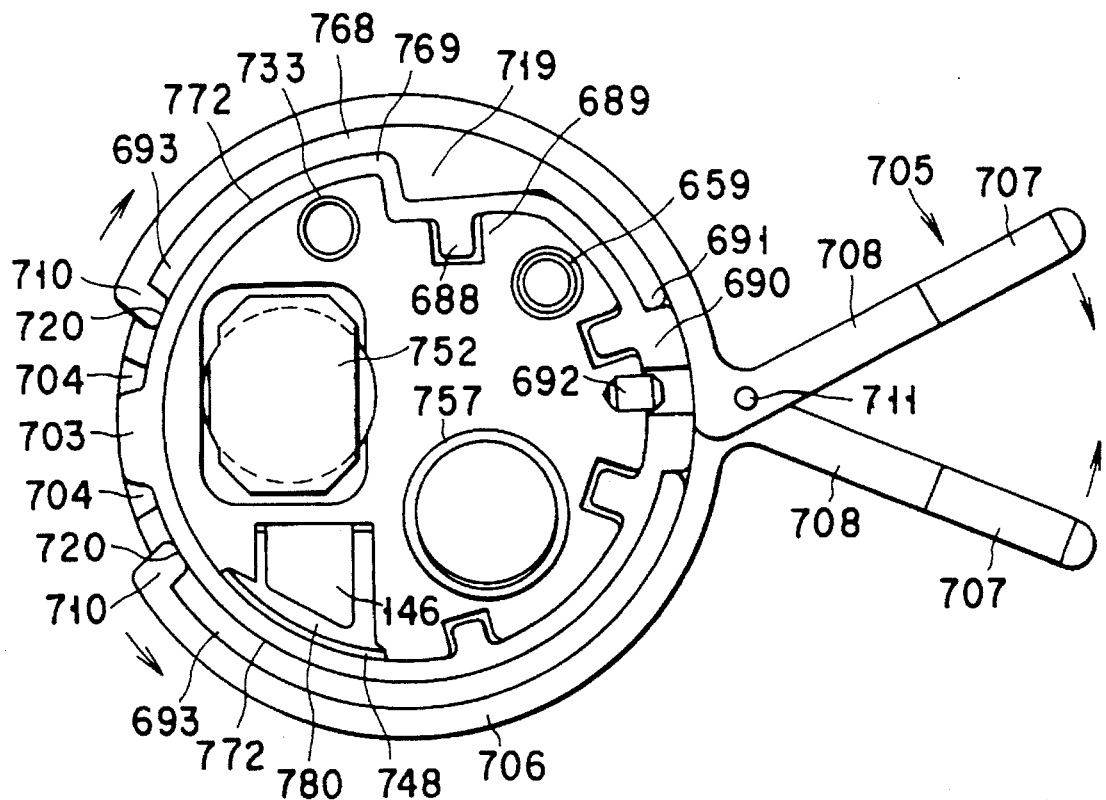
FIG. 110 is a rear view showing still another embodiment of the endoscope distal end cover, and more specifically the relationship between a stationary cover, a detachable cover, and a stripping jig.
Figure 111:
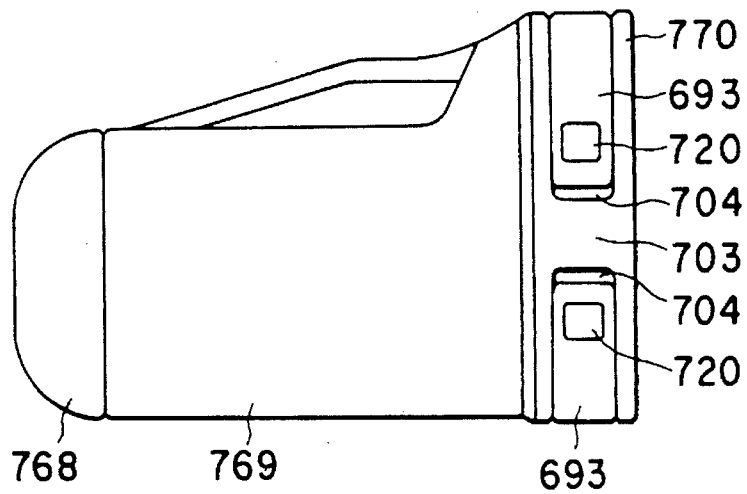
FIG. 111 is a side view showing the stationary cover and the detachable cover in FIG. 110.
Figure 112:
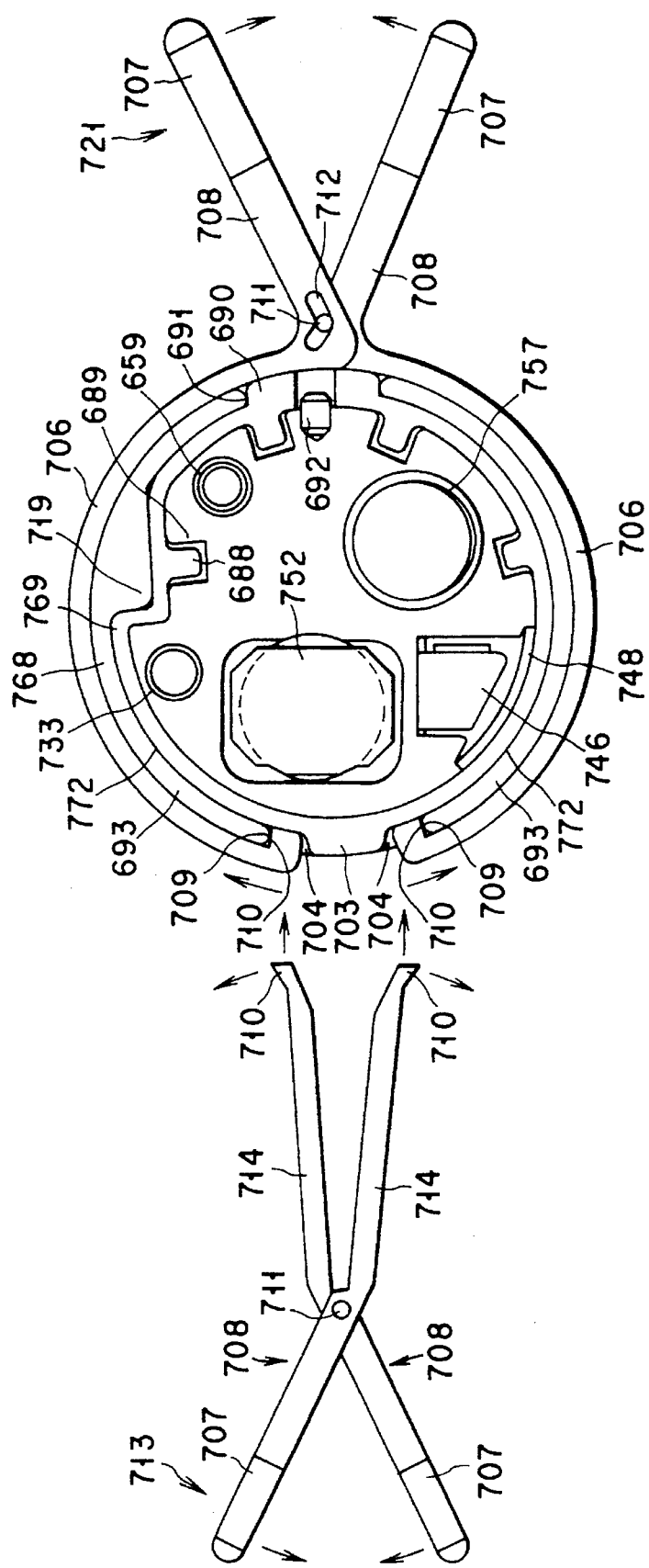

FIGS. 110 to 112 show the forty-fourth embodiment of the present invention. FIG. 110 is a rear view showing a stationary cover 769, a detachable cover 768, and a stripping jig 705. FIG. 111 is a side view showing the stationary cover 769 and the detachable cover 768. FIG. 112 is a rear view showing the stationary cover 769, the detachable cover 768, and a stripping jig 713.

Referring to FIGS. 110 and 111, two hook portions 720 with which the stripping jig 705 is engaged are formed near end portions of two lock pieces 693 of the detachable cover 768. The stripping jig 705 comprises jig members 708 respectively constituted by substantially semicircular circumferential support portions 706 and handle portions 707. The jig members 708 are rotatably connected to each other via a support shaft 711. The circumferential support portions 706 respectively have hook portions 710, which are engaged with the hook portions 720, at their distal end portions.

Referring to FIG. 112, gaps (hook portions) 704 with which a stripping jig 721 is engaged are formed between a projection 703, formed on a recess groove 772 of the stationary cover 769, and end portions of the lock pieces 693. The stripping jig 721 comprises two jig members 708 respectively constituted by substantially semicircular circumferential support portions 706 and handle portions 706. The circumferential support portions 706 respectively have hook portions 710 at their distal end portions. The hook portions 710 are hooked on end portions 709 of the two lock pieces 693 of the detachable cover 768 and are fitted in the gaps 704. One jig member 708 has a groove portion 712 in which a support shaft 711 formed on the other jig member 708 can be freely moved. With this structure, the stripping jig 721 can properly respond to a change in the outer diameter of each lock piece 693 of the detachable cover 768 by moving the support shaft 711 in the groove portion 712.

A stripping jig 713 shown on the left side of FIG. 112 is another example of the stripping jig. The stripping jig 713 comprise two jig members 708 respectively constituted by handle portions 707 and substantially straight support portions 714. The two jig members 708 are connected to each other via a support shaft 711. The support portions 714 respectively have hook portions 710 at their distal end portions. Similar to the above stripping jig, the hook portions 710 are fitted in the gaps 704 and hooked on the end portions 709 of the lock pieces 693.

In the respective embodiments shown in FIGS. 110 and 112, the hook portions 710 of the stripping jigs 705,713, and 721 are engaged with the engaging portions 720 or the gaps 704 of the lock pieces 693, and the handle portions 707 are gripped. With this operation, the circumferential support portions 706 are respectively pivoted upward and downward to break the lock pieces 693. The relationship between the inner diameter of the lock piece 693 of the detachable cover 768 and the outer diameter of the recess groove 772 is defined as follows.

The outer diameter of the recess groove 772 is equal to or larger than the inner diameter of the lock piece 693. In addition, the inner diameter of the lock piece 693 is equal to or larger than a value obtained by adding 0.2 mm to the outer diameter of the recess groove 772. The width of each of the stripping jigs 705, 713, and 721 is smaller than that of the recess groove 772.

FIGS. 113 to 115B are views for explaining a packed state of the forceps base raising unit 685 shown in FIG. 107.

Figure 113:
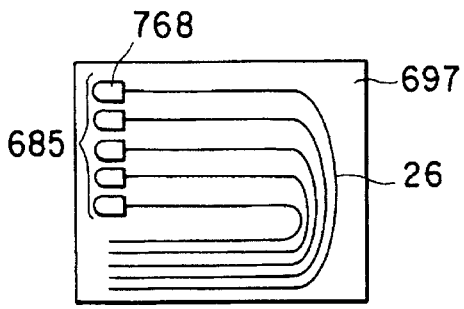

Referring to FIG. 113, a plurality of forceps base raising units 685 are packed in one packing bag 697. The forceps base raising units 685 in the bag are sterilized altogether. Each forceps raising wire 26 is packed in a folded state so as not to increase the size of the package. The curvature of radius of each forceps raising wire 26 is larger than that of the detachable cover 768.

Figure 114A:
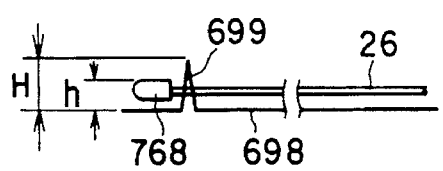
Figure 114B:
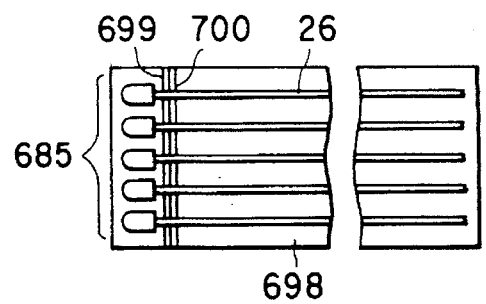
Figure 114C:
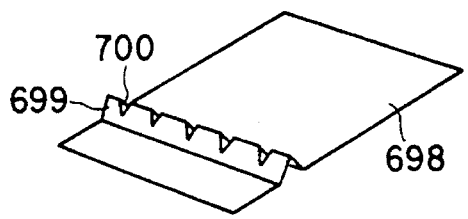
Figure 114D:
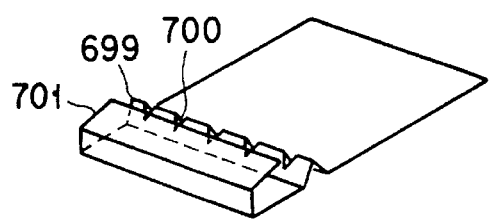

Referring to FIGS. 114A to 114D, a cardboard 698 such as a corrugated cardboard is folded, and a plurality of notches 700 are formed in a folded portion 699. The forceps raising wires 26 of the forceps base raising units 685 are inserted in the notches 700. A height H of the folded portion 699 is larger than the outer diameter of the detachable cover 768. Referring to FIG. 114B, packing is performed in the direction in which a forceps raising base 737 can be seen. Referring to FIG. 114D, a distal end portion of the cardboard 698 is folded, and detachable covers 768 of the forceps base raising units 685 are protected by a folded portion 701.

Figure 115A:
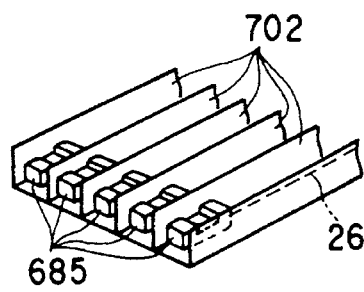
Figure 115B:
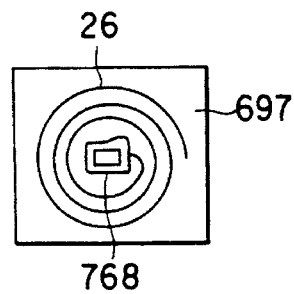

Referring to FIG. 115A, the forceps base raising units 685 are housed in partitions 702 divided by cardboard or the like. Referring to FIG. 115B, each forceps base raising unit 685 is housed in the packing bag 697 while the forceps raising wire 26 is wound around the detachable cover 768.

As is apparent from the above description, according to the endoscopes of the forty-first to forty-fourth embodiments described with reference to FIGS. 104 to 115B, since the hook portions on which the stripping jig is hooked are formed on portions of the lock pieces of the detachable cover of the endoscope distal end portion, the detachable cover can be easily removed by breaking the lock pieces using the stripping jig.

FIGS. 116A to 130B show endoscope cover members designed to minimize breakage of lock portions.

FIGS. 116A to 128D show the forty-fifth embodiment of the present invention, which has such an endoscope cover member.

Figure 116A:
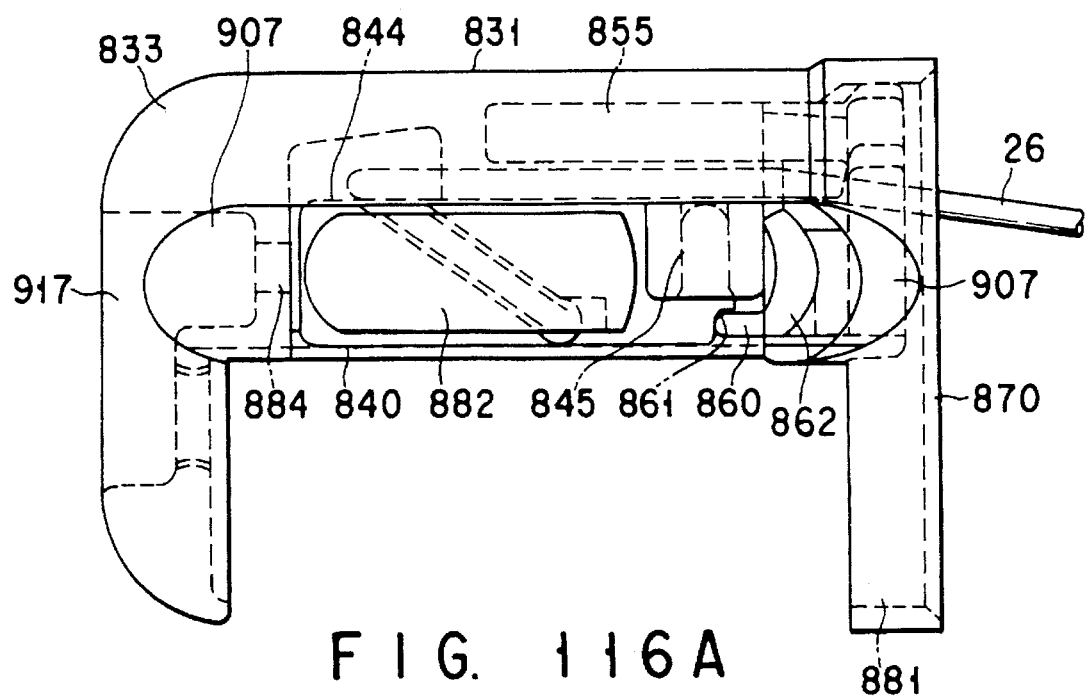
Figure 116B:
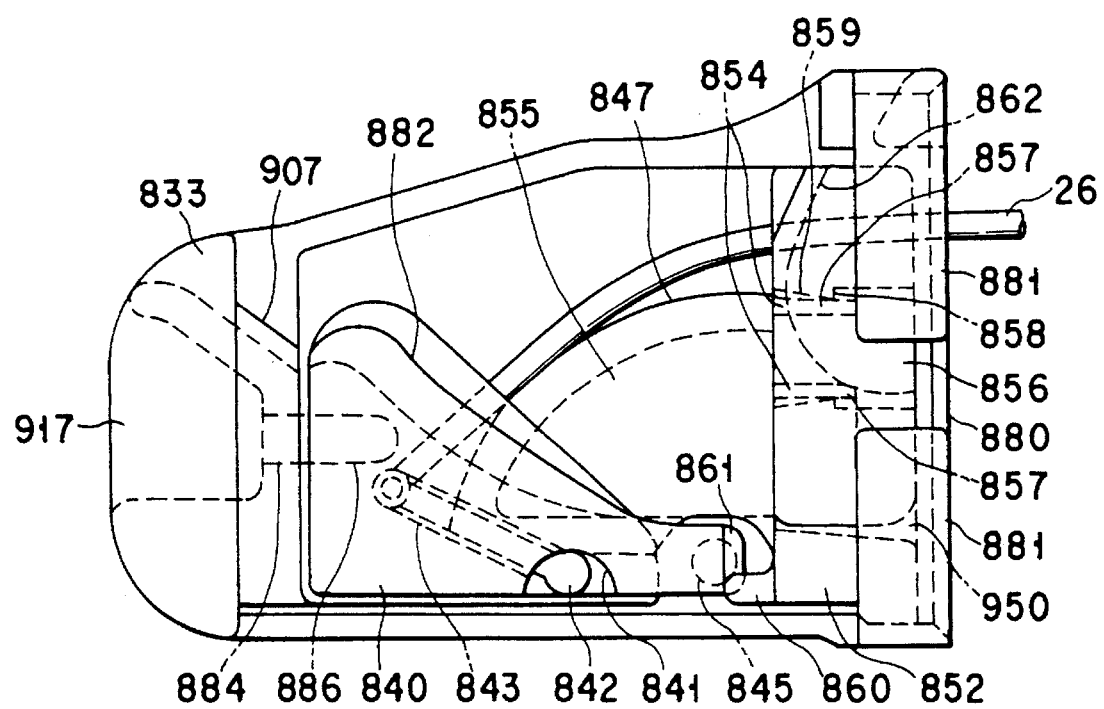

As shown in FIGS. 116A and 116B, a raising base 840 has a tip housing portion 841. A fixed portion tip 842 of a forceps raising wire 26 is housed. The fixed portion tip 842 is obtained by forming the distal end portion of the forceps raising wire 26 into a spherical shape by a plasma process. Note that the fixed portion tip 842 has a diameter larger than the outer diameter of the forceps raising wire 26.

The forceps raising wire 26 extends through a guide hole 843 extending from the tip housing portion 841 as a start point to penetrate through the raising base 840 obliquely upward at an acute angle. The forceps raising wire 26 is then bent in the opposite direction so as to be in contact with a side surface 844 of the raising base 840. In this arrangement, the forceps raising wire 26 and the raising base 840 constitute a raising base assembly such as the one shown in FIGS. 117A and 117B. That is, the forceps raising wire 26 and the raising base 840 are fixed by a simple method using a small number of components.

As shown in FIG. 116A, a cover member 831 can be removed from a distal end body 837 (see FIG. 122A) together with the assembly constituted by three members, i.e., the raising base 840, the forceps raising wire 26, and an insulating block 852. That is, the cover member 831 and the assembly constituted by the three members constitute a forceps raising base unit 853 and are detachably mounted on the distal end body 837.

The raising base 840 is made of an insulating plastic material or the like. A raising shaft 845 integrally formed with the raising base 840 extends from a side surface, of the raising base 840, located on the proximal end side. The raising shaft 845 is fitted in a shaft hole 849 (see FIG. 117B) of a slope portion 847 formed on the cover member 831 to support the raising base 840 to allow it to be rotated within a predetermined angular range.

As shown in FIG. 118, a stationary cover 846 is fitted on the distal end body 837. The stationary cover 846 is mounted on the distal end body 837 by fitting a pin 850 in a side hole 851 of the distal end body 837 and bonding/fixing the pin 850. The cover member 831 detachably mounted on the distal end body 837 is made of an insulating member such as polysulfone or modified PPO.

Referring to FIG. 118, reference numeral 887 denotes a light guide; 888, an adhesive-filled portion 889 filled with an adhesive; 889, a bonding plate; 891, an objective lens group; 892, a lens frame; 893, a set screw for fixing the lens frame 892; 899, a CCD; and 907, a forceps guide groove formed in the cover member 831.

The arrangement of the forceps raising base unit 853 will be described next with reference to FIGS. 116A to 117B.

As shown in FIGS. 117A and 117B, the forceps raising base unit 853 can be disassembled. Recently, various methods of performing endoscopy have been employed. Accordingly, different forceps are used, and different forceps raising operations are performed for the respective medical treatments. Therefore, raising bases 840 having guide grooves 899 with different shapes and different raising angles are replaced with each other in accordance with the size and type of forceps. For this reason, according to the arrangement of the present invention, different types of raising bases 840 have different numbers or colors to be discriminated from each other.

In addition, the cover member 831 can be replaced with a cover member whose insertion is the primary importance or a cover member made of a material resistant to high-frequency treatment. If it is cumbersome to select a raising base 840, a raising base 840 having a guide groove 882 corresponding to an instrument having the maximum outer diameter may be used. Furthermore, the arrangement of a coupling portion between the raising base 840 and the cover member 831 is made to be common to all the types so as to allow coupling between different types of raising bases 840 and different types of cover members 831.

As shown in FIGS. 117A and 117B, the slope portion 847 is formed on the cover member 831 to extend along the traveling path of the forceps raising wire 26, and a lock portion 854 locked to the insulating block 852 is formed on an end portion of the slope portion 847. A first hook portion 857 is formed at an end portion of the lock portion 854. Since the cover member 831 is a molded component consisting of a plastic material or the like, a cavity 855 is formed in the slope portion 847 to prevent formation of a sinkmark, as shown in FIG. 118. Note that the number of thinning holes 855 is not limited to one, and a large number of thinning holes 855 may be formed, as shown in FIGS. 119A and 119B.

The insulating block 852 has a lock hole 856 in which the lock portion 854 of the cover member 831 can be locked. A taper portion 859 and a second hook portion 858 are formed on the inner surface of the lock hole 856.

With this structure, when the lock portion 854 of the cover member 831 is pushed into the lock hole 856 of the insulating block 852 from the taper portion 859 side, the first hook portion 857 of the lock portion 854 is elastically deformed and hooked on the second hook portion 858 of the lock hole 856. As a result, the cover member 831 is connected to the insulating block 852.

When the cover member 831 is to be connected to the insulating block 852 in this manner, the raising shaft 845 of the raising base 840 is fitted in a shaft hole 849 formed in the slope portion 847. With this operation, a projection 860 formed on the insulating block 852 is brought into contact with a flat surface 861 formed near the rear side of the raising shaft 845 of the raising base 840. Therefore, the raising base 840 will not be removed from the shaft hole 849.

When the cover member 831 and the insulating block 852 are connected to each other via the lock hole 856 and the lock portion 854 in this manner, the raising base 840 can also be fixed. For this reason, an adhesive coating operation required for the assembly operation can be omitted, resulting in a reduction of the cost of the forceps raising base unit 853.

As shown in FIGS. 117A and 117B, the insulating block 852 also has a forceps insertion hole 950 and a raising guide portion 862. The forceps insertion hole 950 is formed to be substantially coaxial with a channel distal end opening portion 839 of the distal end body 837. The raising guide portion 862 has a curved surface which is smoothly continuous with the forceps insertion hole 950 and extends along a bent shape of forceps when the forceps are raised.

The smooth slope portion 847 extending along the traveling path of the wire 26 is designed such that the upper end face is smoothly continuous with a parallel bottom surface 864 of a raising wire guide hole 863 extending through the insulating block 852 to reach its upper end face.

As described above, the pin 850 penetrates through the portion between the stationary cover 846 and the distal end body 837. The pin 850 serves to reinforce an O-ring 874 of the stationary cover 846 against force in the twisting direction.

As shown in FIG. 118, a first projection 875 is formed on a lower portion of a side surface, of the distal end body 837, which opposes the raising base 840, and a second projection 876, which is brought into contact with the first projection 875, is formed on the stationary cover 846. When the first and second projections 875 and 876 are brought into contact with each other, rotation of the stationary cover 846 with respect to the distal end body 837 is prevented.

An end portion 870 of a cover member 31 has a C-shaped lock piece 881 having a notched portion 880. The C-shaped lock piece 881 is formed to be elastically deformed and fitted in a recess groove 873 of the stationary cover 846. In addition, a protective portion 833 having an outer diameter almost equal to that of the lock piece 881 is formed on the distal end side of the cover member 831.

Figure 120:
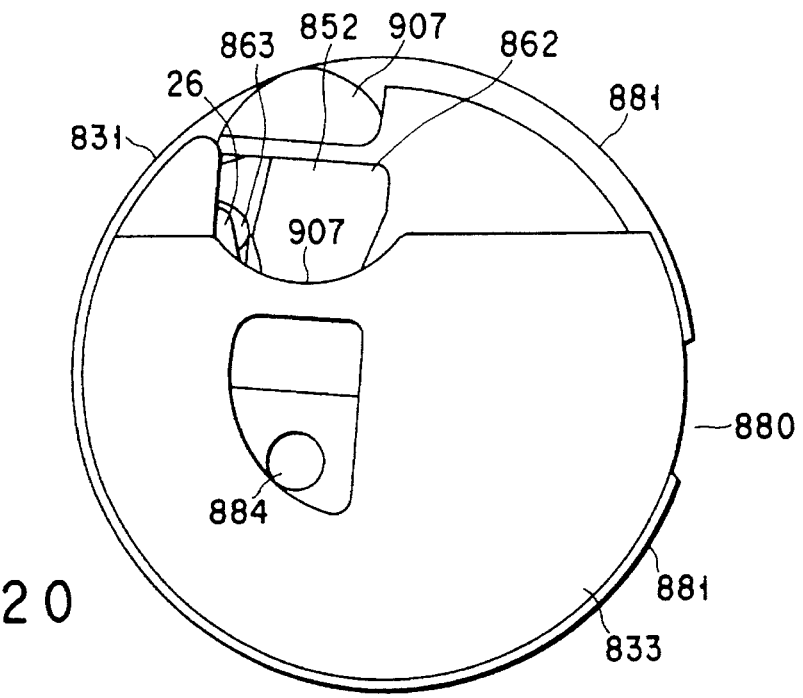
Figure 121A:
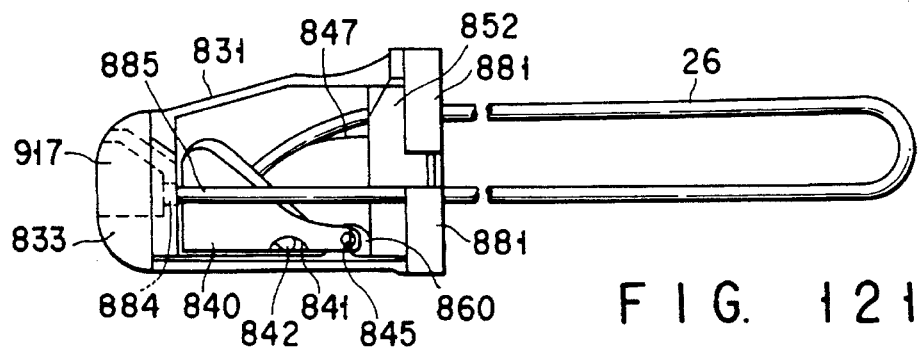

As shown in FIG. 120, the protective portion 833 at the distal end of the cover member 831 has an engaging hole 884 with which a distal end portion 885 of the forceps raising wire 26 can be engaged. When the forceps raising base unit 853 is to be stored, the distal end portion 885 of the wire is engaged with the engaging hole 884, as shown in FIG. 121A. With this operation, no protective member is required for the distal end portion 885, and there is no possibility that the distal end portion 885 breaks a packing member when the forceps raising base unit 853 is packed.

Figure 121B:
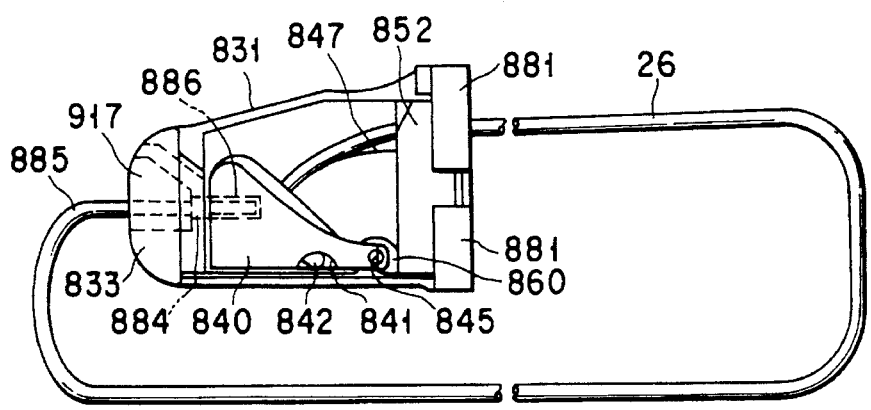

As shown in FIG. 121B, a second engaging hole 886 is formed in the raising base 840. The second engaging hole 886 opposes the engaging hole 884 of the protective portion 833 when the raising base 840 is inverted. Therefore, when the distal end portion 885 of the forceps raising wire 26 is sequentially engaged with the engaging hole 884 and the second engaging hole 886 from the distal end side of the cover member 831, the movement of the raising base 840 can be regulated by the wire 26 when the forceps raising base unit 853 is to be stored or packed.

FIGS. 122A to 125 show an arrangement in which a slop portion is disposed in the distal end body 837. As shown in FIGS. 122A to 123, a slope portion 897 protrudes from the stationary cover 846. As shown in FIG. 124, the insulating block 852 has a through hole 896 through which the slope portion 897 can extend in a fitted state. In this arrangement, when the forceps raising base unit 853 is mounted on a distal end portion 9, the slope portion 897 is fitted in the through hole 896 of the insulating block 852, and the slope portion 897 extends to a side surface 898 of the raising base 840 to regulate the lateral movement of the raising base 840.

An engaging hole 894 is formed in the proximal end portion of the insulating block 852, and an engaging projection 895 extends from the distal end portion of the distal end body 837 in correspondence with the engaging hole 894. With this structure, when the forceps raising base unit 853 is mounted on the distal end body 837, the engaging projection 895 of the distal end body 837 is engaged with the engaging hole 894 of the insulating block 852. Therefore, the rotation of the forceps raising base unit 853 with respect to the distal end body 837 is regulated. After the forceps raising base unit 853 is mounted on the distal end body 837, a very thin film cover 900 is mounted to cover the lock piece 881 of the cover member 831 engaged with the recess groove 873 of the stationary cover 846 and an end portion 871 of the stationary cover 846, thereby preventing removal of the cover member 831.

As described above, the slope portion may be formed on either the distal end body 837 or the cover member 831. In any arrangement, when the cover member 831 is mounted on the distal end body 837, the lock piece 881 of the cover member 831 is may be engaged with the recess groove 873 of the stationary cover 846 of the distal end body 837. In this set state, a rib 877 formed on the cover member 831 is engaged with an engaging hole 878 formed in the stationary cover 846, and a recess 938 formed in the cover member 831 is engaged with a projection 937 formed on the distal end body 837.

FIG. 126 shows a packed state of the forceps raising base units 853. The forceps raising base units 853 are packed in a plastic case 902 whose interior is divided by partitions 901, while the distal end portion 885 of the wire 26 is engaged with the engaging hole 884 of the cover member 831 of each forceps raising base unit 853. In this case, as shown in FIG. 126, the main portions of the forceps raising base units 853 except for the wires 26 are respectively fitted in fitting portions 902a constituted by hook portions 903 extending from the partitions 901, while the wires 26 are disposed in wire housing portions 902b. If the forceps raising base units 853 are packed by using the plastic case 902 having the above arrangement, loosening of the wires 26 can be prevented, and mounting of the forceps raising base unit 853 is facilitated.

FIGS. 128A to 128D show another arrangement of a housing member for housing the forceps raising base unit 853. In general, the wire 26 has a length of 1 m or more. If the wire 26 is bent, a raising operation of the raising base 840 cannot be properly performed. If, however, the wire 26 is packed straight, the size of the package increases. In this case, when an endoscope is put in a carrying case, the package cannot be fitted in the case, resulting in inconvenience in handling.

For this reason, in a forceps raising base unit housing member 912 shown in FIGS. 128A to 128D, the wire 26 can be wound within a radius twice or more the length of the cover member 831 in the axial direction.

The forceps raising base unit housing member 912 (to be referred to as the housing member 912 hereinafter) is constituted by a raising wire wind-up portion 913 (to be referred to as a wind-up portion 913 hereinafter) and a cover member housing portion 914. The cover member housing portion 914 has a housing space 915 having almost the same outer appearance as that of the cover member 831. The cover member 831 of the forceps raising base unit 853 is fitted in the housing space 915. A projection 916 is formed in the housing space 915. An engaging hole 917 (see FIG. 129A) with which the projection 916 can be engaged is formed in the distal end of the cover member 831 (the distal end of the protective portion 833). With this structure, when the cover member 831 is fitted in the housing space 915, the projection 916 in the housing space 915 is engaged with the engaging hole 917 of the cover member 831, and the cover member 831 is fixed in the housing space 915.

As shown in FIGS. 128A to 128D, the engaging hole 917 communicates with the engaging hole 884. A projection 918 extends from the distal end of the projection 916. The projection 918 can be engaged with the engaging hole 884 of the cover member 831 and the second engaging hole 886 of the raising base 840. With this structure, when the cover member 831 is fitted in the housing space 915, the projection 918 is sequentially engaged with the engaging hole 884 and the second engaging hole 886. As a result, both the cover member 831 and the raising base 840 can be fixed in the housing space 915.

An opening portion 924 of the cover member housing portion 914 has an expanded portion 919 having a width larger than the outer diameter of the lock piece 881 of the cover member 831. With this structure, even if the cover member 831 housed in the cover member housing portion 914 is mounted on the distal end body 837, the lock piece 881 is not brought into contact with the inner surface of the housing space 915. In addition, the cover member housing portion 914 has notched portions 920 and 921. The notched portion 920 allows the operator to see the notched portion 880 of the lock piece 881 of the cover member 831 from the outside. The notched portion 921 allows the operator to see the raising base 840 from the outside. Therefore, the operator can check a mounted state of the cover member 831 with respect to the distal end body 837 and a set state of the raising base 840.

A substantially circular wire housing space 922 is formed in the wind-up portion 913. An opening portion 923 of the wind-up portion 913 is open in substantially the same direction as that of an opening portion 924 of the cover member housing portion 914. A notched portion 926 is formed in a wind-up portion upper surface 925 to allow the operator to see a wound state of the wire 26. Note that the wind-up portion upper surface 925 constitutes a floating preventing portion 927 for preventing the wire 26 from floating.

The floating preventing portion 927 is at a level higher than that of the wire 26 extending from the cover member housing portion 914. A hole 928 is formed in the center of the wind-up portion 913, and a wall 929 is formed around the hole 928 to prevent the wire 26 from loosening.

When the forceps raising base unit 853 is to be housed in the housing member 912 having the above arrangement, the cover member 831 of the forceps raising base unit 853 is fixed to the cover member housing portion 914, as described above. Thereafter, the wire 26 is inserted in the opening portion 923 located on the opposite side of the center of the wind-up portion 913 to the cover member housing portion 914. Note that the diameter within which the wire 26 is wound in the wire housing space 922 is set such that the wire 26 is not bent, and the wire housing space 922 can be minimized.

In the housing member 912 having the above arrangement, since the wind-up portion 913 and the cover member housing portion 914 are integrally formed, the forceps raising base unit 853 can be stored in a compact state, and the wire 26 can be wound up and housed without being bent. In addition, when the forceps raising base unit 853 is mounted on the distal end body 837, the raising base 840 need not be inverted.

When the forceps raising base unit 853 is to be mounted on the distal end body 837, the wire 26 is connected to the driving shaft 28 via the connecting portion 29 while the insertion portion 3 is stretched substantially straight, and the raising base 840 is inverted. Thereafter, as shown in FIG. 127, a projection 933 of a wire connection inspection member 932 is fitted in the guide groove 882 of the raising base 840. In addition, the wire 26 is pulled via a raising lever 27 (see FIG. 1) to raise the raising base 840 while a flat surface 934 of the wire connection inspection member 932 is in contact with the insulating block 852. The forceps raising lever 27 is pulled for several seconds while the wire connection inspection member 932 is clamped between the raising base 840 and the insulating block 852 to check whether the connection between a driving shaft 28 and the wire 26 is maintained. Thereafter, an examination is performed by using the endoscope.

As described above, the cover member 831 of the present invention has the protective portion 833 having an outer diameter almost equivalent to the outer shape of the lock piece 881. For this reason, even if an external force acts on the cover member 831, the external force does not concentrate on the lock piece 881 but also acts on the protective portion 833. Hence, an unnecessary large force does not act on the lock piece 881. In contrast to this, according to a conventional endoscope, since the lock piece 881 has the largest diameter in the components of the cover member 831, an external force acts on only the lock piece 881. As a result, the thin lock piece 881 may be broken. According to the cover member 831 of this embodiment, however, the external force acting thereon can be distributed to the lock piece 881 and the protective portion 833. For this reason, the force acting on the lock piece 881 decreases, and the lock piece 881 is not easily broken, as compared with the conventional cover member. Therefore, the detachable function of the cover member 831 is not impaired.

Assume that the cover member 831 needs to be sterilized after it is used, or is used as a disposable member. In either case, the cover member 831 must be sterilized before it is used. When autoclave sterilization is to be performed, each cover member 831 is packed in a pack, which can be peeled off by hand, and supplied to a sterilization step. Thereafter, each peel pack is stored in a storage room for sterilized endoscopes. In this case, the cover member 831 is packed in the pack such that the protective portion 833 and the lock piece 881 are in contact with the inner surface of the pack. In this state, the external force is always distributed to the protective portion 833 and the lock piece 881.

In addition, as shown in FIGS. 116A and 116B, the cover member 831 of this embodiment is designed such that the raising base 840 is exposed via a side portion of the cover member 831. For this reason, when the forceps raising base unit 853 is assembled, the operator can easily check whether foreign substances have entered the raising base housing portion and the raising base 840 and the like are properly assembled.

FIGS. 129A and 129B show the forty-sixth embodiment of the present invention. In this embodiment, the outer diameter of a protective portion 833 is larger than that of a lock piece 881. Other arrangements are the same as those of the first embodiment. In this arrangement, since an external force applied to a cover member 831 acts first on the protective portion 833, the possibility of damaging the lock piece 881 is lower than that in the first embodiment.

FIGS. 130A and 130B show the forty-seventh embodiment of the present invention. In this embodiment, the outer diameter of a protective portion 833 is smaller than that of a lock piece 881, but is larger than the elastic deformation diameter limit, i.e., the outer diameter of the lock piece 881 in a case wherein the lock piece 881 is compressed/deformed up to the elastic limit. Therefore, even if an external force acts on the lock piece 881, the force is distributed to the protective portion 833 before the lock piece 881 reaches the elastic limit, and breakage of the lock piece 881 is minimized.

As described above, each of the endoscope cover members of the forty-fifth to forty-seventh embodiments is designed such that the outer diameter of the protective portion is set to be larger than the elastic deformation diameter limit of the lock piece, i.e., the outer diameter of the lock piece in a case wherein the lock piece is compressed/deformed to reach the elastic limit. Therefore, even if an external force acts on the lock piece, the force is distributed to the protective portion before the lock piece reaches the elastic limit. That is, the external force acting on the cover member does not concentrate on the lock piece but also acts on the protective portion, and an unnecessary large force does not act on the lock piece. Therefore, the force acting on the lock piece is smaller than that acting on the lock piece of a conventional cover member, and the lock piece of this cover member is not easily broken.

FIGS. 131A to 146 show the forty-eighth to fiftieth embodiments of the present invention.

For example, as shown in FIG. 138, in the forty-eighth to fiftieth embodiments, when a forceps raising wire is to be pressed/fixed, an engaging hole 1226 of a protective cover 1216 detachable with respect to the endoscope is engaged with a wire press portion body 1190 of a connecting portion 1029 and is rotated. Since the wire press portion body 1190 of the connecting portion 1029 is rotated by using the protective cover 1216 constituting the endoscope, an unnecessary adjustment tool for an examination can be omitted.

As shown in FIGS. 131A to 132, a breakage preventing member 1108 and a breakage preventing cover 1111 are integrated into a breakage preventing unit 1200. In order to prevent rotation of the breakage preventing member 1108 relative to the breakage preventing cover 1111 when the breakage preventing unit 1200 is threadably engaged with a cylindrical member 1094, rotation preventing projections 1201 are formed on the breakage preventing member 1108, and substantially circular rotation preventing recesses 1202 in which the rotation preventing projections 1201 are fitted are formed in the breakage preventing cover 1111. In addition, each rotation preventing recess 1202 is compressed in a force smaller than that of each rotation preventing projection 1201. Therefore, even if the operator tries to threadably engage the breakage preventing unit 1200 with the cylindrical member 1094 while holding the breakage preventing cover 1111 with his/her hand, there is no possibility that no torque is transmitted to the breakage preventing member 1108. A removal preventing portion 1203 is formed on the operating portion 1 side of the breakage preventing cover 1111 to prevent removal of the breakage preventing cover 1111 from the breakage preventing member 1108 in the axial direction. Furthermore, in order to reduce the outer diameter of the breakage preventing unit 1200, the projections 1201 of the breakage preventing member 1108 are formed by not only a rubber portion 1204 of the breakage preventing member 1108 but also a breakage preventing mouthpiece 1109 of the rubber portion 1204.

The relationship between a clamping portion 1205, of the breakage preventing member 1108, which is designed to clamp an insertion tube 1100, and the clamping ratio of a fitting portion 1206 of the breakage preventing cover 1111 to the insertion tube 1100 will be described next.

The clamping portion 1205 of the breakage preventing member 1108 always clamps the insertion tube 1100 to improve the flexural durability of the insertion tube 1100. If the breakage preventing cover 1111 is to have the same flexural durability improving function as that of the insertion tube 1100, the fitting portion 1206 of the breakage preventing cover 1111 may have the same clamping ratio as that of the clamping portion 1205 of the breakage preventing member 1108. An adhesive is coated on the fitting portion 1206 to provide watertightness for the breakage preventing cover 1111. In order to prevent the adhesive from peeling off, the clamping ratio of the fitting portion 1206 to the insertion tube 1100 may be set to be higher than that of the clamping portion 1205 of the breakage preventing member 1108. If an elastic silicone adhesive is coated between the insertion tube 1100 and the fitting portion 1206, a clearance as a margin for an adhesive may be ensured between the insertion tube 1100 and the fitting portion 1206.

When the insertion tube 1100 is bent, the breakage preventing member 1108 moves relative to the insertion tube 1100. However, the breakage preventing cover 1111 does not move because it is bonded to the insertion tube 1100. For this reason, a clearance is ensured between the breakage preventing member 1108 and the breakage preventing cover 1111 to prevent contact of the breakage preventing member 1108 with the breakage preventing cover 1111 even if the breakage preventing member 1108 moves. If, however, the width of this clearance is maintained between an outer taper portion A 1207 of the breakage preventing member 1108 and a taper portion B 1208 of the breakage preventing cover 1111, the gap between the breakage preventing member 1108 and the breakage preventing cover 1111 becomes too large. Therefore, as shown in FIG. 132, the width of the clearance is made to become smaller from the insertion portion 3 side to the operating portion 1 side.

Figure 18:
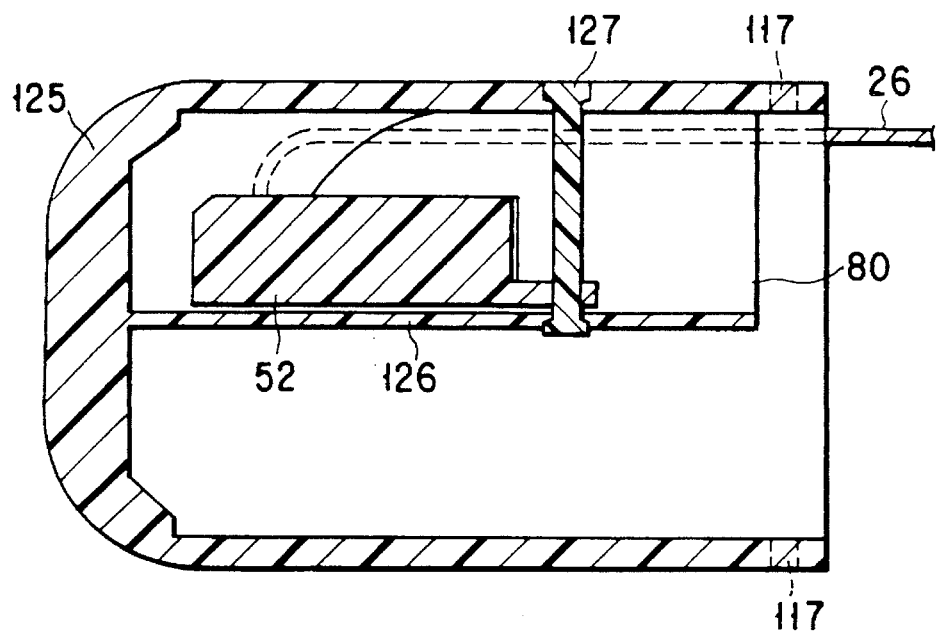
FIG. 18 is a view showing the arrangement of the distal end portion of an endoscope according to the fourth embodiment of the present invention.

FIGS. 133A and 133B are sectional views showing a modification of the arrangement of the connecting portion 1029 in FIG. 18. In this modification, a connecting portion 1029 is not provided for a driving shaft 28, and the driving shaft 28 is inserted in a fitting hole 1210 of a connecting portion body 1209 detachable from the driving shaft 28. In addition, a forceps raising wire 26 is inserted in a guide hole 1211 formed in the driving shaft 28. In this state, a wire press portion body 1212 is rotated to engage a wire press portion 1213 with an engaging hole 1214 of the driving shaft 28, thereby pressing/fixing the forceps raising wire 26.

The forty-ninth embodiment of the present invention will be described next with reference to FIGS. 1, 17, and 134 to 138. FIG. 134 shows a state wherein a protective cover 1216 is removed. FIGS. 135A and 135B show a modification of a positioning hole 1217 formed in a driving shaft opening portion 25. FIG. 136 is a partially sectional view showing a state wherein the protective cover 1216 is mounted. FIGS. 137A and 137B are plan views showing a state after the protective cover 1216 is mounted. FIG. 138 shows a state wherein a wire press portion body 1190 is rotated by the protective cover 1216.

The insulating protective cover 1216 is detachably mounted on an operating portion 1 to protect a connecting portion 1029. The protective cover 1216 is fixed as follows. A positioning projection 1218 of the protective cover 1216 is inserted in the positioning hole 1217 formed in a driving shaft opening portion 1025. The protective cover 1216 is then pushed into the operating portion 1 side, and a syringe taper recess 1220 of the protective cover 1216 is fitted on a syringe taper projection 1219 formed on a forceps raising guide tube mouthpiece 1121, thereby fixing the protective cover 1216.

As shown in FIGS. 135A and 135B, the positioning hole 1217 for receiving the positioning projection 1218 of the protective cover 1216 may constitute a blind alley and a drainage hole 1222 may be formed in the positioning hole 1217 to drain a liquid used for a cleaning operation. As shown in FIG. 136, the syringe taper recess 1220 formed in the protective cover 1216 has a taper notched portion 1223 on the operating portion 1 side so as not to interfere with insertion of the syringe taper projection 1219. Two types of protective covers 1216, i.e., a disposable type and a type to be repeatedly used, are prepared to be selectively used in accordance with the preference of a user. In order to identify these types, no surface treatment may be performed with respect to the protective cover 1216 of the disposable type, whereas a surface treatment such as satinizing may be performed with respect to the protective cover 1216 of the type to be repeatedly used.

The positioning hole 1217 formed in the driving shaft opening portion 25 is positioned at an upper portion on the drawing surface of each of FIGS. 137A and 137B to allow the operator to easily grip the grip portion. The driving shaft opening portion 1025, the protective cover 1216, and a guide portion 1224 of a forceps wire opening portion body 1096 are made of the same material and arranged in a substantially straight line at a substantially same level in consideration of an outer appearance. In addition, the axial center of these components is shifted from the center of a grip portion 2 to an upper portion on the drawing surface of each of FIGS. 137A and 137B.

A forceps raising wire 26 is pressed/fixed as follows. As shown in FIG. 138, an engaging hole 1226 (tool portion) of a protective cover 1216 is engaged with a rotating projection 1225 formed on the wire press portion body 1190 of the connecting portion 1029, which projection is directed obliquely upward in a mounted state, and the wire press portion body 1190 is rotated, thereby fixing the forceps raising wire 26. In this case, a projection 1227 (FIGS. 136 to 138) is formed to allow the operator to easily recognize the position of the engaging hole 1226. In addition, as shown in FIG. 138, a notched portion 1228 is formed in the protective cover 1216 to prevent the protective cover 1216 from interfering with the grip portion 2. A seal with instructions to a user who mounts the forceps raising wire 26, e.g., "Please check whether the forceps raising wire is reliably mounted", is adhered to a portion, of the grip portion 2, which is covered with the protective cover 1216.

Since the wire press portion body 1190 of the connecting portion 1029 is rotated by using the protective cover 1216 as a component of the endoscope, an unnecessary tool for an examination can be omitted. Since a tool as an accessary need not be prepared, the number of components can be decreased. In addition, a commercially available tool such as a screwdriver need not be purchased, the expense born by the user can be reduced. Assume that a forceps raising wire guide tube 1128 is applied to a direct-vision endoscope. In this case, if a syringe is attached to the syringe taper projection 1219 of the forceps raising guide tube mouthpiece 1121 to supply water to the forceps raising wire guide tube 1128, the forceps raising wire guide tube 1128 can be used as a tube path for cleaning a morbid portion. When no water is to be supplied, a cap made of an elastic member and having a syringe taper portion is attached to the forceps raising guide tube mouthpiece 1121.

FIG. 139 is a side view showing a modification of the protective cover 1216 according to the present invention. In the above embodiment, the width of the gap between the protective cover 1216 and the driving shaft opening portion 1025, formed when protective cover 1216 is mounted, is set such that a finger of the operator cannot be inserted in the gap to ensure the insulation of the exposed portion of the driving shaft 28. In this modification, a projection 1237 is formed on the protective cover 1216 to perfectly prevent a finger of the operator from touching the driving shaft 28 and protect a seal portion 1180 (FIG. 134).

FIGS. 140A to 140C show a modification of the arrangement of the connecting portion 1029 to which the present invention is applied. FIG. 140A is a side view. FIG. 140B is a plan view. FIG. 140C is a sectional view. A wire guide portion 1239 is fitted in a connecting portion body 1238 of a driving shaft 28. A screw 1241 is then threadably engaged with an engaging hole 240 of the wire guide portion 1239 to fix the wire guide portion 1239. A taper portion 1242 is formed on the wire guide portion 1239 to allow easy insertion of a forceps raising wire 26. In addition, a U-shaped groove 243 is formed in the wire guide portion 1239 to position the forceps raising wire 26. The connecting portion body 1238 has a threaded portion 1244 formed obliquely, with which a wire press portion body 1245 for pressing/fixing the forceps raising wire 26 is threadably engaged.

The wire press portion body 1245 has a press portion 1246 which is brought into contact with the forceps raising wire 26 in a parallel state. The forceps raising wire 26 is fixed as follows. The forceps raising wire 26 is inserted along the U-shaped groove 1243 of the wire guide portion 1239 until it is brought into contact with an abutment portion 1247. An engaging hole 1226 of a protective cover 1216 is engaged with a rotating projection 1248 of the wire press portion body 1245, and the protective cover 1216 is rotated, thereby pressing/fixing the forceps raising wire 26 with the press portion 1246 of the wire press portion body 1245. The press portion 1246 may be knurled to more firmly press/fix the forceps raising wire 26. In this case, since the rotating projection 1248 faces obliquely upward and in the sliding direction of the driving shaft 28 when the forceps raising wire 26 is pressed/fixed, the height and width of the protective cover 1216 can be further decreased.

FIG. 141 is a plan view showing the fiftieth embodiment of the present invention. The same reference numerals in the fiftieth embodiment denote the same parts as in the embodiment shown in FIG. 1, and a description thereof will be omitted. In the above embodiment, since the protective cover 1216 is designed to be detachable from the endoscope, the cover may be lost. In this embodiment, in order to rotate a wire press portion body 1190, of a connecting portion 1029, designed to press/fix a forceps raising wire 26, an engaging hole 1249 engaged with a rotating projection 1225 of the wire press portion body 1190 is formed in a connector 5 of the endoscope. In this embodiment, since the rotation means is arranged at a portion of the endoscope itself, there is no possibility of losing the rotation means. In the embodiment, the tool portion as the rotation means is formed on the connector 5. However, the tool portion may be formed on a water supply tank or a connection adaptor, which is connected to the connector in an examination, or a water/air supply piston or a suction piston, which is a component of the endoscope. That is, the rotation means can be arranged on any member as long as it is connected to the endoscope to be used in an examination, or a component of the endoscope.

FIG. 142 is a side view showing another modification of the arrangement of the connecting portion to which the present invention is applied. In the above embodiment, when the rotation means is to be mounted on the rotating projection 1225 in the vertical direction, the forceps and the angle knob may interfere with the mounting operation. In addition, as is apparent, if the rotating projection 1225 faces in a direction lower than the horizontal direction in a mounted state, the operating portion 1 interferes with an operation performed by the operator. For this reason, in this modification, a rotating projection 1225, of a connecting portion 1029, placed on a desk 1250 is directed obliquely upward by an angle i with respect to the horizontal surface of the desk 1250. With this arrangement, the user can easily mount and rotate the rotation tool. By obliquely setting the rotating projection 1225 which protrudes most, a protective cover 1229 covering the connecting portion 1029 and an operating portion 1 can be reduced in size. Note that the rotating projection 1225 of the connecting portion 1029 faces obliquely to the right on the drawing surface of FIG. 142. This direction of the rotating projection 1225 is changed in accordance with the structures of the endoscope and the connecting portion 1029, but is not limited as long as the rotating projection 1225 is set in a substantially horizontal position or horizontal position in a mounted state.

This embodiment exemplifies the connection of the forceps raising wire 26. However, the above description also applies to an endoscope having a connecting portion designed to perform connection by using a connecting tool or an adjusting portion designed to perform adjustment by using an adjusting tool.

FIG. 143 is a sectional view showing a modification of the arrangement of the connecting portion 1029. In this modification, an abutment portion 1195 formed on a wire guide portion 1191 of the connecting portion 1029 is omitted. In this case, when a forceps raising wire 26 is slackened by repetitive use, an engaging hole 1252 of a rotation tool 1251 is engaged with a rotating projection 1225 of a wire press portion body 1190, and the rotation tool 1251 is rotated to loosen the pressed/fixed forceps raising wire 26. Thereafter, in this state, the forceps raising wire 26 is pushed into the operating portion 1 side, and the engaging hole 1252 of the rotation tool 1251 is engaged with the rotating projection 1225 to rotate the rotation tool 1251 again so as to press/fix the forceps raising wire 26. With this operation, the tension of the forceps raising wire 26 can be adjusted. At this time, the rotating projection 1225 faces obliquely upward with respect to the horizontal direction, similar to the case shown in FIG. 142. The rotation tool 1251 is used as an adjusting means. As described above, the adjusting means may be mounted on the protective cover 1216 which is detachable from the endoscope or a connector 5 as a component of the endoscope to perform adjustment.

FIGS. 144 to 146 show arrangements associated with the endoscope of the present invention. FIGS. 144 and 145 are side views showing a modification of the arrangement of the operating portion. In the above embodiment, the stopper (denoted by reference numeral 325 in FIGS. 39B, 40, and 41) for determining the raising/inverting stroke of the forceps raising base 36 is disposed in the operating portion 1. If, however, as shown in FIG. 107, a plurality of types of forceps raising bases 737 are to selectively used as needed, the raising/inverting stroke varies depending on the type of a forceps raising base used. For this reason, it is difficult to make a connecting portion common to all the types of forceps raising bases.

In addition, since the raising/inverting stopper is incorporated in the operating portion, the raising/inverting stroke of the forceps raising base cannot be adjusted as desired by the user. If, therefore, a raising operation failure occurs due to a slack of the forceps raising wire 26, the endoscope must be disassembled. That is, there is still room for improvement.

Referring to FIGS. 144 and 145, a stopper mount portion 1229 is formed on a portion, of a grip portion 2, located on the connecting portion 1029 side of a forceps raising wire 26, and a raising stopper 1230 and an inverting stopper 1231 are fixed to the protective cover 1229 with screws 1232. The raising/inverting stroke of the forceps raising base is determined by the positions where the connecting portion 1029 is brought into contact with the raising and inverting stoppers 1230 and 1231. In addition, the stroke is adjusted by selectively replacing raising stoppers 1230 having different widths and inverting stoppers 1231 having different widths with each other.

In this arrangement, the raising and inverting stoppers 1230 and 1231 for determining the raising/inverting stroke of the forceps raising base 36 are mounted on the grip portion 2 located outside the endoscope. Therefore, an operating portion unit common to all types of endoscopes having forceps raising bases with different raising/inverting strokes can be realized by selectively mounting the raising and inverting stoppers 1230 and 1231. In addition, if the user requires a raising angle larger than the initial raising angle, the raising angle can be adjusted to the required angle by mounting a raising stopper 1230 having a smaller width. When a raising angle error occurs because of a slack of the forceps raising wire 26, the tension of the forceps raising wire 26 can be adjusted by only replacing the raising stopper 1230 outside the endoscope. For this reason, repairs can be easily performed without disassembling the endoscope, unlike the case wherein the stoppers are arranged in the operating portion.

Referring to FIG. 145, a plurality of stopper set screw holes 1233 are formed in the protective cover 1229 so that the mounting positions of the raising and inverting stoppers 1230 and 1231 can be changed to adjust the raising/inverting stroke of the forceps raising base. In this case, one type of a raising stopper 1230 and one type of a inverting stopper 1231 are required only.

FIG. 146 is a sectional view showing modifications of the breakage preventing member 1108 and the breakage preventing cover 1111 in FIGS. 131A and 131B. A breakage preventing member 1108 and a breakage preventing cover 1111 of these modifications are fixed by bonding/fixing a pin 1234 made of an insulating material such as a resin material to a breakage preventing mouthpiece 1109. The outer diameter of a fitting portion 1235 of the breakage preventing member 1108, in which the pin 1234 is fitted, is set to be larger than the inner diameter of a fitting hole 1236 on the breakage preventing member 1108 side. For this reason, a rubber portion 1204 of the breakage preventing member 1108 always presses the pin 1234, watertightness can be ensured. In these modifications, the rotational torque of the breakage preventing cover 1111 can be sufficiently transmitted to the breakage preventing member 1108 through only the pin 1234, and removal in the axial direction can be prevented.

According to the endoscopes described with reference to FIGS. 131 to 146, since the tool portion for connecting and adjusting the components of the endoscope is arranged on part of the components of the endoscope, connecting and adjusting tools which are not necessary for examinations can be omitted. Therefore, the number of components can be decreased, and the expense born by the user can be reduced.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An endoscope including:

an operating portion placed outside a living body;

an elongated insertion portion having a proximal end portion coupled to said operating portion, a distal end portion to be inserted in the living body, and an instrument insertion channel extending through said insertion portion;

a raising mechanism, having an operation wire, for directing a distal end portion of an instrument, caused to extend through the instrument insertion channel, to a predetermined position; and operation means, provided in said operating portion, for operating said operation wire, said operation means comprising:

a distal end body portion arranged at the distal end portion of said elongated insertion portion and incorporating observation means for observing an interior of the living body;

a support member for forming at least a portion of an outer surface of said distal end portion of the endoscope, said support member being detachable from said distal end body portion of said operation means;

a raising base which is supported on said support member such that an angle at which said raising base is arranged is adjustable;

wherein said operation wire has an end which is fitted in said raising base; and a transmission member having an end detachably coupled to another end of said operation wire; and wherein said operation means is arranged to cause said transmission member to operate said operation wire such that said operation wire adjusts an angle of said raising base.

2. An endoscope according to claim 1, wherein said end of said operation wire which is fitted in said raising base is fixed to said raising base.

3. An endoscope according to claim 1, wherein:

said raising base is movable between a lower resting position and a raised position; and said support member has a stopper for determining a raised position of said raising base.

4. An endoscope according to claim 1, wherein:

said operating portion comprises a housing to which the proximal end portion of said insertion portion is coupled; and said end of said transmission member to which said operation wire is detachably coupled, is located outside the housing.

5. An endoscope according to claim 4, further comprising guide means for causing said operation wire to extend outward through said housing, said guide means having a guide tube enclosing said operation wire, and said guide tube being liquidtightly sealed with respect to said housing and guiding said operation wire to cause said operation wire to extend outward through said housing.

6. An endoscope according to claim 4, further comprising coupling means for coupling one end of said transmission member to said operation wire, said coupling means coupling said transmission member to said operation wire such that said transmission member and said operation wire are arranged in substantially a straight line.

7. An endoscope according to claim 1, coupled, and further comprising means for coupling said end of said transmission member to said operation wire, said coupling means being capable of adjusting a coupling position of said operation wire with respect to said end of said transmission member, thereby maintaining a moving range of said raising base regardless of a length of said operation wire.

8. An endoscope according to claim 1, wherein:

said operating portion comprises a grip which an operator can grip, and an operating knob for operating a direction of the distal end portion; and the endoscope further comprising coupling means for coupling said end of said transmission member to said operation wire, said coupling means being arranged on a same side as that of said operation knob at a position near to a distal end portion side of said grip.

9. An endoscope according to claim 4, further comprising guide means for causing the operation wire to extend outward through the housing, said guide means having a flexible tube for causing said operation wire to loosely extend therethrough and to be movable in an axial direction, and said operating portion having holding means, arranged in the housing, for holding said flexible tube.

10. An endoscope according to claim 1, further comprising coupling means for coupling said end of said transmission member to said operation wire, said coupling means comprising:

adjusting means for adjusting a coupling position of said operation wire with respect to said end of said transmission member; and cooperation means arranged on part of said endoscope and capable of operating in cooperation with said adjusting means to operate said adjusting means.

11. An endoscope according to claim 1, wherein said operation wire and said raising base are detachable from each other.

12. An endoscope including:

an operating portion placed outside a living body;

an elongated insertion portion having a proximal end portion coupled to said operating portion, a distal end portion to be inserted into the living body, and an instrument insertion channel extending through said insertion portion;

a raising mechanism, having an operating wire, for directing a distal end portion of an instrument, caused to extend through instrument insertion channel, to a predetermined position; and operation means, provided in said operating portion, for operating said operation wire, said operation means comprising:

a distal end body portion arranged at the distal end portion of said elongated insertion portion and incorporating observation means for observing an interior of the living body;

a support member for forming at least a portion of an outer surface of said distal end portion of the endoscope, said support member including a lock member which is elastic and which is detachable from said distal end body portion of said operation means; and a raising base which is supported by said support member such that an angle of said raising base is adjustable by said operation wire;

and wherein said operation wire is detachable from said operation means.

13. An endoscope according to claim 12, wherein said lock member comprises:

a mount portion having elasticity, and which mount portion is firmly mounted on said distal end body portion; and lock means arranged on said mount portion for locking a detaching jig for detaching said support member against an elastic force of said mount portion.

14. An endoscope according to claim 12, wherein said lock member has an outer shape designed to be more resistant to an influence of an external force than other portions.

15. An endoscope according to claim 14, wherein said support member has a shape decreasing in diameter toward a distal end side.

* * * * *